(12) United States Patent
Kitamura et al.

(10) Patent No.: US 9,812,650 B2
(45) Date of Patent: *Nov. 7, 2017

(54) ORGANIC ELECTROLUMINESCENT ELEMENT, COMPOUND AND MATERIAL FOR ORGANIC ELECTROLUMINESCENT ELEMENT, USED IN THE SAME, AND LIGHT EMITTING DEVICE, DISPLAY DEVICE AND ILLUMINATION DEVICE, USING THE ELEMENT

(71) Applicant: UDC Ireland Limited, Dublin (IE)

(72) Inventors: Tetsu Kitamura, Kanagawa (JP); Koji Takaku, Kanagawa (JP); Wataru Sotoyama, Kanagawa (JP); Yasunori Yonekuta, Kanagawa (JP); Toru Watanabe, Kanagawa (JP); Masaru Kinoshita, Kanagawa (JP)

(73) Assignee: UDC Ireland Limited, Dublin (IE)

( * ) Notice: Subject to any disclaimer, the term of this patent is extended or adjusted under 35 U.S.C. 154(b) by 758 days.

This patent is subject to a terminal disclaimer.

(21) Appl. No.: 14/349,874

(22) PCT Filed: Oct. 5, 2012

(86) PCT No.: PCT/IB2012/001981
§ 371 (c)(1),
(2) Date: Oct. 16, 2014

(87) PCT Pub. No.: WO2013/108069
PCT Pub. Date: Jul. 25, 2013

(65) Prior Publication Data
US 2015/0076462 A1    Mar. 19, 2015

(30) Foreign Application Priority Data

Oct. 6, 2011 (JP) ................................. 2011-222207
Mar. 30, 2012 (JP) ................................. 2012-083250

(51) Int. Cl.
*H01L 51/00* (2006.01)
*C07D 307/77* (2006.01)
(Continued)

(52) U.S. Cl.
CPC ........ *H01L 51/0061* (2013.01); *C07D 307/77* (2013.01); *C09B 57/001* (2013.01);
(Continued)

(58) Field of Classification Search
CPC ..... C07D 307/77; C09B 57/001; C09K 11/06; H01L 51/0054; H01L 51/0061;
(Continued)

(56) References Cited

U.S. PATENT DOCUMENTS

2004/0076853 A1* 4/2004 Jarikov .................. C09K 11/06
428/690
2014/0008621 A1* 1/2014 Kaminaga ........... H01L 51/0052
257/40

FOREIGN PATENT DOCUMENTS

JP    2010-205986    9/2010

OTHER PUBLICATIONS

International Patent Application No. PCT/IB2012/001981, International Preliminary Report on Patentability, dated Apr. 17, 2014, 7 pages.

* cited by examiner

*Primary Examiner* — Dawn Garrett
(74) *Attorney, Agent, or Firm* — Riverside Law LLP

(57) ABSTRACT

An organic electroluminescent element comprising a substrate, a pair of electrodes including an anode and a cathode, disposed on the substrate, and at least one organic layer which is arranged between the electrodes and which includes a light emitting layer, wherein the organic layer contains a compound represented by general formula (1) in
(Continued)

at least one layer. The organic electroluminescent element has a high luminous efficiency, excellent blue color purity, and little chromaticity change due to drive deterioration. (In the formula, the two Xs either both represent an O atom or both represent an S atom, and $R^1$-$R^{10}$ each independently represents a hydrogen atom or a substituent group).

20 Claims, 1 Drawing Sheet

(51) Int. Cl.
 *C09B 57/00* (2006.01)
 *C09K 11/06* (2006.01)
 *H01L 51/50* (2006.01)
(52) U.S. Cl.
 CPC ...... *H01L 51/0054* (2013.01); *H01L 51/0071* (2013.01); *H01L 51/0073* (2013.01); *H01L 51/0074* (2013.01); *H01L 51/0094* (2013.01); *C09K 11/06* (2013.01); *H01L 51/0072* (2013.01); *H01L 51/5012* (2013.01); *H01L 51/5056* (2013.01); *H01L 51/5072* (2013.01); *H01L 51/5088* (2013.01); *H01L 51/5092* (2013.01)
(58) Field of Classification Search
 CPC ............. H01L 51/0071; H01L 51/0072; H01L 51/0073; H01L 51/0074; H01L 51/0094; H01L 51/5012; H01L 51/5056; H01L 51/5072; H01L 51/5088; H01L 51/5092
 See application file for complete search history.

[FIG. 1]
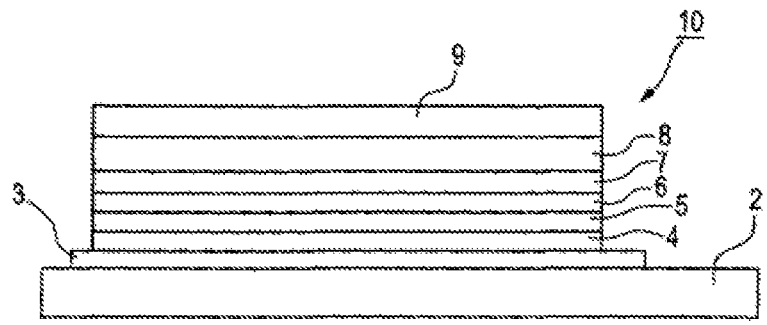
[FIG. 2]
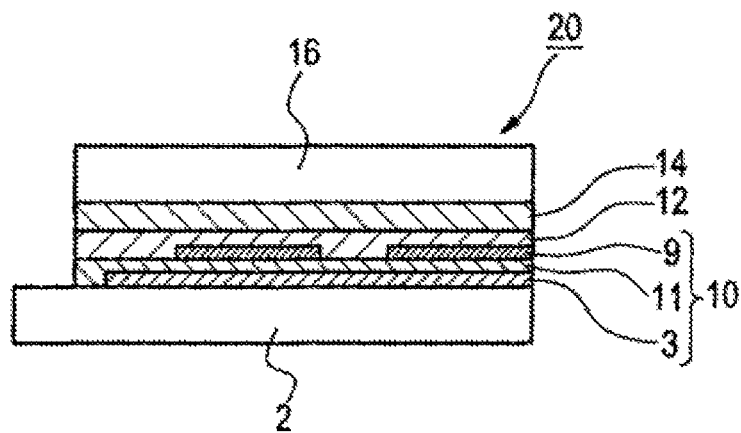
[FIG. 3]
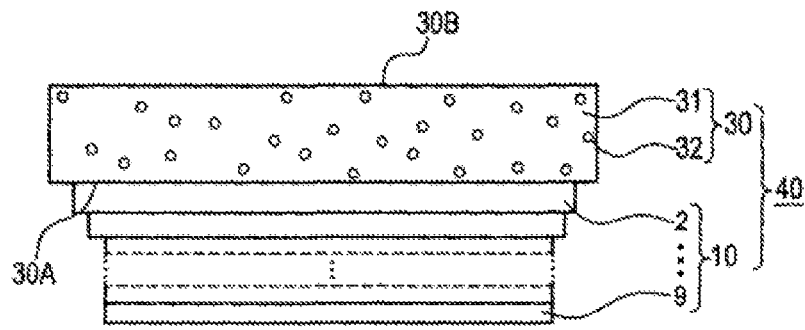

ORGANIC ELECTROLUMINESCENT ELEMENT, COMPOUND AND MATERIAL FOR ORGANIC ELECTROLUMINESCENT ELEMENT, USED IN THE SAME, AND LIGHT EMITTING DEVICE, DISPLAY DEVICE AND ILLUMINATION DEVICE, USING THE ELEMENT

CROSS-REFERENCE TO RELATED APPLICATIONS

The present application is a 35 U.S.C. §371 national phase application from, and claiming priority to, International Application PCT/IB2012/001981, filed Oct. 5, 2012, which claims priority to Japanese Patent Application No. 2011-222207, filed Oct. 6, 2011, and Japanese Patent Application No. 2012-083250, filed Mar. 30, 2012, all of which applications are incorporated by reference herein in their entireties.

TECHNICAL FIELD

The present invention relates to an organic electroluminescent element, as well as a compound and material for an organic electroluminescent element that can be used therein. Furthermore, the present invention relates to a light emitting device, display device, and illumination device using the organic electroluminescent element.

BACKGROUND ART

Research and development have been actively conducted because the organic electroluminescent element (referred to below as "element" or "organic EL element") can achieve light emission with high luminance using a low voltage drive. The organic electroluminescent element has an organic layer between a pair of electrodes, an electron injected from a cathode and an electron hole injected from an anode are rebonded in the organic layer, and the energy of a generated exciton is used for light emission. The organic electroluminescent element can be provided as an element having various light emitting wavelengths, and can be expected to be applied in a wide range of applications due to fast response time, relative thinness, and light weight. Of these, the development of an organic electroluminescent element with fast response speed and high luminous efficiency is important in applications for full color displays and the like, and various development and research results have been reported in the past.

For example, patent document 1 describes obtaining an organic electroluminescent element where the light emission color is blue or blue-green, with favorable luminous efficiency, and improved longevity, using a compound where a heterocyclic ring containing a nitrogen atom is condensed in the major axis (positions 1, 2, 3, 6, 7, and 8) direction of a pyrene skeleton. Patent document 2 describes enabling light emission and increasing longevity in the blue region of an element, using a material that forms a ring by a single bond, methylene chain, or the like with regards to a condensed structure such as pyrene or the like.

On the other hand, the pyrene skeleton compound is conventionally used in other fields, and patent document 3 describes using a compound or the like with a condensed ether substitution group, such as a benzene ring linked to the pyrene skeleton through an oxygen atom or a sulfur atom, in an electrophotographic photoreceptor as a photoconductive material. Furthermore, patent document 4 describes an organic transistor using a compound where a heterocyclic ring containing a sulfur atom, oxygen atom, or nitrogen atom is condensed in the major axis (positions 1, 2, 3, 6, 7, and 8) direction of a pyrene skeleton, but does not allude to the use of an organic electroluminescent element. Note that in patent document 4, a compound having a substitution group in the minor axis (positions 4, 5, 9, and 10) direction of pyrene was not specifically examined.

PRIOR TECHNOLOGY DOCUMENTS

Patent Documents

Patent Document 1: Japanese Unexamined Patent Application 2010-205986
Patent Document 2: WO 2010012328
Patent Document 3: Japanese Unexamined Patent Application H2-120747
Patent Document 4: Japanese Unexamined Patent Application 2011-51984

SUMMARY OF THE INVENTION

Problem to be Resolved by the Invention

However, as a result of examination by the present inventors, the organic electroluminescent element described in the aforementioned patent document 1 in many cases did not have sufficient blue color purity. Furthermore, of the compounds described the same document, organic electroluminescent elements using a compound where the color purity is favorable to a certain degree was seen to have a change in chromaticity due to drive deterioration where the light emitting strength is reduced (also referred to below as color change due to drive deterioration). Furthermore, after examining the organic electroluminescent element described in patent document 2, the organic electroluminescent element of patent document 2 displays blue light emission, but according to the studies by the present inventors, it is clear that the compounds described in the same document have low luminous efficiency, and that there are points of improvement for color change due to drive deterioration.

Furthermore, after the compounds described in patent document 3 were applied in the organic electroluminescent element, it is clear that the compounds described in the document also have low luminous efficiency, and that there are points of improvement for color change due to deterioration. It is clear that the compounds described in the document are improved with regards to color change due to deterioration when the compounds described in patent document 4 are applied to an organic electroluminescent element.

Means for Resolving Problems

Therefore, the present inventors performed intensive studies in order to provide an organic electroluminescent element with high luminous efficiency, excellent blue color purity, and low color change due to drive deterioration. As a result, it was discovered that the aforementioned problems can be resolved if a pyrene derivative having a specific structure is used, thereby achieving the present invention as described below.

[1] An organic electroluminescent element, comprising:
 a substrate;
 a pair of electrodes including an anode and a cathode, disposed on the substrate; and at least one organic layer which is arranged between the electrodes and which includes a light emitting layer; wherein the organic layer contains a compound expressed by general formula (1) in at least one layer.

General Formula (1)

[Formula 1]

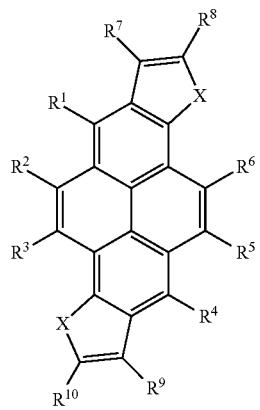

In general formula (1), the two X's represent the same linking group, and either both represent oxygen atoms or both represent sulfur atoms, R1 through $R^{10}$ independently represent a hydrogen atom or a substitution group, and $R^1$ through $R^{10}$ may jointly form a ring. However, if the two X's represent sulfur atoms, at least one of $R^2$, $R^3$, $R^5$, and $R^6$ represents a substitution group.)

[2] The organic electroluminescent element according to [1], wherein the compound expressed by general formula (1) is expressed by general formula (2).

General Formula (2)

[Formula 2]

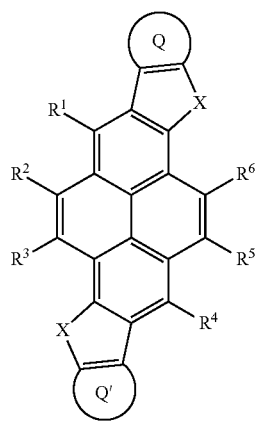

(In general formula (2), the two X's represent the same linking group, and either both represent oxygen atoms or both represent sulfur atoms, $R^1$ through $R^6$ independently represent a hydrogen atom or a substitution group, and $R^1$ through $R^6$ may jointly form a ring. Q and Q' independently represent an aromatic five membered ring or an aromatic six-membered ring. However, if the two X's represent sulfur atoms, at least one of $R^2$, $R^3$, $R^5$, and $R^6$ represents a substitution group.)

[3] The organic electroluminescent element according to [2], wherein the compound expressed by general formula (2) is expressed by general formula (3).

General Formula (3)

[Formula 3]

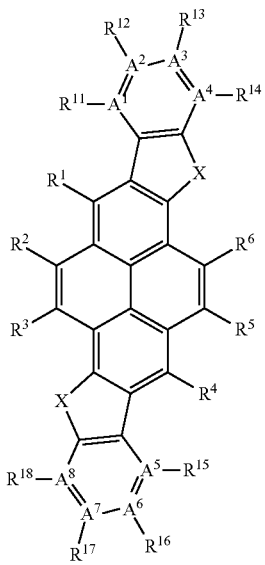

(In general formula (3), the two X's represent the same linking group, and either both represent oxygen atoms or both represent sulfur atoms, $R^1$ through $R^6$ independently represent a hydrogen atom or a substitution group, and $R^1$ through $R^6$ may jointly form a ring. $R^{11}$ through $R^{18}$ independently represent a hydrogen atom or a substitution group. $A^1$ through $A^8$ independently represent a carbon atom or a nitrogen atom, and if $A^1$ through $A^8$ represent a nitrogen atom, $R^{11}$ through $R^{18}$ that bonds thereto does not exist. However, if the two X's represent sulfur atoms, at least one of $R^2$, $R^3$, $R^5$, and $R^6$ represents a substitution group.)

[4] The organic electroluminescent element according to [3], wherein the compound expressed by general formula (3) is expressed by general formula (4).

[Formula 4]

General Formula (4)

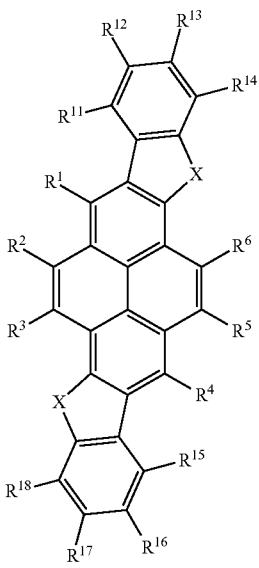

(In general formula (4), the two X's represent the same linking group, and either both represent oxygen atoms or both represent sulfur atoms, $R^1$ through $R^6$ independently represent a hydrogen atom or a substitution group, and $R^1$ through $R^6$ may jointly form a ring. $R^{11}$ through $R^{18}$ independently represent a hydrogen atom or a substitution group. However, if the two X's represent sulfur atoms, at least one of $R^2$, $R^3$, $R^5$, and $R^6$ represents a substitution group.)

[5] The organic electroluminescent element according to [4], where in general formula (4), at least one of $R^1$ through $R^6$ and through $R^{18}$ is a substitution group containing one of a fluorine atom, alkyl group, sylyl group, or amino group.

[6] The organic electroluminescent element according to [4] or [5], wherein the compound expressed by general formula (4) is expressed by general formula (5).

General Formula (5)

[Formula 5]

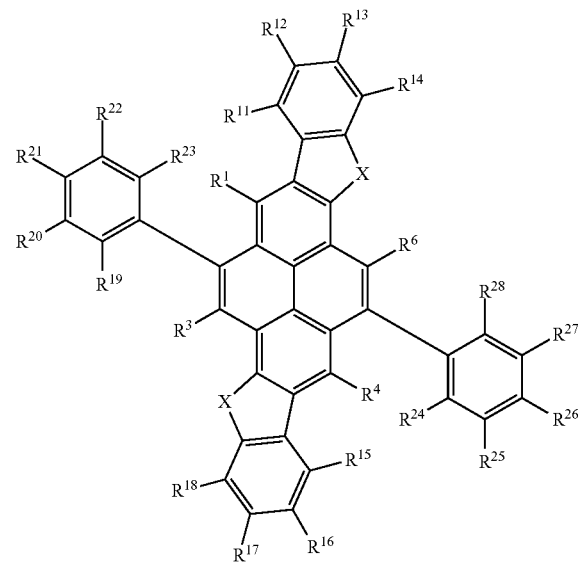

(In general formula (5), the two X's represent the same linking group, and either both represent oxygen atoms or both represent sulfur atoms, and $R^1$, $R^3$, $R^4$, and $R^6$ independently represent a hydrogen atom or a substitution group. $R^{11}$ through $R^{28}$ independently represent a hydrogen atom or a substitution group. However, at least one of $R^3$ through $R^6$ and $R^{11}$ through $R^{18}$ is a substitution group containing one of a fluorine atom, alkyl group, sylyl group, or amino group, or at least one of $R^{19}$ through $R^{28}$ is a fluorine atom, alkyl group, sylyl group, or amino group.)

[7] The organic electroluminescent element according to [6], where in general formula (5), $R^{13}$ is a substitution group.

[8] The compound according to [6], wherein the compound expressed by general formula (5) is expressed by general formula (6).

[Formula 6]

General Formula (6)

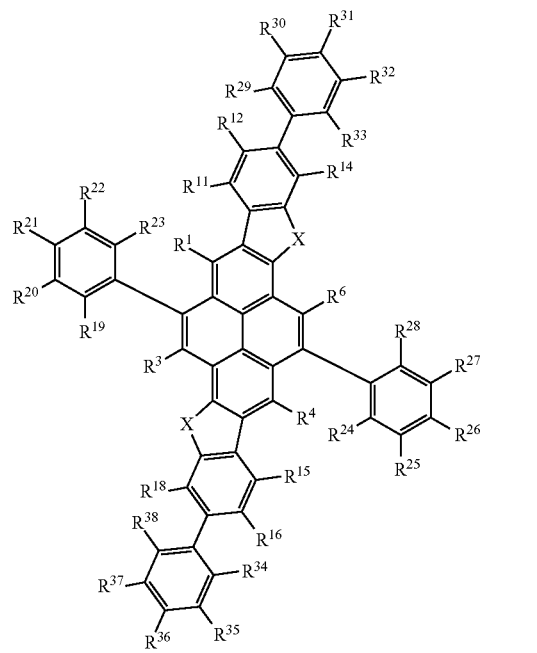

(In general formula (6), the two X's represent the same linking group, and either both represent oxygen atoms or both represent sulfur atoms, and $R^1$, $R^3$, $R^4$, and $R^6$ independently represent a hydrogen atom or a substitution group. $R^{11}$ through $R^{38}$ independently represent a hydrogen atom or a substitution group.)

[9] The compound according to [4], wherein the compound expressed by general formula (4) is expressed by general formula (7).

[Formula 7]

General Formula (4)

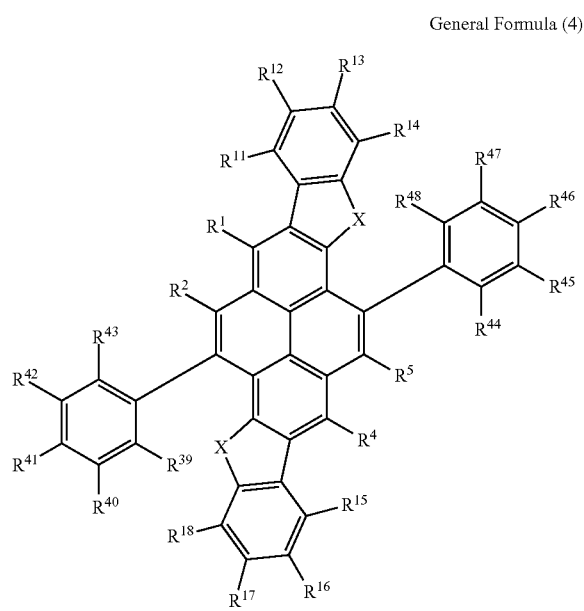

(In general formula (7), the two X's represent the same linking group, and either both represent oxygen atoms or both represent sulfur atoms, and $R^1$, $R^2$, $R^4$, and $R^5$ independently represent a hydrogen atom or a substitution group. A ring may be jointly formed by a plurality of $R^1$, $R^2$, $R^4$, and $R^5$. $R^{11}$ through $R^{48}$ independently represent a hydrogen atom or a substitution group.)

[10] The organic electroluminescent element according to [9], where in general formula (7), $R^{13}$ is a substitution group.

[11] The compound according to [9], wherein the compound expressed by general formula (7) is expressed by general formula (8).

[Formula 8]

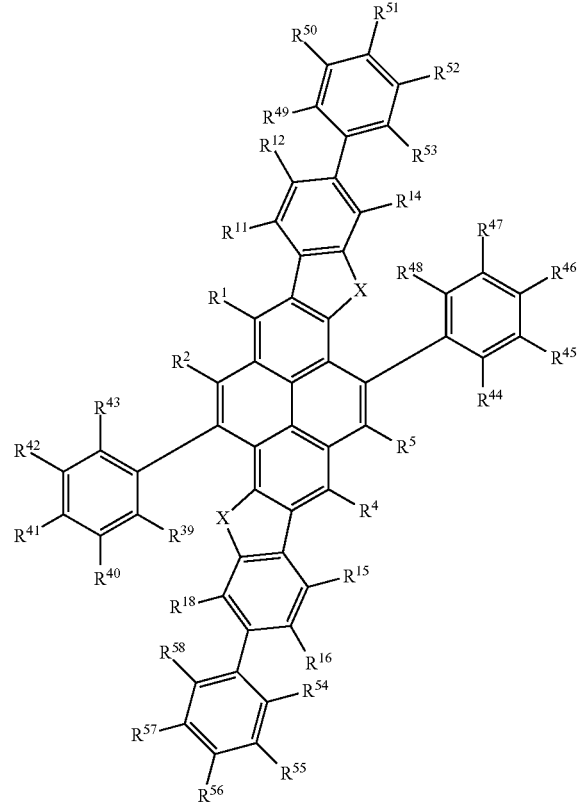

General Formula (8)

(In general formula (8), the two X's represent the same linking group, and either both represent oxygen atoms or both represent sulfur atoms, and $R^1$, $R^2$, $R^4$, and $R^5$ independently represent a hydrogen atom or a substitution group. A ring may be jointly formed by a plurality of $R^1$, $R^2$, $R^4$, and $R^5$. $R^{11}$ through $R^{58}$ independently represent a hydrogen atom or a substitution group.)

[12] The compound according to [4], wherein the compound expressed by general formula (4) is expressed by general formula (9).

[Formula 9]

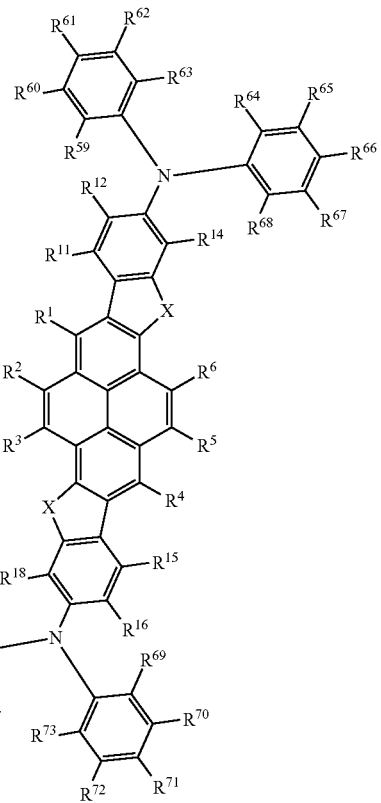

General Formula (9)

(In general formula (9), the two X's represent the same linking group, and either both represent oxygen atoms or both represent sulfur atoms, and $R^1$ through $R^6$ independently represent a hydrogen atom or a substitution group. A ring may be jointly formed by a plurality of $R^1$, $R^2$, $R^4$, and $R^6$. $R^{11}$ through $R^{78}$ independently represent a hydrogen atom or a substitution group.)

[13] The organic electroluminescent element according to [12], where in general formula (9), at least one of $R^2$, $R^3$, $R^5$, and $R^6$ is a substitution group.

[14] The organic electroluminescent element according to any one of [1] through [13], where in general formula (1), both X's represent oxygen atoms.

[15] The organic electroluminescent element according to any one of [1] through [14], wherein the molecular weight of the compound expressed by general formula (1) is 900 or less.

[16] The organic electroluminescent element according to any one of [1] through [15], wherein at least one layer of the organic layer containing the compound expressed by general formula (1) is a light emitting layer.

[17] The organic electroluminescent element according to any one of [1] through [16], wherein the compound expressed by general formula (1) is a light emitting material.

[18] The organic electroluminescent element according to any one of [1] through [17], wherein a compound expressed by the following general formula (An-1) is included in at least one layer of the organic layer.

[Formula 10]

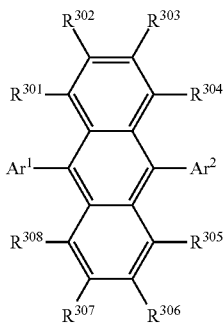

General Formula (An-1)

(In general formula (An-1), $Ar^1$ and $Ar^2$ independently represent an aryl group or a heteroaryl group, $R^{301}$ through $R^{308}$ independently represent a hydrogen atom or a substitution group. $R^{301}$ and $R^{302}$, $R^{302}$ and $R^{303}$, $R^{303}$ and $R^{304}$, $R^{305}$ and $R^{306}$, $R^{306}$ and $R^{307}$, and $R^{307}$ and $R^{308}$ can be bonded together to form a ring.)

[19] The organic electroluminescent element according to [18], wherein the compound expressed by general formula (An-1) is a compound expressed by the following formula (An-2).

[Formula 11]

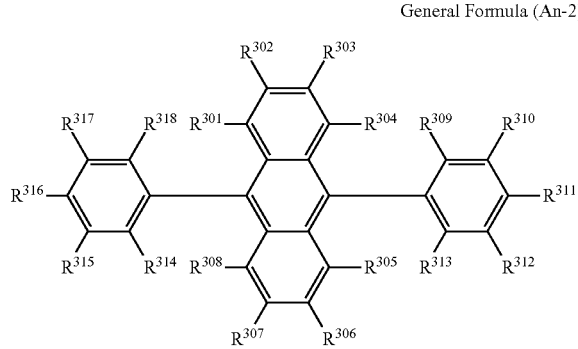

General Formula (An-2)

(In general formula (An-2), $R^{301}$ through $R^{318}$ independently represent a hydrogen atom or a substitution group. $R^{301}$ and $R^{302}$, $R^{302}$ and $R^{303}$, $R^{303}$ and $R^{304}$, $R^{305}$ and $R^{306}$, $R^{306}$ and $R^{307}$, $R^{307}$ and $R^{308}$, $R^{309}$ and $R^{310}$, $R^{310}$ and $R^{311}$, $R^{311}$ and $R^{312}$, $R^{312}$ and $R^{313}$, $R^{314}$ and $R^{315}$, $R^{315}$ and $R^{316}$, $R^{316}$ and $R^{317}$, and $R^{317}$ and $R^{318}$ can be bonded together to form a ring.)

[20] The organic electroluminescent element according to [18] or [19], wherein at least one layer of the organic layer containing a compound expressed by general formula (An-1) is a light emitting layer.

[21] The organic electroluminescent element according to any one of [1] through [20], wherein a compound expressed by the following general formula (P-1) is included in at least one layer of the organic layer.

[Formula 12]

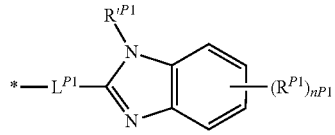

General Formula (P-1)

(In general formula (P-1), $R^{P1}$ and $R^{\prime P1}$ each represent an alkyl group, aryl group, or heteroaryl group. $n^{P1}$ represents an integer of 0 through 4, and if plural, the plurality of $R^{P1}$ may be the same or different. $L^{P1}$ represents either a single bond or a bivalent linking group containing an aryl ring or a heteroaryl ring. * represents a site for bonding to the anthracene ring of general formula (P)).

[22] The organic electroluminescent element according to any one of [1] through [21], wherein a compound expressed by the following general formula (P-2) is included in at least one layer of the organic layer.

[Formula 13]

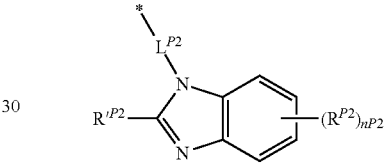

General Formula (P-2)

In general formula (P-2), $R^{P2}$ and $R^{\prime P2}$ each represent an alkyl group, aryl group, or heteroaryl group. $n^{P2}$ represents an integer of 0 through 4, and if plural, the plurality of $R^{P2}$ may be the same or different. $L^{P2}$ represents either a single bond or a bivalent linking group containing an aryl ring or a heteroaryl ring. * represents a site for bonding to the anthracene ring of general formula (P)).

[23] The organic electroluminescent element according to any one of [1] through [22], wherein a compound expressed by the following general formula (P-3) is included in at least one layer of the organic layer.

[Formula 14]

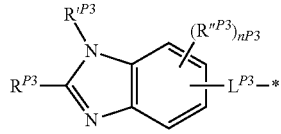

General Formula (P-3)

(In general formula (P-3), $R^{P3}$, $R^{\prime P3}$, and $R^{\prime\prime P3}$ each represent an alkyl group, aryl group, or heteroaryl group. $n^{P3}$ represents an integer of 0 through 4, and if plural, the plurality of $R^{P3}$ may be the same or different. $L^{P3}$ represents either a single bond or a bivalent linking group containing an aryl ring or a heteroaryl ring. * represents a site for bonding to the anthracene ring of general formula (P)).

[24] The organic electroluminescent element according to any one of [1] through [23], wherein a compound expressed by the following general formula (P-4) is included in at least one layer of the organic layer.

[Formula 15]

General Formula (P-4)

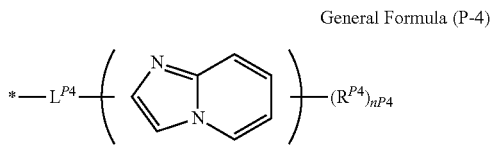

(In general formula (P-4), $R^{P4}$ represents an alkyl group, aryl group, or heteroaryl group. $n^{P4}$ represents an integer of 0 through 4, and if plural, the plurality of $R^{P4}$ may be the same or different. $L^{P4}$ represents either a single bond or a bivalent linking group containing an aryl ring or a heteroaryl ring. * represents a site for bonding to the anthracene ring of general formula (P).)

[25] The organic electroluminescent element according to any one of [1] through [24], wherein a compound expressed by the following general formula (P-5) is included in at least one layer of the organic layer.

[Formula 16]

General Formula (P-5)

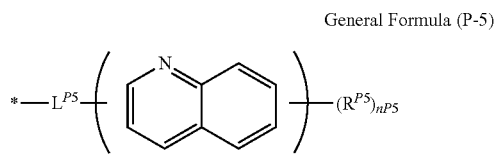

(In general formula (P-5), $R^{P5}$ represents an alkyl group, aryl group, or heteroaryl group. $n^{P5}$ represents an integer of 0 through 4, and if plural, the plurality of $R^{P5}$ may be the same or different. $L^{P5}$ represents either a single bond or a bivalent linking group containing an aryl ring or a heteroaryl ring. * represents a site for bonding to the anthracene ring of general formula (P).)

[26] The organic electroluminescent element according to any one of [1] through [25], comprising a step of forming a light emitting layer using a vacuum vapor deposition process.

[27] The organic electroluminescent element according to any one of [1] through [25], comprising a step of forming a light emitting layer using a wet process.

[28] A light emitting device using an organic electroluminescent element according to any one of [1] through [27].

[29] A display device using an organic electroluminescent element according to any one of [1] through [27].

[30] A lighting device using an organic electroluminescent element according to any one of [1] through [27].

[31] A compound expressed by the following general formula (1).

[Formula 17]

General Formula (1)

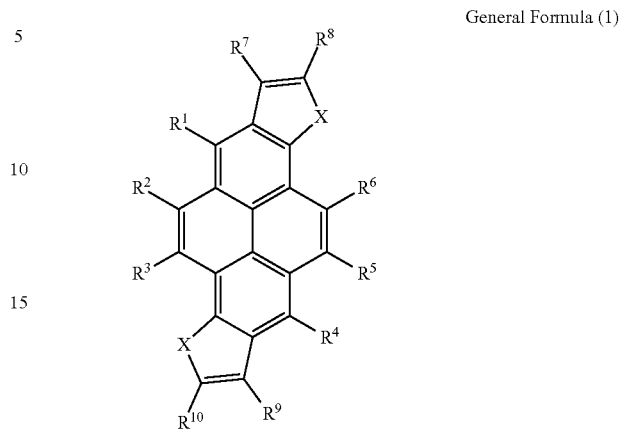

(In general formula (1), the two X's represent the same linking group, and either both represent oxygen atoms or both represent sulfur atoms, $R^1$ through $R^{10}$ independently represent a hydrogen atom or a substitution group, and $R^1$ through $R^{10}$ may jointly form a ring. However, if the two X's represent sulfur atoms, at least one of $R^2$, $R^3$, $R^5$, and $R^6$ represents a substitution group.)

[32] The compound according to [31], wherein the compound expressed by general formula (1) is expressed by general formula (2).

[Formula 18]

General Formula (2)

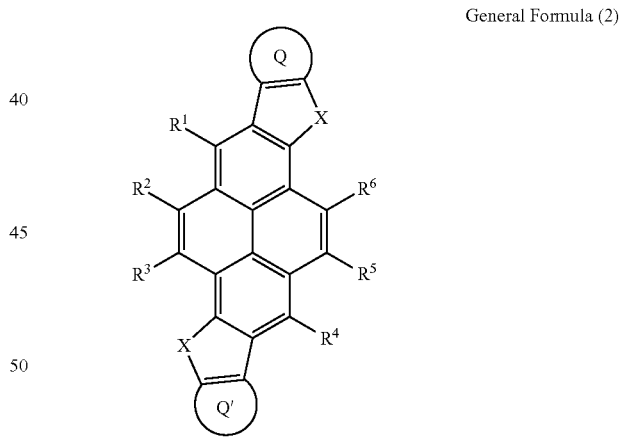

(In general formula (2), the two X's represent the same linking group, and either both represent oxygen atoms or both represent sulfur atoms, $R^1$ through $R^6$ independently represent a hydrogen atom or a substitution group, and $R^1$ through $R^6$ may jointly form a ring. Q and Q' independently represent an aromatic five membered ring or an aromatic six-membered ring. However, if the two X's represent sulfur atoms, at least one of $R^2$, $R^3$, $R^5$, and $R^6$ represents a substitution group.)

[33] The compound according to [32], wherein the compound expressed by general formula (2) is expressed by general formula (3).

[Formula 19]

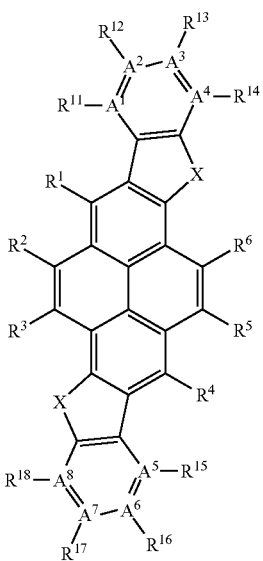

General Formula (3)

(In general formula (3), the two X's represent the same linking group, and either both represent oxygen atoms or both represent sulfur atoms, $R^1$ through $R^6$ independently represent a hydrogen atom or a substitution group, and $R^1$ through $R^6$ may jointly form a ring. $R^{11}$ through $R^{18}$ independently represent a hydrogen atom or a substitution group. $A^1$ through $A^8$ independently represent a carbon atom or a nitrogen atom, and if $A^1$ through $A^8$ represent a nitrogen atom, $R^{11}$ through $R^{18}$ that bonds thereto does not exist. However, if the two X's represent sulfur atoms, at least one of $R^2$, $R^3$, $R^5$, and $R^6$ represents a substitution group.)

[34] The compound according to [33], wherein the compound expressed by general formula (3) is expressed by general formula (4).

[Formula 20]

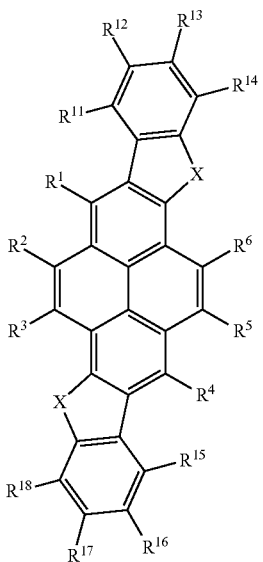

General Formula (4)

(In general formula (4), the two X's represent the same linking group, and either both represent oxygen atoms or both represent sulfur atoms, $R^1$ through $R^6$ independently represent a hydrogen atom or a substitution group, and $R^1$ through $R^6$ may jointly form a ring. $R^{11}$ through $R^{18}$ independently represent a hydrogen atom or a substitution group. However, if the two X's represent sulfur atoms, at least one of $R^2$, $R^3$, $R^5$, and $R^6$ represents a substitution group.)

[35] The compound according to [34], where in general formula (4), at least one of $R^1$ through $R^6$ and $R^{11}$ through $R^{18}$ is a substitution group containing one of a fluorine atom, alkyl group, sylyl group, or amino group.

[36] The compound according to [34], wherein the compound expressed by general formula (4) is expressed by general formula (5).

[Formula 21]

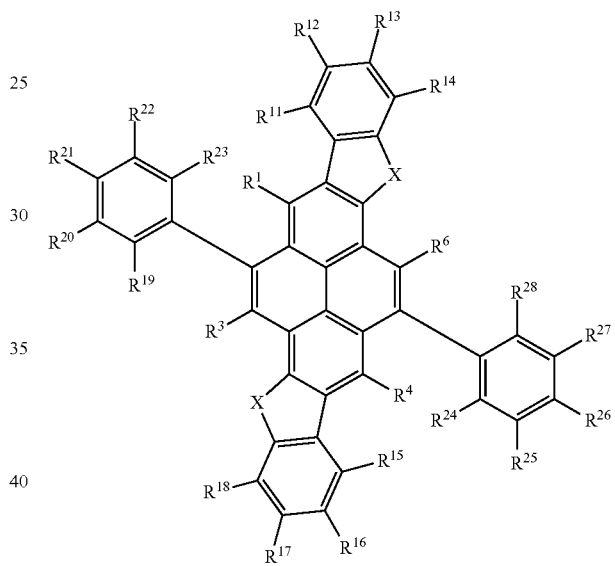

General Formula (5)

(In general formula (5), the two X's represent the same linking group, and either both represent oxygen atoms or both represent sulfur atoms, and $R^1$, $R^3$, $R^4$, and $R^5$ independently represent a hydrogen atom or a substitution group. $R^{11}$ through $R^{28}$ independently represent a hydrogen atom or a substitution group. However, at least one of $R^3$ through $R^6$ and $R^{11}$ through $R^{18}$ is a substitution group containing one of a fluorine atom, alkyl group, sylyl group, or amino group, or at least one of $R^{19}$ through $R^{28}$ is a fluorine atom, alkyl group, sylyl group, or amino group.)

[37] The organic electroluminescent element according to [36], where in general formula (5), $R^{13}$ is a substitution group.

[38] The compound according to [36], wherein the compound expressed by general formula (3) is expressed by general formula (6).

[Formula 22]

General Formula (6)

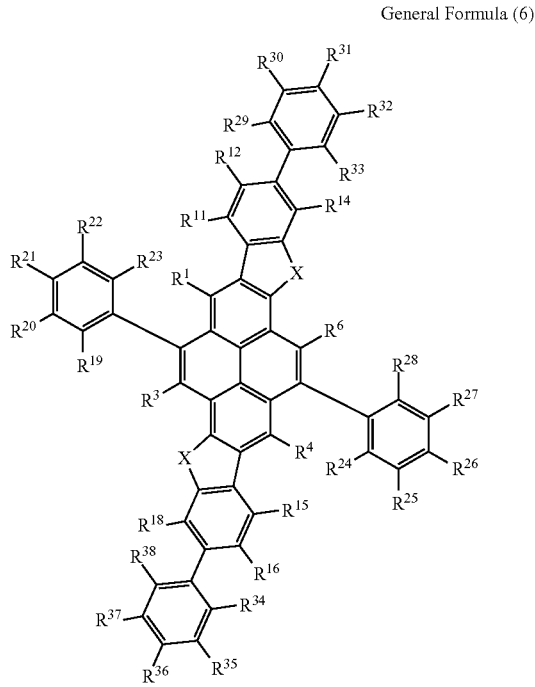

(In general formula (6), the two X's represent the same linking group, and either both represent oxygen atoms or both represent sulfur atoms, and $R^1$, $R^3$, $R^4$, and $R^6$ independently represent a hydrogen atom or a substitution group. $R^{11}$ through $R^{38}$ independently represent a hydrogen atom or a substitution group.)

[39] The compound according to [34], wherein the compound expressed by general formula (4) is expressed by general formula (7).

[Formula 23]

General Formula (7)

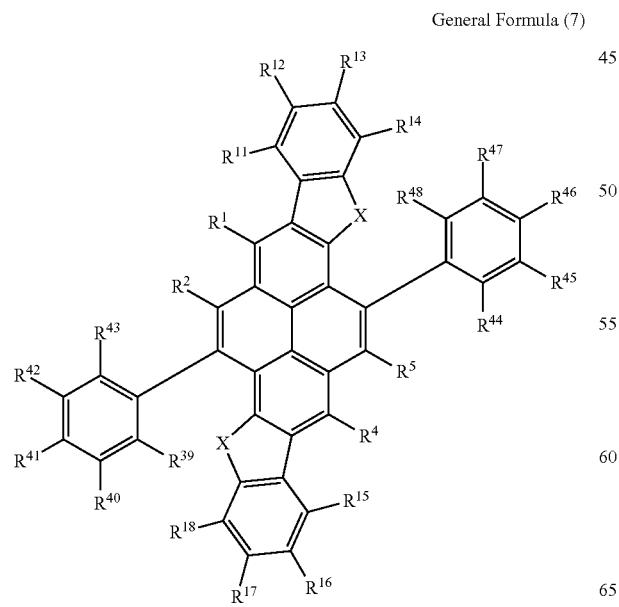

(In general formula (7), the two X's represent the same linking group, and either both represent oxygen atoms or both represent sulfur atoms, and $R^1$, $R^2$, $R^4$, and $R^5$ independently represent a hydrogen atom or a substitution group. A ring may be jointly formed by a plurality of $R^1$, $R^2$, $R^4$, and $R^5$. $R^{11}$ through $R^{48}$ independently represent a hydrogen atom or a substitution group.)

[40] The organic electroluminescent element according to [39], where in general formula (7), $R^{13}$ is a substitution group.

[41] The compound according to [39], wherein the compound expressed by general formula (7) is expressed by general formula (8).

[Formula 24]

General Formula (8)

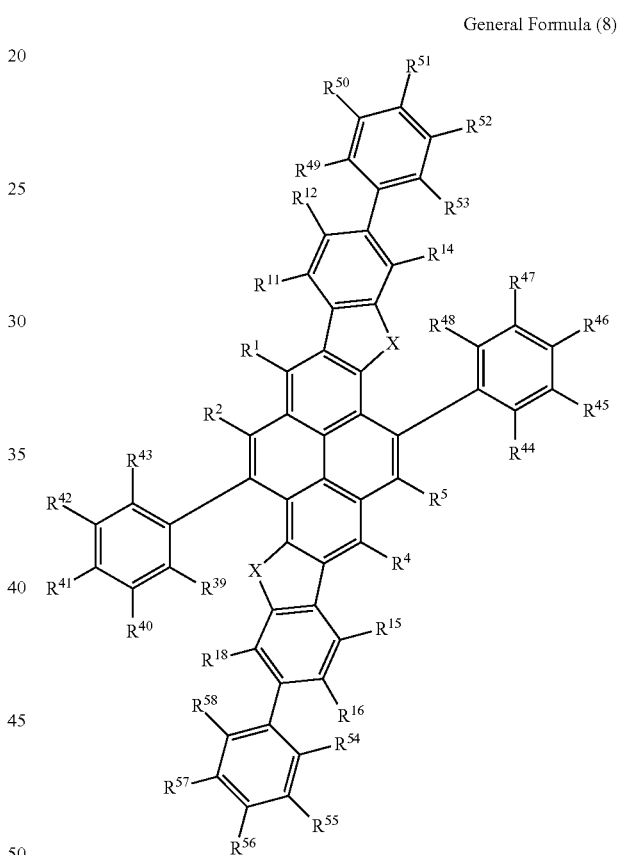

(In general formula (8), the two X's represent the same linking group, and either both represent oxygen atoms or both represent sulfur atoms, and $R^1$, $R^2$, $R^4$, and $R^5$ independently represent a hydrogen atom or a substitution group. A ring may be jointly formed by a plurality of $R^1$, $R^2$, $R^4$, and $R^5$. $R^{11}$ through $R^{58}$ independently represent a hydrogen atom or a substitution group.)

[42] The compound according to [34], wherein the compound expressed by general formula (4) is expressed by general formula (9).

[Formula 25]

General Formula (9)

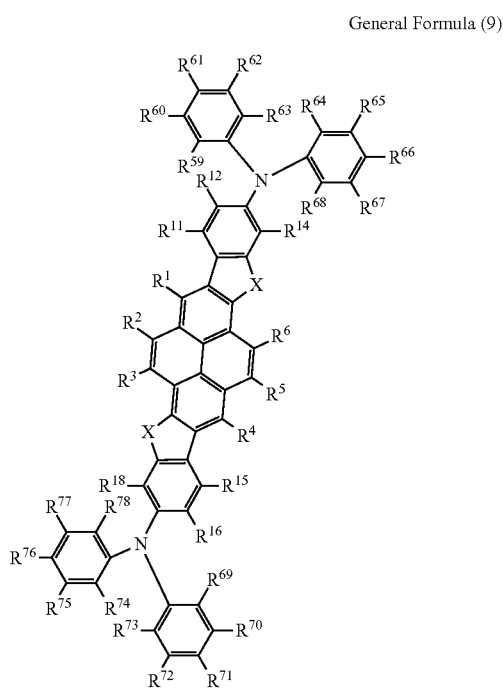

(In general formula (9), the two X's represent the same linking group, and either both represent oxygen atoms or both represent sulfur atoms, and $R^1$ through $R^6$ independently represent a hydrogen atom or a substitution group. A ring may be jointly formed by a plurality of $R^1$ through $R^6$. $R^{11}$ through $R^{78}$ independently represent a hydrogen atom or a substitution group.)

[43] The organic electroluminescent element according to [42], where in general formula (9), at least one of $R^2$, $R^3$, $R^5$, and $R^6$ is a substitution group.

[44] The compound according to any one of [31] through [43], where in general formula (1), both X's represent oxygen atoms.

[45] The compound according to any one of [31] through [44], wherein the molecular weight of the compound expressed by general formula (1) is 900 or less.

[46] A material for an organic electroluminescent element containing a compound according to any one of [31] through [45].

[47] The material for an organic electroluminescent element according to [46], which is a light emitting material.

Effect of the Invention

The organic electroluminescent element of the present invention has advantageous effects such as high luminous efficiency, excellent blue color purity, and low color change due to drive deterioration. Furthermore, if the compounds of the present invention are used, an excellent organic electroluminescent element can be easily manufactured. Furthermore, the light emitting device, display device, and illumination device of the present invention has advantageous effects such as low power consumption, excellent blue color purity, and resistance to color change even after prolonged use.

BRIEF DESCRIPTION OF THE DRAWINGS

FIG. 1 is a schematic view illustrating an example of the configuration of an organic electroluminescent element according to the present invention;

FIG. 2 is a schematic view illustrating an example of a light emitting device according to the present invention; and FIG. 3 is a schematic view illustrating an example of an illumination device according to the present invention.

DESCRIPTION OF THE PREFERRED EMBODIMENTS

The details of the present invention are described below in detail. A description of the configuration requirements is provided below based on embodiments and specific examples of the present invention, but the present invention is not restricted to these embodiments or specific examples. Note that in the present specification, the numerical range expressed using "to" refers to a range including the numerical values mentioned before and after "to" as the minimum value and maximum value.

Organic Electroluminescent Element

An organic electroluminescent element contains: a substrate; a pair of electrodes including an anode and a cathode, disposed on the substrate; and at least one organic layer which is arranged between the electrodes and which includes a light emitting layer; wherein the organic layer contains a compound expressed by general formula (1) in at least one layer.

[Formula 26]

General Formula (1)

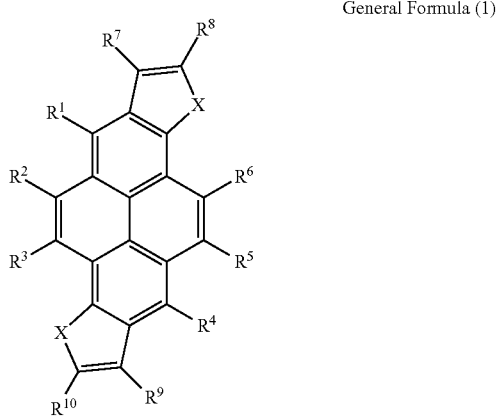

In the formula (1), the two X's both represent oxygen atoms or both represent sulfur atoms, $R^1$ through $R^{10}$ independently represent a hydrogen atom or a substitution group, and $R^1$ through $R^{10}$ may jointly form a ring. However, if the two X's represent sulfur atoms, at least one of $R^2$, $R^3$, $R^5$, and $R^6$ represents a substitution group.)

The organic electroluminescent element has characteristics such as a sharpened light emitting spectrum, and favorable blue color purity, by including the compound expressed by the aforementioned general formula (1) in at least one layer of the organic layer. Shortening the light emission wavelength is known to be useful for improving the blue color purity. However, when the light emission wavelength of the light emitting material is shortened, the $S_1$ of the light emitting material (lowest excitation singlet energy level) increases, and therefore, the difference between the $S_1$ of the light emitting material and the $S_1$ of the host material is reduced, or the $S_1$ of the host material increases more than the $S_1$ of the light emitting material. Therefore, a problem occurs where the sub-light emission of the host material is mixed, and the blue color purity is reduced, in conjunction with the reduction of the luminous efficiency. Correspondingly, if the compound expressed by general formula (1) is used in accordance with the present invention, the spectrum can be sharpened while achieving high luminous efficiency, and thus the blue color purity can be improved. In particular, if the two X's in the aforementioned general formula (1) are oxygen atoms for example, the compound condensing an ether substituted group and pyrene ring of the present invention expressed by the aforementioned general formula (1) has a rigid structure, and therefore, the structural change between the ground state and excited state is reduced, and the light emitting spectrum is sharpened, as compared to a compound introducing an ether substituted group on pyrene rings described in Japanese Unexamined Patent Application H2-120747.

In comparison to the compound where the condensed cross-linking position with regards to the pyrene skeleton (position corresponding to the two X's in the aforementioned general formula (1)) is C atom and N atom, the aforementioned condensed cross-linking position is oxygen atom and sulfur atom for the compound of the present invention as expressed by the aforementioned general formula (1), and therefore, planarity of the molecule is high, and orientation in the film is simple. Therefore, with the compound of the present invention expressed by the aforementioned general formula (1), light extraction efficiency is increased, and a highly efficient organic electroluminescent element can be obtained. However, the compound of the present invention expressed by the aforementioned general formula (1) easily causes excimer light emission by forming an association between pyrene rings where the aforementioned condensed cross-linking position is an sulfur atom, and therefore, an organic electroluminescent element with high luminous efficiency and excellent blue color purity is provided by introducing a substitution group to a specific position.

On the other hand, association formation of pyrene due to light emitting position change due to change in the element charge balance (optical interference effects thereby), heat generation in accordance with the drive, and the like, light emitting component creation due to chemical reaction degradation of light emitting material and/or host material due to element drive, and the like are considered as a cause of color change due to drive deterioration, and thus a material where all of these is less likely to occur is required. The compounds of the present invention are stable with regards to holes (oxidation) and electrons (reduction), injectability/transportability of the charge is high, association formation of the pyrene rings is less likely to occur, and chemical reaction degradation due to element drive is less likely to occur, and therefore, color change is less likely to occur.

Furthermore, association of the pyrene rings is less likely to occur with the compounds of the present invention, and therefore, a light emitting layer can be independently formed without using a host material.

Compound Expressed by General Formula (1)

First, the compound expressed by the aforementioned general formula (1) is described below in detail.

With the present invention, the hydrogen atom in the description of the general formula (1) also includes isotopes (deuterium or the like), and the atoms configuring the substitution groups also include the isotopes.

In the present invention, a "substitution group" may also have another substitution group. For example, in the present invention, "alkyl group" includes an alkyl group that was substituted with a fluorine atom (for example, a trifluoromethyl group), an alkyl group that was substituted with an aryl group (for example, a triphenylmethyl group), and the like, but an "alkyl group with 1 to 6 carbon atoms" indicates 1 to 6 carbon atoms for all groups including the substituted alkyl groups.

In the general formula (1), the two X's are the same linking groups, and both represent an oxygen atom or sulfur atom.

The two X's are preferably oxygen atoms in the general formula (1) with the compounds of the present invention.

In the general formula (1), $R^1$ through $R^{10}$ independently represent a hydrogen atom or a substitution group, and $R^1$ through $R^{10}$ may jointly form a ring. However, if the two X's represent sulfur atoms, at least one of $R^2$, $R^3$, $R^5$, and $R^6$ represents a substitution group. Note that a pyrene skeleton is preferably not included in aforementioned $R^1$ to $R^{10}$.

An example of the substitution group expressed by $R^1$ to $R^{10}$ in the general formula (1) includes the following substitution group A.

Substitution Group A

Examples include alkyl groups (preferably with 1 to 30 carbon atoms, more preferably with 1 to 20 carbon atoms, and particularly preferably with 1 to 10 carbon atoms, and examples include (methyl, ethyl, isopropyl, t-butyl, n-octyl, n-decyl, n-hexadecyl, cyclopropyl, cyclopentyl, cyclohexyl, and the like.), alkenyl groups (preferably with 2 to 30 carbon atoms, more preferably with 2 to 20 carbon atoms, and particularly preferably with 2 to 10 carbon atoms, and examples include vinyl, allyl, 2-butenyl, 3-pentenyl, and the like.), alkynyl groups (preferably with 2 to 30 carbon atoms, more preferably with 2 to 20 carbon atoms, and particularly preferably with 2 to 10 carbon atoms, and examples include propargyl, 3-pentynyl, and the like.), aryl groups (preferably with 6 to 30 carbon atoms, more preferably with 6 to 20 carbon atoms, and particularly preferably with 6 to 12 carbon atoms, and examples include phenyl, p-methylphenyl, napthyl, anthranyl, and the like.), amino groups (the amino group can have a substitution group, and the entire amino group preferably has 0 to 30 carbon atoms including the substitution group, more preferably has 0 to 20 carbon atoms, and particularly preferably has 0 to 10 carbon atoms; and examples include amino, methylamino, dimethylamino, diethylamino, dibenzylamino, diphenylamino, ditolylamino, and the like.), alkoxy groups (preferably with 1 to 30 carbon atoms, more preferably with 1 to 20 carbon atoms, and particularly preferably with 1 to 10 carbon atoms, and examples include methoxy, ethoxy, butoxy, 2-ethylhexyloxy, and the like.), aryloxy groups (preferably with 6 to 30 carbon atoms, more preferably with 6 to 20 carbon atoms, and particularly preferably with 6 to 12 carbon atoms, and examples include phenyloxy, 1-napthyloxy, 2-napthyloxy, and the like.), heterocyclic oxy groups (preferably with 1 to 30 carbon atoms, more preferably 1 to 20 carbon atoms, and particularly preferably with 1 to 12 carbon atoms, and examples include pyridyloxy, pyrazyloxy, pyrimidyloxy, quinolyloxy, and the like.), acyl groups (preferably with 2 to 30 carbon atoms, more preferably with 2 to 20 carbon atoms, and particularly preferably with 2 to 12 carbon atoms, and examples include acetyl, benzoyl, formyl, pivaloyl, and the like.), alkoxycarbonyl groups (preferably with 2 to 30 carbon atoms, more preferably with 2 to 20 carbon atoms, and particularly preferably with 2 to 12 carbon atoms, and examples include methoxycarbonyl, ethoxycarbonyl, and the like.), aryloxycarbonyl groups (preferably with 7 to 30 carbon atoms, more preferably with 7 to 20 carbon atoms, and particularly preferably with 7 to 12 carbon atoms, and examples include phenyloxycarbonyl, and the like.), acyloxy groups (preferably with 2 to 30 carbon atoms, more preferably with 2 to 20 carbon atoms, and particularly preferably with 2 to 10 carbon atoms, and examples include acetoxy, benzoyloxy, and the like.), acylamino groups (preferably with 2 to 30 carbon atoms, more preferably with 2 to 20 carbon atoms, and particularly preferably with 2 to 10 carbon atoms, and examples include acetylamino, benzoylamino, and the like.), alkoxycarbonyl amino groups (preferably with 2 to 30 carbon atoms, more preferably with 2 to 20 carbon atoms, and particularly preferably with 2 to 12 carbon atoms, and examples include methoxycarbonyl amino, and the like.), aryloxycarbonyl amino groups (preferably with 7 to 30 carbon atoms, more preferably with 7 to 20 carbon atoms, and particularly preferably with 7 to 12 carbon atoms, and examples include phenyloxycarbonyl amino, and the like.) sulfonylamino groups (preferably with 1 to 30 carbon atoms, more preferably with 1 to 20 carbon atoms, and particularly preferably with 1 to 12 carbon atoms, and examples include methane sulfonylamino, benzene sulfonylamino, and the like.), sulfamoyl groups (preferably with 0 to 30 carbon atoms, more preferably with 0 to 20 atoms, and particularly preferably with 0 to 12 carbon atoms, and examples include sulfamoyl, methylsulfamoyl, dimethylsulfamoyl, phenylsulfamoyl, and the like.), carbamoyl groups (preferably with 1 to 30 carbon atoms, more preferably with 1 to 20 carbon atoms, and particularly preferably with 1 to 12 carbon atoms, and example include carbamoyl, methylcarbamoyl, dimethylcarbamoyl, phenylcarbamoyl, and the like.), alkylthio groups (preferably with 1 to 30 carbon atoms, more preferably with 1 to 20 carbon atoms, and particularly preferably with 1 to 12 carbon atoms, and examples include methylthio, ethylthio, and the like.), arylthio groups (preferably with 6 to 30 carbon atoms, more particularly with 6 to 20 carbon atoms, and particularly preferably with 6 to 12 carbon atoms, and examples include phenylthio and the like.), heterocyclic thio groups (preferably with 1 to 30 carbon atoms, more preferably with 1 to 20 carbon atoms, and particularly preferably with 1 to 12 carbon atoms, and examples include pyridylthio, 2-benzimidazolylthio, 2-benzoxazolylthio, 2-benzthiazolylthio, and the like.), sulfonyl groups (preferably with 1 to 30 carbon atoms, more preferably with 1 to 20 carbon atoms, and particularly preferably with 1 to 12 carbon atoms, and examples include mesyl, tosyl, and the like.), sulfinyl groups (preferably with 1 to 30 carbon atoms, more preferably with 1 to 20 carbon atoms, and particularly preferably with 1 to 12 carbon atoms, and examples include methane sulfinyl, benzene sulfinyl, and the like.), ureido groups (preferably with 1 to 30 carbon atoms, more preferably with 1 to 20 carbon atoms, and particularly preferably with 1 to 12 carbon atoms, and examples include ureido, methylureido, phenylureido, and the like.), amide phosphate groups (preferably with 1 to 30 carbon atoms, more preferably with 1 to 20 carbon atoms, and particularly preferably with 1 to 12 carbon atoms, and examples include diethylamidophosphate, phenylamidophosphate, and the like.), hydroxy groups, mercapto groups, halogen atoms (such as fluorine atoms, chlorine atoms, bromine atoms, and iodine atoms), cyano groups, sulfo groups, carboxyl groups, nitro groups, hydroxamic acid groups, sulfino groups, hydrazino groups, imino groups, heterocyclic groups (including aromatic heterocyclic groups, preferably with 1 to 30 carbon atoms, and more preferably with 1 to 12 carbon atoms; and examples of a hetero atom include nitrogen atoms, oxygen atoms, sulfur atoms, phosphorous atoms, silicon atoms, selenium atoms, and tellurium atoms, and specific examples include pyridyl, pyrazinyl, pyrimidyl, pyridazinyl, pyrrolyl, pyrazolyl, triazolyl, imidazolyl, oxazolyl, thiazolyl, isoxazolyl, isothiazolyl, quinolyl, furyl, thienyl, selenophenyl, tellurophenyl, piperidyl, piperidino, morpholino, pyrrolidyl, pyrrolidino, benzoxazolyl, benzothiazolyl, carbazolyl groups, azepinyl groups, silolyl groups, and the like.), silyl groups (the silyl group can have a substitution group, and the entire silyl group preferably has 3 to 40 carbon atoms including the substitution group, more preferably has 3 to 30 carbon atoms, and particularly preferably has 3 to 24 carbon atoms; and examples include trimethylsilyl, triphenylsilyl, phenyl dimethylsilyl, and the like.), silyloxy group (preferably with 3 to 40 carbon atoms, more preferably with 3 to 30 carbon atoms, and particularly preferably with 3 to 24 carbon atoms, and examples include trimethylsilyloxy, triphenylsilyloxy, and the like.), and phosphoryl groups (examples include diphenyl phosphoryl groups, dimethyl phosphoryl groups, and the like.). The substitution groups can be further substituted, and examples of these additional substitution groups can include a group selected from substitution group A described above. Furthermore, the substitution group substituted in the substitution group can be further substituted, and examples of these additional substitution groups can include a group selected from substitution group A described above. Furthermore, the substitution group substituted in the substitution group substituted in the substitution group can be further substituted, and examples of additional substitutions groups can include a group selected from substitution group A described above.

With the compounds of the present invention, if the two X's represent sulfur atoms in the aforementioned general formula (1), at least one of $R^2$, $R^3$, $R^5$, and $R^6$ represents a substitution group.

In general, pyrene compounds have properties where long wave association light emission (excimer light emission) is prone to occur due to monomer light emission, thereby possibly leading to a reduction in color purity by association light emission. In the compounds of the present invention, when comparing a compound where the position corresponding to the two X's in the aforementioned general formula (1) is an oxygen atom to a compound where the position is a sulfur atom, the compound where the two X's are sulfur atoms have a stronger intermolecular interaction, and association light emission is more prone to occur. With the present invention, it was discovered that when the two X's are sulfur atoms, association light emission can be effectively suppressed without adversely affecting color tone, by introducing a substitution group in positions $R^2$, $R^3$, $R^5$, and $R^6$. In other words, the compounds of the present invention have a substitution group in positions $R^2$, $R^3$, $R^5$, and $R^6$ on a pyrene ring when the two X's are sulfur atoms, and therefore, association between the compounds expressed in the aforementioned general formula (1) is less likely to occur in the light emitting layer, and thus blue color purity can be increased.

With the compounds of the present invention, if the two X's represent sulfur atoms in the aforementioned general formula (1), two of $R^2$, $R^3$, $R^5$, and $R^6$ are more preferably substitution groups.

With the compounds of the present invention, at least one of $R^7$ to $R^{10}$ is preferably a substitution group, two or more are more preferably substitution groups, and all four are particularly preferably substitution groups. By providing a substitution group in the positions of the pyrene ring, association between the compounds expressed by the general formula (1) is less likely to occur in the organic layer, and thus blue color purity can be increased.

With the compounds of the present invention, $R^7$ and $R^8$ of $R^7$ to $R^{10}$ in the general formula (1) are both substitution groups, and preferably jointly form a ring. Furthermore, with the compounds of the present invention, $R^9$ and $R^{10}$ of $R^7$ to $R^{10}$ are both substitution groups, and preferably jointly form a ring. Furthermore, with the compounds of the present invention, $R^7$ and $R^8$ of $R^7$ to $R^{10}$ are more preferably both substitution groups, jointly forming a ring, and $R^9$ and $R^{10}$ are more preferably both substitution groups, jointly forming a ring. Furthermore, the rings jointly formed by $R^7$ and $R^8$, or by $R^9$ and $R^{10}$ in the general formula (1) are preferably five or six-membered rings.

Note that with the compounds of the present invention, $R^1$ to $R^6$ preferably do not jointly form a ring. However, in so far as gist of the present invention is not violated, two adjacent point of $R^1$ to $R^6$ can jointly form a ring, and the ring formed in this case is preferably a five or six-membered ring.

The five or six-membered ring jointly formed by $R^7$ and $R^8$, $R^9$ and $R^{10}$, or two adjacent points of $R^1$ to $R^6$ in the aforementioned general formula (1) can be any of cycloalkenyl rings, benzene rings, or heteroaryl rings. The heteroaryl ring can include 1 to 3 hetero atoms selected from a group consisting of nitrogen atoms, oxygen atoms, and sulfur atoms, of the atoms configuring the ring. Specific examples include pryidine rings, pyrazine rings, pryidazine rings, pyrimidine rings, imidazole rings, oxazole rings, thiazole rings, pyrazole rings, thiophene rings, furan rings, and the like. The formed five or six-membered rings can have a substitution group, and examples of the substitution groups on the carbon atom include the aforementioned substitution group A, and examples of the substitution group on the nitrogen atom include the following substitution group B.

Substitution Group B

Examples include alkyl groups (preferably with 1 to 30 carbon atoms, more preferably with 1 to 20 carbon atoms, and particularly preferably with 1 to 10 carbon atoms, and examples include (methyl, ethyl, isopropyl, t-butyl, n-octyl, n-decyl, n-hexadecyl, cyclopropyl, cyclopentyl, cyclohexyl, and the like.), alkenyl groups (preferably with 2 to 30 carbon atoms, more preferably with 2 to 20 carbon atoms, and particularly preferably with 2 to 10 carbon atoms, and examples include vinyl, allyl, 2-butenyl, 3-pentenyl, and the like), alkynyl groups (preferably with 2 to 30 carbon atoms, more preferably with 2 to 20 carbon atoms, and particularly preferably with 2 to 10 carbon atoms, and examples include propargyl, 3-pentynyl, and the like.), aryl groups (preferably with 6 to 30 carbon atoms, more preferably with 6 to 20 carbon atoms, and particularly preferably with 6 to 12 carbon atoms, and examples include phenyl, p-methylphenyl, napthyl, anthranyl, and the like), cyano groups, heterocyclic groups (including aromatic heterocyclic groups, preferably with 1 to 30 carbon atoms, and more preferably with 1 to 12 carbon atoms; and examples of a hetero atom include nitrogen atoms, oxygen atoms, sulfur atoms, phosphorous atoms, silicon atoms, selenium atoms, and tellurium atoms, and specific examples include pyridyl, pyrazinyl, pyrimidyl, pyridazinyl, pyrrolyl, pyrazolyl, triazolyl, imidazolyl, oxazolyl, thiazolyl, isoxazolyl, isothiazolyl, quinolyl, furyl, thienyl, selenophenyl, tellurophenyl, piperidyl, piperidino, morpholino, pyrrolidyl, pyrrolidino, benzoxazolyl, benzothiazolyl, carbazolyl groups, azepinyl groups, silolyl groups, and the like.) The substitution groups can be further substituted, and examples of these additional substitution groups can include a group selected from substitution group B described above. Furthermore, the substitution group substituted in the substitution group can be further substituted, and examples of these additional substitution groups can include a group selected from substitution group B described above. Furthermore, the substitution group substituted in the substitution group substituted in the substitution group can be further substituted, and examples of additional substitutions groups can include a group selected from substitution group B described above.

In other words, with the compounds of the present invention, the compound expressed by the aforementioned general formula (1) is preferably expressed by the following general formula (2).

[Formula 27]

General Formula (2)

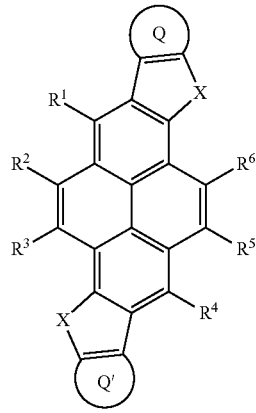

In general formula (2), the two X's both represent oxygen atoms or both represent sulfur atoms, $R^1$ through $R^6$ independently represent a hydrogen atom or a substitution group, and $R^1$ through $R^6$ may jointly form a ring. Q and Q' independently represent an aromatic five membered ring or an aromatic six-membered ring. However, if the two X's represent sulfur atoms, at least one of $R^2$, $R^3$, $R^5$, and $R^6$ represents a substitution group.

The preferred range of the two X's in the aforementioned general formula (2) is the same preferred range as the two X's in the aforementioned general formula (1).

The description and preferred range of $R^1$ to $R^6$ in the general formula (2) is the same as the description and preferred range of $R^1$ to $R^6$ in the general formula (1).

The description and preferred range of the substitution group expressed by at least one of $R^2$, $R^3$, $R^5$, and $R^6$ when the two X's are both sulfur atoms in the general formula (2) is the same as the description and preferred range of the substitution group expressed by at least one of $R^2$, $R^3$, $R^5$, and $R^6$ when the two X's are both sulfur atoms in the description of the general formula (1).

In general formula (2), examples of aromatic five-membered rings or aromatic six-membered rings expressed by the aforementioned Q are the same as the examples of the five or six-membered rings jointly formed by $R^7$ and $R^8$ in general formula (1). Examples of aromatic five-membered rings or aromatic six-membered rings expressed by the aforementioned Q' are the same as the examples of the five or six-membered rings jointly formed by $R^7$ and $R^8$ in general formula (1).

Preferably Q and Q' each independently represent aromatic six-membered rings.

With the compounds of the present invention, the compound expressed by the aforementioned general formula (2) is preferably expressed by the following general formula (3).

[Formula 28]

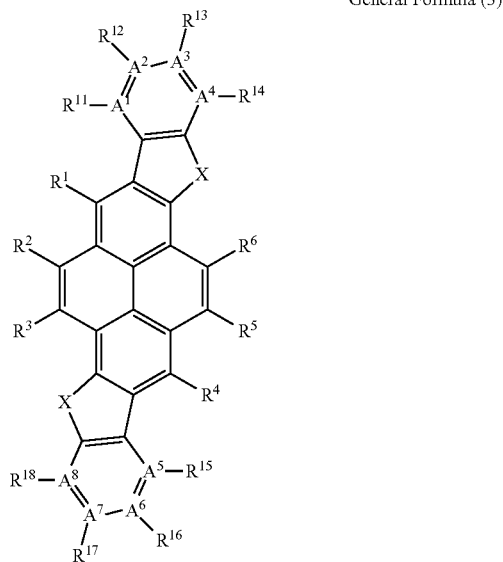

General Formula (3)

In general formula (3), the two X's both represent oxygen atoms or both represent sulfur atoms, $R^1$ through $R^6$ independently represent a hydrogen atom or a substitution group, and $R^1$ through $R^6$ may jointly form a ring. R11 through R18 independently represent a hydrogen atom or a substitution group. $A^1$ through $A^8$ independently represent a carbon atom or a nitrogen atom, and if $A^1$ through $A^8$ represent a nitrogen atom, $R^{11}$ through $R^{18}$ that bonds thereto does not exist. However, if the two X's represent sulfur atoms, at least one of $R^2$, $R^3$, $R^5$, and $R^6$ represents a substitution group.

The preferred range of the two X's in the aforementioned general formula (3) is the same preferred range as the two X's in the aforementioned general formula (1).

The description and preferred range of $R^1$ to $R^6$ in the general formula (3) is the same as the description and preferred range of $R^1$ to $R^6$ in the general formula (1).

The description and preferred range of the substitution group expressed by at least one of $R^2$, $R^3$, $R^5$, and $R^6$ when the two X's are both sulfur atoms in the general formula (3) is the same as the description and preferred range of the substitution group expressed by at least one of $R^2$, $R^3$, $R^5$, and $R^6$ when the two X's are both sulfur atoms in the description of the general formula (1).

In general formula (3), to $R^{18}$ independently represent a hydrogen atom or a substitution group. $A^1$ through $A^8$ independently represent a carbon atom or a nitrogen atom, and if $A^1$ through $A^8$ represent a nitrogen atom, through $R^{18}$ that bonds thereto does not exist.

In general formula (3), of $A^1$ to $A^4$, the number of nitrogen atoms is preferably 0 to 2 from the perspective of chemical stability of the compound, more preferably 0 or 1 from the perspective of further increasing blue color purity, and particularly preferably 0 from the perspective of improving color change due to drive deterioration. Of $A^1$ to $A^4$, the position of the nitrogen atom is not particularly restricted.

In general formula (3), of $A^5$ to $A^8$, the number of nitrogen atoms is preferably 0 to 2 from the perspective of chemical stability of the compound, more preferably 0 or 1 from the perspective of further increasing blue color purity, and particularly preferably 0 from the perspective of improving chromaticity change due to drive deterioration. Of $A^5$ to $A^8$, the position of the nitrogen atom is not particularly restricted.

In general formula (3), an example of the substitution group expressed by $R^{11}$ to $R^{18}$ can include the aforementioned substitution group A. In general formula (3), $R^{13}$ is preferably a substitution group from the perspective of orientation in the film of the molecule.

When two or more of $A^1$ to $A^4$ in the general formula (3) represent a carbon atom, the substitution groups (corresponding $R^{11}$ to $R^{14}$) having two adjacent carbon atoms preferably do not jointly form a five or six-membered ring in the present invention, but can form a five or six-membered ring. The formed five or six-membered rings can be any of cycloalkenyl rings, benzene rings, or heteroaryl rings. The heteroaryl ring can include 1 to 3 hetero atoms selected from a group consisting of nitrogen atoms, oxygen atoms, and sulfur atoms, of the atoms configuring the ring. Specific examples include pryidine rings, pyrazine rings, pryidazine rings, pyrimidine rings, imidazole rings, oxazole rings, thiazole rings, pyrazole rings, thiophene rings, furan rings, and the like. The formed five or six-membered rings can have a substitution group, and examples of the substitution groups on the carbon atom include the aforementioned substitution group A, and examples of the substitution group on the nitrogen atom include the aforementioned substitution group B. The formed five or six-membered rings can be benzene rings, and are more preferably unsubstituted benzene rings.

When two or more of $A^1$ to $A^4$ in the general formula (3) represent a carbon atom, the substitution groups (corresponding $R^{15}$ to $R^{18}$) having the two adjacent carbon atoms thereof can form a five or six-membered ring, but preferably do not jointly form a five or six-membered ring in the present invention. When two or more of $A^1$ to $A^4$ in the general formula (3) represent a carbon atoms, the description and preferred range of the form five or six-membered rings is the same as the description and preferred range when the substituted group having two adjacent carbon atoms thereof jointly form five or six-membered rings.

With the compounds of the present invention, the compound expressed by the aforementioned general formula (3) is preferably expressed by the following general formula (4).

[Formula 29]

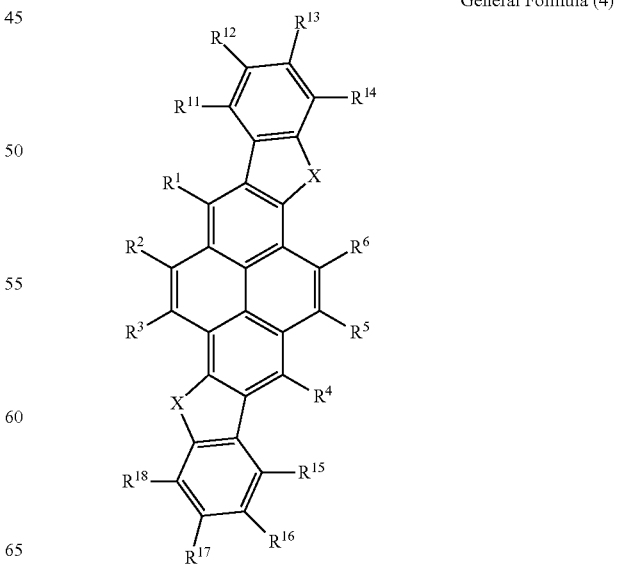

General Formula (4)

In general formula (4), the two X's both represent oxygen atoms or both represent sulfur atoms, $R^1$ through $R^6$ independently represent a hydrogen atom or a substitution group, and $R^1$ through $R^6$ may jointly form a ring. $R^{11}$ through $R^{18}$ independently represent a hydrogen atom or a substitution group. However, if the two X's represent sulfur atoms, at least one of $R^2$, $R^3$, $R^5$, and $R^6$ represents a substitution group.

The preferred range of the two X's in the aforementioned general formula (4) is the same preferred range as the two X's in the aforementioned general formula (1).

The description of $R^1$ to $R^6$ in general formula (4) is the same as the description in $R^1$ to $R^6$ in the aforementioned general formula (1).

$R^1$ to $R^6$ in general formula (4) is preferably within the preferred range of $R^1$ to $R^6$ in general formula (1).

The description and preferred range of the substitution group expressed by at least one of $R^2$, $R^3$, $R^5$, and $R^6$ when the two X's are both sulfur atoms in the general formula (4) is the same as the description and preferred range of the substitution group expressed by at least one of $R^2$, $R^3$, $R^5$, and $R^6$ when the two X's are both sulfur atoms in the description of the general formula (1).

In general formula (4), an example of the substitution group expressed by $R^{11}$ to $R^{18}$ can include the aforementioned substitution group A. In general formula (4), any of $R^{12}$, $R^{13}$, $R^{16}$, and $R^{17}$ are preferably substitution groups, and either $R^{13}$ or $R^{17}$ is more preferably a substitution group. In particular, $R^{13}$ is preferably a substitution group from the perspective of orientation in the film of the molecule.

With the compound of the present invention, at least one of $R^1$ to $R^6$ and $R^{11}$ to $R^{18}$ is preferably a substitution group having any of a fluorine atom, alkyl group, silyl group, and amino group, from the perspective of chemical stability and association suppression. These substitution groups with a specific structure are substituted in these position of the pyrene ring, and therefore, association is less likely to form, and drive color change can be reduced more than other pyrene ring compounds where only other substitution groups such as substituted phenyl groups and the like are substituted in these positions for example.

The compound expressed by general formula (4) is preferably a compound where at least two points of $R^1$ to $R^6$ and $R^{11}$ to $R^{18}$ are substituted, from the perspective of enabling suppression of association between pyrene compounds.

Of these, in general formula (4), $R^2$ and $R^5$ are more preferably independently substitution groups having any of a fluorine atom, alkyl group, silyl group, and amino group as an additional substitution group, from the perspective of suppressing association, and are particularly preferably nitrogen containing heterocyclic groups or aryl groups having any of a fluorine atom, alkyl group, silyl group, and amino group as an additional substitution group. The number of ring members of the aryl groups or nitrogen containing heteroxylic groups in this case is not restricted, but the number of ring members is preferably fewer to some degree from the perspective of suppressing association, and is preferably 5 to 12 ring members, and more preferably 6 to 10 ring members. The aryl group or nitrogen containing heterocyclic group in this case is preferably a phenyl group, pyridyl group, or pyrimidyl, more preferably a phenyl group or pyridyl group, and more particularly preferably a phenyl group.

With the compounds of the present invention, the compound expressed by the aforementioned general formula (4) is preferably expressed by the following general formula (5).

[Formula 30]

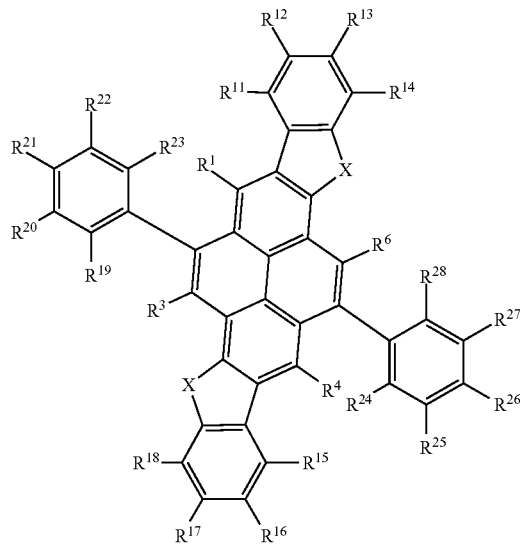

General Formula (5)

In the formula (5), the two X's both represent oxygen atoms or both represent sulfur atoms, and $R^1$, $R^2$, $R^4$, and $R^6$ independently represent a hydrogen atom or a substitution group. $R^{11}$ through $R^{38}$ independently represent a hydrogen atom or a substitution group. However, at least one of $R^3$ through $R^6$ and $R^{11}$ through $R^{18}$ is a substitution group containing one of a fluorine atom, alkyl group, sylyl group, or amino group, or at least one of $R^{19}$ through $R^{28}$ is a fluorine atom, alkyl group, sylyl group, or amino group.

The preferred range of the two X's in the aforementioned general formula (5) is the same preferred range as the two X's in the aforementioned general formula (1).

The description and preferred range of $R^1$, $R^3$, $R^4$, and $R^6$ in general formula (5) is the same as the description and preferred range of $R^1$, $R^3$, $R^4$, and $R^6$ in the aforementioned general formula (1).

$R^1$ and $R^4$ in general formula (5) is more preferably a hydrogen atom.

In general formula (5), at least one of $R^3$, $R^6$ and $R^{11}$ through $R^{18}$ is a substitution group containing one of a fluorine atom, alkyl group, sylyl group, or amino group, or at least one of $R^{19}$ through $R^{28}$ is a fluorine atom, alkyl group, sylyl group, or amino group.) Furthermore, in general formula (5), at least one of $R^3$, $R^6$ and $R^{11}$ to $R^{18}$ is preferably a substitution group containing one of a fluorine atom, alkyl group, sylyl group, or amino group, and at least one of $R^{19}$ to $R^{28}$ is preferably a fluorine atom, alkyl group, sylyl group, or amino group. Furthermore, in general formula (5), $R^{13}$ is preferably a substitution group from the perspective of orientation in the film of the molecule.

For the compound of the present invention, the substitution groups which may be on $R^3$, $R^6$ and $R^{11}$ to $R^{18}$ in general formula (5) are more preferably independently substitution groups having any of a fluorine atom, alkyl group, silyl group, and amino group as an additional substitution group, from the perspective of suppressing association, and are particularly preferably amino groups, aryl groups, or nitrogen containing heterocyclic groups having any of a fluorine atom, alkyl group, silyl group, and amino group as an additional substitution group.

The amino group in this case in not particularly restricted, but is preferably a diarylamino group (in other words, a diarylamino group having any of a fluorine atom, alkyl group, silyl group, and amino group on the aryl group portion as an additional substitution group) from the perspective of suppressing association, and is more preferably a diphenylamino group. The number of ring members of the aryl groups or nitrogen containing heteroxylic groups in this case is not restricted, but the number of ring members is preferably fewer to some degree from the perspective of suppressing association, and is preferably 5 to 12 ring members, and more preferably 6 to 10 ring members. The aryl group or nitrogen containing heterocyclic group in this case is preferably a phenyl group, pyridyl group, or pyrimidyl, more preferably a phenyl group or pyridyl group, and more particularly preferably a phenyl group.

For the substitution group having any one of the fluorine atom, alkyl group, silyl group, and amino group as an additional substitution group, examples of the alkyl groups as the additional substitution group can include the alkyl groups in the aforementioned substitution group A, and unsubstituted straight chain alkyl groups, unsubstituted branched alkyl groups, unsubstituted cycloalkyl group, and perfluoroalkyl groups are preferable, straight chain alkyl groups with 1 to 6 carbon atoms, branched alkyl groups with 1 to 6 carbon atoms, and perfluoroalkyl groups with 1 to 6 carbon atoms are more preferable, methyl group, ethyl groups, isopropyl groups, t-butyl groups, t-amyl group, neopentyl groups, and trifluoromethyl groups are particularly preferable, and methyl groups, ethyl groups, isopropyl groups, and t-butyl groups are more particularly preferable.

For the substitution group having any one of the fluorine group, alkyl group, silyl group, and amino group as an additional substitutional group, examples of the silyl groups as the additional substitution group can include the silyl groups in the aforementioned substitution group A, and alkylsilyl groups are preferable, and trialkylsilyl groups or dialkylsilyl groups are more preferable. The alkyl groups of the trialklysilyl groups or aryldialkylsilyl groups are preferably independently methyl groups, ethyl groups, and isopropyl groups, and more preferably methyl groups. The aryl groups of the aryldialkylsilyl groups are preferably phenyl groups. The silyl groups as the additional substitution groups are particularly preferably trimethylsilyl groups.

For the substitution groups having any one of the fluorine atom, alkyl group, silyl group, and amino group as an additional substitution group, examples of the amino groups as the additional substitution groups can include the amino groups in the aforementioned substitution group A, and diarylamino groups are preferable, and diphenylamino groups are more preferable.

Of these, for the compound expressed by general formula (5), at least one of $R^3$, $R^6$, and $R^{11}$ to $R^{18}$ is more preferably a substitution group having an alkyl group or silyl group as an additional substitution group from the perspective of further increasing blue color purity, and is particularly preferably a substitution group having an alkyl group as an additional substitution group.

Furthermore, for the compound expressed by general formula (5), at least one of $R^3$, $R^6$, and $R^{11}$ and $R^{18}$ is particularly preferably a para-alkyl substituted phenyl group from the perspective of chemical stability and a high association suppressing effect, without reducing color purity.

Of $R^3$, $R^6$, and $R^{11}$ to $R^{18}$ in general formula (5), the number of substitution groups having any one of the fluorine atom, alkyl group, silyl group, and amino group as an additional substitution group is not particularly restricted, but of the $R^3$, $R^6$, and $R^{11}$ to $R^{18}$ in general formula (5), 0 to 4 points is preferable, 0 to 2 points is more preferable, and 2 points is particularly preferable. However, of the $R^3$, $R^6$, and $R^{11}$ to $R^{18}$ in general formula (5), if the substitution group having any one of the fluorine atom, alkyl group, silyl group, and amino group is at position 0, at least one of $R^{19}$ to $R^{28}$ described below represent a fluorine atom, alkyl group, silyl group, or amino group.

Of the $R^3$, $R^6$, and $R^{11}$ to $R^{18}$ in general formula (5), the position of the substitution group having any one of the fluorine atom, alkyl group, silyl group, and amino group as an additional substitution group is preferably $R^{12}$, $R^{13}$, $R^{16}$, and $R^{17}$, and more preferably a combination of two point $R^{12}$ and $R^{16}$, or two points of $R^{13}$ and $R^{17}$.

Of $R^3$, $R^6$, and $R^{11}$ to $R^{18}$ in general formula (5), $R^3$ and $R^6$ are preferably hydrogen atoms. Of the $R^3$, $R^6$, and $R^{11}$ to $R^{18}$ in general formula (5), the substitution group having any one of the fluorine atom, alkyl group, silyl group, and amino group of $R^{11}$ to $R^{14}$ is preferably at 2 points or less, and more preferably at 0 or 1 point. When $R^{11}$ to $R^{14}$ in general formula (5) represent a group other than a substitution group having any one of the fluorine atom, alkyl group, silyl group, and amino group as an additional substitution group, examples of the $R^{11}$ to $R^{14}$ can include a hydrogen atom, alkyl group, aryl group, alkoxy group, fluorine atom, and cyano group, and a hydrogen atom or aryl group is preferable, a hydrogen atom or phenyl group is more preferable, and a hydrogen atom is particularly preferable.

Of the $R^3$, $R^6$, and $R^{11}$ to $R^{18}$ in general formula (5), the preferred range of $R^{15}$ to $R^{18}$ is the same as the preferred range of $R^{11}$ to $R^{14}$.

For the compound of the present invention, at least one of $R^{19}$ to $R^{28}$ in general formula (5) is preferably a fluorine atom, alkyl group, silyl group, or amino group. In general formula (5), the preferred range of the fluorine atom, alkyl group, silyl group, and amino group preferably represented by $R^{19}$ to $R^{28}$ is the same as the preferred range of the fluorine atom, alkyl group, silyl group, and amino group of the substitution group having any one of the fluorine atom, alkyl group, silyl group, and amino group which may be on $R^3$, $R^6$, and $R^{11}$ to $R^{18}$ in general formula (5) as an additional substitution group.

In general formula (5), the number of substitution fluorine atoms, alkyl groups, silyl group, and amino groups of $R^{19}$ to $R^{28}$ is not particularly restricted, but of $R^3$, $R^6$, and $R^{11}$ to $R^{18}$ in general formula (5), 2 to 6 points are preferable, and 2 to 4 points are more preferable.

In general formula (5), the fluorine atom, alkyl group, silyl group, and amino group of $R^{19}$ to $R^{28}$ preferably has 1 to 3 points that are not adjacent of $R^{19}$ to $R^{23}$, and 1 to 3 points that are not adjacent of $R^{24}$ to $R^{28}$, and more preferably 1 or 2 points that are not adjacent of $R^{19}$ to $R^{23}$, and 1 or 2 points that are not adjacent of $R^{24}$ to $R^{28}$, for the position of the fluorine atom, alkyl group, silyl group, and amino group of $R^{19}$ to $R^{28}$.

For the compounds of the present invention, the compound expressed by general formula (4) is expressed by the following general formula (7), and therefore, X atoms are sterically protected, and thus is preferable from the perspective of durability.

[Formula 31]

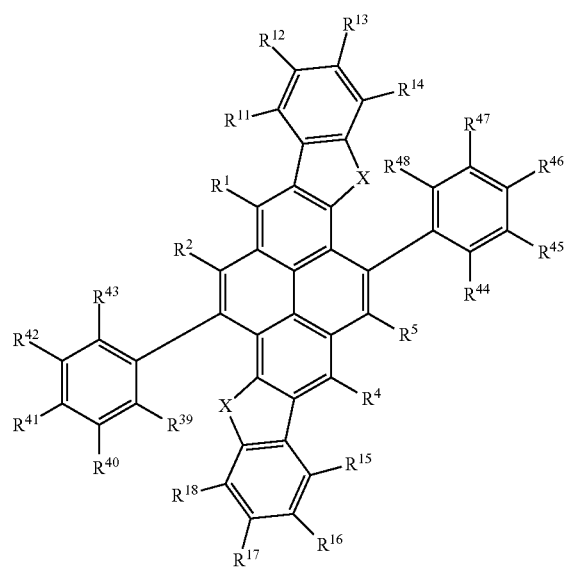

General Formula (7)

[Formula 32]

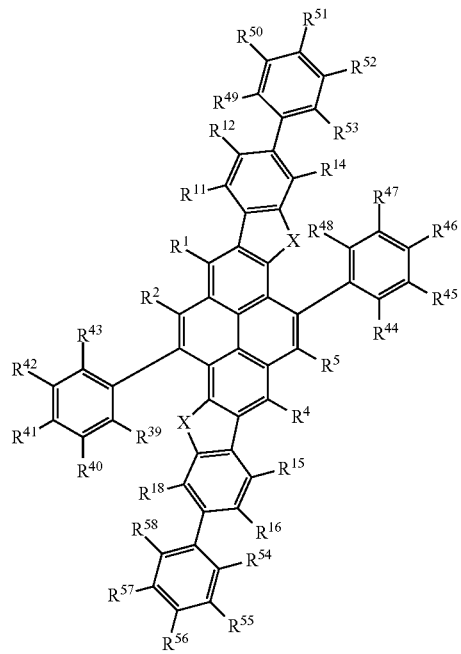

General Formula (8)

In the formula (7), the two X's both represent oxygen atoms or both represent sulfur atoms, and $R^1$, $R^2$, $R^4$, and $R^5$ independently represent a hydrogen atom or a substitution group. A ring may be jointly formed by a plurality of $R^1$, $R^2$, $R^4$, and $R^5$. $R^{11}$ through $R^{48}$ independently represent a hydrogen atom or a substitution group.

The preferred range of the two X's in the aforementioned general formula (7) is the same preferred range as the two X's in the aforementioned general formula (1).

The description and preferred range of $R^1$, $R^2$, $R^4$, and $R^5$ in general formula (7) are the same as the description and preferred range of $R^1$, $R^2$, $R^4$, and $R^5$ in the aforementioned general formula (1).

An example of the substitution group expressed by $R^{11\ to\ 18}$ and $R^{41\ to\ 48}$ in general formula (7) can include the aforementioned substitution group A. The description and preferred range of $R^{11}$ to $R^{18}$ in the general formula (7) is the same as the description and preferred range of $R^1$ to $R^6$ in the general formula (1). Furthermore, in general formula (7), $R^{13}$ is preferably a substitution group from the perspective of orientation in the film of the molecule.

With the compounds of the present invention, the compound expressed by the aforementioned general formula (7) is preferably expressed by the following general formula (8).

In the formula (8), the two X's both represent oxygen atoms or both represent sulfur atoms, and $R^1$, $R^2$, $R^4$, and $R^5$ independently represent a hydrogen atom or a substitution group. A ring may be jointly formed by a plurality of $R^1$, $R^2$, $R^4$, and $R^5$. $R^{11}$ through $R^{58}$ independently represent a hydrogen atom or a substitution group.)

The preferred range of the two X's in the aforementioned general formula (8) is the same preferred range as the two X's in the aforementioned general formula (1).

The description and preferred range of $R^1$, $R^2$, $R^4$, and $R^5$ in general formula (8) is the same as the description and preferred range of $R^1$, $R^2$, $R^4$, and $R^5$ in the aforementioned general formula (1).

An example of the substitution group expressed by $R^{11\ to\ 18}$ and $R^{41\ to\ 58}$ in general formula (8) can include the aforementioned substitution group A. The description and preferred range of $R^{11}$ to $R^{58}$ in the general formula (8) is the same as the description and preferred range of $R^{11}$ to $R^{18}$ in the general formula (4).

With the compounds of the present invention, the compound expressed by the aforementioned general formula (9) is preferably expressed by the following general formula (4). By introducing an amino group, oscillator strength increases, and therefore, is preferable from the perspective of luminous efficiency.

[Formula 33]

General Formula (9)

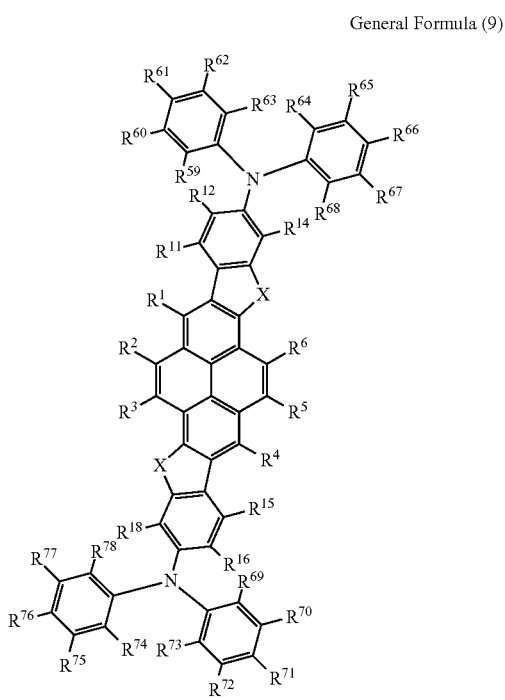

In the formula (9), the two X's both represent oxygen atoms or both represent sulfur atoms, and $R^1$ through $R^6$ independently represent a hydrogen atom or a substitution group. A ring may be jointly formed by a plurality of $R^1$ through $R^6$. $R^{11}$ through $R^{78}$ independently represent a hydrogen atom or a substitution group.

The preferred range of the two X's in the aforementioned general formula (9) is the same preferred range as the two X's in the aforementioned general formula (1).

The description and preferred range of $R^1$ to $R^6$ in the general formula (9) is the same as the description and preferred range of $R^1$ to $R^6$ in the general formula (1). In particular, at least one of $R^2$, $R^3$, $R^5$, and $R^6$ is preferably a substitution group due to effective suppression of association light emission.

An example of the substitution group expressed by $R^{11\ to\ 18}$ and $R^{59\ to\ 78}$ in general formula (9) can include the aforementioned substitution group A. The description and preferred range of $R^{11}$ to $R^{58}$ in the general formula (9) is the same as the description and preferred range of $R^{11}$ to $R^{18}$ in the general formula (4).

When the compound expressed by general formula (1) is used as the light emitting material, the maximum light emission wavelength of the organic electroluminescent element is normally less than 460 nm. 400 nm or more and less than 460 nm is preferable, 420 nm or more and less than 455 nm is more preferable, 430 nm or more and less than 455 nm is even more preferable, and 440 or more and less than 455 nm is most preferable from the perspective of achieving blue color light emission with high color purity.

For the compound expressed by general formula (1), a molecular weight of 900 or less is preferable, 850 or less is more preferable, and 800 or less is even more preferable. By reducing the molecular weight, the sublimation temperature can be reduced, and therefore, pyrolysis of the compound during deposition can be prevented. Furthermore, by reducing the deposition time, energy required for deposition can be reduced. Herein, pyrolysis may occur during long term deposition with material with a high sublimation temperature, and therefore, the sublimation temperature is preferably not too high from the perspective of deposition suitability. The sublimation temperature (in the present specification, this refers to the temperature that provides a 10% reduction in mass) of the compound expressed by general formula (1) is preferably 300° C., more preferably 285° C. or less, and even more preferably 270° C. or less.

Specific examples of the compound expressed by general formula (1) are exemplified below, but the compound expressed by general formula (1) that can be used in the present invention should not be interpreted as to be restricted by these specific examples.

[Formula 34]

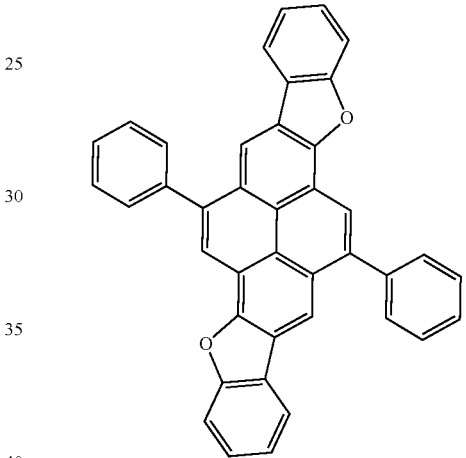

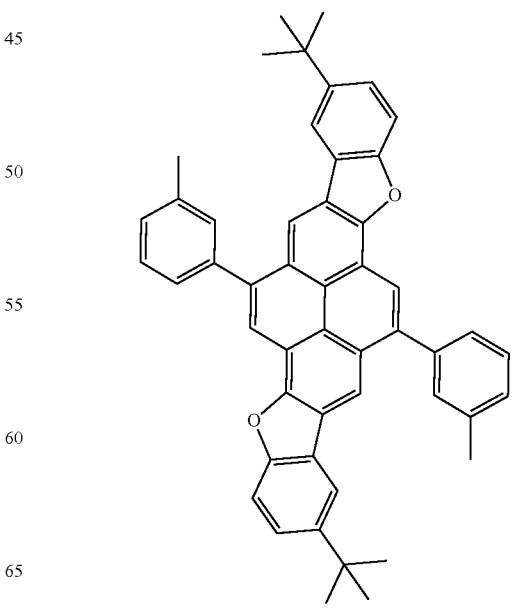

35
-continued
36
-continued
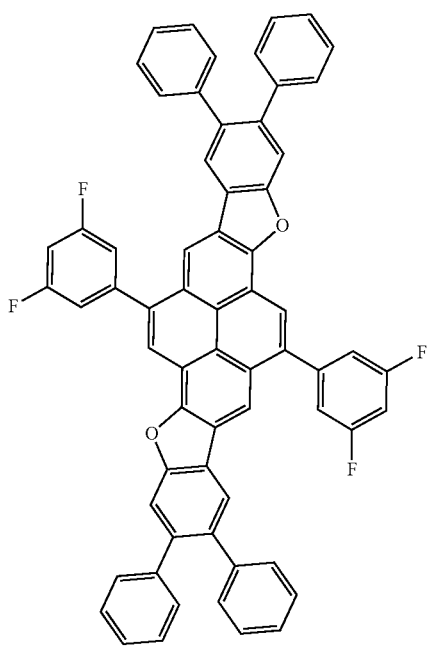
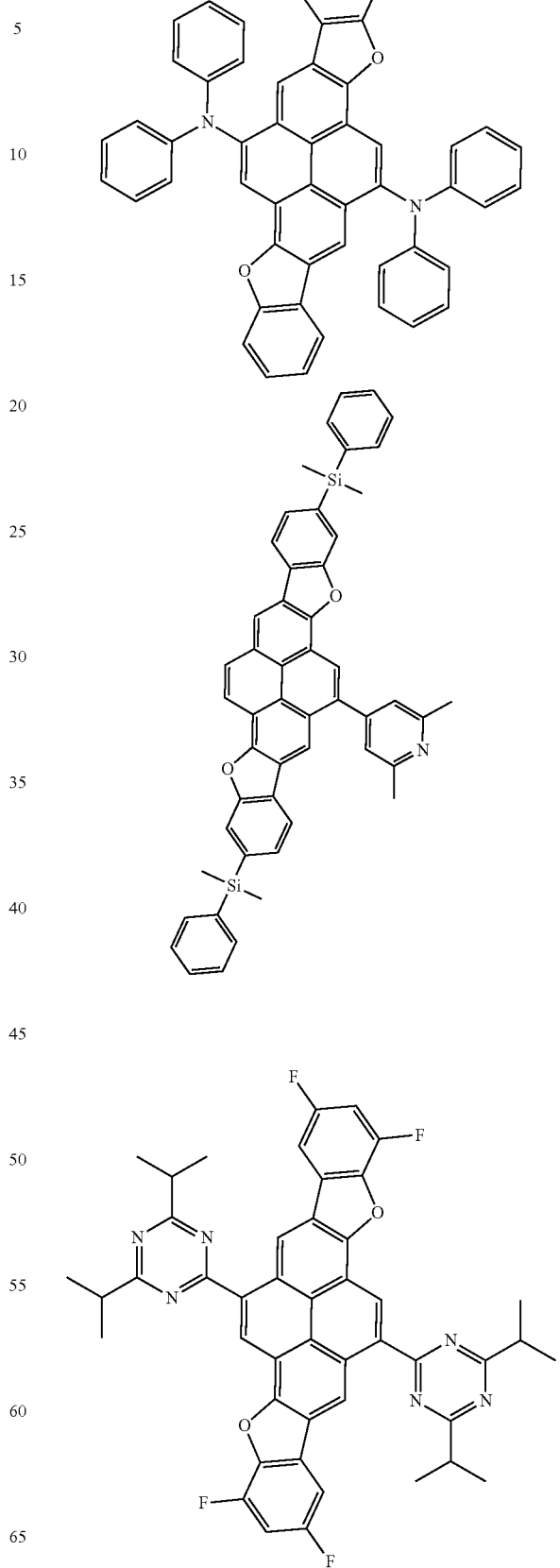
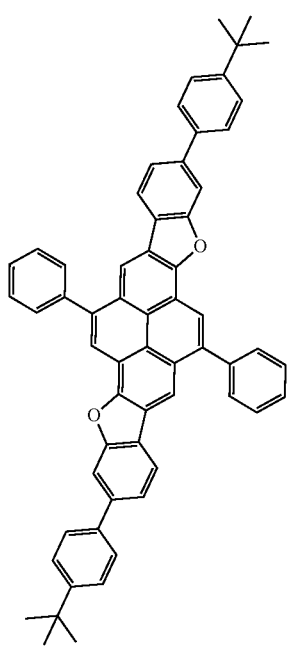

37
-continued
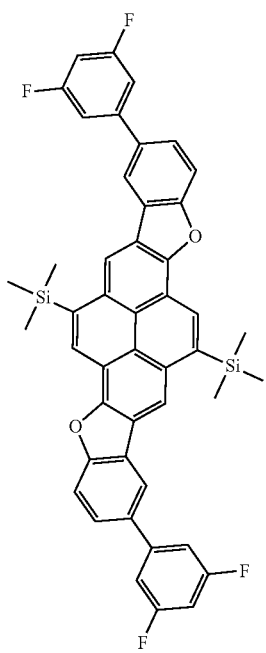
38
-continued
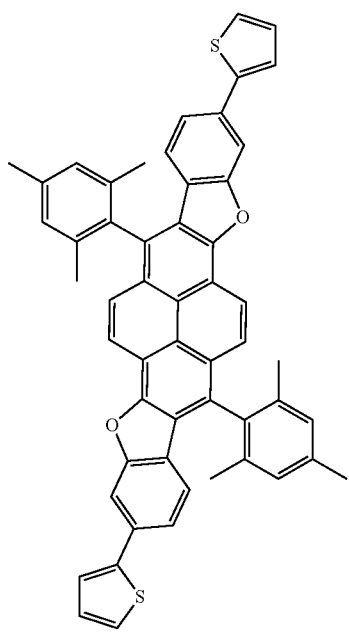
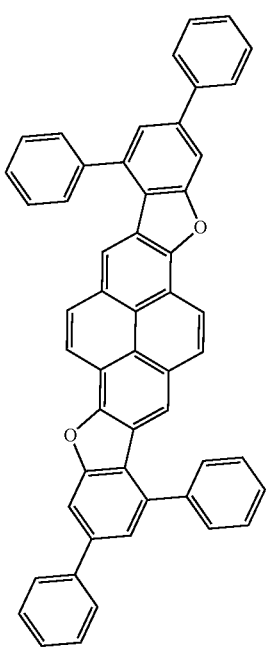

39
-continued
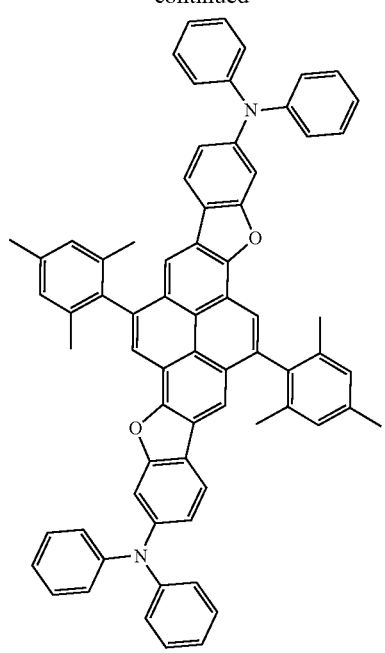
[Formula 35]
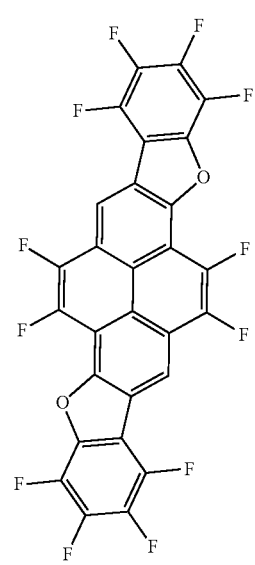
40
-continued
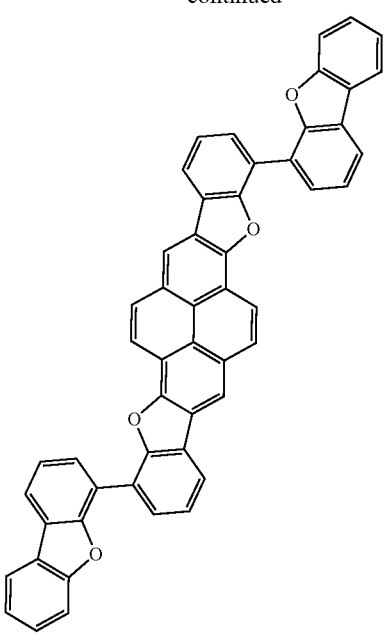
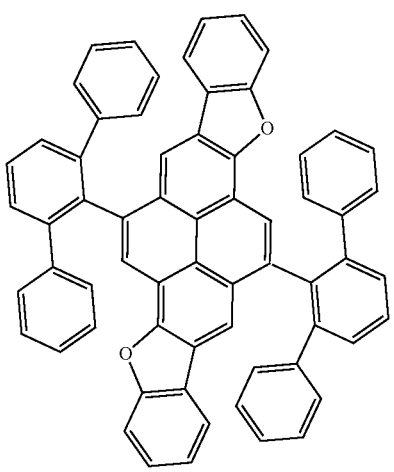
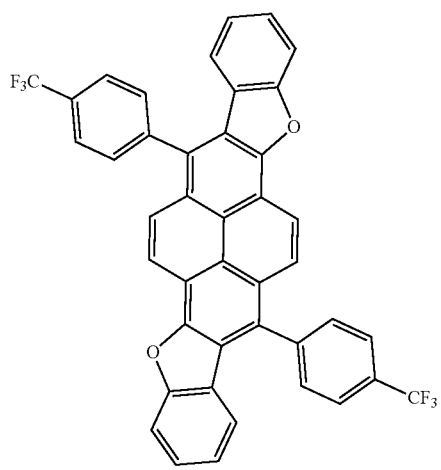

41
-continued
42
-continued
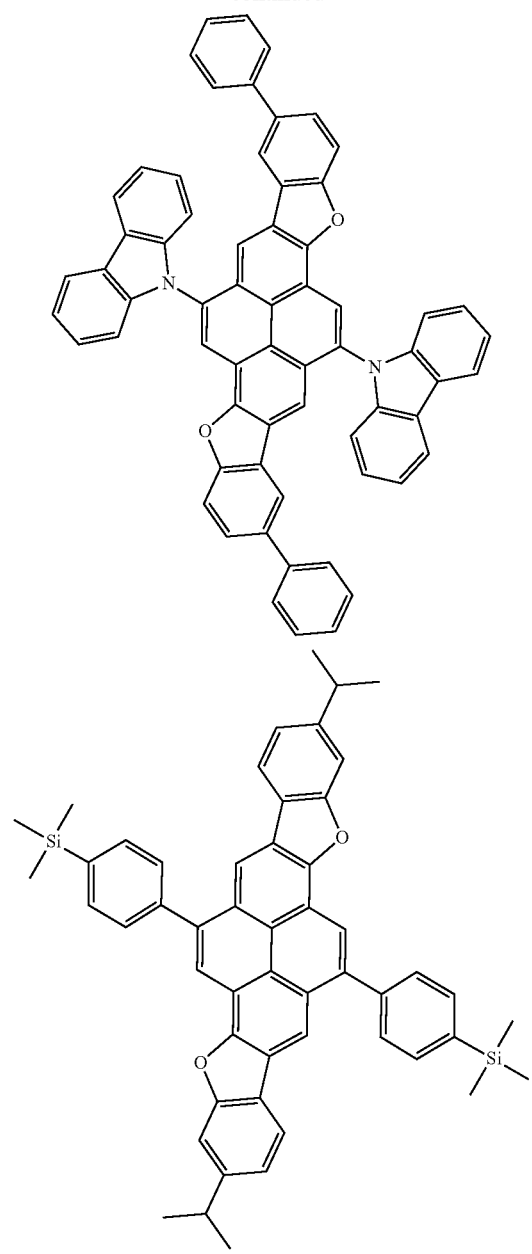
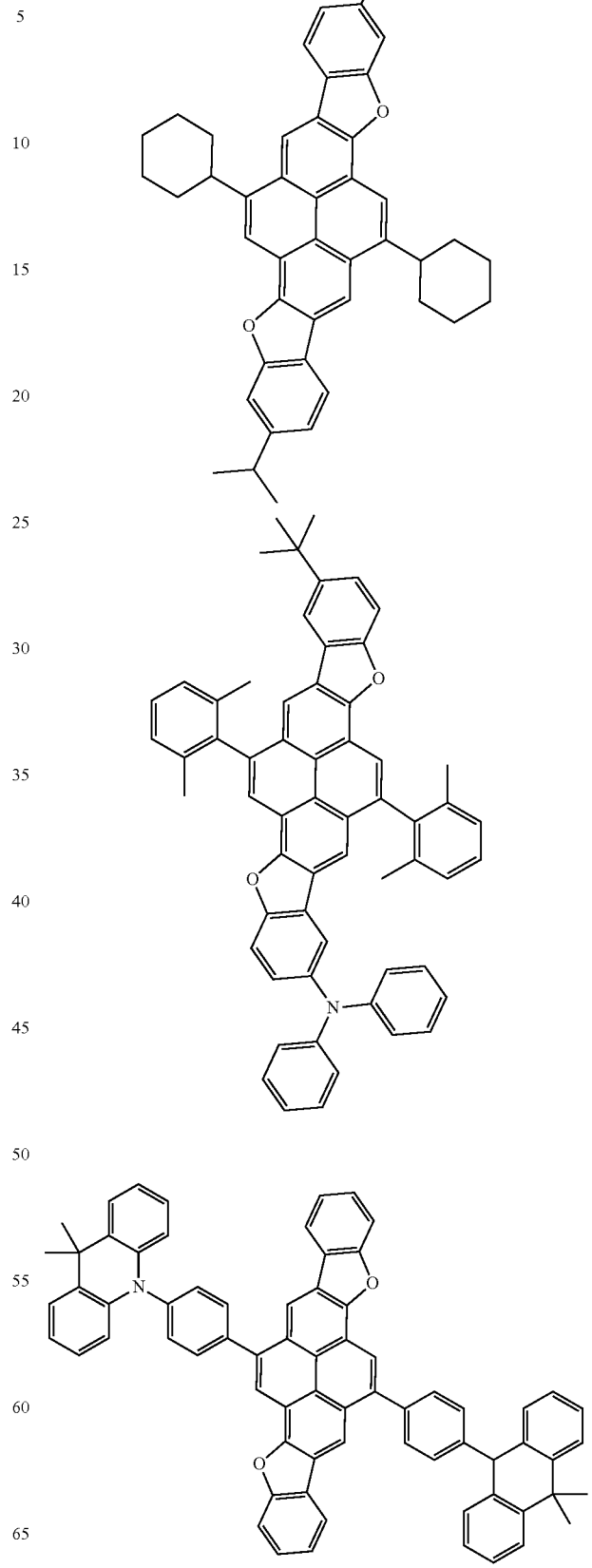

[Formula 36]
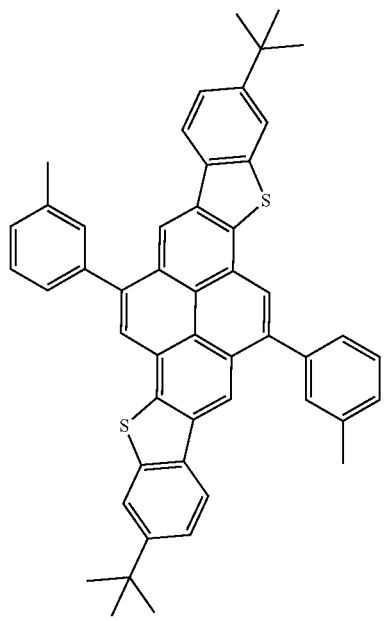
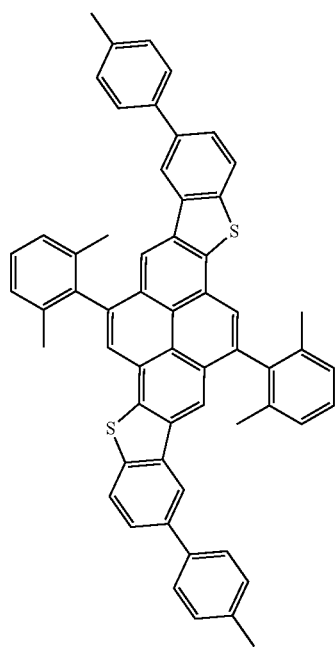
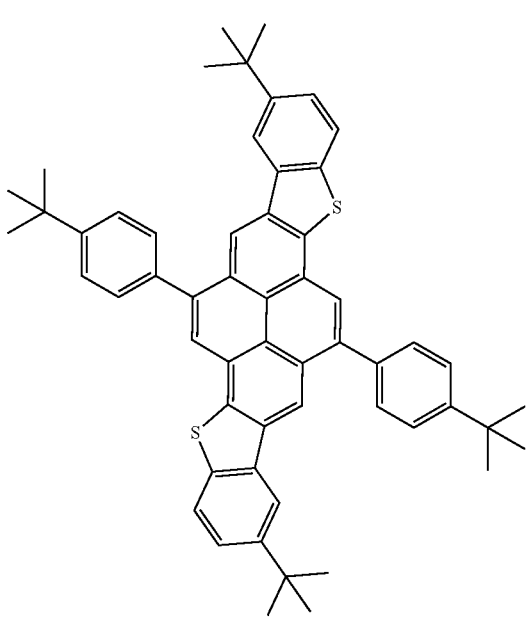
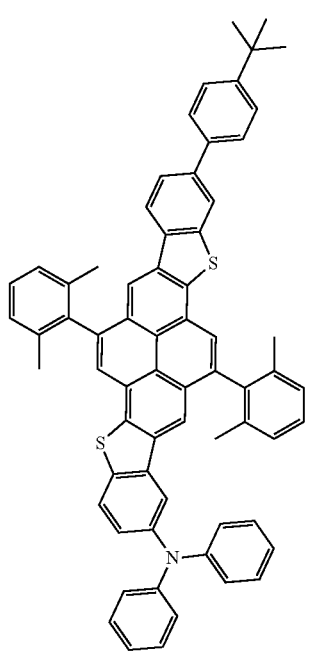

45
-continued
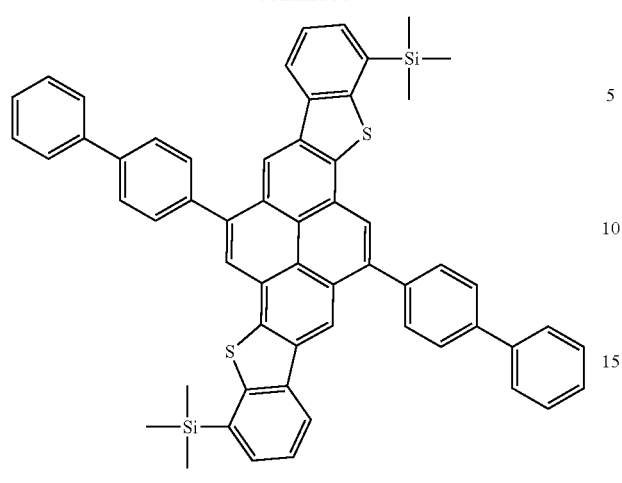
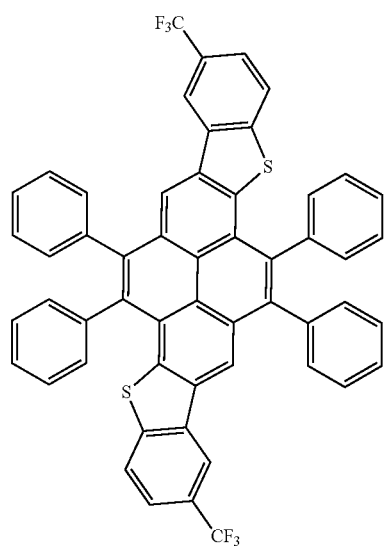
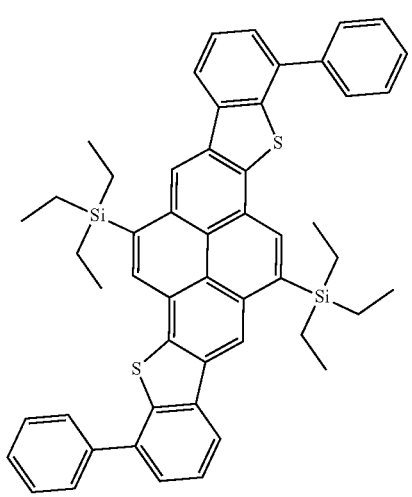
46
-continued
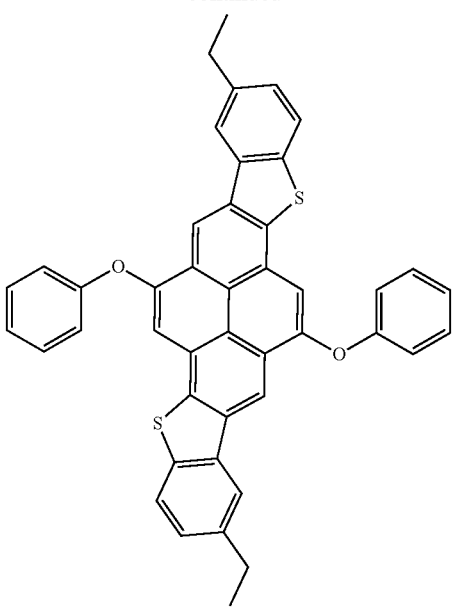
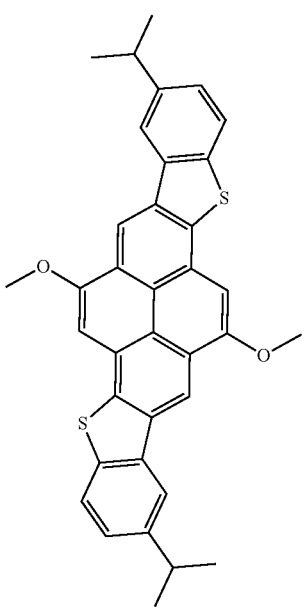

47
-continued
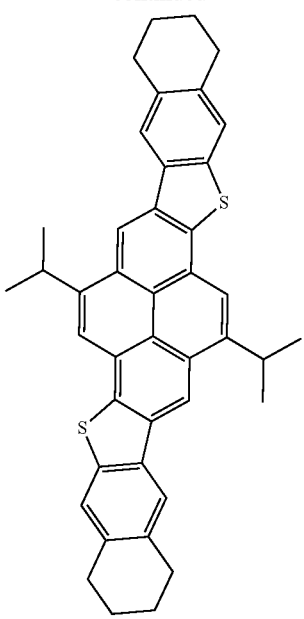
48
-continued
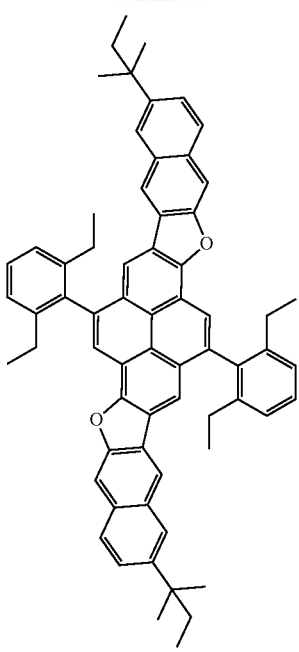
[Formula 37]
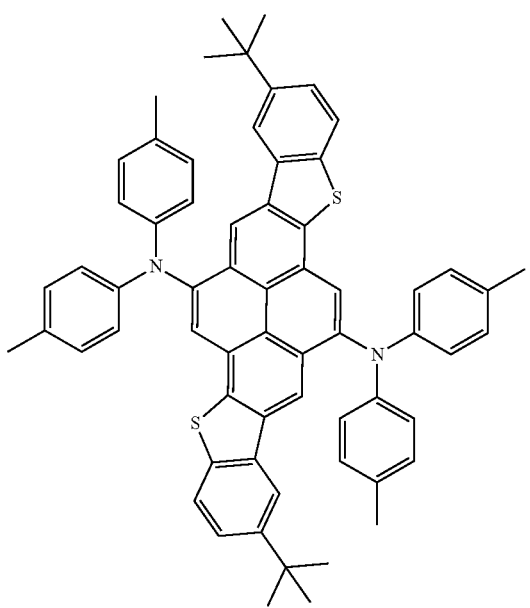
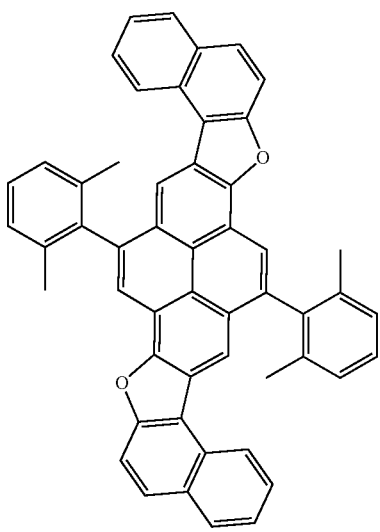

49
-continued
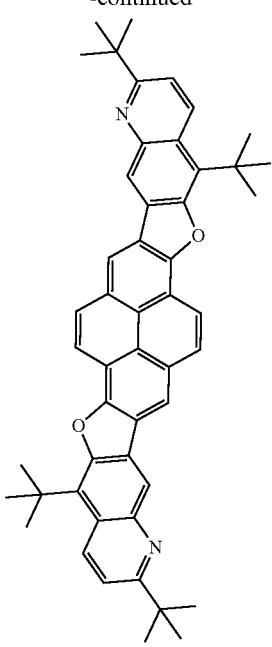
50
-continued
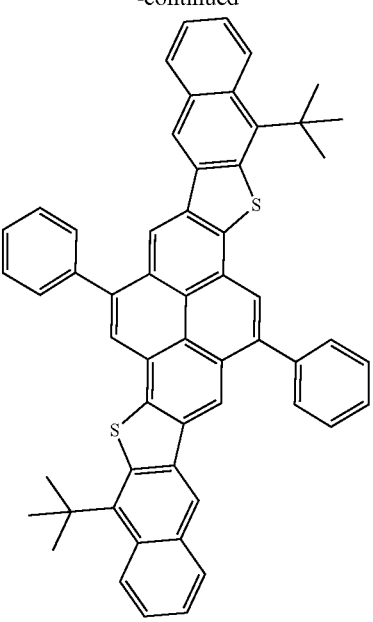
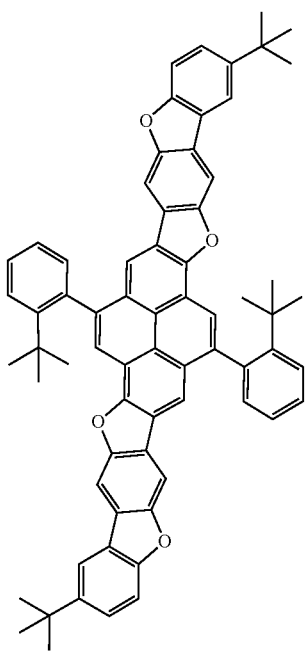
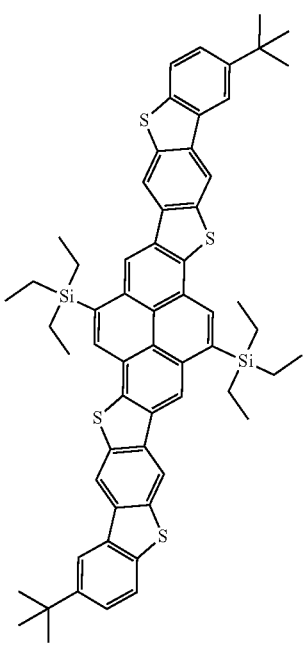

-continued
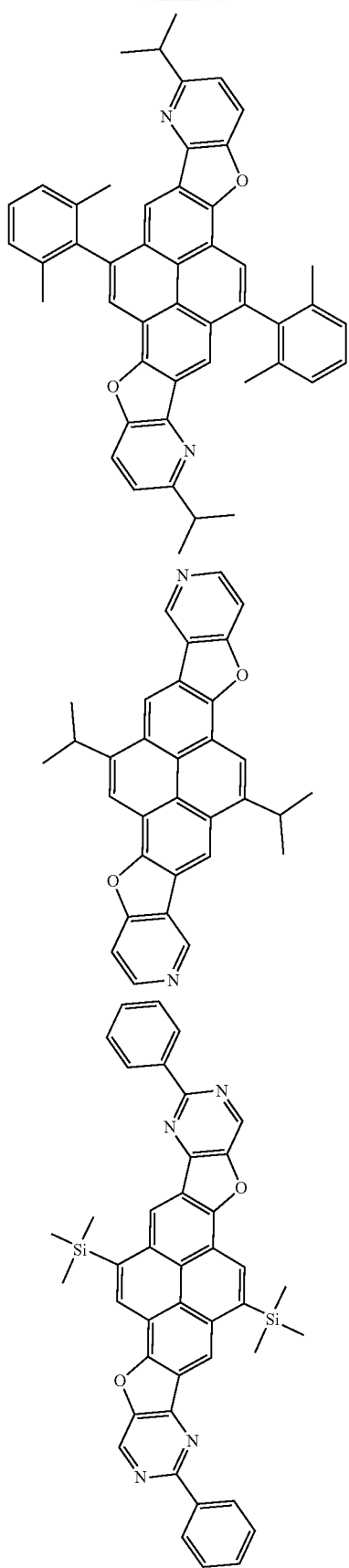
[Formula 38]
-continued

53
-continued
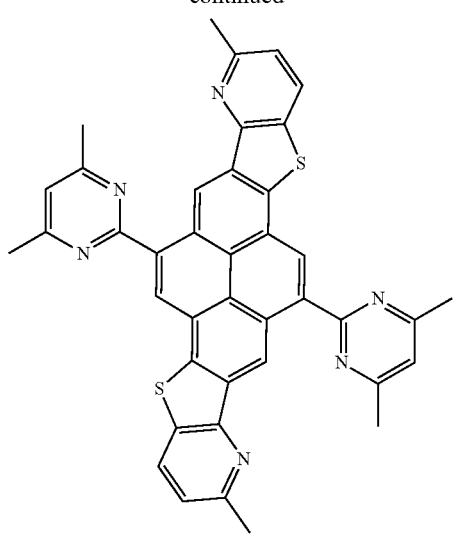
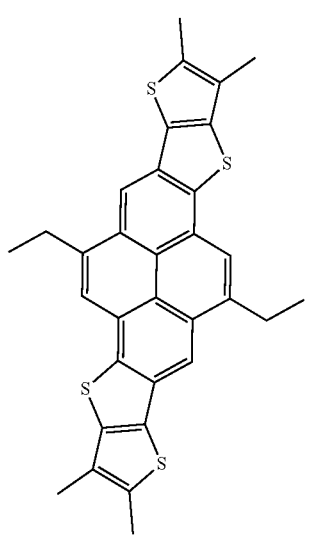
54
-continued
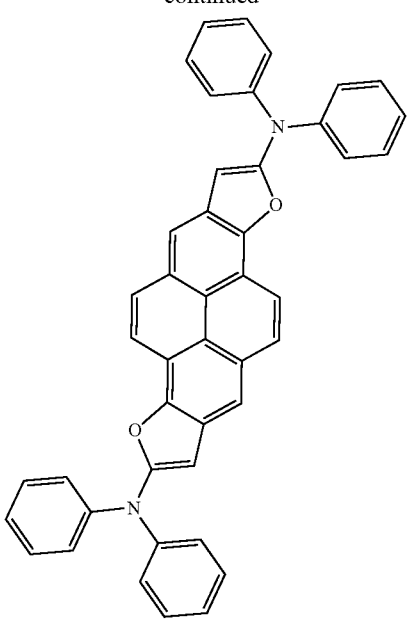
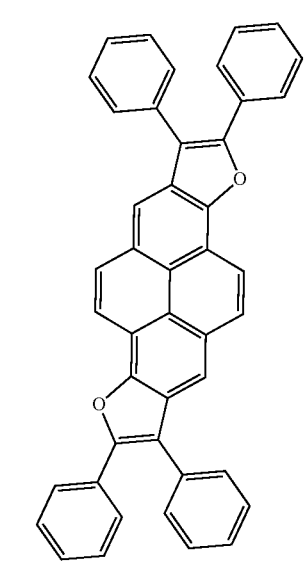

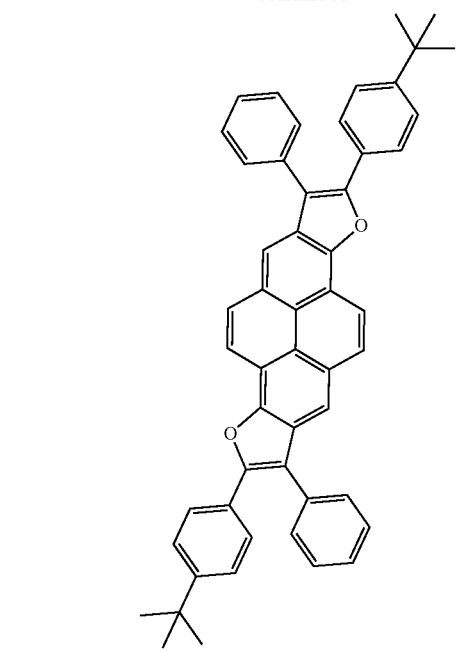
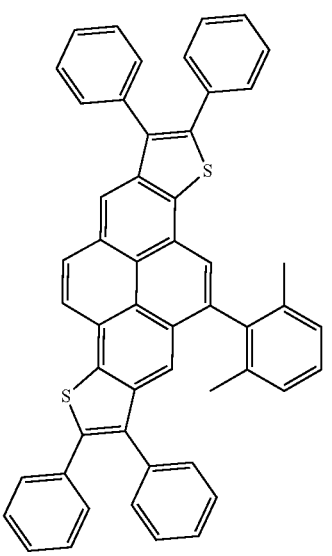
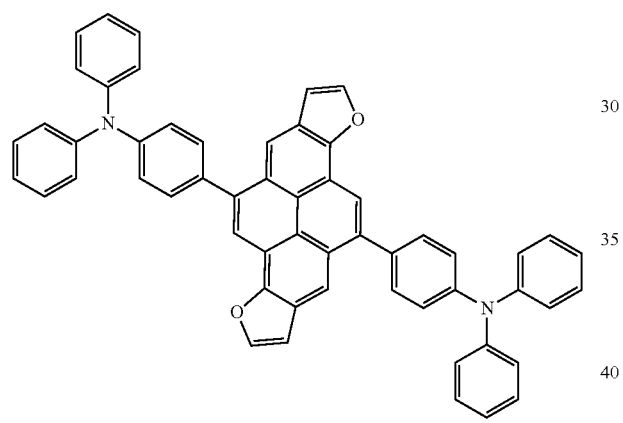
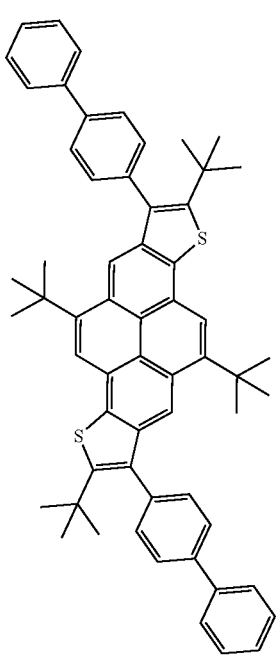
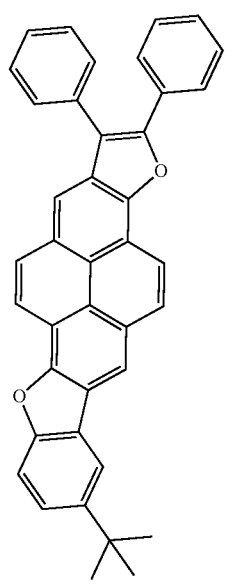
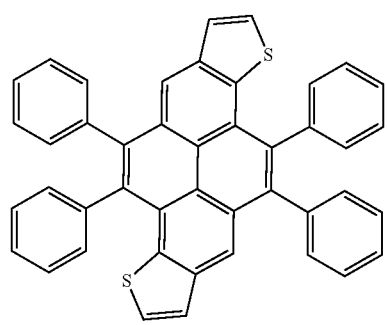
[Formula 39]

57
-continued
58
-continued
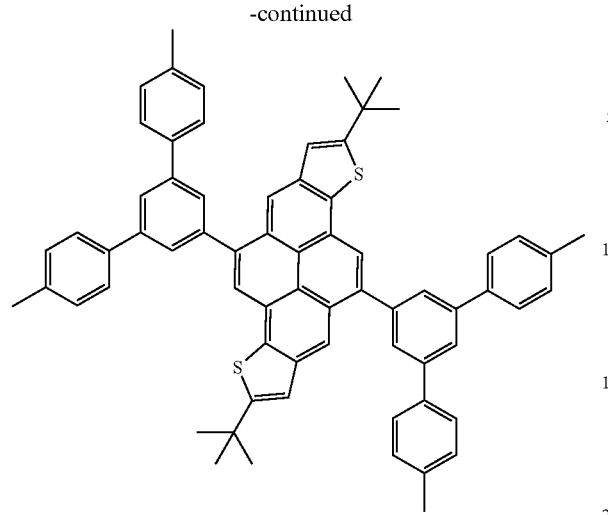
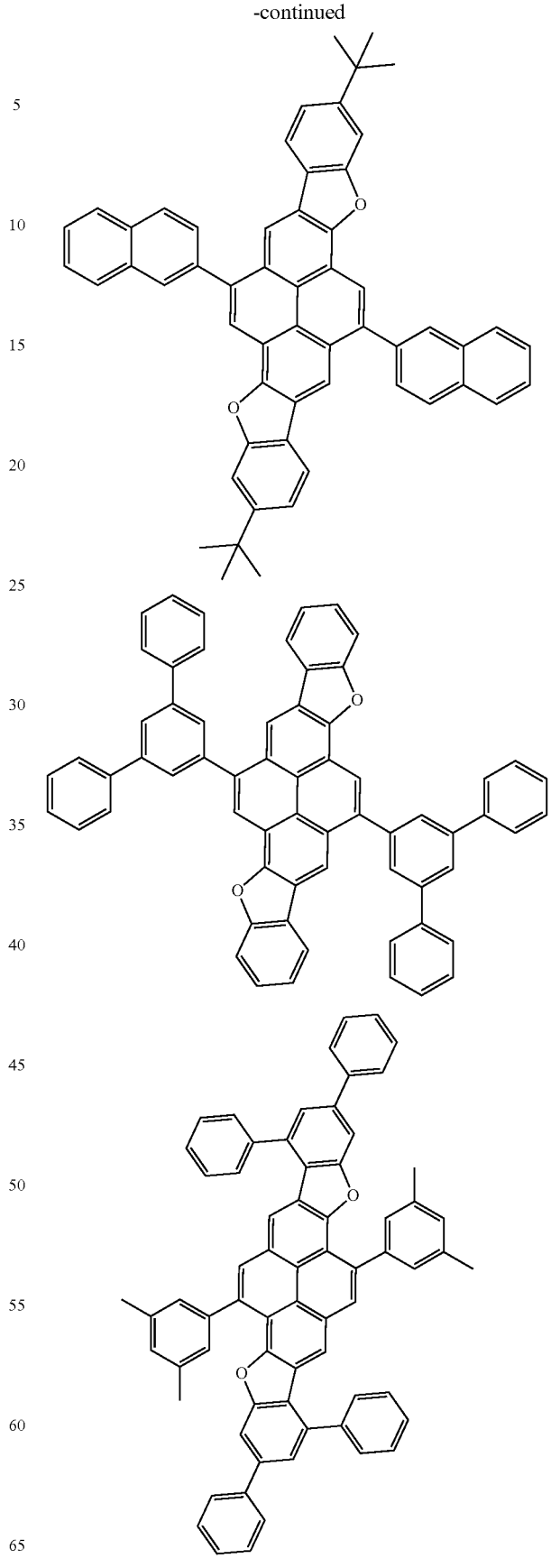

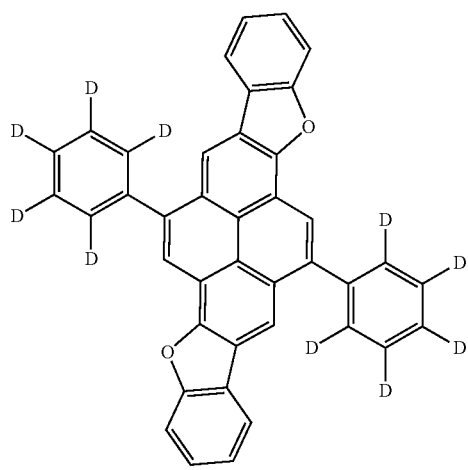
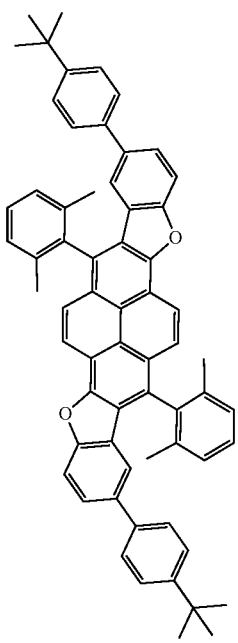
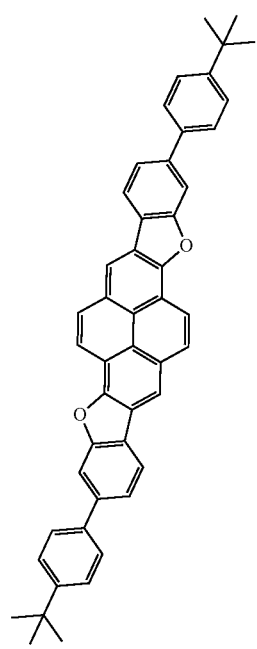
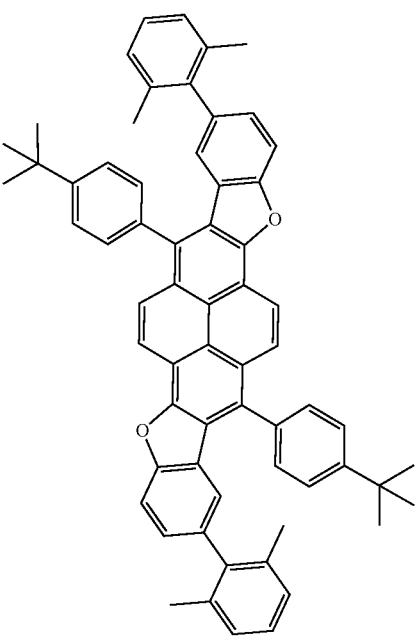

61
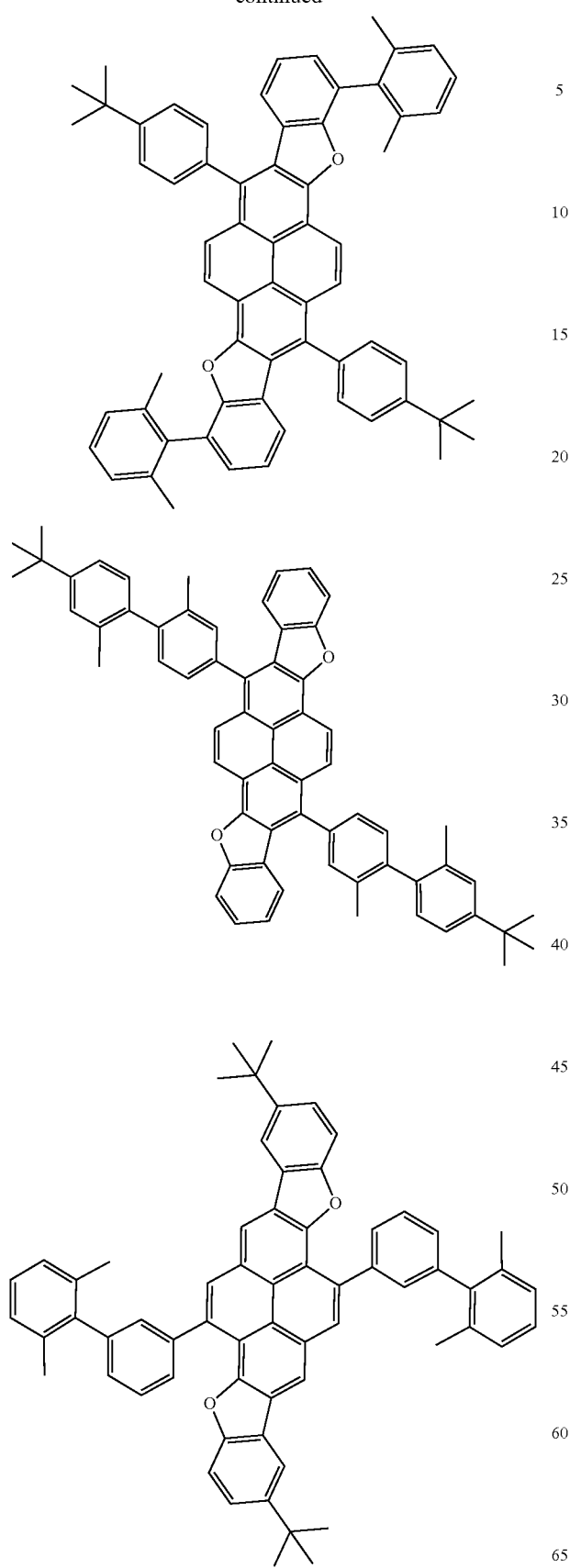
62
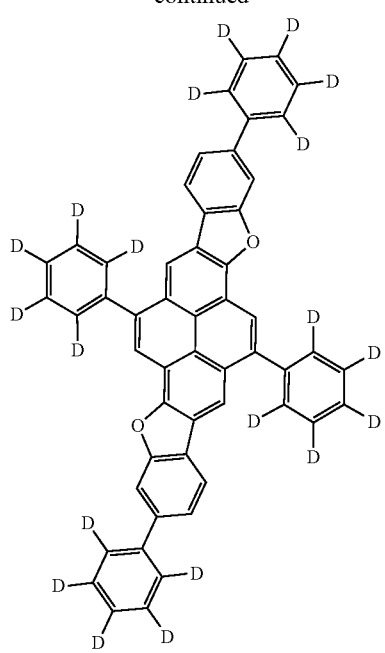
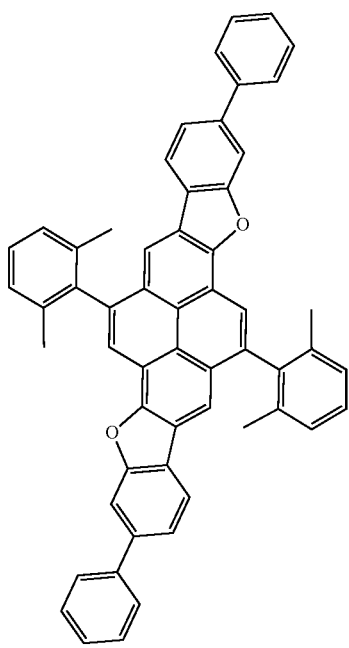

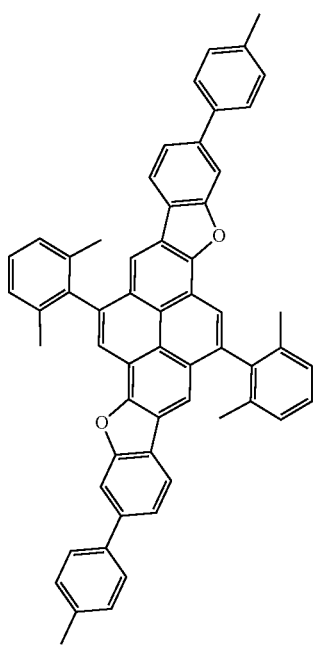
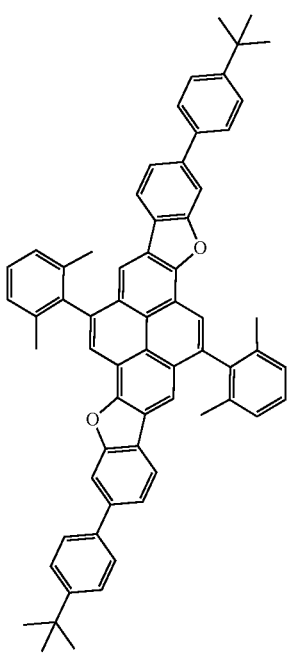 [SMILES: Cc1cccc(C)c1-c1cc2c3oc4cc(-c5ccc(C(C)(C)C)cc5)ccc4c3cc3c(-c4c(C)cccc4C)cc4c5oc6cc(-c7ccc(C(C)(C)C)cc7)ccc6c5cc1c4c32]
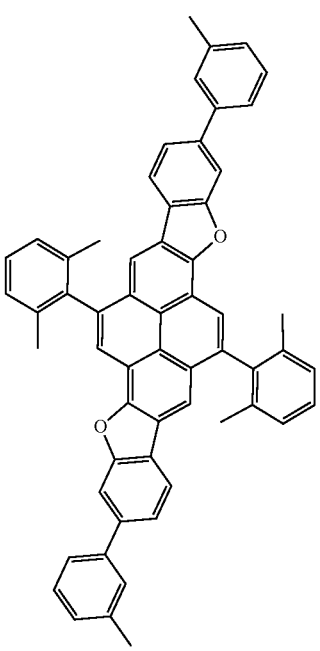
[Formula 40]
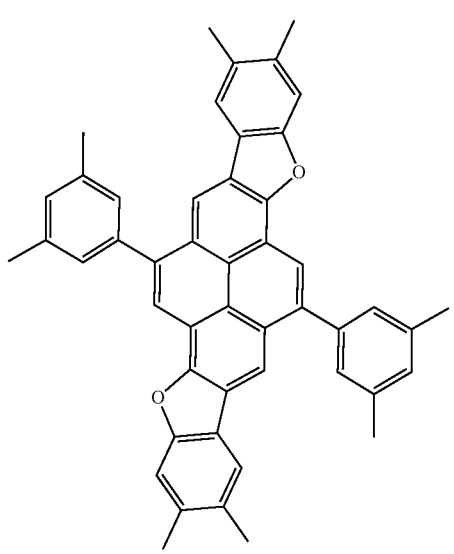

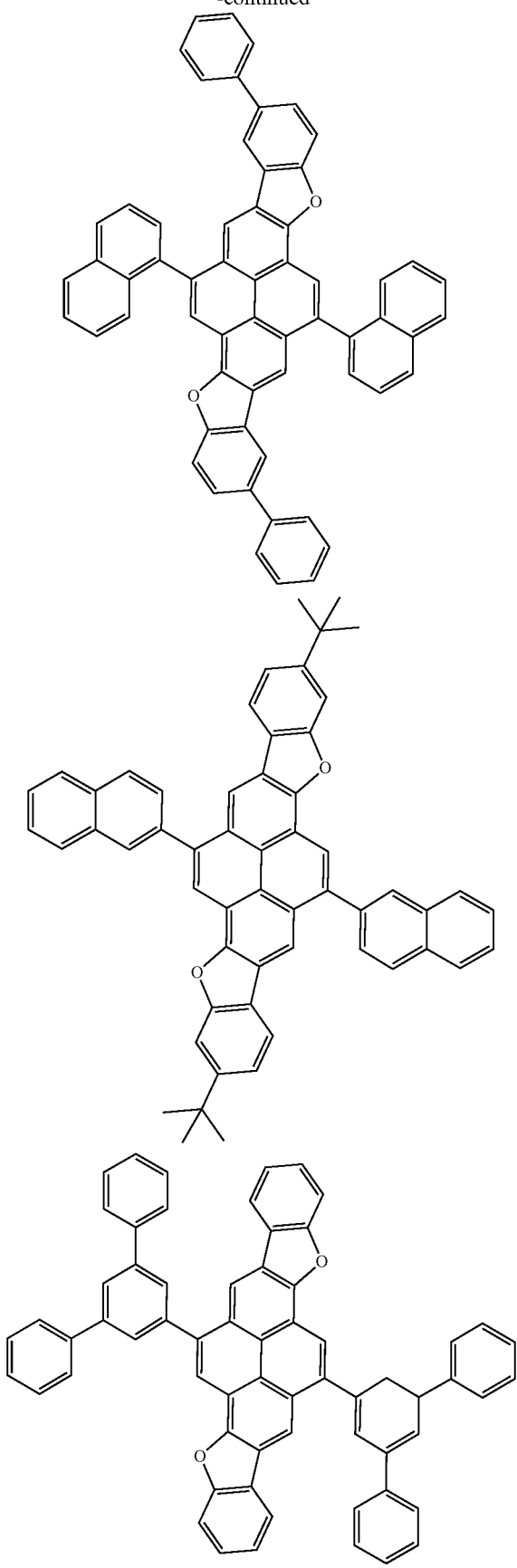
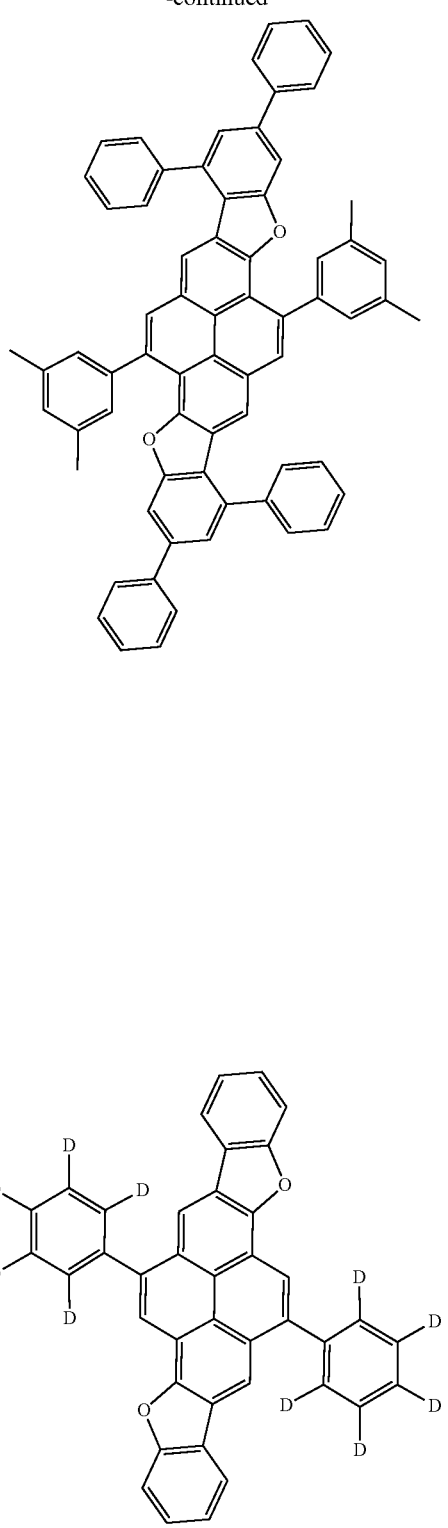

67
-continued
68
-continued
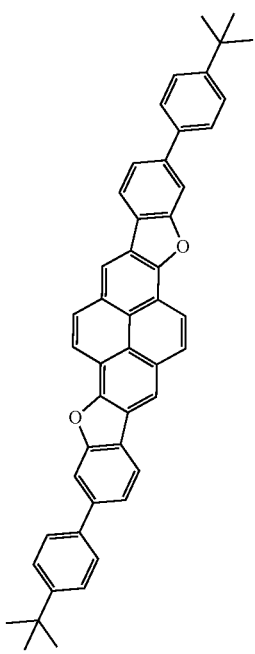
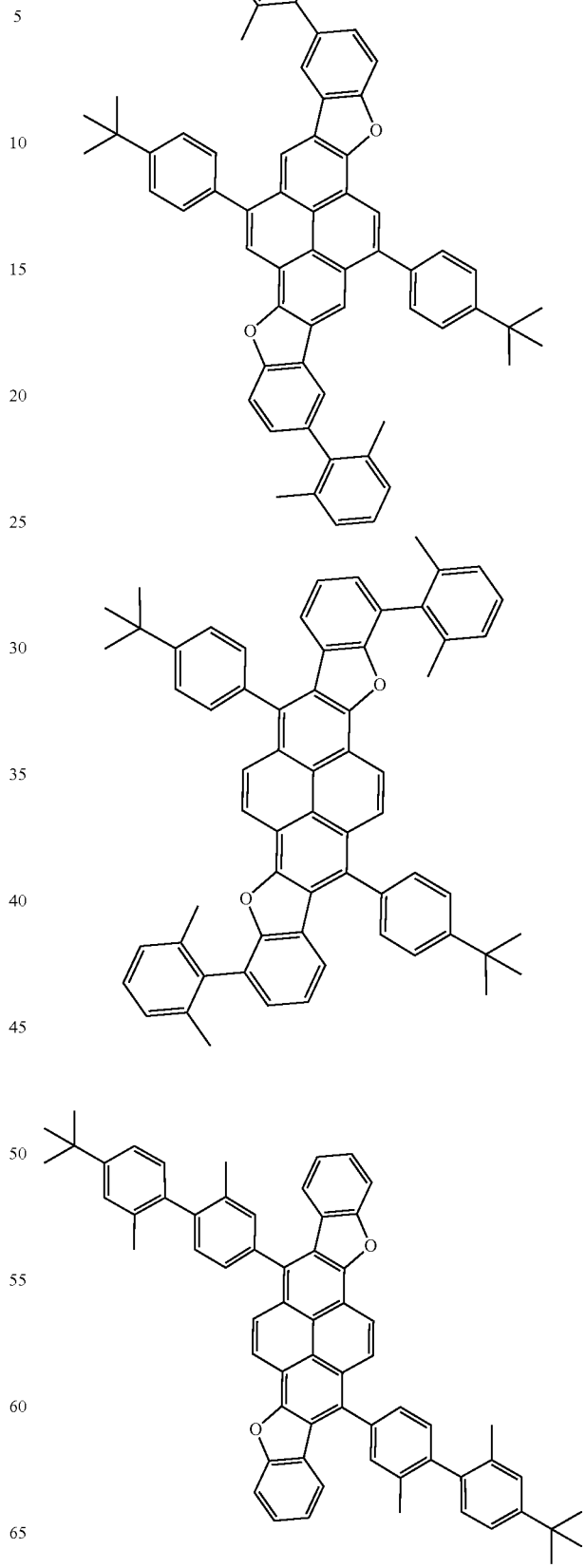

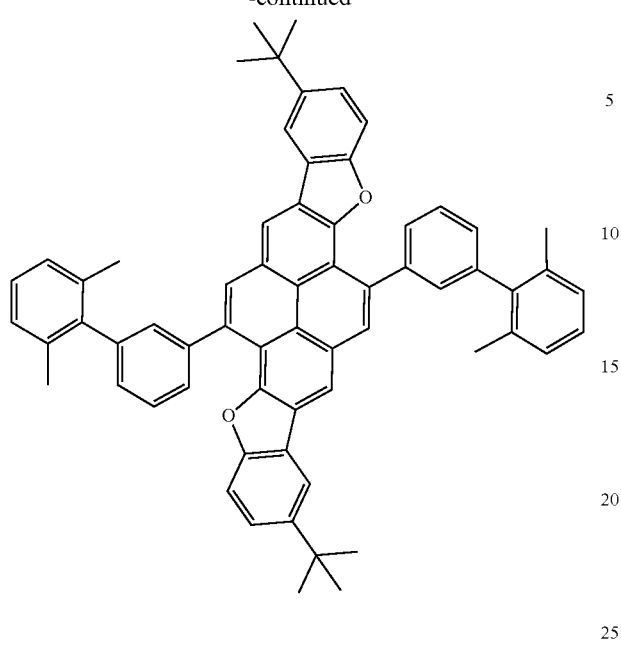
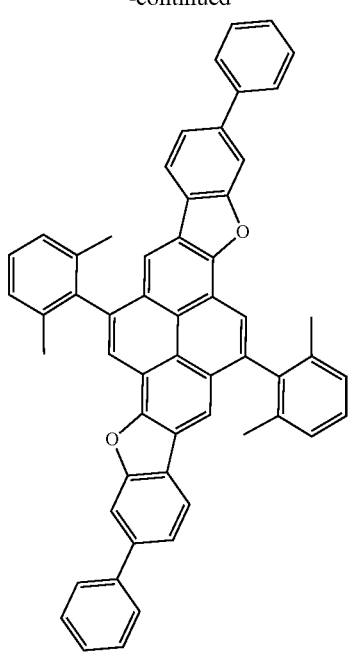
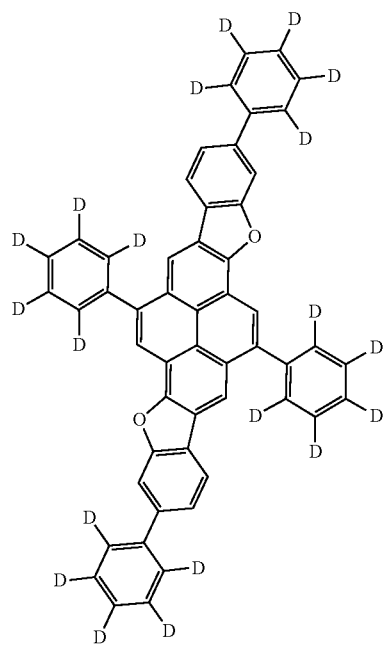
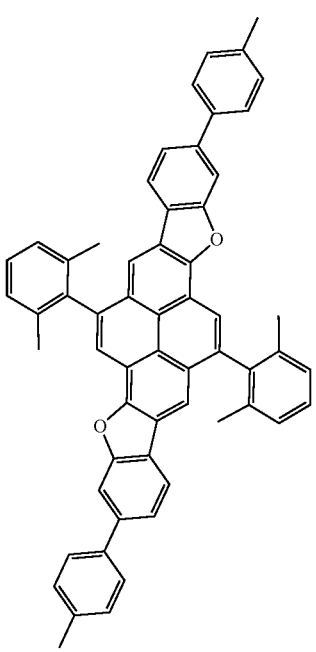

71
-continued
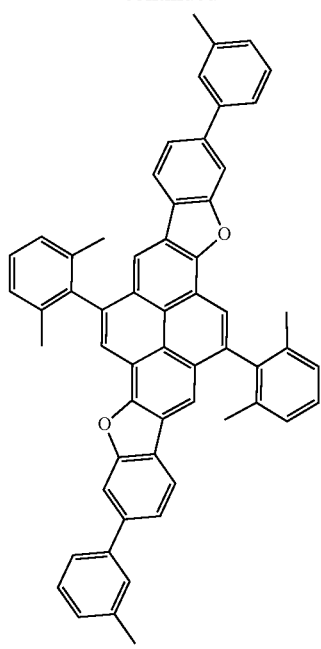
72
-continued
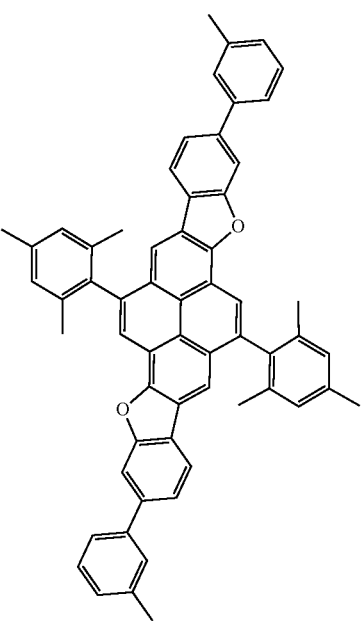
[Formula 41]
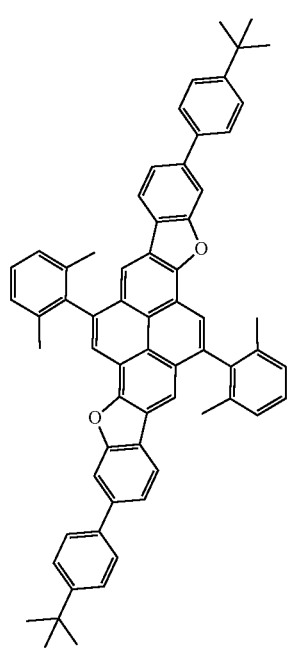 [SMILES: Cc1cccc(C)c1-c1cc2c3oc4cc(-c5ccc(C(C)(C)C)cc5)ccc4c3cc3c(-c4c(C)cccc4C)cc4c5oc6cc(-c7ccc(C(C)(C)C)cc7)ccc6c5cc1c4c32]
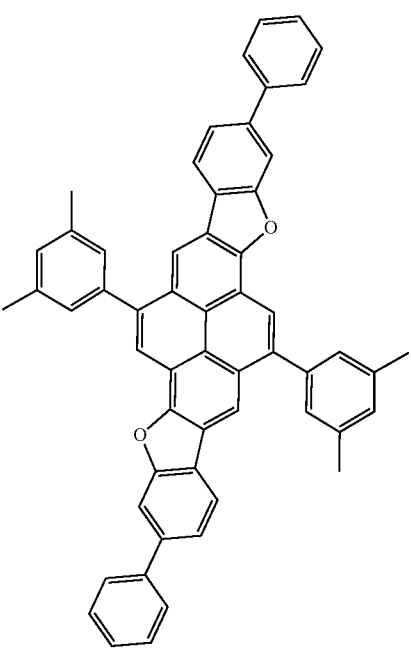

73
-continued
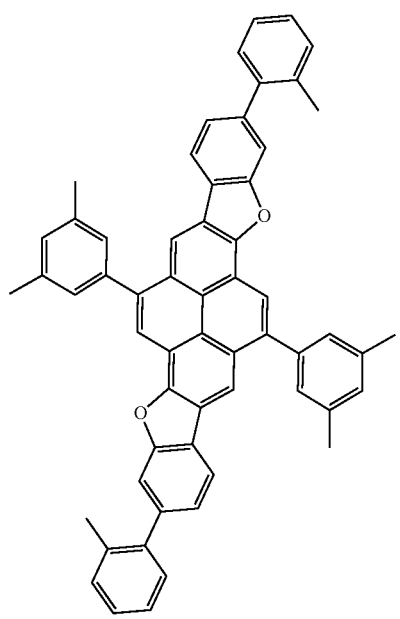
74
-continued
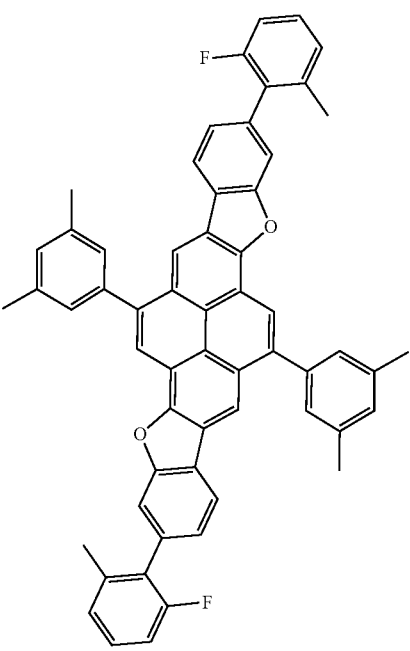
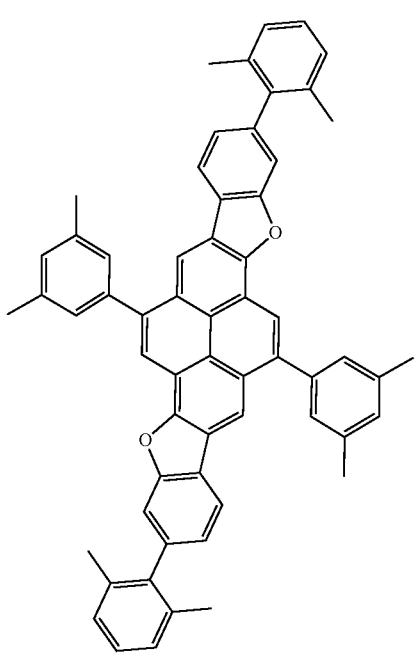
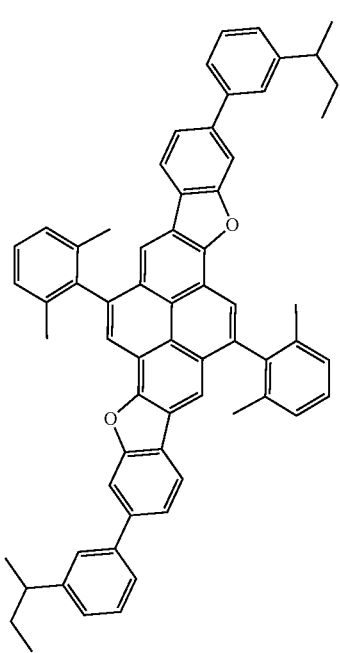

75
-continued
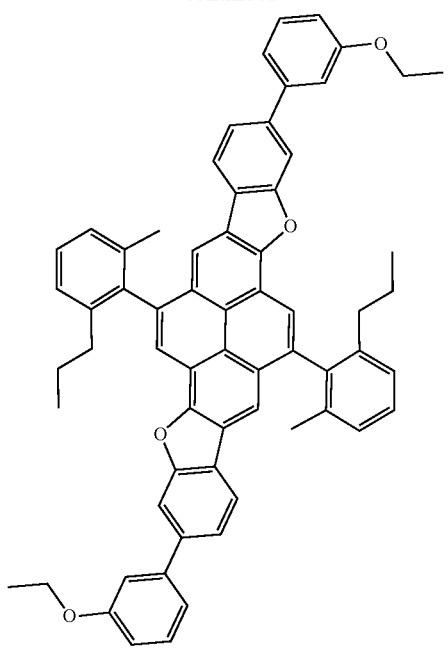
76
-continued
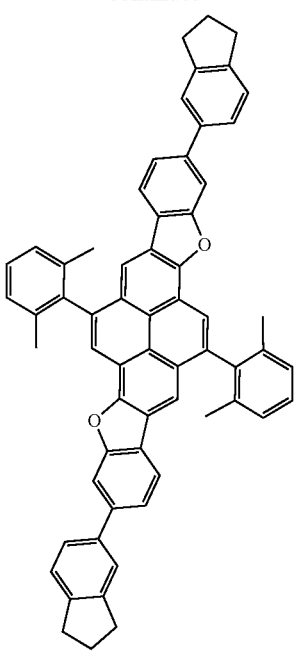
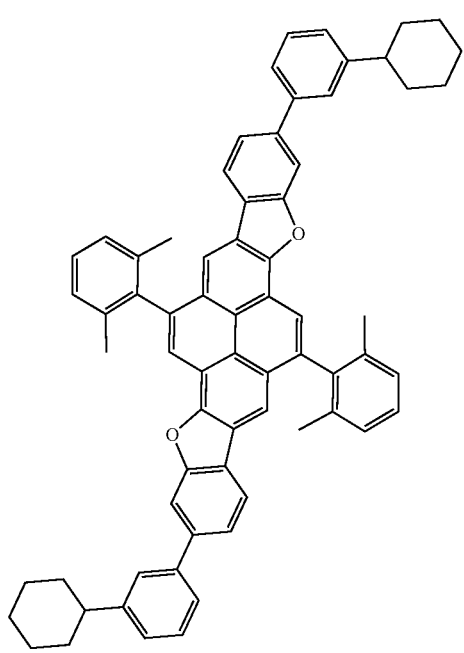
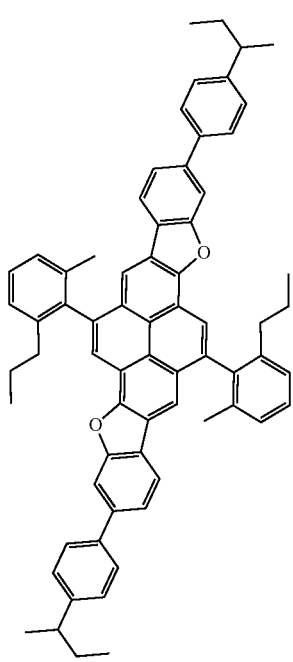 [SMILES: CCCc1cccc(C)c1-c1cc2c3oc4cc(-c5ccc(C(C)CC)cc5)ccc4c3cc3c(-c4c(C)cccc4CCC)cc4c5oc6cc(-c7ccc(C(C)CC)cc7)ccc6c5cc1c4c32]

[Formula 42]
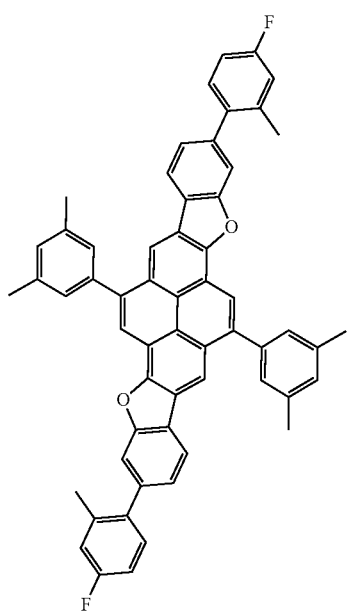
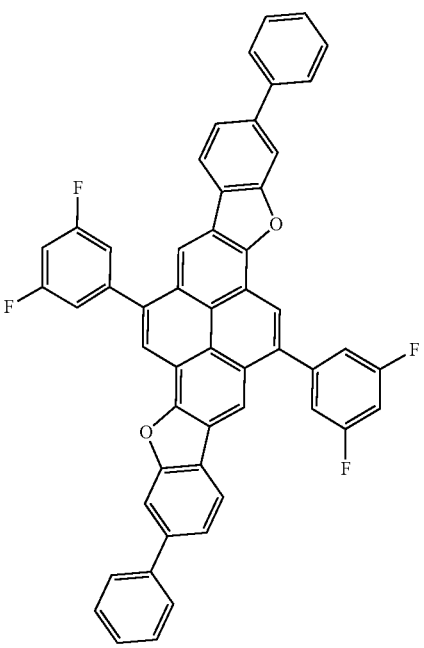
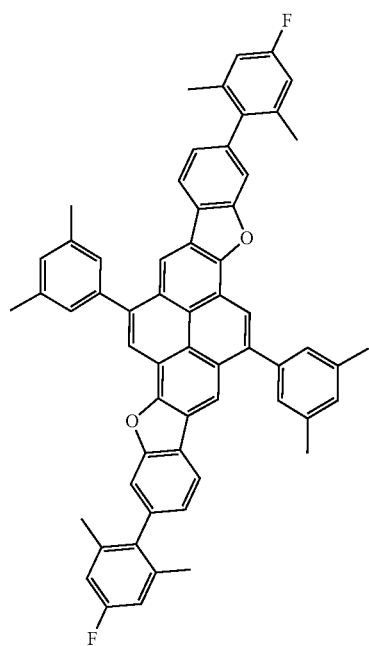
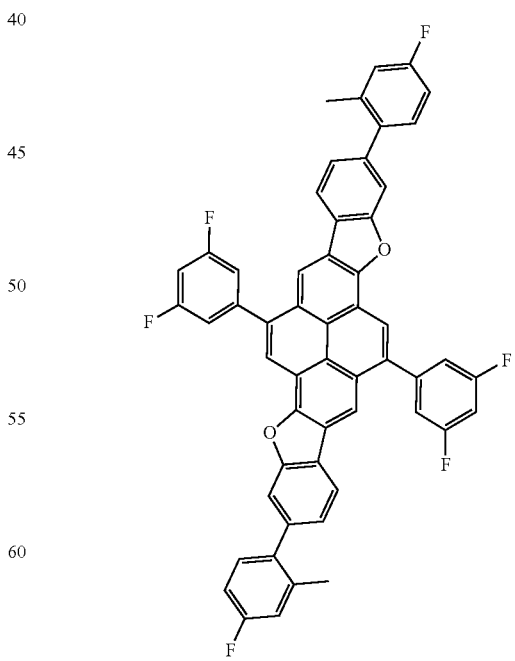

79
-continued
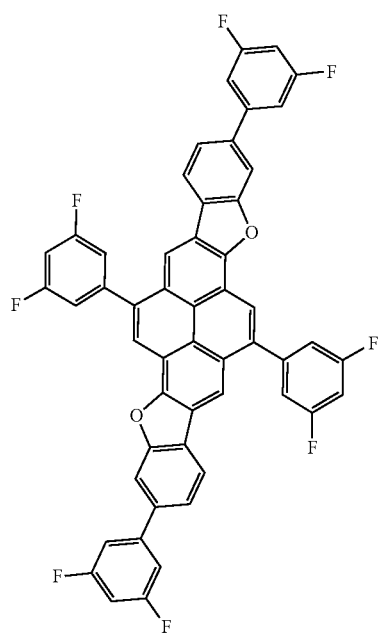
80
-continued
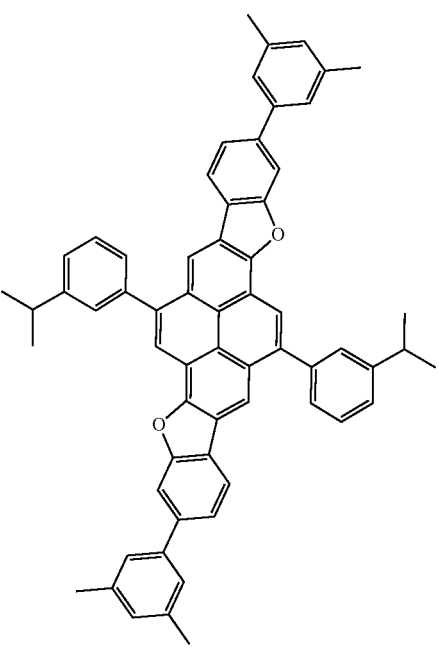
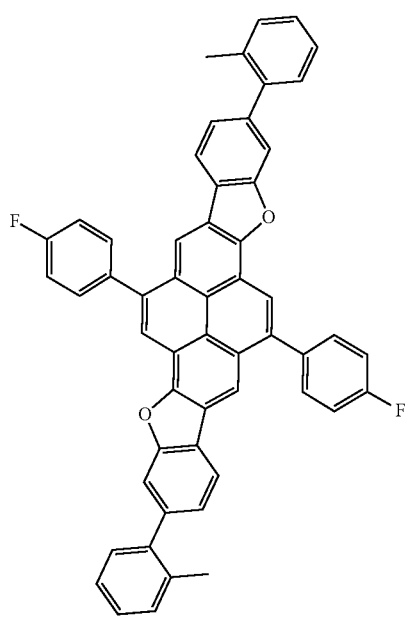
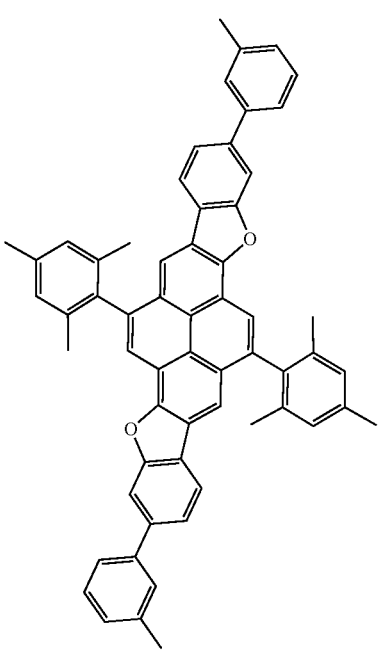

81
-continued
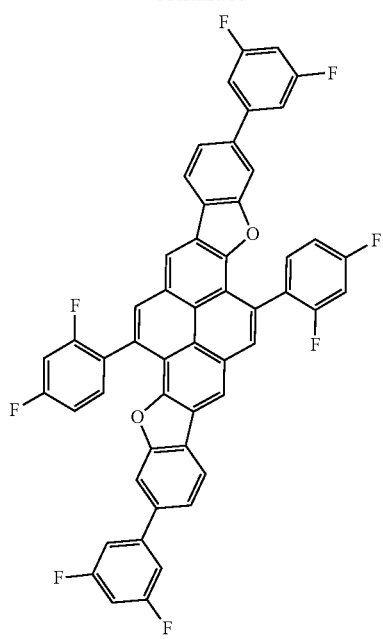
82
-continued
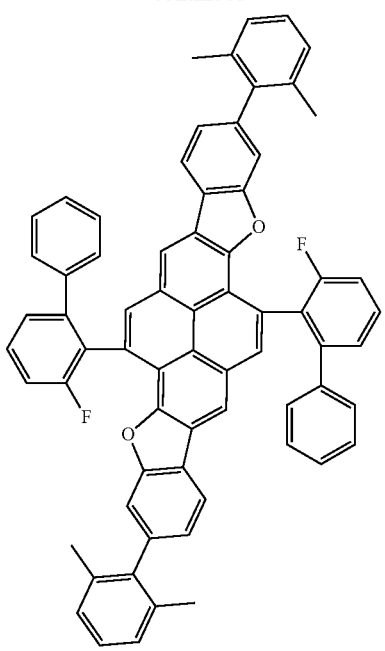
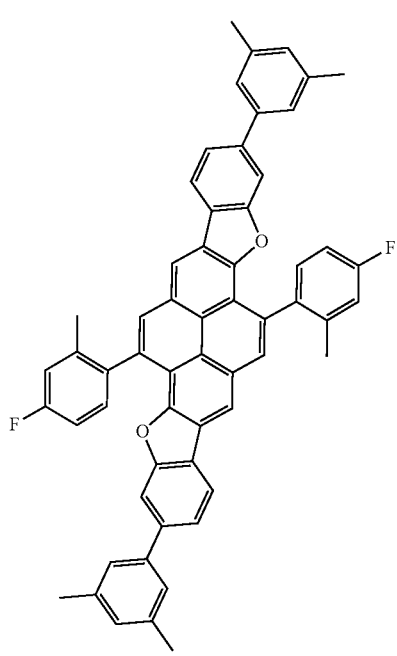
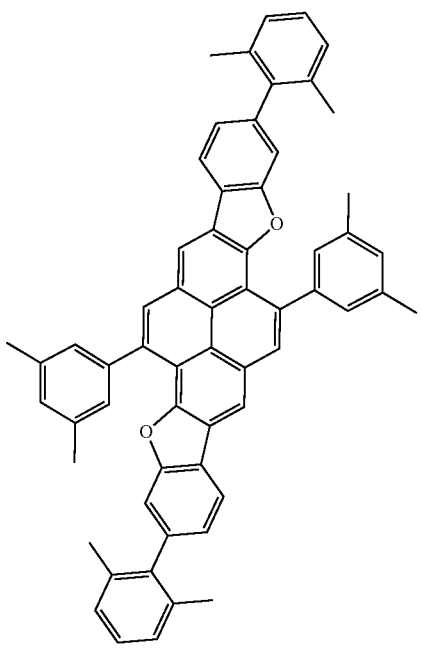

[Formula 43]
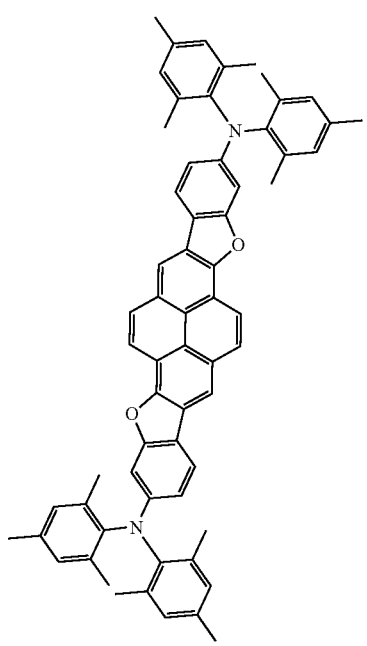
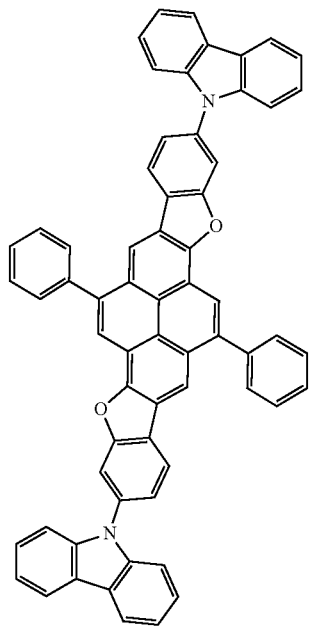
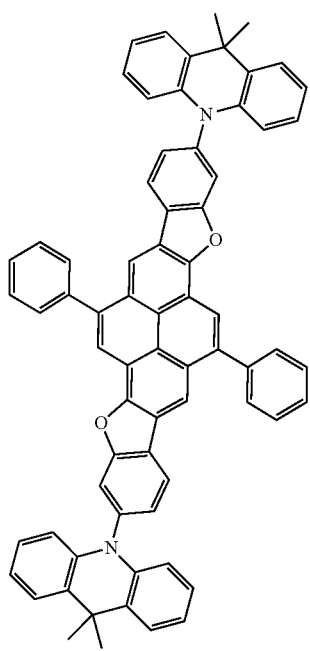
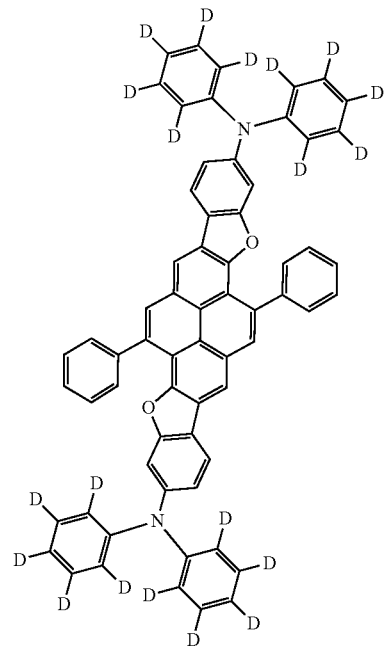

85
-continued
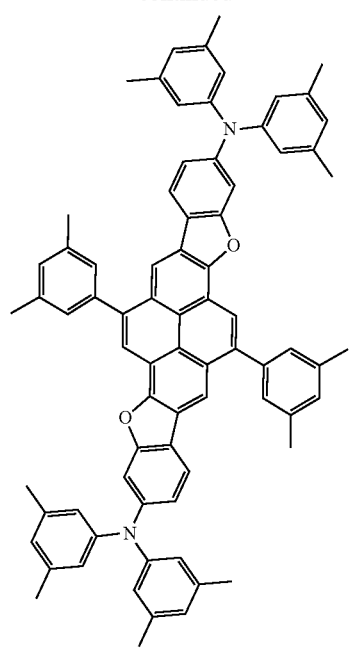
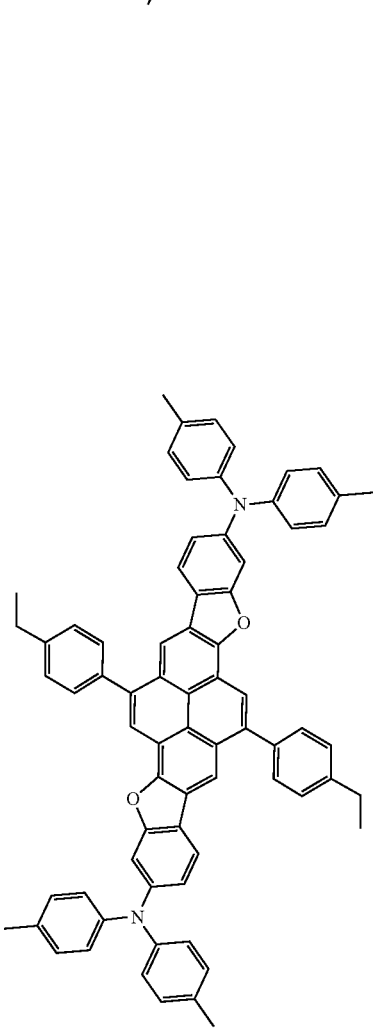
86
-continued
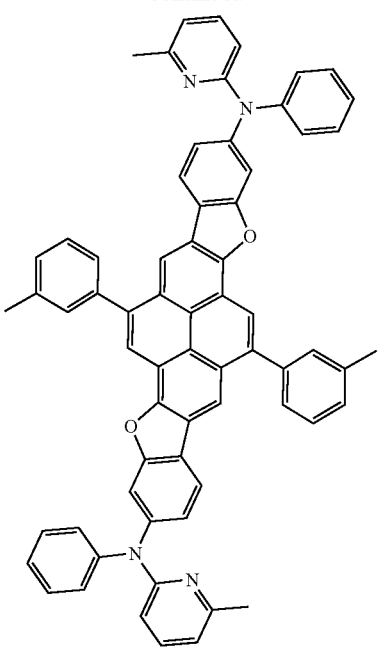
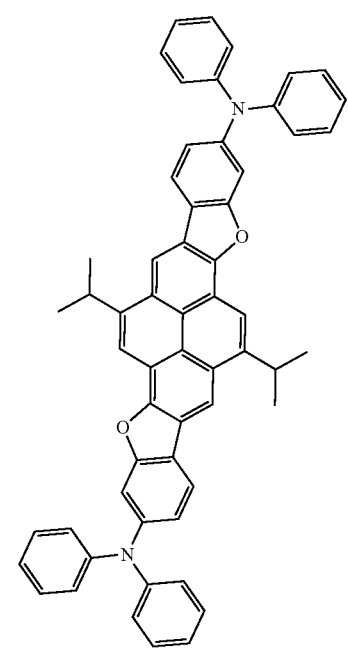
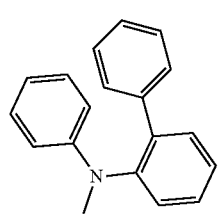

87
-continued
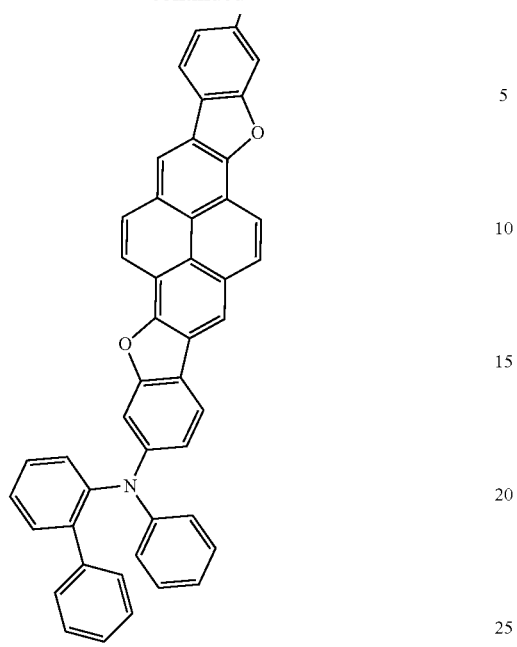
88
-continued
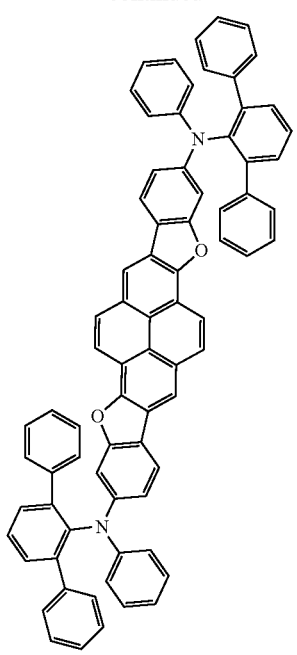
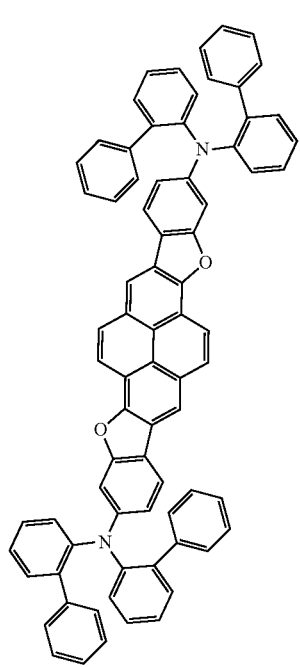
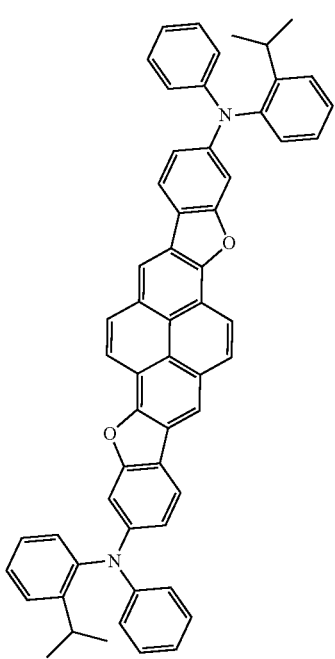

89
-continued
90
-continued
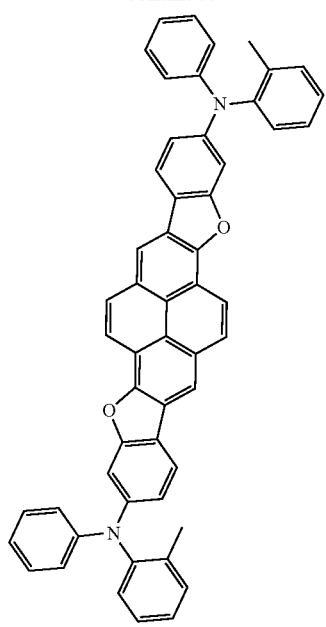 [SMILES: Cc1ccccc1N(c1ccccc1)c1ccc2c(c1)oc1c2cc2ccc3c4oc5cc(N(c6ccccc6)c6ccccc6C)ccc5c4cc4ccc1c2c43]
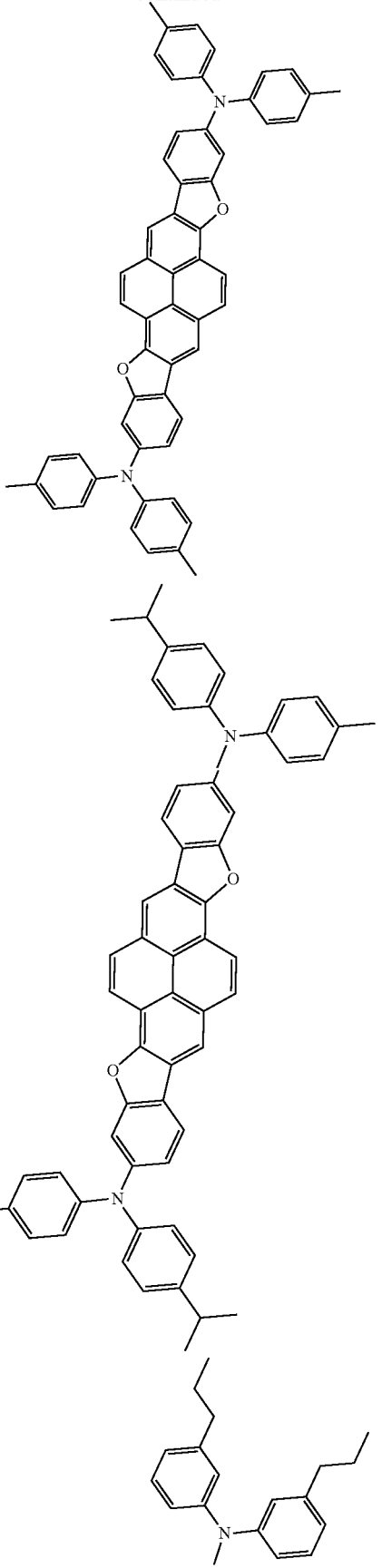

91
-continued
92
-continued
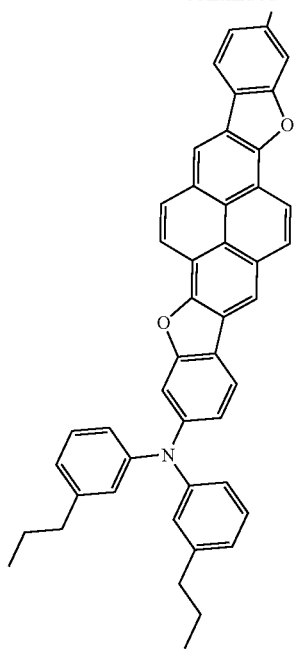
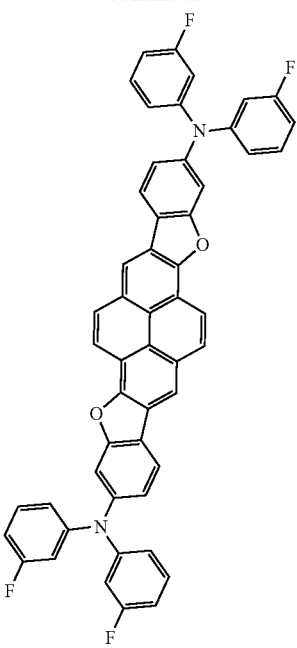
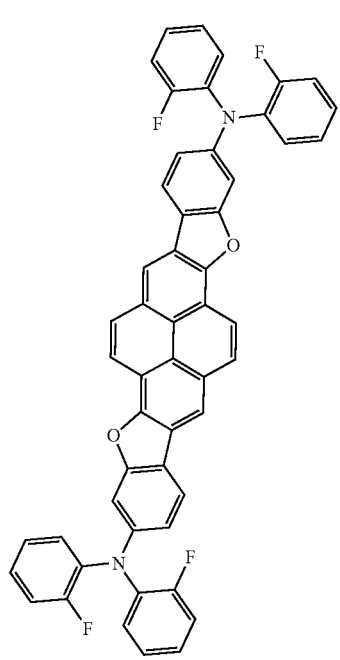

93
-continued
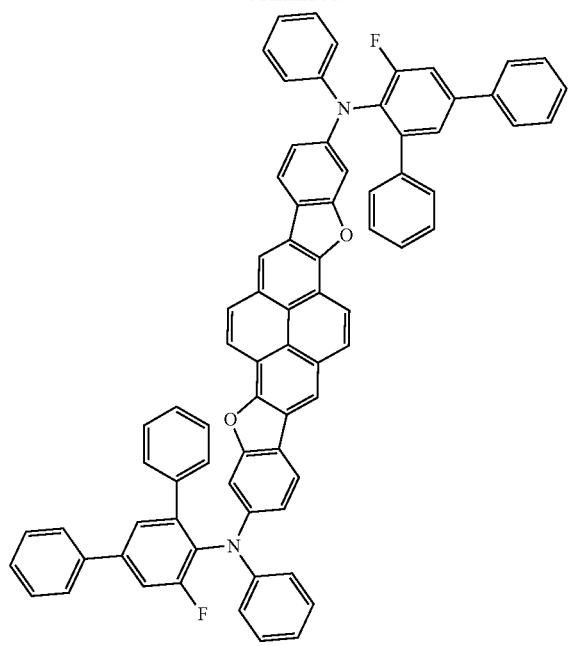
94
-continued
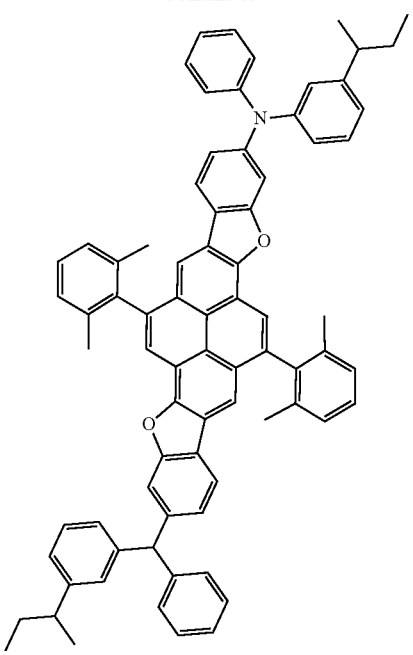
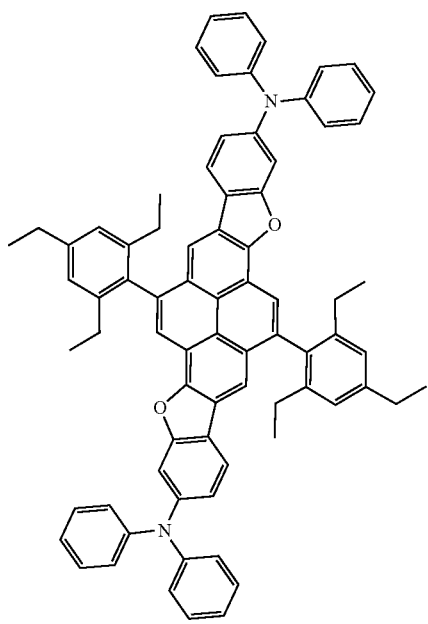
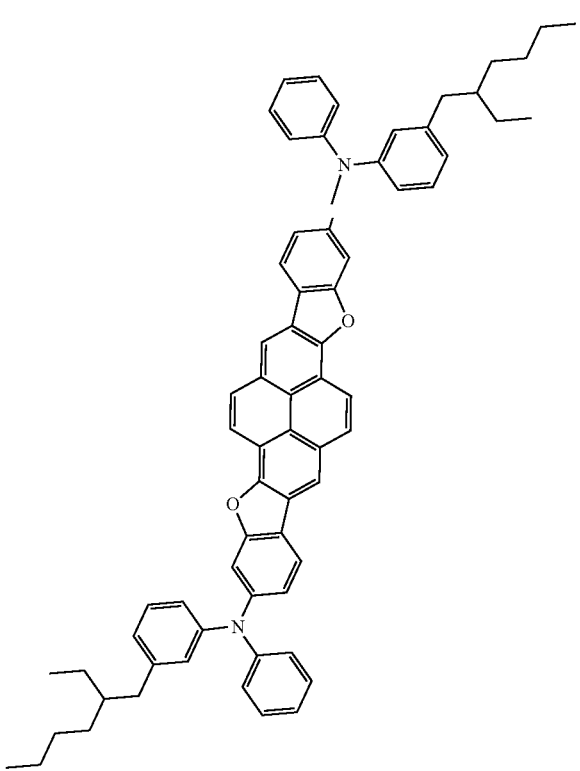

[Formula 45]
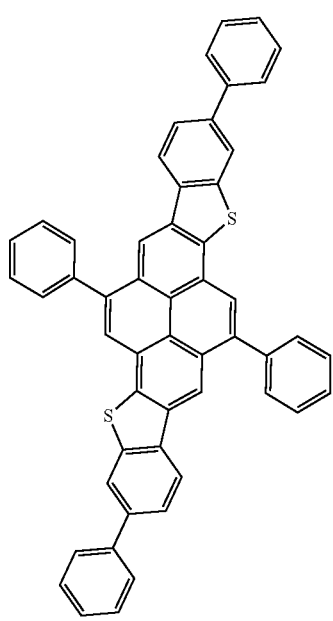
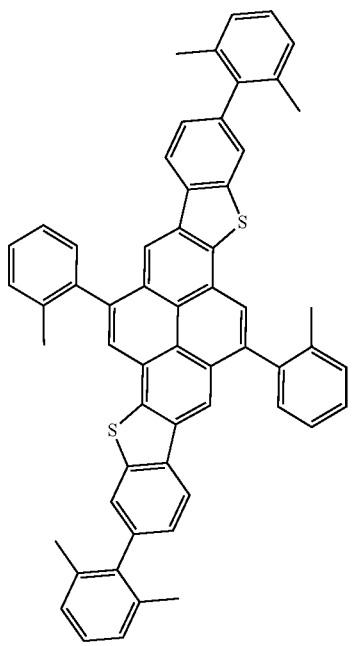
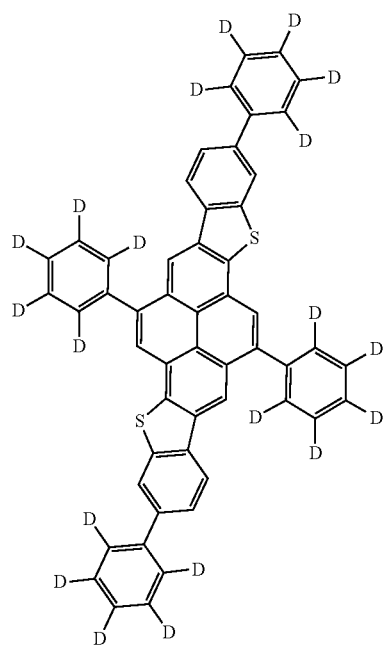
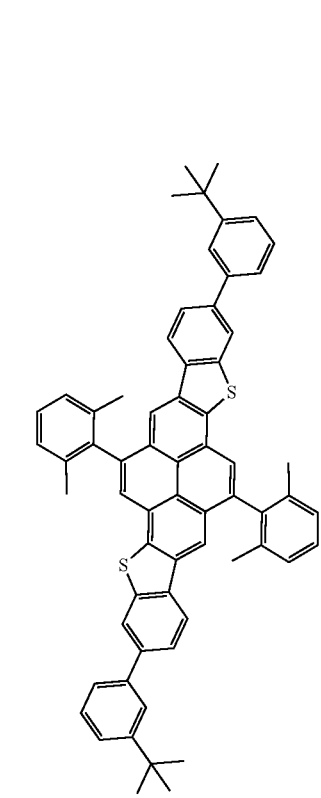

97
-continued
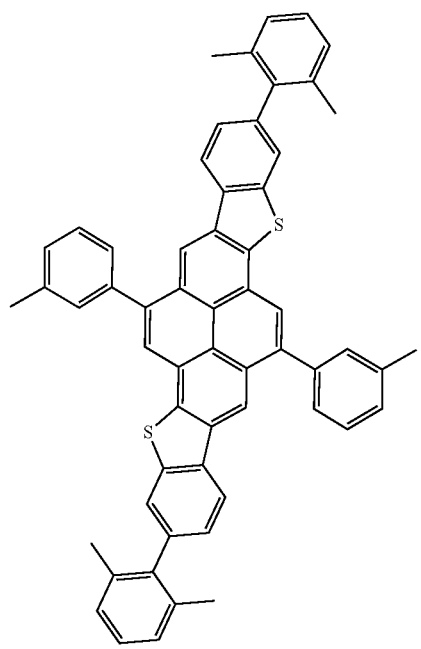
98
-continued
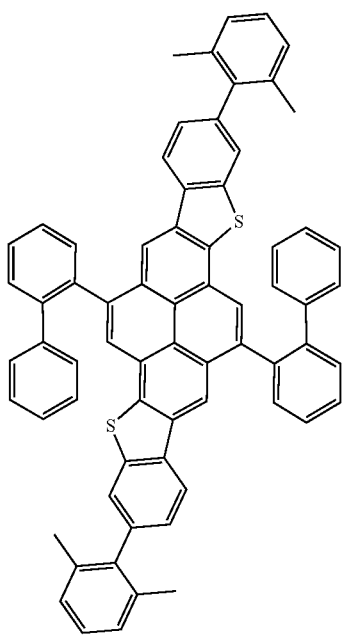
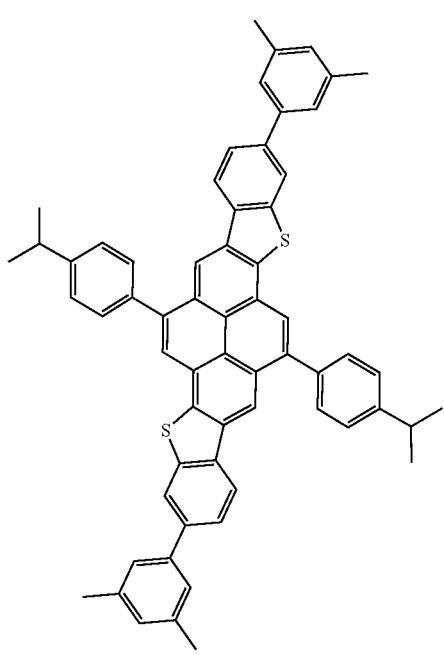
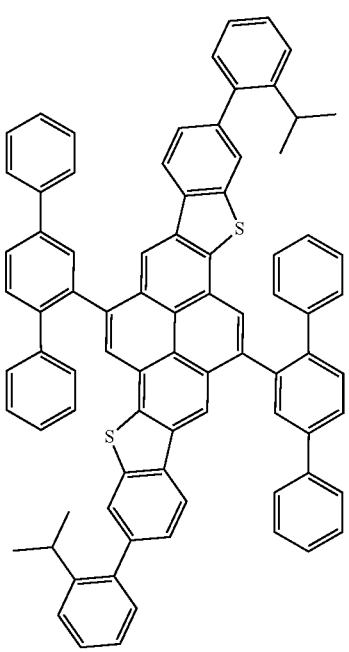

99
-continued
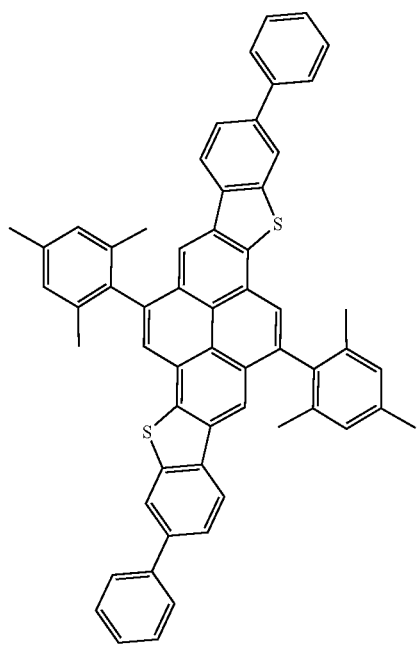
100
-continued
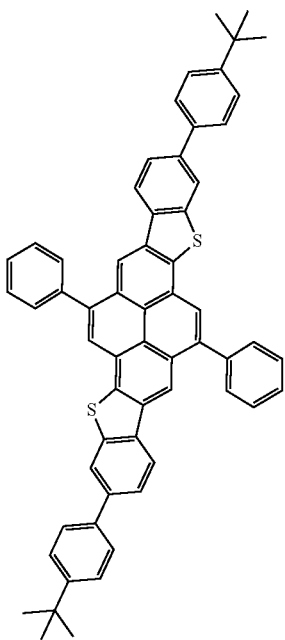
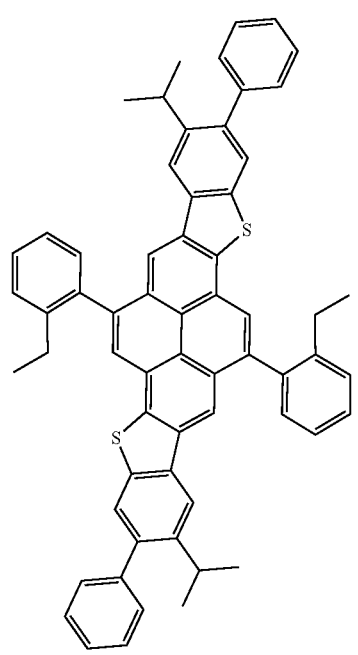
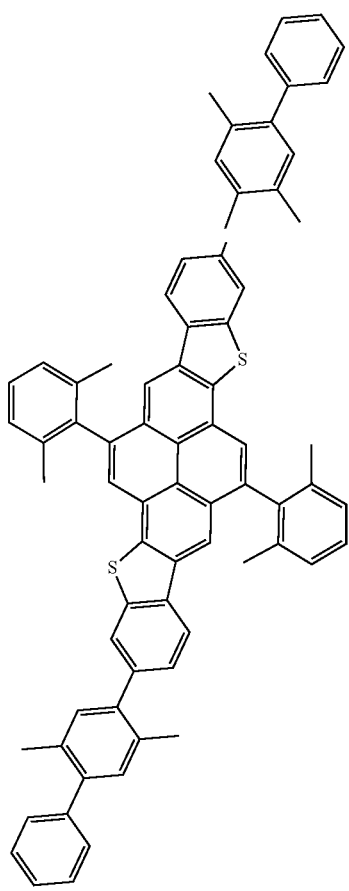

101
-continued
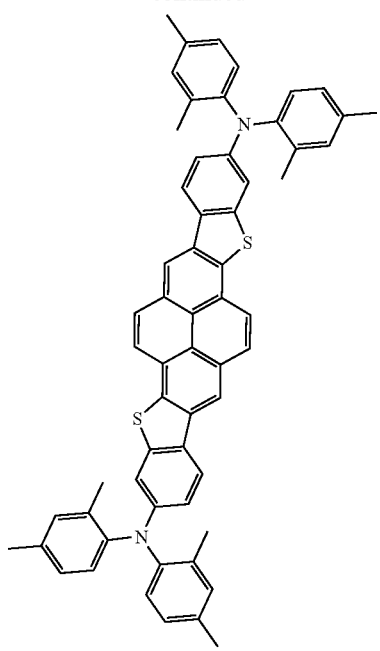
102
-continued
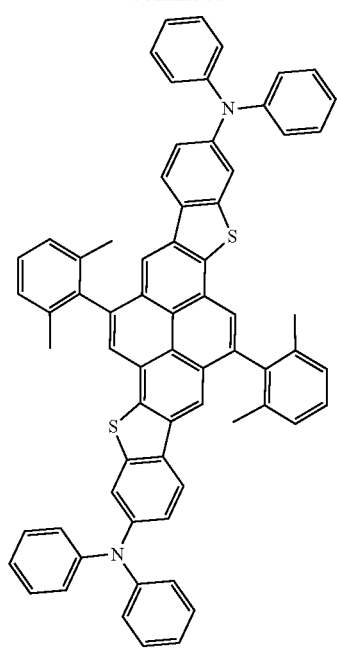
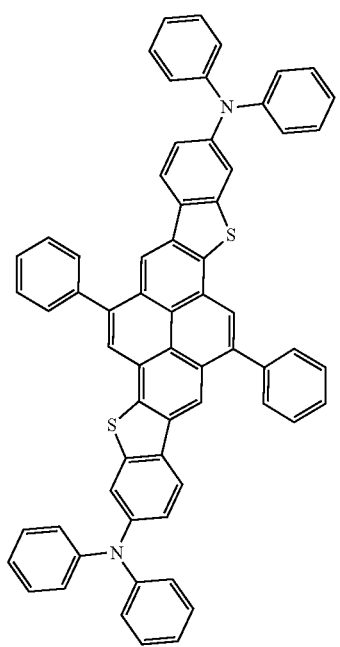
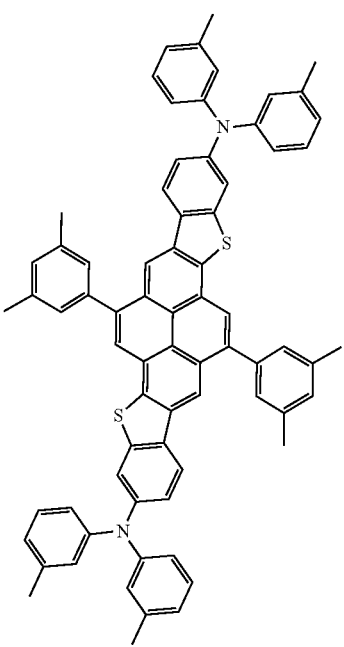

-continued

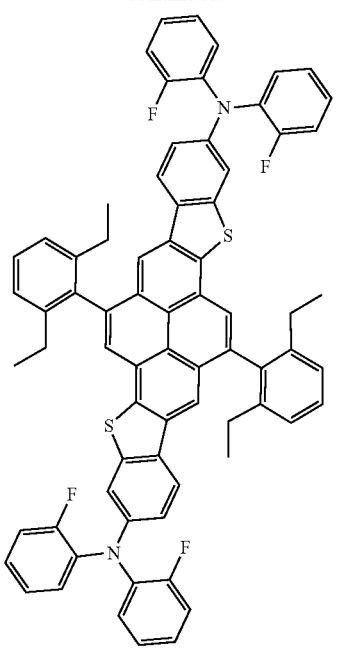 [SMILES: CCc1cccc(CC)c1-c1cc2c3sc4cc(N(c5ccccc5F)c5ccccc5F)ccc4c3cc3c(-c4c(CC)cccc4CC)cc4c5sc6cc(N(c7ccccc7F)c7ccccc7F)ccc6c5cc1c4c32]

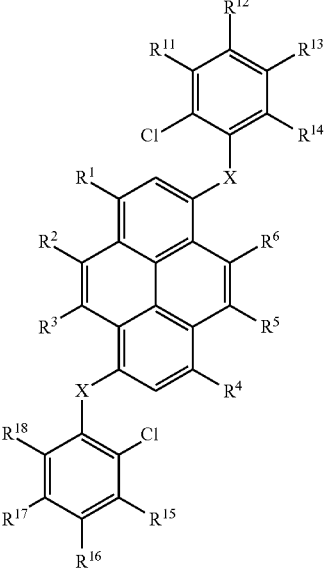

Synthesis
Intermediate B

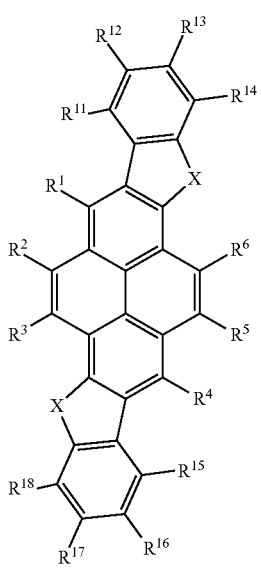

Compound of the Present Invention
(or Synthesis Intermediate C)

The compound expressed by general formula (1) can be synthesized by combining the methods described in Japanese Unexamined Patent Application 2010-205986, J. Org. Chem. 1975, 40, 1365-1367, J. Am. Chem. Soc. 2006, 128, 581-590, Japanese Unexamined Patent Application 2008-133277, WO2004/063159, Japanese Unexamined Patent Application 2009-108066, and the like or other conventionally known reactions. Furthermore, synthesis can be performed based on the following schemes for example.

[Formula 46]

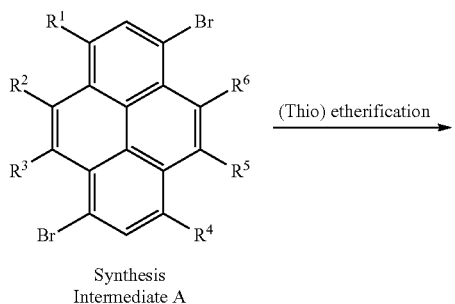

Synthesis
Intermediate A

The synthesis intermediate A having various substitution groups can be synthesized by combining conventionally known reactions. For example, the compound having a substitution group on $R^1$ and $R^4$ can be synthesized by the methods described in WO2005/108348, US2010/0164374, and the like. Furthermore, the compound having a substitution group on $R^2$, $R^3$, $R^5$, and $R^6$ can be synthesized by the methods described in Synthesis, 1980, 356-359, Japanese Unexamined Patent Application 2008-127291, J. Am. Chem. Soc. 2001, 133, 10716-10719, and the like. The (thio) etherification step can be performed in various conventionally known reaction conditions, and the cyclization reaction step can be performed in a reaction condition described in J. Am. Chem. Soc. 2006, 128, 581-590. for example. Furthermore, each substitution group can be introduced at any intermediate stage. After synthesizing, purification is performed by column chromatography, recrystallization, or the like, and then purification is preferably performed by sublimation purification. Not only can organic impurities be separated, but inorganic salt, residual solvents, and the like can be effectively removed by sublimation purification.

When used as the light emitting material using the compound expressed by general formula (1), the maximum light emission wavelength in a thin film state is preferably less than 460 nm, more preferably 400 nm or more and 460 or less, particularly preferably 420 nm or more and less than 455 nm, even more preferably 430 nm or more and less than 455 nm, and most preferably 440 nm or more and less than 455 nm, from the perspective of achieving blue color light emission with high color purity.

Organic Electroluminescent Element

An organic electroluminescent element contains: a substrate; a pair of electrodes including an anode and a cathode, disposed on the substrate; and at least one light emitting layer which is arranged between the electrodes and which includes a light emitting layer; wherein the organic layer contains a compound expressed by general formula (1) in at least one layer.

The configuration of the organic electroluminescent element of the present invention is not particularly restricted. FIG. 1 illustrates an example of the configuration of the organic electroluminescent element of the present invention. An organic electroluminescent element 10 in FIG. 1 has an organic layer between a pair of electrode (anode 3 and cathode 9) on a substrate 2.

The element configuration, substrate, anode, and cathode of the organic electroluminescent element are described in detail in Japanese Unexamined Patent Application 2008-270736 for example, and items described in the publication can be applied in the present invention. Preferred aspects of the organic electroluminescent element of the present invention are described below in detail in order of substrate, electrodes, organic layer, protective layer, sealed container, driving method, light emission wavelength, and application.

Substrate

The organic electroluminescent element of the present invention has a substrate.

The substrate used in the present invention is preferably a substrate that does not scatter or attenuate light emitted from the organic layer. If an organic material is used, the material preferably has excellent heat resistance, dimensional stability, solvent resistance, electrical insulating properties, and processability.

Electrode

The organic electroluminescent element of the present invention has a pair of electrodes which include an anode and a cathode, disposed on the substrate.

Due to the nature of the luminescent element, at least one electrode of the anode and cathode which make the pair of electrodes is preferably transparent or semi-transparent.

Anode

The anode normally has a function as an electrode supplying electron holes to the organic layer, and the form, structure, size, and the like thereof is not particularly restricted. The anode can be appropriately selected from conventionally known electrode material based on application and purpose of the luminescent element. As described above, the anode is normally provided as a transparent anode.

Cathode

The cathode normally has a function as an electrode injecting electrons to the organic layer, and the form, structure, size, and the like thereof is not particularly restricted. The anode can be appropriately selected from conventionally known electrode material based on application and purpose of the luminescent element.

Organic Layer

The organic electroluminescent element of the present invention has at least one organic layer which includes a light emitting layer, disposed between the electrodes, and the compound expressed by general formula (1) is included in at least one layer of the light emitting layer. The organic layer is not particularly restricted, and can be appropriately selected based on application and purpose of the organic electroluminescent element, but is preferably formed on the transparent electrode or semi-transparent electrode. In this case, the organic layer is formed on all surfaces or one surface of the transparent electrode or semi-transparent electrode.

The form, size, thickness, and the like of the organic layer is not particularly restricted, but can be appropriately selected based on the objective.

The configuration of the organic layer, forming method of the organic layer, a preferred aspect of each layer configuring the organic layer, and the material used in each layer for the organic electroluminescent element of the present invention is described in order below.

Configuration of Organic Layer

The organic layer includes a light emitting layer in the organic electroluminescent element of the present invention. The organic layer preferably includes a charge transport layer. The charge transport layer refers to a layer where charge transfer occurs when a voltage is applied to the organic electroluminescent element. Specific examples include electron hole injecting layers, electron hole transport layers, electron blocking layers, light emitting layers, electron hole blocking layers, electron transport layers, and electron injecting layers. If the charge transport layer is an electron hole injecting layer, electron hole transport layer, electron blocking layer, or light emitting layer, manufacturing of a low cost and highly efficient organic electroluminescent element is possible.

The compound expressed by general formula (1) is included in at least one layer of the light emitting layers in the organic layer disposed between the electrodes of the organic electroluminescent element.

However, in so far as the gist of the present invention is not violated, the compound expressed by general formula (1) can be included in another organic layer of the organic electroluminescent element of the present invention. Examples of organic layers other than the light emitting layer that can include the compound expressed by general formula (1) can include electron hole injecting layers, electron hole transport layers, electron transport layers, electron injecting layers, exciton blocking layers, charge blocking layers (such as electron hole blocking layers, electron blocking layers), and the like. Any one of the exciton blocking layers, charge blocking layers, electron transport layers, and electron injecting layers is preferable, and the exciton blocking layers, charge blocking layers, or electron transport layers are more preferable.

When the compound expressed by general formula (1) is included in the light emitting layer, 0.1 to 100 mass % of the compound expressed by general formula (1) is preferably included based on the total weight of the light emitting layer, more preferably 1 to 50 mass %, and even more preferably 2 to 20 mass %.

When the compound expressed by general formula (1) is included in an organic layer other than the light emitting layer, 70 to 100 mass % of the compound expressed by general formula (1) is preferably included based on the total weight of the light emitting layer, more preferably 80 to 100 mass %, and even more preferably 90 to 100 mass %.

Method of Forming of Organic Layer

With the organic electroluminescent element of the present invention, each organic layer can be suitably formed by either a dry film forming method such as a deposition method, sputtering method, and the like, or a wet film forming method (solution coating method) such as a transfer method, printing method, spin coating method, bar coating method, and the like. For the organic electroluminescent element, at least one layer of the organic layer disposed between the pair of electrodes is preferably formed by deposition of a composition including the compound expressed by general formula (1).

Light Emitting Layer

The light emitting layer receives electron holes from the anode, electron holes injecting layer, or electron hole transport layer, and receives electrons from the cathode, electron injecting layer, or electron transport layer, when an electric field is applied, and is a layer that has a function of light emission by providing a place for rebonding the electron holes and electrons. However, the light emitting layer according to the present invention is not necessarily restricted to light emission by this mechanism.

The light emitting layer according to the organic electroluminescent element of the present invention can be configured by only the light emitting materials, or can be configured using a mixed layer of host material and the light emitting material. The light emitting material can be one type, or can be two or more types. The host material is preferably a charge transporting material. The host material can be one type, or can be two or more types, and an example includes a configuration combining an electron transportable host material and a hole transportable host material. Furthermore, the light emitting layer does not have charge transporting properties, and can included material that does not emit light.

Furthermore, the light emitting layer can be a single layer, or can be multiple layers of two or more, and the same light emitting material and host material can be included in each layer, or different materials can be included in each layer. If there is a plurality of light emitting layers, each light emitting layer can emit light with different light emitting colors.

The thickness of the light emitting layers is not particularly restricted, but is normally preferably 2 nm to 500 nm, and above all, 3 nm to 200 nm is more preferable, and 5 nm to 100 nm is even more preferable, from the perspective of external quantaum efficiency.

With the organic electroluminescent element of the present invention, the light emitting layer contains the compound expressed by general formula (1), and the compound expressed by general formula (1) is more preferably used as the light emitting material of the light emitting layer. Herein, in the present specification, the host material is a compound that is mainly responsible for injection and transport of the charge in the light emitting layer, and that itself is a compound that does not substantially emit light. Herein, "does not substantially emit light" means that the light emission amount from the compound that does not substantially emit light is 5% or less of the entire light emitting layer in the entire element, more preferably 3% or less, and even more preferably 1% or less. The compound expressed by general formula (1) can be used as the host material of the light emitting layer.

Light Emitting Material

In the organic electroluminescent element of the present invention, the compound expressed by the general formula (1) is preferably used as the light emitting material, but even in this case, the compound expressed by general formula (1) can be used by combining with another light emitting material. Furthermore, in the organic electroluminescent element of the present invention, when the compound expressed by general formula (1) is used as the host material of the light emitting layer, and when used in an organic layer other than the light emitting layer, a light emitting material that is different from the compound expressed by general formula (1) is used in the light emitting layer.

The light emitting material that can be used in the present invention can be any one of a phosphorescent light emitting material, fluorescent light emitting material, or the like. Furthermore, the light emitting layer in the present invention can include two or more light emitting materials in order to improve the color purity, and to extend the light emission wavelength region.

A fluorescent light emitting material and a phosphorescent light emitting material that can be used in the organic electroluminescent element of the present invention is described in paragraphs [0100] through [0164] of Japanese Unexamined Patent Application 2008-270736, and paragraphs [0088] through [0090] of Japanese Unexamined Patent Application 2007-266458 in detail for example, and the items described in the publications can be applied in the present invention.

Examples of the phosphorescent light emitting material that can be used in the present invention include phosphorescent light emitting material described in patent documents such as U.S. Pat. Nos. 6,303,238, 6,097,147, WO00/57676, WO00/70655, WO01/08230, WO01/39234, WO01/41512, WO02/02714, WO02/15645, WO02/44189, WO05/19373, Japanese Unexamined Patent Application 2001-247859, Japanese Unexamined Patent Application 2002-302671, Japanese Unexamined Patent Application 2002-117978, Japanese Unexamined Patent Application 2003-133074, Japanese Unexamined Patent Application 2002-235076, Japanese Unexamined Patent Application 2003-123982, Japanese Unexamined Patent Application 2002-170684, European Patent Publication 1211257, Japanese Unexamined Patent Application 2002-226495, Japanese Unexamined Patent Application 2002-234894, Japanese Unexamined Patent Application 2001-247859, Japanese Unexamined Patent Application 2001-298470, Japanese Unexamined Patent Application 2002-173674, Japanese Unexamined Patent Application 2002-203678, Japanese Unexamined Patent Application 2002-203679, Japanese Unexamined Patent Application 2004-357791, Japanese Unexamined Patent Application 2006-256999, Japanese Unexamined Patent Application 2007-19462, Japanese Unexamined Patent Application 2007-84635, Japanese Unexamined Patent Application 2007-96259, and the like, and of these, even more preferable examples of light emitting materials include phosphorescent light emittable metal complex compound such as Ir complexes, Pt complexes, Cu complexes, Re complexes, W complexes, Rh complexes, Ru complexes, Pd complexes, Os complexes, Eu complexes, Tb complexes, Gd complexes, Dy complexes, Ce complexes, and the like. Ir complexes, Pt complexes, or Re complexes are particularly preferable, and of these, the Ir complexes, Pt complexes, or Re complexes preferably include at least one coordination of metal-carbon bonds, metal-nitrogen bonds, metal-oxygen bonds, and metal-sulfur bonds. Furthermore, Ir complexes and Pt complexes are particularly preferable, and Ir complexes are most preferable from the perspective of luminous efficiency, drive durability, color tone, and the like.

The type of fluorescent light emitting material that can be used in the present invention is not particularly restricted, and examples include benzoxaole, benzimidazole, benzothiazole, styrylbenzene, polyphenyl, diphenyl butadiene, tetraphenyl butadiene, naphthalimide, coumarin, pyran, perynone, oxadiazole, aldazine, pyralidine, cyclopentadiene, bisstyrylanthracene, quinacridone, pyrrolopyridine, thiadiazolopyridine, cyclopentadiene, styrylamine, condensed polycyclic aromatic compounds, anthracene, phenanthroline, pyrene, perylene, rubrene, pentacene, or the like), metal complexes of 8-quinolinol, various metal complexes represented by pyrromethane complexes and rare earth complexes, polymer compounds such as polythiphene, polyphenylene, polyphenylenevinylene, and the like, organic silane, derivatives thereof, and the like, in addition to the compound expressed by general formula (1).

In addition, compounds described in [0082] of Japanese Unexamined Patent Application 2010-111620 can also be used as the light emitting material.

The light emitting layer according to the organic electroluminescent element of the present invention can be configured by only the light emitting materials, or can be configured using a mixed layer of host material and the light emitting material. The type of the light emitting material can be one type, or can be two types or more. The host material is preferably a charge transporting material. The host material can be one type, or can be two or more types, and an example includes a configuration combining an electron transportable host material and a hole transportable host material. Furthermore, the light emitting layer does not have charge transporting properties, and can included material that does not emit light.

Furthermore, the light emitting layer can be a single layer, or can be multiple layers of two or more, and the same light emitting material and host material can be included in each layer, or different materials can be included in each layer. If there is a plurality of light emitting layers, each light emitting layer can emit light with different light emitting colors.

Host Material

The host material is a compound that is mainly responsible for injection and transport of the charge in the light emitting layer, and that itself is a compound that does not substantially emit light. Herein, "does not substantially emit light" means that the light emission amount from the compound that does not substantially emit light is 5% or less of the entire light emitting layer in the entire element, more preferably 3% or less, and even more preferably 1% or less.

Examples of the host material that can be used in the organic electroluminescent element of the present invention includes the following compounds in addition to the compound expressed by general formula (1).

Examples can include pyrrole, indole, carbazole, azaindole, azacarbazole, triazole, oxazole, oxadiazole, pyrazole, imidazole, thiophene, benzothiphene, dibenzothiophene, furan, benzofuran, dibenzofuran, polyarylalkane, pyrazoline, pyrazolone, phenylenediamine, arylamine, amino substituted chalcone, styrylanthracene, fluorenone, hydrazone, stilbene, silazane, aromatic tertiary amine compounds, styrylamine compounds, porphyrin compounds, condensed aromatic hydrocarbon compounds (fluorene, napthalene, phenanthrene, triphenylene, and the like), polysilane compounds, poly(N-vinylcarbazole), aniline copolymers, thiophene oligomers, polythiophene, and other conductive polymer oligomers, organic silane, carbon film, pyridine, pyrimidine, triazine, imidazole, pyrazole, triazole, oxazole, oxadiazole, fluorenone, anthraquinodimethane, anthrone, diphenylquinone, thipyrandioxide, carbodiimide, fluorenylidenemethane, distyrylpyrazine, fluorine substituted aromatic compounds, napthaleneperylene, and other heterocyclic tetracarboxylic acid anhydrides, phthalocyanine, various metal complexes represented by metal complexes of 8-quinolinol derivatives, and metal complexes using metal phthalocyanine, benzoxazole, and benzothiazole as a ligand, derivatives thereof (may have a substitution group or be condensed), and the like. In addition, compounds described in [0081] and [0083] of Japanese Unexamined Patent Application 2010-111620 can be used.

Of these, carbazole, dibenzothiophene, dibenzofuran, arylamine, condensed aromatic hydrocarbon compounds, and metal complexes are preferable, and condensed aromatic hydrocarbon compounds are particularly preferable due to stability. The condensed aromatic hydrocarbon compounds are preferably naphthalene compounds, anthracene compounds, phenanthrene compounds, triphenylene compounds, or pyrene compounds, and anthracene compounds and pyrene compounds are more preferable, and anthracene compounds are particularly preferable. The anthracene compounds are particularly preferably that which is described in [0033] through [0064] in WO2010/134350, and examples can include infra-compounds H-1 and H-2.

The luminescent element of the present invention preferably contains a compound expressed by the following general formula (An-1) as a host material.

[Formula 47]

General Formula (An-1)

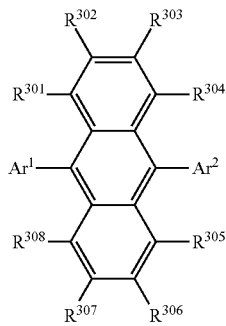

In general formula (An-1), Ar1 and $Ar^2$ independently represent an aryl group or a heteroaryl group, $R^{301}$ through $R^{308}$ independently represent a hydrogen atom or a substitution group. $R^{301}$ and $R^{302}$, $R^{302}$ and $R^{303}$, $R^{303}$ and $R^{304}$, $R^{305}$ and $R^{306}$, $R^{306}$ and $R^{307}$, and $R^{307}$ and $R^{308}$ can be bonded together to form a ring.

In general formula (An-1), the aryl group represented by $Ar^1$ and $Ar^2$ is preferably an aryl group with 6 to 36 carbon atoms, more preferably an aryl group with 6 to 18 carbon atoms, particularly preferably an aryl group with 6 to 14 carbon atoms, and more particularly preferably a phenyl group or naphthyl group.

The heteroaryl group represented by $Ar^1$ and $Ar^2$ is preferably a heteroaryl group with 5 to 20 ring members, and more preferably a heteroaryl group with 5 to 13 ring members. The heteror atom included in the heteroaryl group represented by $Ar^1$ and $Ar^2$ is preferably a nitrogen atom, an oxygen atom, and sulfur atom, and more preferably a nitrogen atom. The number of hetero atoms included in the heteroaryl group represented by $Ar^1$ and $Ar^1$ is preferably 1 to 3, more preferably 1 or 2, and particularly preferably 1. The heteroaryl group represented by $Ar^1$ and $Ar^2$ is particularly preferably a pyridyl group, carbazolyl group, dibenzofuryl group, or dibenzothiphenyl group.

$Ar^1$ and $Ar^2$ are preferably a phenyl group, naphthyl group, pyridyl group, carbazolyl group, dibenzofuryl group, dibenzothiophenyl group, or a combination thereof. Of these, $Ar^1$ and $Ar^2$ are more preferably a phenyl group and naphthyl group, and at least one of $Ar^1$ and $Ar^2$ is particularly preferably a substituted or unsubstituted phenyl group.

$Ar^1$ and $Ar^2$ can further have a substitution group, and examples of the substitution group can include, an aryl group, heteroaryl group, fluorine atom, alkly group (preferably with 1 to 4 carbon atoms), alkenyl group, silyl group, and cyano group.

In general formula (An-1), examples of the substitution group represented by $R^{301}$ to $R^{308}$ can include an aryl group, heteroaryl group, fluorine atom, alkyl group, silyl group, cyano group, and a combination thereof, and are preferably a phenyl group, naphthyl group, pyridyl group, carbazolyl group, dibenzofuryl group, dibenzothiophenyl group, fluorine atom, alkyl group, silyl group, cyano group, or a combination thereof, and more preferably a phenyl group, naphthyl group, or alkyl group with 1 to 5 carbon atoms (particularly preferably a tert-butyl group).

In general formula (An-1), $R^{301}$ to $R^{308}$ can further have a substitution group, and examples of the substitution group can include an aryl group, heteroaryl group, and alkyl group, and are preferably an aryl group or heteroaryl group, and more preferably an aryl group with 6 to 18 carbon atoms.

In general formula (An-1), the number of substitution groups included in $R^{301}$ to $R^{308}$ is preferably 0 to 4, more preferably 0 or 2, particularly preferably 0 or 1, and more particularly preferably 0.

In general formula (An-1), the position of the substitution group included in $R^{301}$ to $R^{308}$ is preferably $R^{302}$, $R^{303}$, $R^{306}$, and $R^{307}$, and more preferably one of either $R^{302}$ or $R^{303}$, or one of either $R^{306}$ or $R^{307}$.

In general formula (An-1), $R^{301}$ and $R^{302}$, $R^{302}$ and $R^{303}$, $R^{303}$ and $R^{304}$, and $R^{305}$ and $R^{306}$, $R^{306}$ and $R^{307}$, $R^{307}$ and $R^{308}$ can be bonded together to form a ring, but preferably do not bond together to form a ring.

The compound expressed by general formula (An-1) is preferably a compound expressed by the following (An-2).

[Formula 48]

General Formula (An-2)

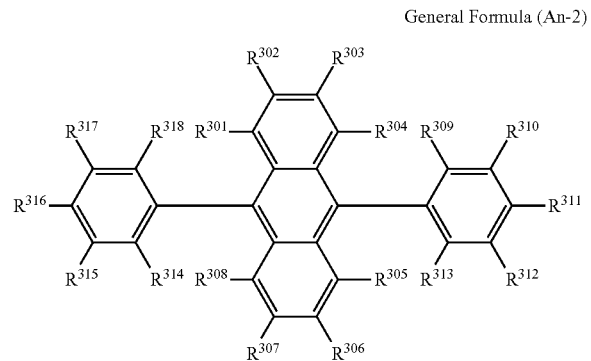

(In general formula (An-2), $R^{301}$ through $R^{318}$ independently represent a hydrogen atom or a substitution group. $R^{301}$ and $R^{302}$, $R^{302}$ and $R^{303}$, $R^{303}$ and $R^{304}$, $R^{305}$ and $R^{306}$, $R^{306}$ and $R^{307}$, $R^{307}$ and $R^{308}$, $R^{309}$ and $R^{310}$, $R^{310}$ and $R^{311}$, $R^{311}$ and $R^{312}$, $R^{312}$ and $R^{313}$, $R^{314}$ and $R^{315}$, $R^{315}$ and $R^{316}$, $R^{316}$ and $R^{317}$, and $R^{317}$ and $R^{318}$ can be bonded together to form a ring.)

The preferred ranged of $R^{301}$ to $R^{308}$ in general formula (An-2) is the same as the preferred range of $R^{301}$ to $R^{308}$ in general formula (An-1).

Examples of the substitution group represented by $R^{309}$ to $R^{318}$ in general formula (An-2) can include an aryl group, heteroaryl group, fluorine atom, alkyl group, silyl group, cyano group, and a combination thereof, and preferably are an aryl group with 6 to 18 carbon atoms, heteroaryl group with 5 to 20 ring members, fluorine atom, alkyl group, alkenyl group, silyl group, cyano group, or a combination thereof, more preferably a phenyl group, naphthyl group, pyridyl group, carbazolyl group, dibenzofuryl group, dibenzothiphenyl group, fluorine atom, alkyl group, alkenyl group, silyl group, cyano group, or a combination thereof, and particularly preferably a phenyl group, naphthyl group, or carbazolyl group.

In general formula (An-1), $R^{309}$ to $R^{318}$ can further have a substitution group. Examples of the substitution group can include an aryl group, alkyl group, fluorine atom, and the like, and the substitution groups can bond together to form a ring.

In general formula (An-1), the number of substitution groups included in $R^{309\ to\ 318}$ is preferably 0 to 4, more preferably 0 or 2, particularly preferably 0 or 1, and more particularly preferably 0.

In general formula (An-1), the position of the substitution group included in $R^{309}$ to $R^{318}$ is not particularly restricted, but if a substitution group is included, at least one of $R^{311}$ and $R^{316}$ preferably has the substitution group.

In general formula (An-1), $R^{309}$ and $R^{310}$, $R^{310}$ and $R^{311}$, $R^{311}$ and $R^{312}$, $R^{312}$ and $R^{313}$, $R^{314}$ and $R^{315}$, $R^{315}$ and $R^{316}$, $R^{316}$ and $R^{317}$, and $R^{317}$ and $R^{318}$ can be bonded together to form a ring, and the formed rings are preferably five or six-membered rings, and more preferably a five-membered ring.

Specific examples of the compound expressed by general formula (An-1) are exemplified below, but the compound expressed by general formula (An-1) that can be used in the present invention should not be interpreted as to be restricted by these specific examples.

[Formula 49]

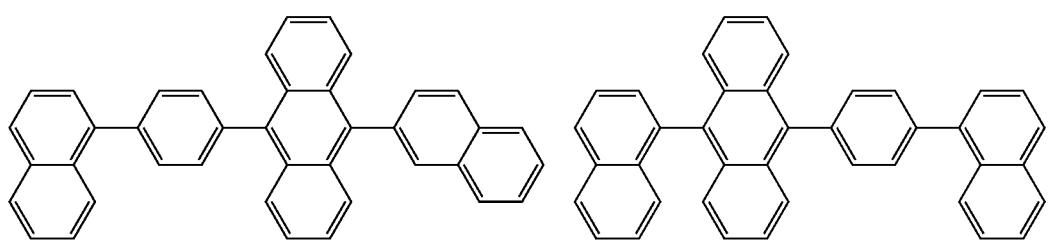

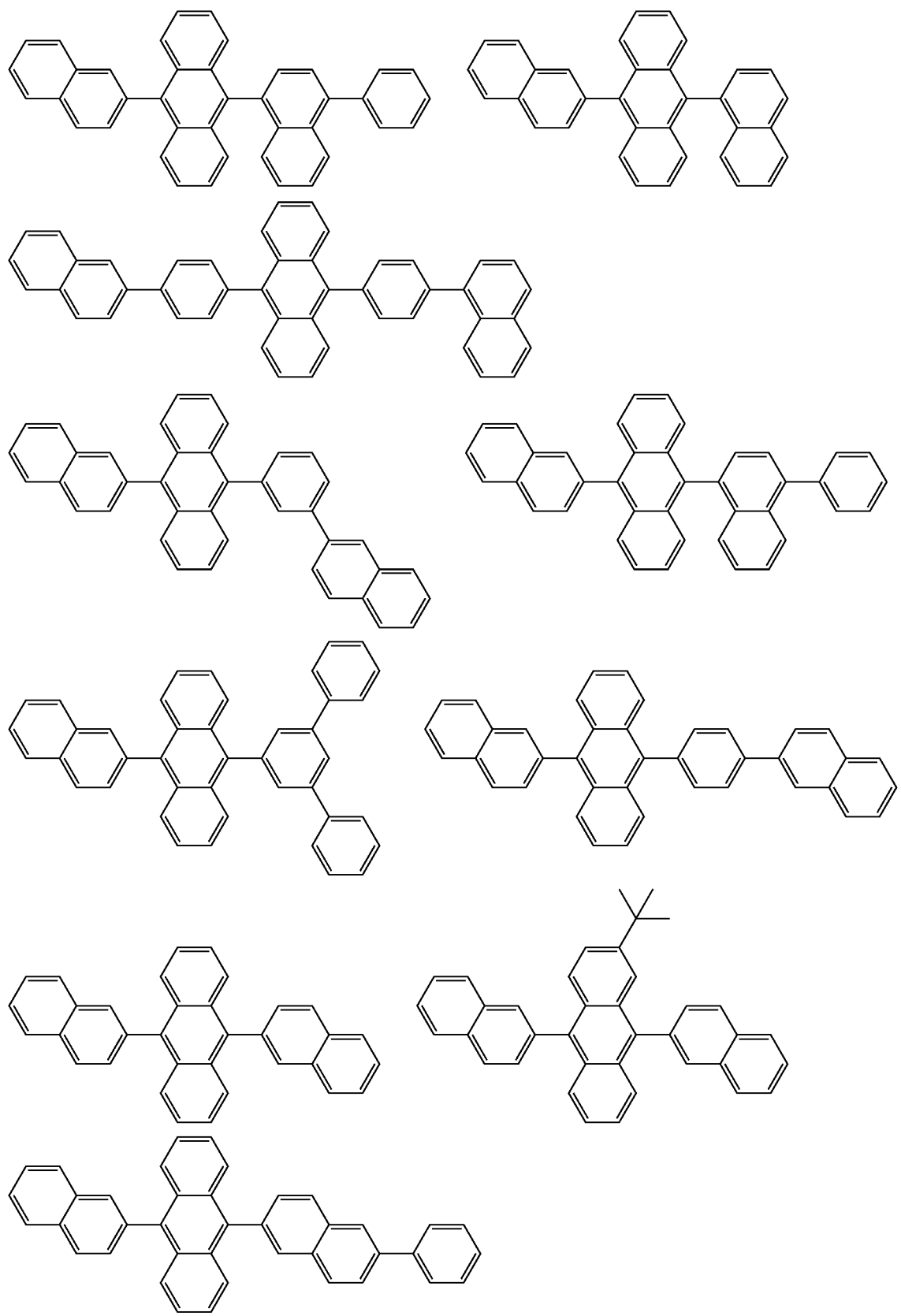

-continued
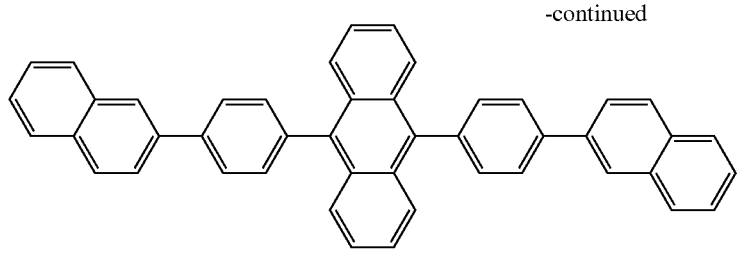
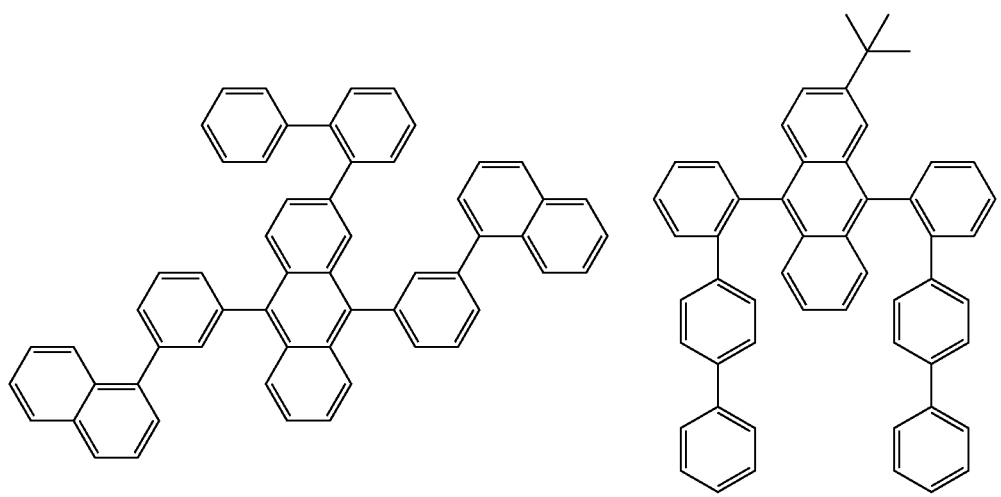
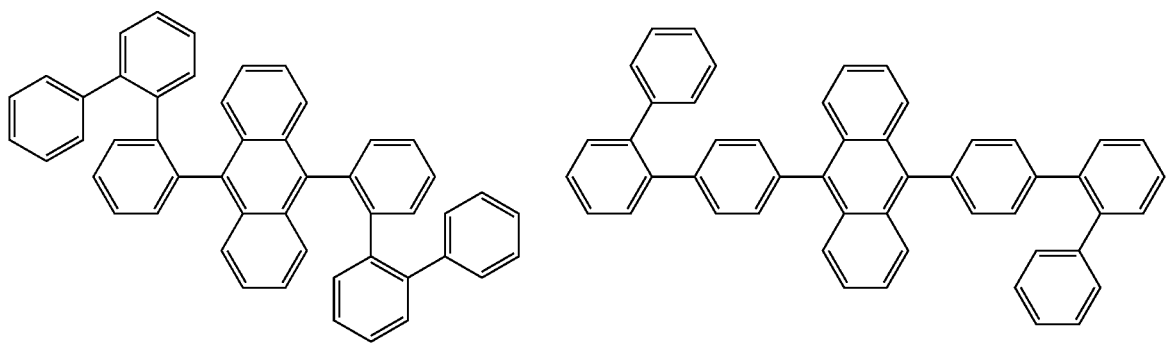
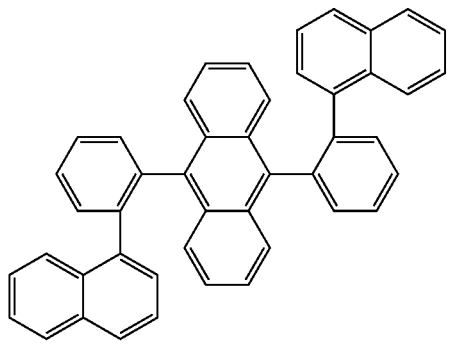

[Formula 50]
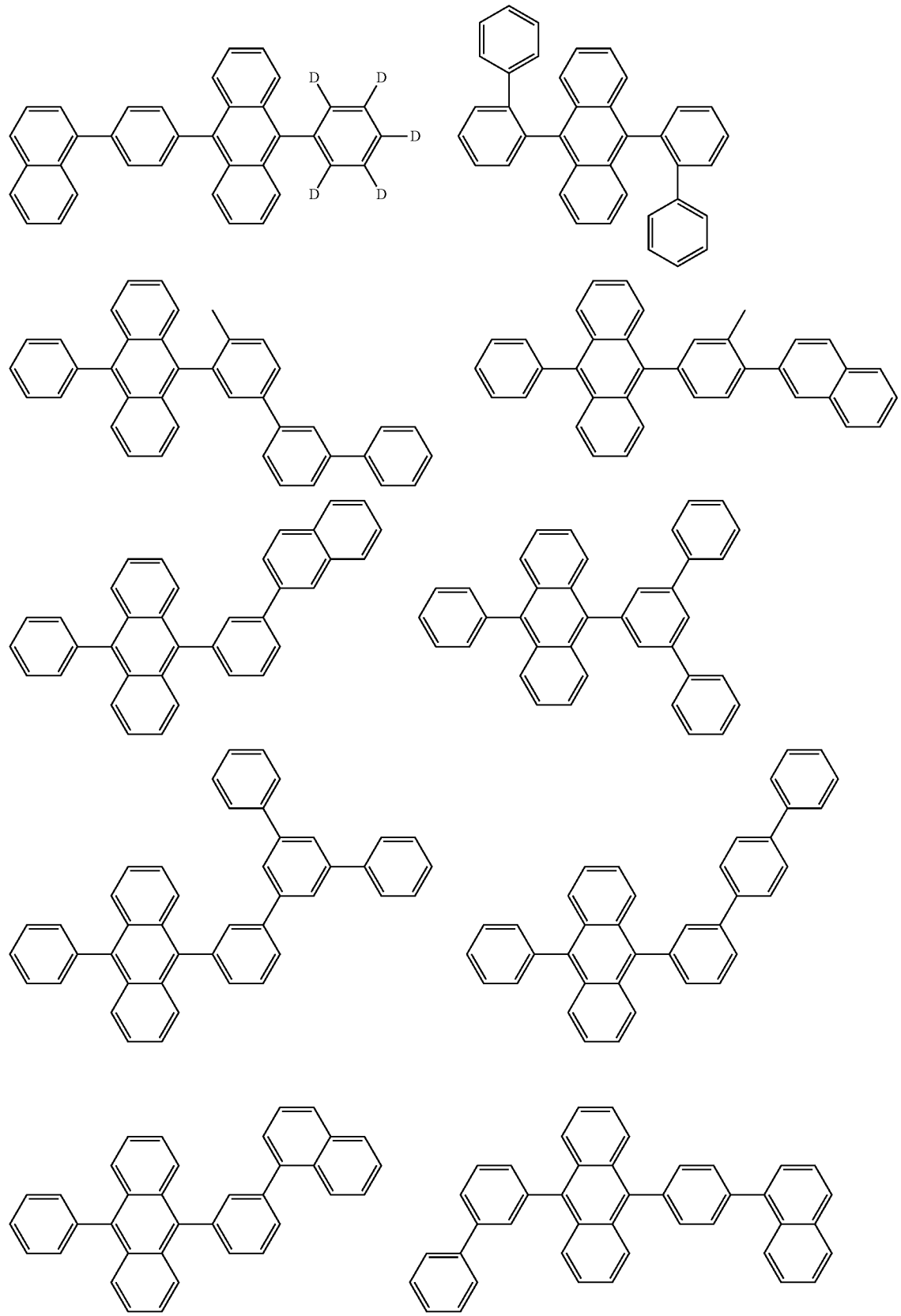

-continued
119
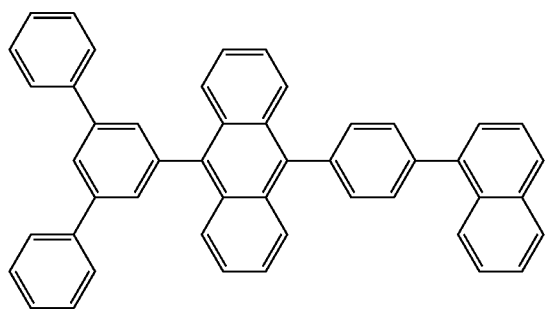
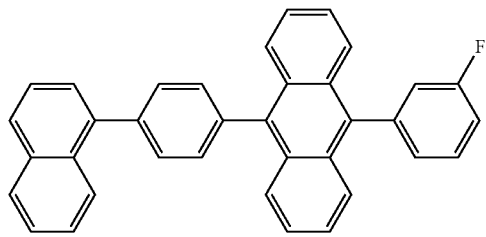
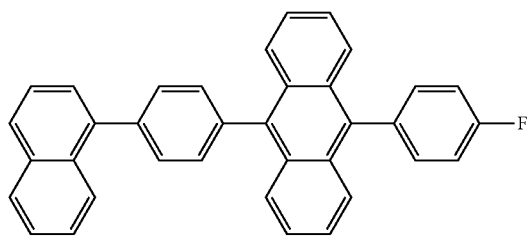
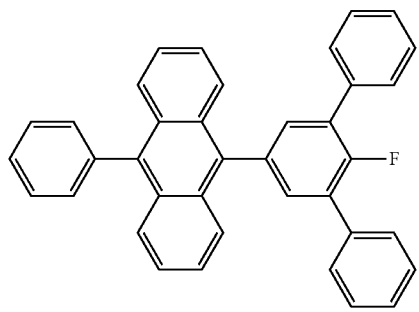
120
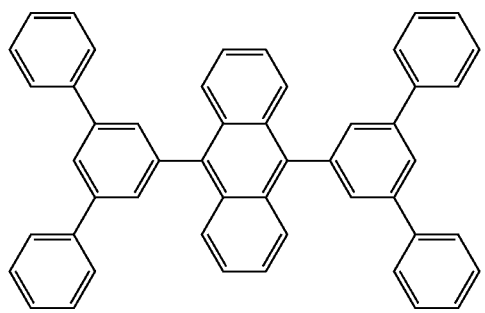
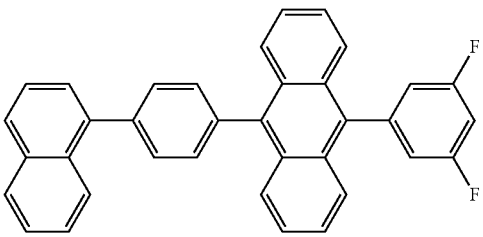
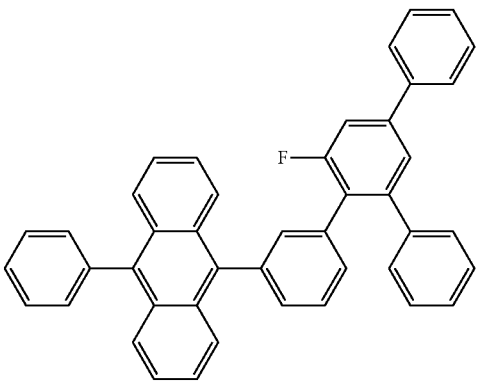
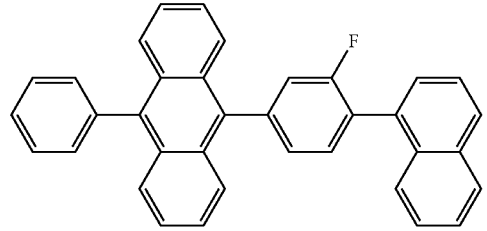
[Formula 51]
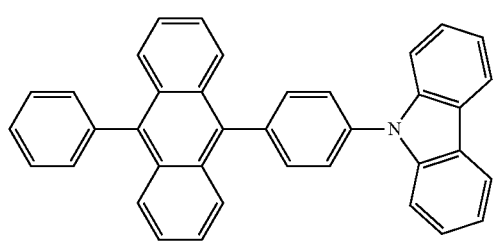
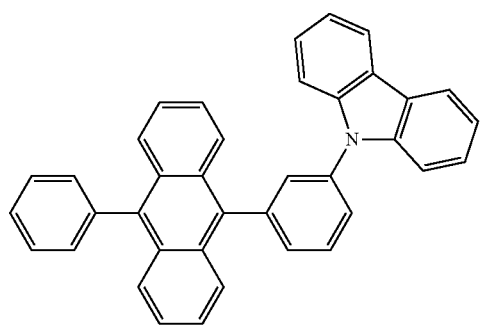

-continued
| 121 | 122 |
|---|---|
| 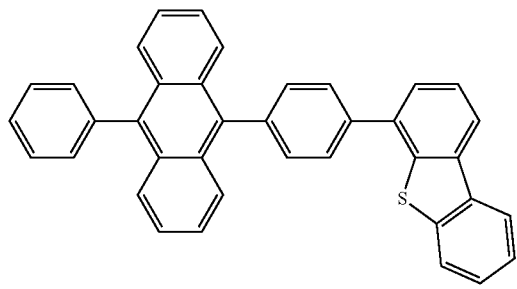 | 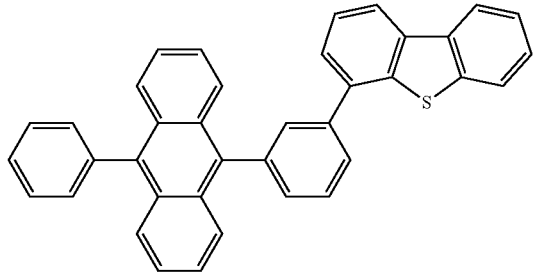 |
| 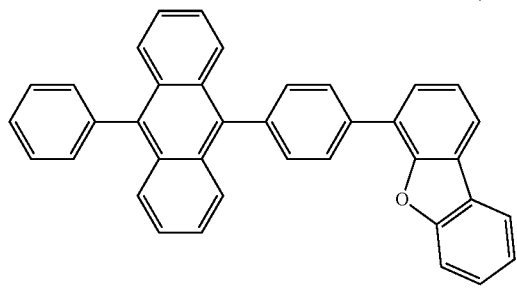 | 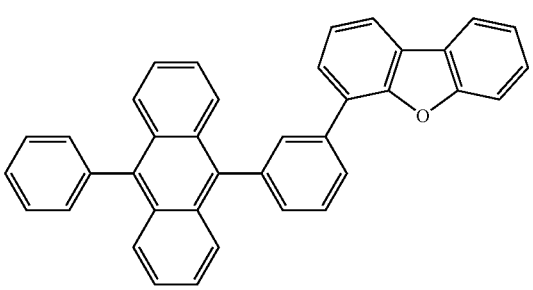 |
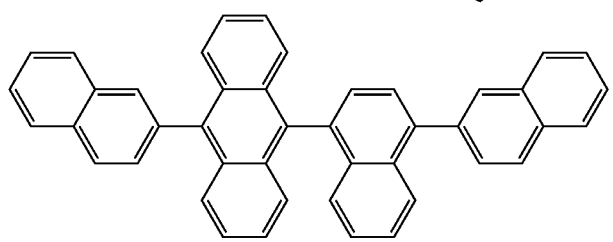
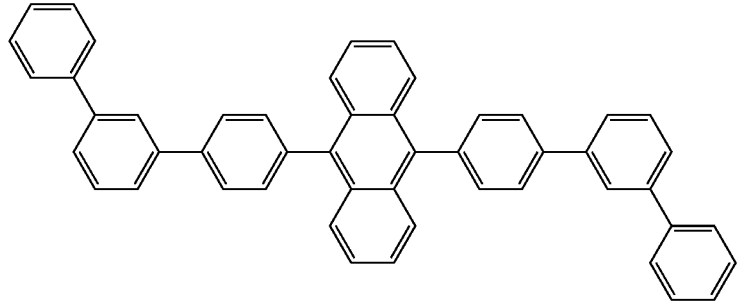
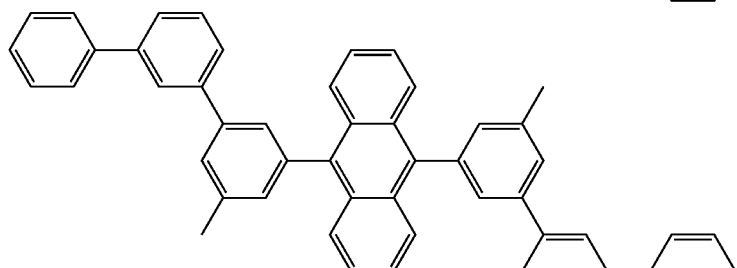
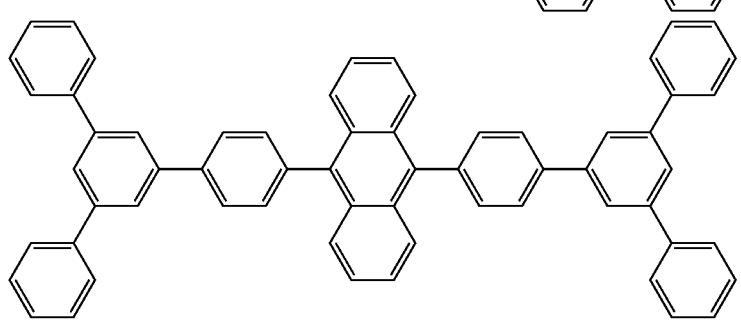

-continued
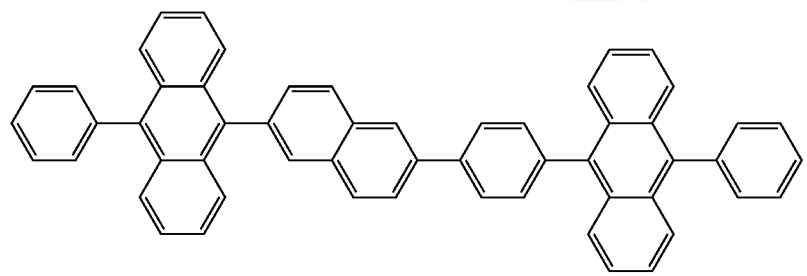

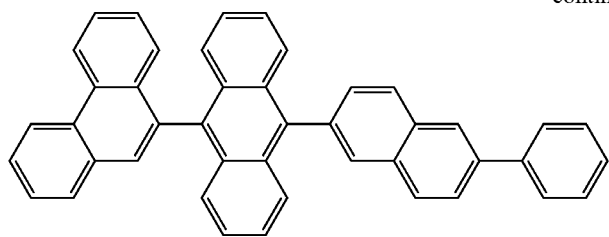
[Formula 52]
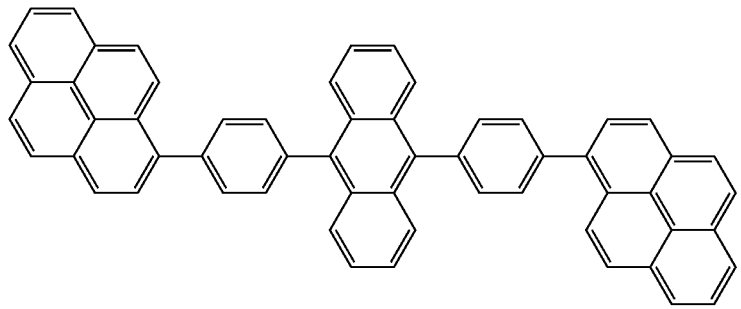
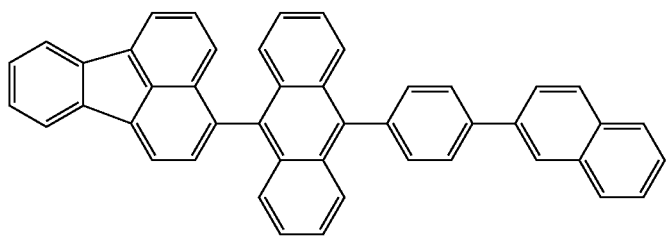
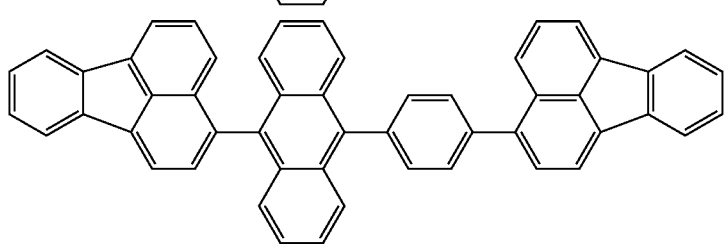
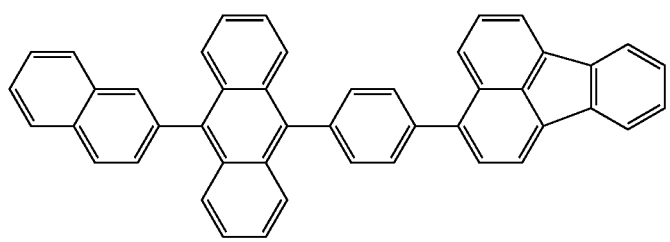
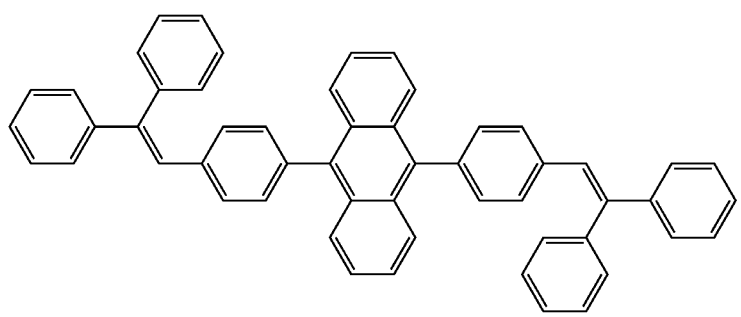

-continued
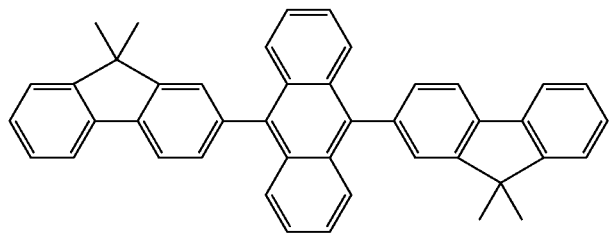
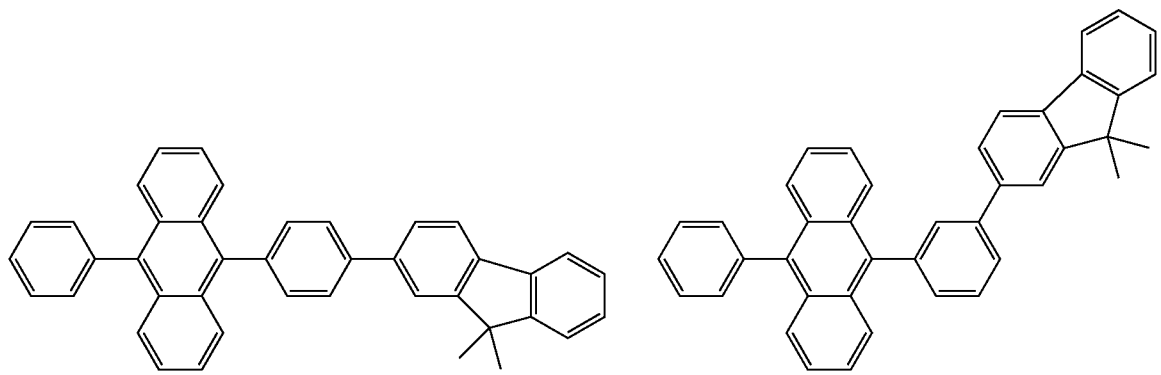
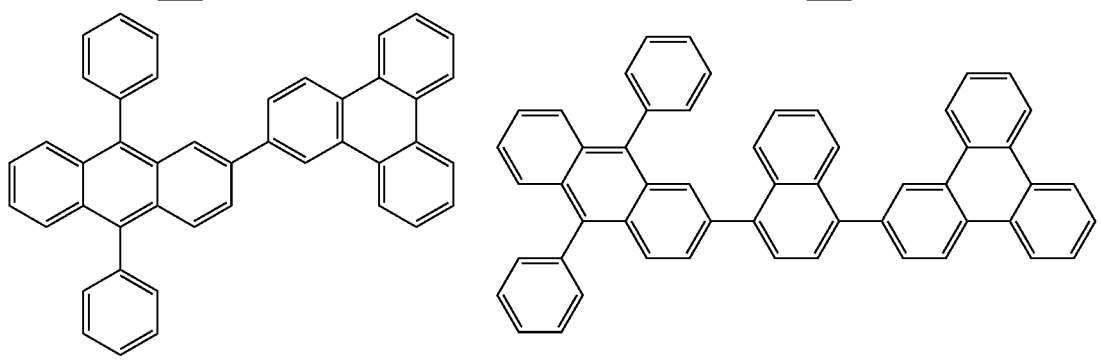
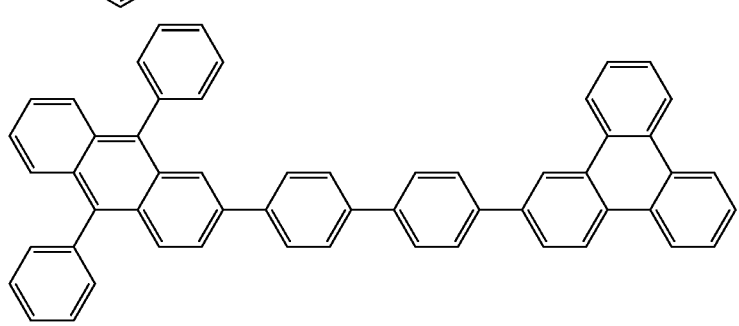
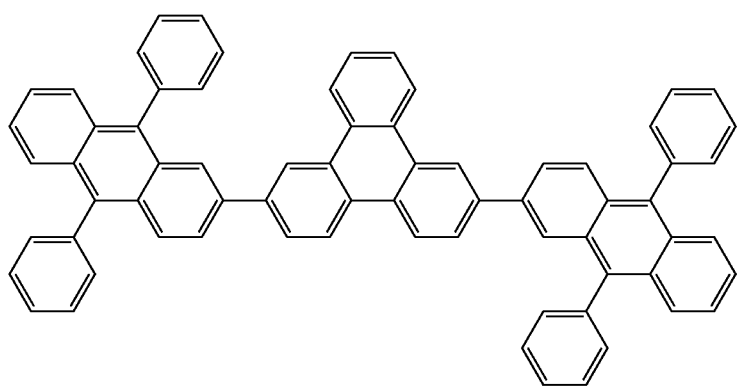

-continued
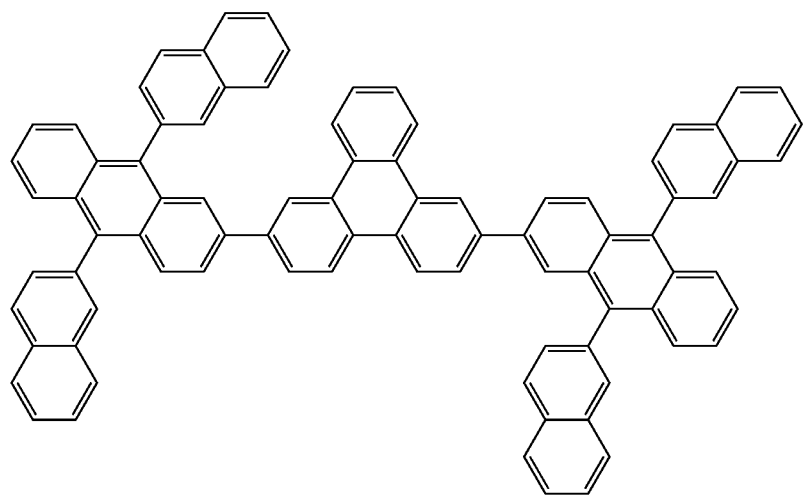
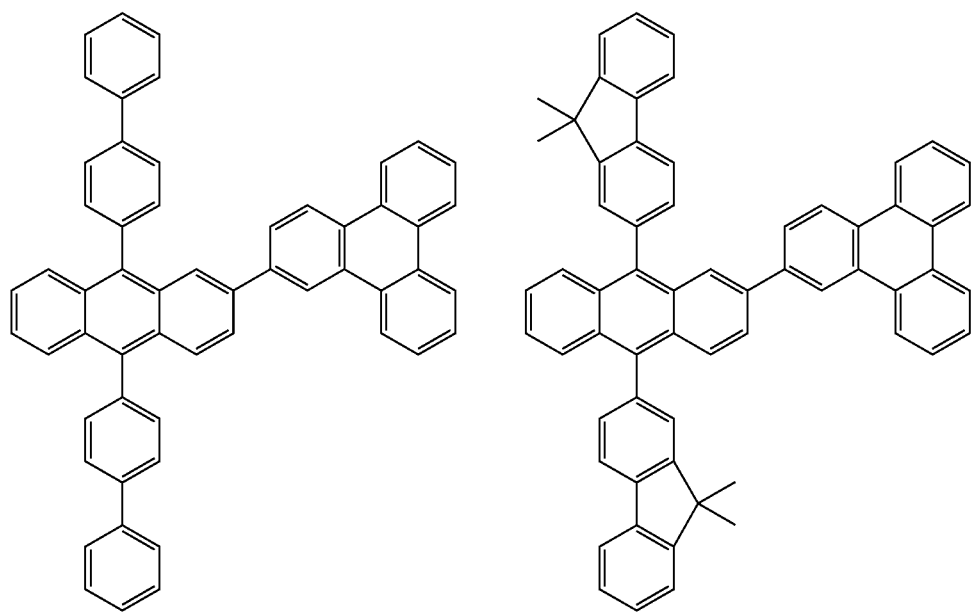
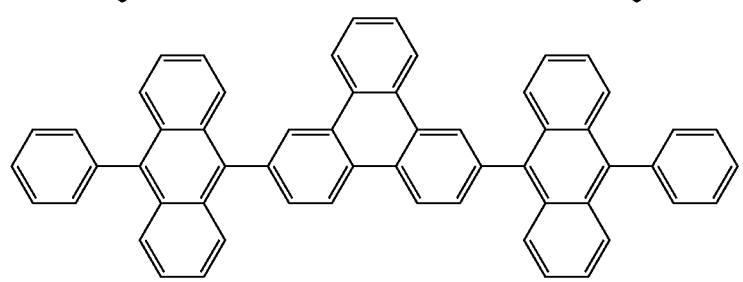
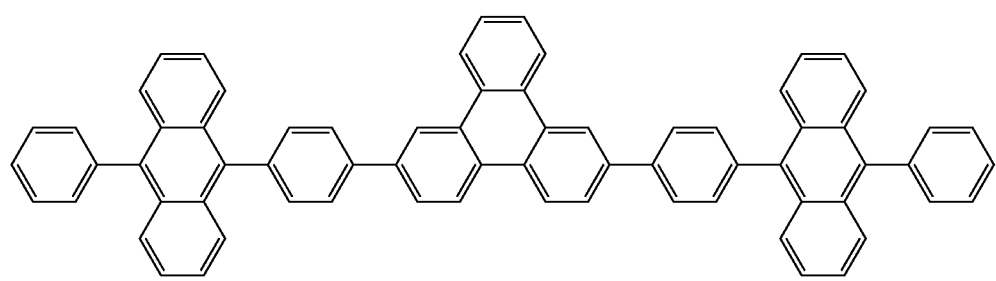

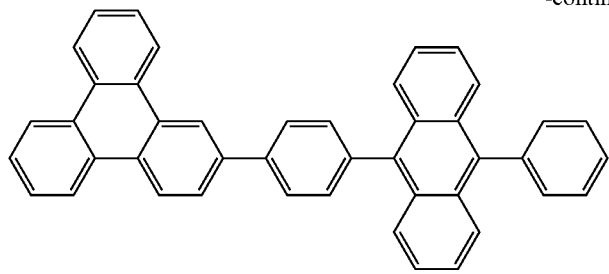

The host material that can be used in the light emitting layer in the organic electroluminescent element of the present invention can be an electron hole transportable host material, or an electron transportable host material.

In the light emitting layer, the singlet lowest excitation energy ($S_1$ energy) in the film state of the host material is preferably higher than the $S_1$ energy of the light emitting material from the perspective of color purity, luminous efficiency, and drive durability. The $S_1$ of the host material is preferably 0.1 eV or more larger than $S_1$ of the light emitting material, more preferably 0.2 eV or more larger, and even more preferably 0.3 eV or more larger.

Light emission is quenched when S1 in the film state of the host material is smaller than $S_1$ of the light emitting material, and therefore, the host material preferably has $S_1$ that is larger than the light emitting material. Furthermore, even if the $S_1$ of the host material is larger than the light emitting material, if the difference between the $S_1$ of both is small, a reverse energy transfer will partially occur from the light emitting layer to the host material, thereby becoming a cause for reducing efficiency, color purity, and durability. Therefore, a host material with sufficiently large $S_1$, with high chemical stability, and carrier injectability, transportability is required.

Furthermore, the content of the host material in the light emitting layer in the organic electroluminescent element of the present invention is not particularly restricted, but is preferably 15 to 95 mass % to the total compound mass forming the light emitting layer, from the perspective of luminous efficiency and drive voltage. If a plurality of various host compounds including the compound expressed by general formula (1) is included in the light emitting layer, the compound expressed by general formula (1) is preferably 50 to 99 mass % or less in the entire host compound.

Other Layers

The organic electroluminescent element of the present invention can have another layer other than the aforementioned light emitting layer.

Examples of other organic layers other than the light emitting layer that can be provided in the organic layer can include, electron hole injecting layers, electron hole transport layers, blocking layers (electron hole blocking layers, exciton blocking layers, and the like), electron transport layers, and the like. Specific examples of the layer configuration include the following, but the present invention is not restricted to these configurations.

Anode/electron hole transport layer/light emitting layer/electron transport layer/cathode, Anode/electron hole transport layer/light emitting layer/blocking layer/electron transport layer/cathode, Anode/electron hole transport layer/light emitting layer/blocking layer/electron transport layer/electron injecting layer/cathode, Anode/electron hole injecting layer/electron hole transport layer/light emitting layer/blocking layer/electron transport layer/cathode, Anode/electron hole injecting layer/electron hole transport layer/light emitting layer/electron transport layer/electron injecting layer/cathode, Anode/electron hole injecting layer/electron hole transport layer/light emitting layer/blocking layer/electron transport layer/electron injecting layer/cathode, and Anode/electron hole injecting layer/electron hole transport layer/blocking layer/light emitting layer/blocking layer/electron transport layer/electron injecting layer/cathode.

The organic electroluminescent element of the present invention preferably includes (A) at least one layer of the organic layer that is preferably disposed between the anode and the light emitting layer. Examples of the organic layer preferably disposed between the anode and the light emitting layer of the aforementioned (A) can include from the anode side an electron hole injecting layer, electron hole transport layer, and electron blocking layer.

The organic electroluminescent element of the present invention preferably includes (B) at least one layer of the organic layers preferably disposed between the cathode and the light emitting layer. Examples of the organic layer preferably disposed between the cathode and the light emitting layer of the aforementioned (B) can include from the cathode side an electron injecting layer, electron transport layer, and electron hole blocking layer.

In particular, an examples of a preferred aspect of the organic electroluminescent element of the present invention is an aspect described in FIG. 1, and is an aspect where an anode 3, electron hole injecting layer 4, electron hole transport layer 5, light emitting layer 6, electron hole blocking layer 7, and electron transport layer 8 are laminated in this order as the organic layer.

Other layers other than the light emitting layer that can be provided in the organic electroluminescent element of the present invention are described below.

(A) Organic layer preferably disposed between the anode and the light emitting layer First, (A) the organic layer that is preferably disposed between the anode and the light emitting layer is described.

(A-1) Electron Hole Injection Layer, Electron Hole Transport Layer

The electron hole injection layer and the electron hole transport layer are layers that have the functionality to receive electron holes from the anode or cathode side, and transport the electron hole to the cathode side.

The light emitting element of the present invention preferably includes at least one organic layer between the light emitting layer and the anode, and preferably includes at least one type of compound of those compounds expressed by the following general formula (Sa-1), general formula (Sb-1), and general formula (Sc-1) in the organic layer.

[Formula 53]

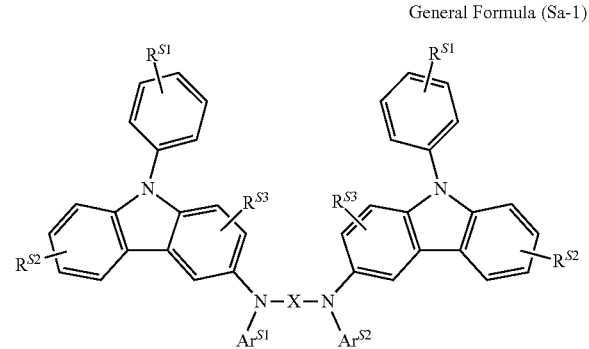

General Formula (Sa-1)

(In the formula, X represents a substituted or unsubstituted alkylene in group with 1 to 30 carbon atoms, a substituted or unsubstituted alkenylene group with 2 to 30 carbon atoms, a substituted or unsubstituted arylene group with 6 to 30 carbon atoms, a substituted or unsubstituted heteroarylene group with 2 to 30 carbon atoms, a substituted or unsubstituted hetero cyclic group with 2 to 30 carbon atoms, or a group that is a combination of these groups. $R^{S1}$, $R^{S2}$, and $R^{S3}$ independently represent a hydrogen atom, substituted or unsubstituted alkyl group with 1 to 30 carbon atoms, substituted or unsubstituted alkoxy group with 1 to 30 carbon atoms, a substituted or unsubstituted aryl group with 6 to 30 carbon atoms, a substituted or unsubstituted aryloxy group with 6 to 30 carbon atoms, a substituted or unsubstituted hetero cyclic ring with 2 to 30 carbon atoms, a substituted or unsubstituted condensed polycyclic group with 5 to 30 carbon atoms, a hydroxy group, a cyano group, or a substituted or unsubstituted amino group. Adjacent $R^{S1}$, $R^{S2}$, and $R^{S3}$ can be bonded together to form a saturated carbon ring or an unsaturated carbon ring. $Ar^{S1}$ and $Ar^{S2}$ independently represent a substituted or unsubstituted aryl group with 6 to 30 carbon atoms, or a substituted or unsubstituted heteroaryl group with 2 to 30 carbon atoms.)

[Formula 54]

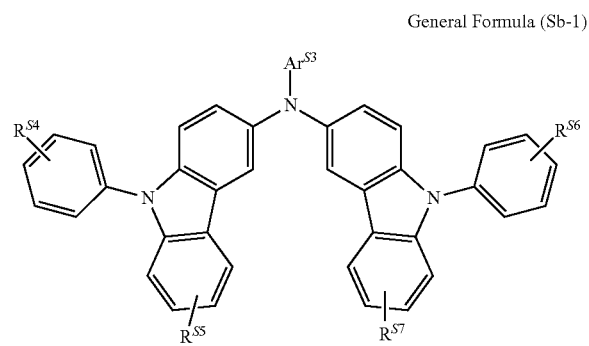

General Formula (Sb-1)

(In the formula, $R^{S4}$, $R^{S5}$, $R^{S6}$, and $R^{S7}$ independently represent a hydrogen atom, substituted or unsubstituted alkyl group with 1 to 30 carbon atoms, substituted or unsubstituted alkoxy group with 1 to 30 carbon atoms, a substituted or unsubstituted aryl group with 6 to 30 carbon atoms, a substituted or unsubstituted aryloxy group with 6 to 30 carbon atoms, a substituted or unsubstituted hetero cyclic ring with 2 to 30 carbon atoms, a substituted or unsubstituted condensed polycyclic group with 5 to 30 carbon atoms, a hydroxy group, a cyano group, or a substituted or unsubstituted amino group. Adjacent $R^{S4}$, $R^{S5}$, $R^{S6}$, and $R^{S7}$ can be bonded together to form a saturated carbon ring or an unsaturated carbon ring. $Ar^{S3}$ represents a substituted or unsubstituted aryl group with 6 to 30 carbon atoms, or a substituted or unsubstituted heteroaryl group with 2 to 30 carbon atoms.)

[Formula 55]

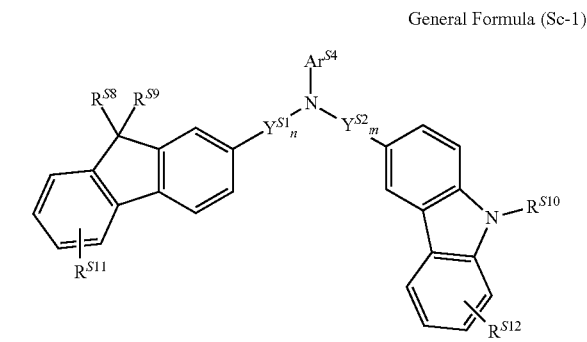

General Formula (Sc-1)

(In the formula, $R^{S8}$ and $R^{S9}$ independently represent a hydrogen atom, substituted or unsubstituted alkyl group with 1 to 30 carbon atoms, a substituted or unsubstituted aryl group with 6 to 30 carbon atoms, a substituted or unsubstituted heterocyclic ring with 2 to 30 carbon atoms, or a substituted or unsubstituted condensed polycyclic group with 5 to 30 carbon atoms. $R^{S10}$ represents a substituted or unsubstituted alkyl group with 1 to 30 carbon atoms, a substituted or unsubstituted aryl group with 6 to 30 carbon atoms, a substituted or unsubstituted heterocyclic ring with 2 to 30 carbon atoms, or a substituted or unsubstituted condensed polycyclic group with 5 to 30 carbon atoms. $R^{S11}$ and $R^{S12}$ independently represent a hydrogen atom, substituted or unsubstituted alkyl group with 1 to 30 carbon atoms, substituted or unsubstituted alkoxy group with 1 to 30 carbon atoms, a substituted or unsubstituted aryl group with 6 to 30 carbon atoms, a substituted or unsubstituted aryloxy group with 6 to 30 carbon atoms, a substituted or unsubstituted hetero cyclic ring with 2 to 30 carbon atoms, a substituted or unsubstituted condensed polycyclic group with 5 to 30 carbon atoms, a hydroxy group, a cyano group, or a substituted or unsubstituted amino group. Adjacent $R^{S11}$ and $R^{S12}$ can be bonded together to form a saturated carbon ring or an unsaturated carbon ring. $Ar^{S4}$ represents a substituted or unsubstituted aryl group with 6 to 30 carbon atoms, or a substituted or unsubstituted heteroaryl group with 2 to 30 carbon atoms.) $Y^{S1}$ and $Y^{S2}$ independently represent a substituted or unsubstituted alkylene group with 1 to 30 carbon atoms, or a substituted or unsubstituted arylene group with 6 to 30 carbon atoms. n and m independently represent integers from 0 to 5.)

The general formula (Sa-1) is described below.

In general formula (Sa-1), X represents a substituted or unsubstituted alkylene in group with 1 to 30 carbon atoms, a substituted or unsubstituted alkenylene group with 2 to 30 carbon atoms, a substituted or unsubstituted arylene group with 6 to 30 carbon atoms, a substituted or unsubstituted heteroarylene group with 2 to 30 carbon atoms, a substituted or unsubstituted hetero cyclic group with 2 to 30 carbon atoms, or a group that is a combination of these groups. X is preferably a saturated or unsaturated arylene group with 6 to 30 carbon atoms, more preferably a substituted or unsubstituted phenylene, substituted or unsubstituted biphenylene, substituted or unsubstituted naphthalene, and even more preferably a substituted or unsubstituted biphenylene group.

$R^{S1}$, $R^{S2}$, and $R^{S3}$ independently represent a hydrogen atom, substituted or unsubstituted alkyl group with 1 to 30 carbon atoms, substituted or unsubstituted alkoxy group with 1 to 30 carbon atoms, a substituted or unsubstituted aryl group with 6 to 30 carbon atoms, a substituted or unsubstituted aryloxy group with 6 to 30 carbon atoms, a substituted or unsubstituted hetero cyclic ring with 2 to 30 carbon atoms, a substituted or unsubstituted condensed polycyclic group with 5 to 30 carbon atoms, a hydroxy group, a cyano group, or a substituted or unsubstituted amino group. Adjacent $R^{S1}$, $R^{S2}$ and $R^{S3}$ can be bonded together to form a saturated carbon ring or an unsaturated carbon ring. Examples of saturated carbon rings and unsaturated carbon rings include naphthalene, azulene, anthracene, fluorene, phenalene, and the like. $R^{S1}$, $R^{S2}$, and $R^{S3}$ preferably represent a hydrogen atom, substituted or unsubstituted alkyl group with 1 to 30 carbon atoms, a substituted or unsubstituted aryl group with 6 to 30 carbon atoms, a substituted or unsubstituted condensed polycyclic group with 5 to 30 carbon atoms, or a cyano group, and more preferably represent a hydrogen atom.

$Ar^{S1}$ and $Ar^{S2}$ independently represent a substituted or unsubstituted aryl group with 6 to 30 carbon atoms, or a substituted or unsubstituted heteroaryl group with 2 to 30 carbon atoms. $Ar^{S1}$ and $Ar^{S2}$ are preferably a substituted or unsubstituted phenyl group.

Next, the general formula (Sb-1) is described below.

In general formula (Sb-1), $R^{S4}$, $R^{S5}$, $R^{S6}$, and $R^{S7}$ independently represent a hydrogen atom, substituted or unsubstituted alkyl group with 1 to 30 carbon atoms, substituted or unsubstituted alkoxy group with 1 to 30 carbon atoms, a substituted or unsubstituted aryl group with 6 to 30 carbon atoms, a substituted or unsubstituted aryloxy group with 6 to 30 carbon atoms, a substituted or unsubstituted hetero cyclic ring with 2 to 30 carbon atoms, a substituted or unsubstituted condensed polycyclic group with 5 to 30 carbon atoms, a hydroxy group, a cyano group, or a substituted or unsubstituted amino group. Adjacent $R^{S4}$, $R^{S5}$, $R^{S6}$, and $R^{S7}$ can be bonded together to form a saturated carbon ring or an unsaturated carbon ring. Examples of saturated carbon rings and unsaturated carbon rings include naphthalene, azulene, anthracene, fluorene, phenalene, and the like. $R^{S4}$, $R^{S5}$, $R^{S6}$, and $R^{S7}$ preferably represent a hydrogen atom, substituted or unsubstituted alkyl group with 1 to 30 carbon atoms, a substituted or unsubstituted aryl group with 6 to 30 carbon atoms, a substituted or unsubstituted condensed polycyclic group with 5 to 30 carbon atoms, or a cyano group, and more preferably represent a hydrogen atom.

$Ar^{S3}$ represents a substituted or unsubstituted aryl group with 6 to 30 carbon atoms, or a substituted or unsubstituted heteroaryl group with 2 to 30 carbon atoms. $Ar^{S3}$ is preferably a substituted or unsubstituted phenyl group.

Next, the general formula (Sc-1) is described below.

In general formula (Sc-1), $R^{S8}$ and $R^{S9}$ independently represent a hydrogen atom, substituted or unsubstituted alkyl group with 1 to 30 carbon atoms, a substituted or unsubstituted aryl group with 6 to 30 carbon atoms, a substituted or unsubstituted heterocyclic ring with 2 to 30 carbon atoms, or a substituted or unsubstituted condensed polycyclic group with 5 to 30 carbon atoms. $R^{S8}$ and $R^{S9}$ preferably represent a substituted or unsubstituted alkyl group with 1 to 30 carbon atoms, or a substituted or unsubstituted aryl group with 6 to 30 carbon atoms, and more preferably a methyl group or a phenyl group. $R^{S10}$ represents a substituted or unsubstituted alkyl group with 1 to 30 carbon atoms, a substituted or unsubstituted aryl group with 6 to 30 carbon atoms, a substituted or unsubstituted heterocyclic ring with 2 to 30 carbon atoms, or a substituted or unsubstituted condensed polycyclic group with 5 to 30 carbon atoms. $R^{S10}$ preferably represents a substituted or unsubstituted aryl group with 6 to 30 carbon atoms, but more preferably is a phenyl group. $R^{S11}$ and $R^{S12}$ independently represent a hydrogen atom, substituted or unsubstituted alkyl group with 1 to 30 carbon atoms, substituted or unsubstituted alkoxy group with 1 to 30 carbon atoms, a substituted or unsubstituted aryl group with 6 to 30 carbon atoms, a substituted or unsubstituted aryloxy group with 6 to 30 carbon atoms, a substituted or unsubstituted hetero cyclic ring with 2 to 30 carbon atoms, a substituted or unsubstituted condensed polycyclic group with 5 to 30 carbon atoms, a hydroxy group, a cyano group, or a substituted or unsubstituted amino group. Adjacent $R^{S11}$ and $R^{S12}$ can be bonded together to form a saturated carbon ring or an unsaturated carbon ring. Examples of saturated carbon rings and unsaturated carbon rings include naphthalene, azulene, anthracene, fluorene, phenalene, and the like. $R^{S11}$ and $R^{S12}$ preferably represent a hydrogen atom, substituted or unsubstituted alkyl group with 1 to 30 carbon atoms, a substituted or unsubstituted aryl group with 6 to 30 carbon atoms, a substituted or unsubstituted condensed polycyclic group with 5 to 30 carbon atoms, or a cyano group, and more preferably represent a hydrogen atom. $Ar^{S4}$ represents a substituted or unsubstituted aryl group with 6 to 30 carbon atoms, or a substituted or unsubstituted heteroaryl group with 2 to 30 carbon atoms. $Y^{S1}$ and $Y^{S2}$ represent a substituted or unsubstituted alkylene group with 1 to 30 carbon atoms, or a substituted or unsubstituted arylene group with 6 to 30 carbon atoms. $Y^{S1}$ and $Y^{S2}$ preferably represent a substituted or unsubstituted arylene group with 6 to 30 carbon atoms, but more preferably a substituted or unsubstituted phenylene group. n is an integer from 0 to 5, preferably 0 to 3, more preferably 0 to 2, and even more preferably 0. m is an integer from 0 to 5, preferably 0 to 3, more preferably 0 to 2, and even more preferably 1.

The compound of general formula (Sa-1) is preferably a compound expressed by the following general formula (Sa-2).

[Formula 56]

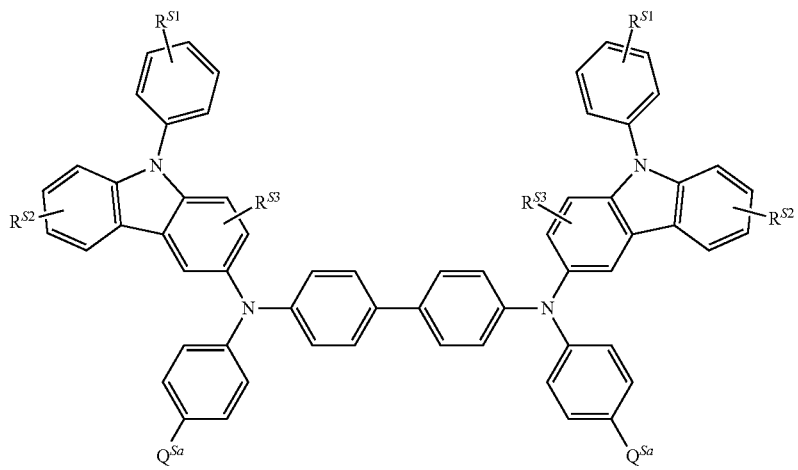

General Formula (Sa-2)

(In the formula, $R^{S1}$, $R^{S2}$, and $R^{S3}$ independently represent a hydrogen atom, substituted or unsubstituted alkyl group with 1 to 30 carbon atoms, substituted or unsubstituted alkoxy group with 1 to 30 carbon atoms, a substituted or unsubstituted aryl group with 6 to 30 carbon atoms, a substituted or unsubstituted aryloxy group with 6 to 30 carbon atoms, a substituted or unsubstituted hetero cyclic ring with 2 to 30 carbon atoms, a substituted or unsubstituted condensed polycyclic group with 5 to 30 carbon atoms, a hydroxy group, a cyano group, or a substituted or unsubstituted amino group. Adjacent $R^{S1}$, $R^{S2}$, and $R^{S3}$ can be bonded together to form a saturated carbon ring or an unsaturated carbon ring. $Q^{Sa}$ represents a hydrogen atom, cyano group, fluorine atom, substituted or unsubstituted alkoxy group with 1 to 30 carbon atoms, substituted or unsubstituted alkyl group with 1 to 30 carbon atoms, a substituted or unsubstituted aryloxy group with 6 to 30 carbon atoms, a substituted or unsubstituted aryl group with 6 to 30 carbon atoms, a substituted or unsubstituted heterocyclic ring with 2 to 30 carbon atoms, or a substituted or unsubstituted amino group.

Next, the general formula (Sa-2) is described below. $R^{S1}$, $R^{S2}$, and $R^{S3}$ have the same meaning as in general formula (Sa-1), and the preferable range is also the same. $Q^{Sa}$ represents a hydrogen atom, cyano group, fluorine atom, substituted or unsubstituted alkoxy group with 1 to 30 carbon atoms, substituted or unsubstituted alkyl group with 1 to 30 carbon atoms, a substituted or unsubstituted aryloxy group with 6 to 30 carbon atoms, a substituted or unsubstituted aryl group with 6 to 30 carbon atoms, a substituted or unsubstituted heterocyclic ring with 2 to 30 carbon atoms, or a substituted or unsubstituted amino group. $Q^{Sa}$ preferably represents a hydrogen atom, a cyano group, a fluorine atom, substituted or unsubstituted alkyl group with 1 to 30 carbon atoms, or a substituted or unsubstituted aryl group with 6 to 30 carbon atoms, more preferably a hydrogen atom, or a substituted or unsubstituted alkyl group with 1 to 30 carbon atoms, and even more preferably a hydrogen atom.

The compound of general formula (Sb-1) is preferably a compound expressed by the following general formula (Sb-2).

[Formula 57]

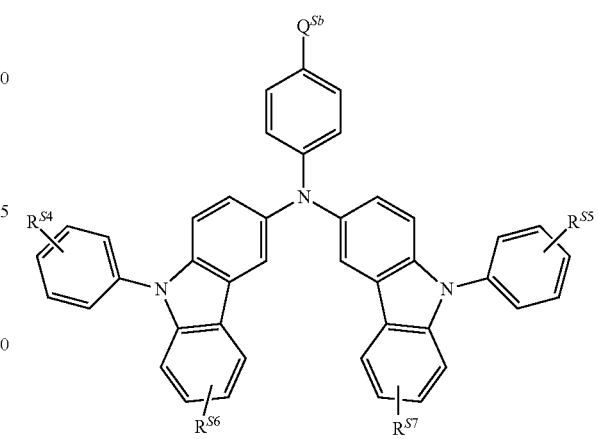

General Formula (Sb-2)

(In the formula, $R^{S4}$, $R^{S5}$, $R^{S6}$, and $R^{S7}$ independently represent a hydrogen atom, substituted or unsubstituted alkyl group with 1 to 30 carbon atoms, substituted or unsubstituted alkoxy group with 1 to 30 carbon atoms, a substituted or unsubstituted aryl group with 6 to 30 carbon atoms, a substituted or unsubstituted aryloxy group with 6 to 30 carbon atoms, a substituted or unsubstituted hetero cyclic ring with 2 to 30 carbon atoms, a substituted or unsubstituted condensed polycyclic group with 5 to 30 carbon atoms, a hydroxy group, a cyano group, or a substituted or unsubstituted amino group. Adjacent $R^{S4}$, $R^{S5}$, $R^{S6}$, and $R^{S7}$ can be bonded together to form a saturated carbon ring or an unsaturated carbon ring. $Q^{Sb}$ represents a hydrogen atom, cyano group, fluorine atom, substituted or unsubstituted alkoxy group with 1 to 30 carbon atoms, substituted or unsubstituted alkyl group with 1 to 30 carbon atoms, a substituted or unsubstituted aryloxy group with 6 to 30 carbon atoms, a substituted or unsubstituted aryl group with 6 to 30 carbon atoms, a substituted or unsubstituted heterocyclic ring with 2 to 30 carbon atoms, or a substituted or unsubstituted amino group.)

Next, the general formula (Sb-2) is described below. $R^{S4}$, $R^{S5}$, $R^{S6}$, and $R^{S7}$ have the same meaning as in general formula (Sb-1), and the preferable range is also the same. $Q^{Sb}$ represents a hydrogen atom, cyano group, fluorine atom, substituted or unsubstituted alkoxy group with 1 to 30 carbon atoms, substituted or unsubstituted alkyl group with 1 to 30 carbon atoms, a substituted or unsubstituted aryloxy group with 6 to 30 carbon atoms, a substituted or unsubstituted aryl group with 6 to 30 carbon atoms, a substituted or unsubstituted heterocyclic ring with 2 to 30 carbon atoms, or a substituted or unsubstituted amino group. $Q^{Sb}$ preferably represents a hydrogen atom, a cyano group, a fluorine atom, substituted or unsubstituted alkyl group with 1 to 30 carbon atoms, or a substituted or unsubstituted aryl group with 6 to 30 carbon atoms, more preferably a hydrogen atom, or a substituted or unsubstituted alkyl group with 1 to 30 carbon atoms, and even more preferably a hydrogen atom.

The compound of general formula (Sc-1) is preferably a compound expressed by the following general formula (Sc-2).

[Formula 58]

General Formula (Sc-2)

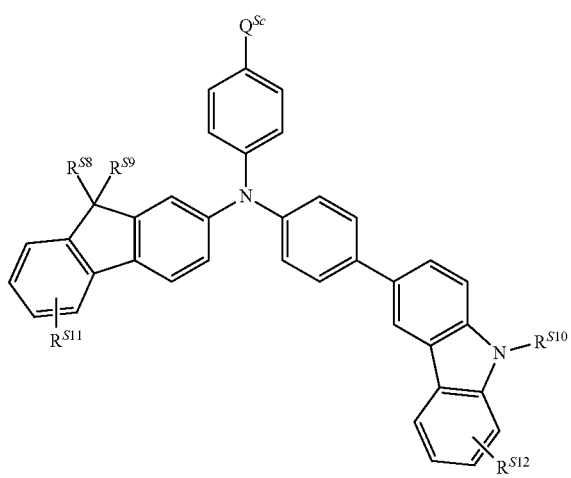

(In the formula, $R^{S8}$ and $R^{S9}$ independently represent a hydrogen atom, substituted or unsubstituted alkyl group with 1 to 30 carbon atoms, a substituted or unsubstituted aryl group with 6 to 30 carbon atoms, a substituted or unsubstituted heterocyclic ring with 2 to 30 carbon atoms, or a substituted or unsubstituted condensed polycyclic group with 5 to 30 carbon atoms. $R^{S10}$ represents a substituted or unsubstituted alkyl group with 1 to 30 carbon atoms, a substituted or unsubstituted aryl group with 6 to 30 carbon atoms, a substituted or unsubstituted heterocyclic ring with 2 to 30 carbon atoms, or a substituted or unsubstituted condensed polycyclic group with 5 to 30 carbon atoms. $R^{S11}$ and $R^{S12}$ independently represent a hydrogen atom, substituted or unsubstituted alkyl group with 1 to 30 carbon atoms, substituted or unsubstituted alkoxy group with 1 to 30 carbon atoms, a substituted or unsubstituted aryl group with 6 to 30 carbon atoms, a substituted or unsubstituted aryloxy group with 6 to 30 carbon atoms, a substituted or unsubstituted hetero cyclic ring with 2 to 30 carbon atoms, a substituted or unsubstituted condensed polycyclic group with 5 to 30 carbon atoms, a hydroxy group, a cyano group, or a substituted or unsubstituted amino group. Adjacent $R^{S11}$ and $R^{S12}$ can be bonded together to form a saturated carbon ring or an unsaturated carbon ring. $Q^{Sb}$ represents a hydrogen atom, cyano group, fluorine atom, substituted or unsubstituted alkoxy group with 1 to 30 carbon atoms, substituted or unsubstituted alkyl group with 1 to 30 carbon atoms, a substituted or unsubstituted aryloxy group with 6 to 30 carbon atoms, a substituted or unsubstituted aryl group with 6 to 30 carbon atoms, a substituted or unsubstituted heterocyclic ring with 2 to 30 carbon atoms, or a substituted or unsubstituted amino group.)

Next, the general formula (Sc-2) is described below. $R^{S8}$, $R^{S9}$, $R^{S10}$, $R^{S11}$, and $R^{S12}$ have the same meaning as in general formula (Sc-1), and the preferable range is also the same. $Q^{Sc}$ represents a hydrogen atom, cyano group, fluorine atom, substituted or unsubstituted alkoxy group with 1 to 30 carbon atoms, substituted or unsubstituted alkyl group with 1 to 30 carbon atoms, a substituted or unsubstituted aryloxy group with 6 to 30 carbon atoms, a substituted or unsubstituted aryl group with 6 to 30 carbon atoms, a substituted or unsubstituted heterocyclic ring with 2 to 30 carbon atoms, or a substituted or unsubstituted amino group. $Q^{Sc}$ preferably represents a hydrogen atom, a cyano group, a fluorine atom, substituted or unsubstituted alkyl group with 1 to 30 carbon atoms, or a substituted or unsubstituted aryl group with 6 to 30 carbon atoms, more preferably a hydrogen atom, or a substituted or unsubstituted aryl group with 6 to 30 carbon atoms, and even more preferably a phenyl group.

Specific examples of the compounds expressed by general formulas (Sa-1), (Sb-1), and (Sc-1) are provided below. However, the present invention is not restricted to the following specific examples.

[Formula 59]

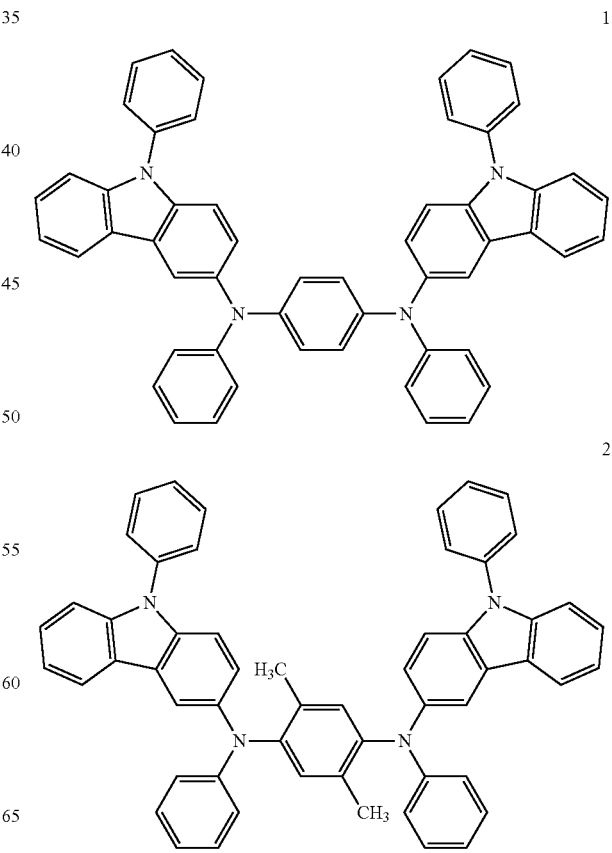

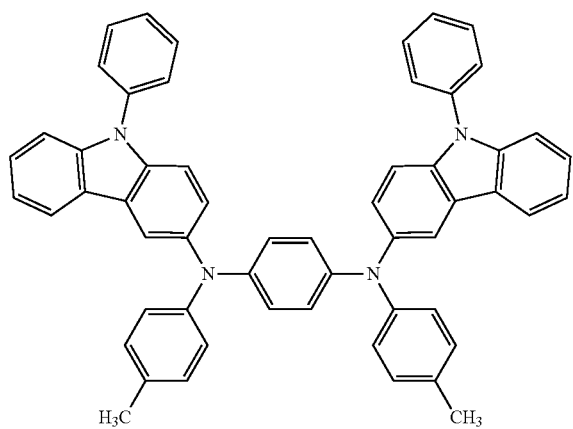
3
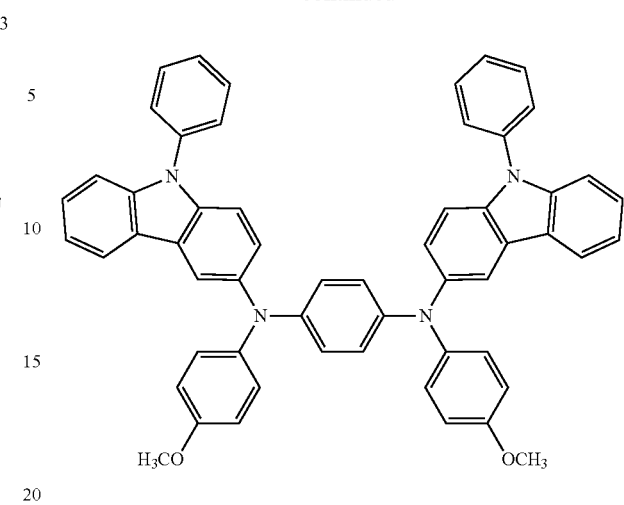
6
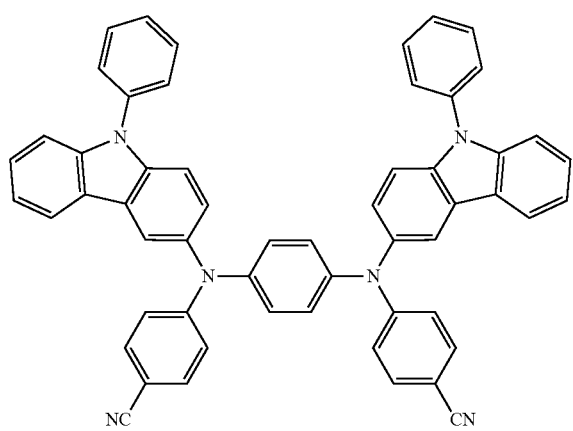
4
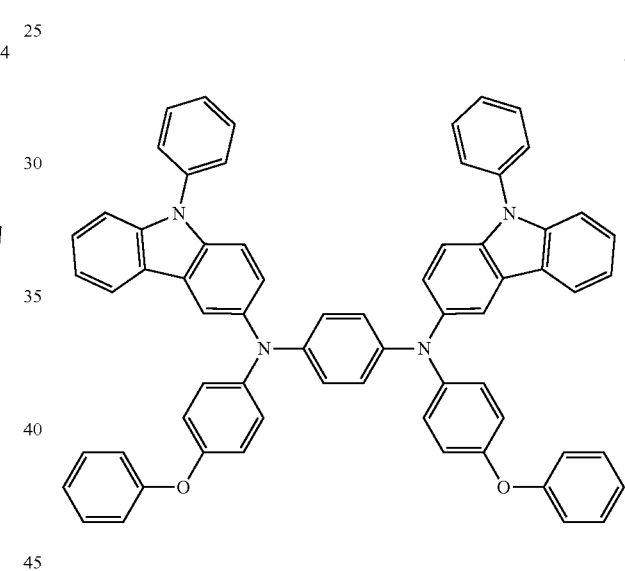
7
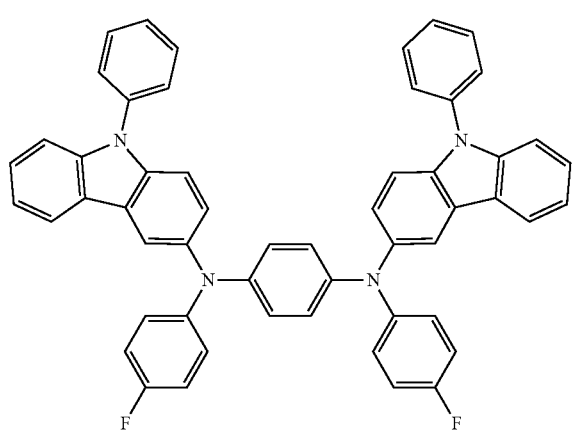
5
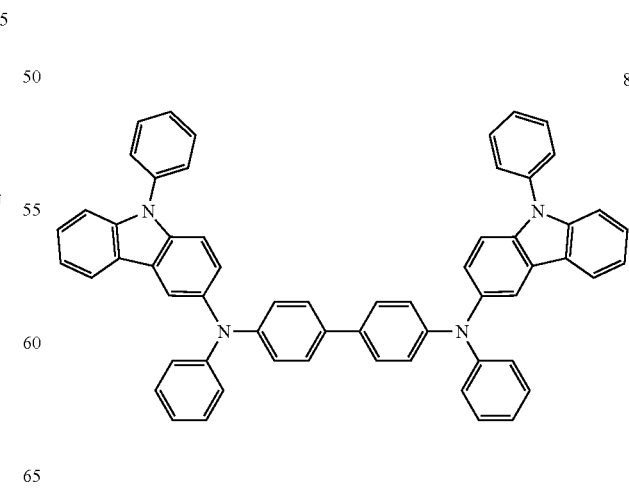
8

[Formula 60]
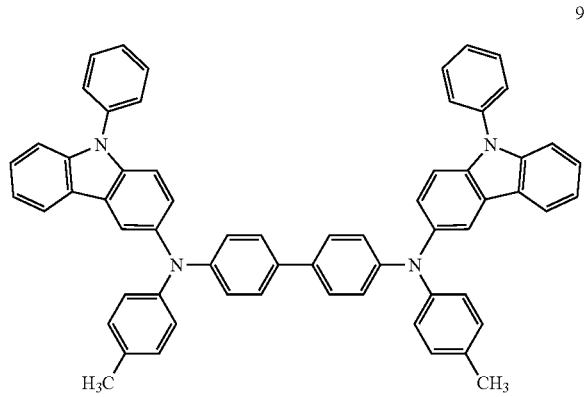
9
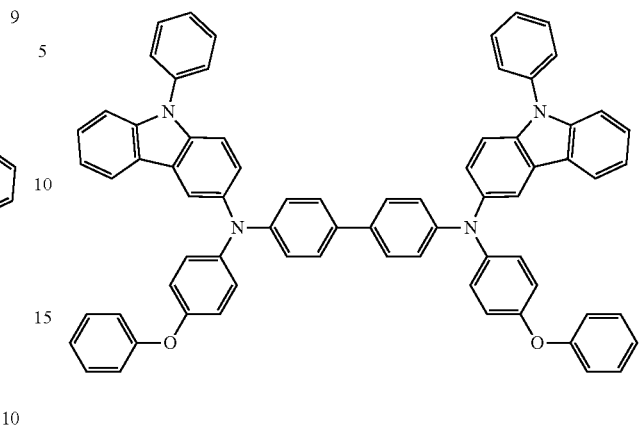
13
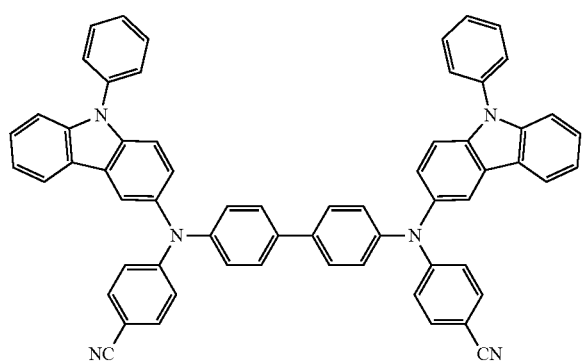
10
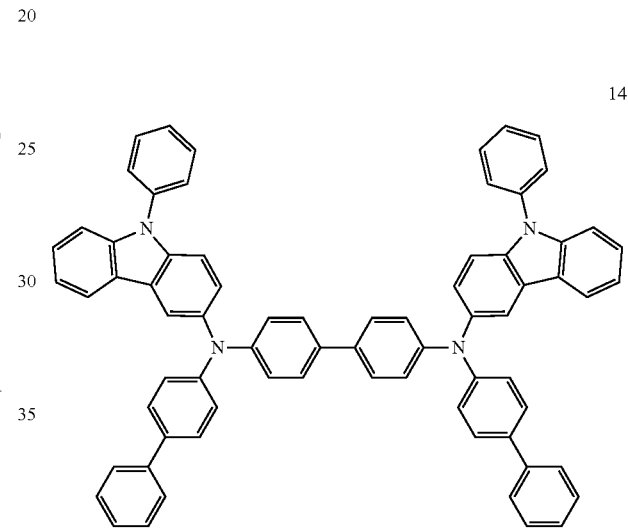
14
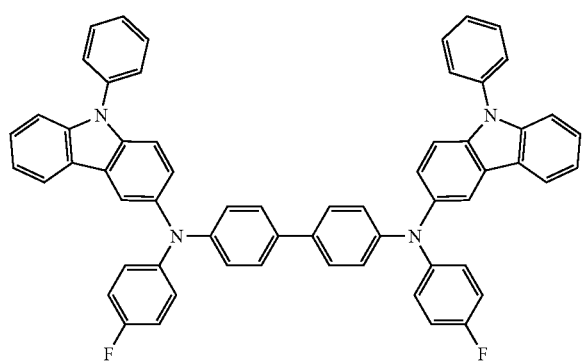
11
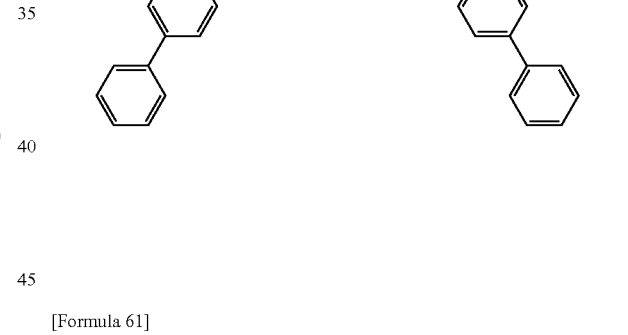
[Formula 61]
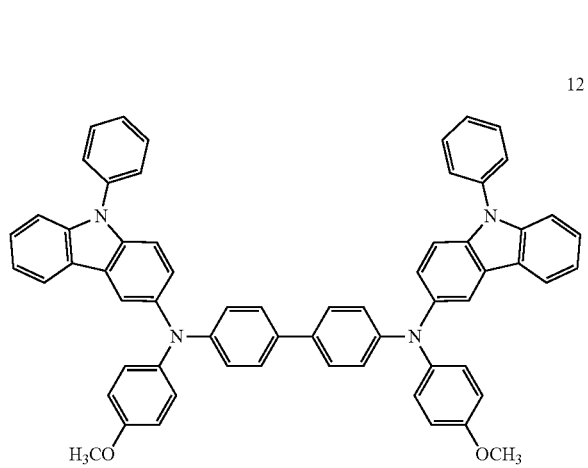
12
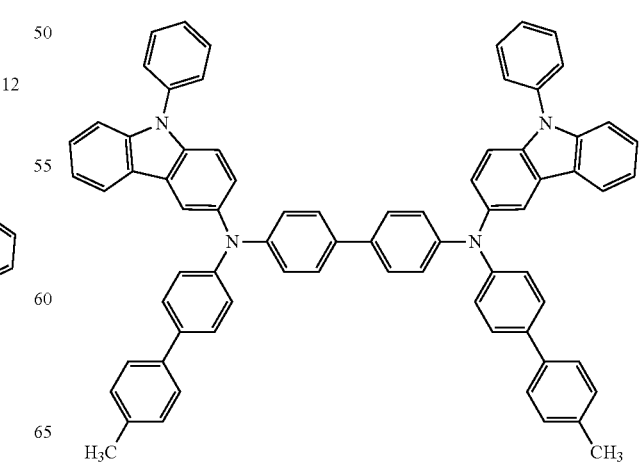
15

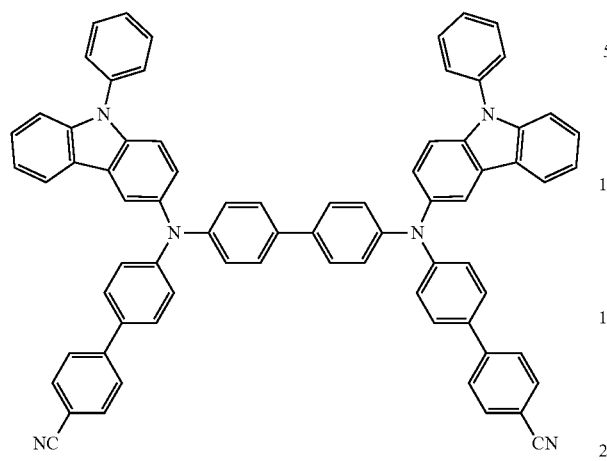
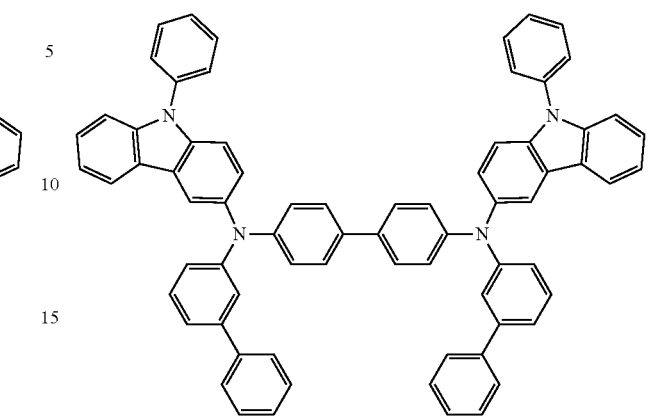
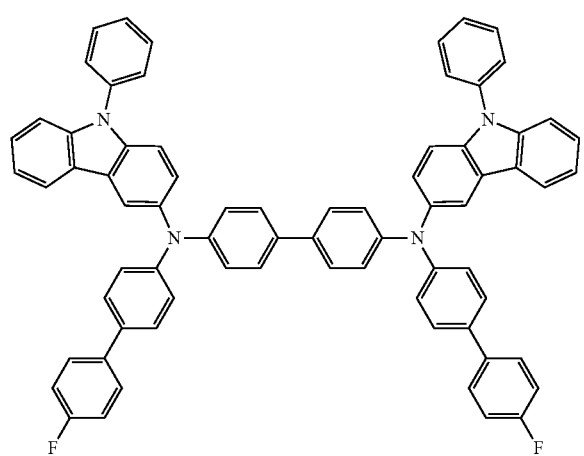
[Formula 62]
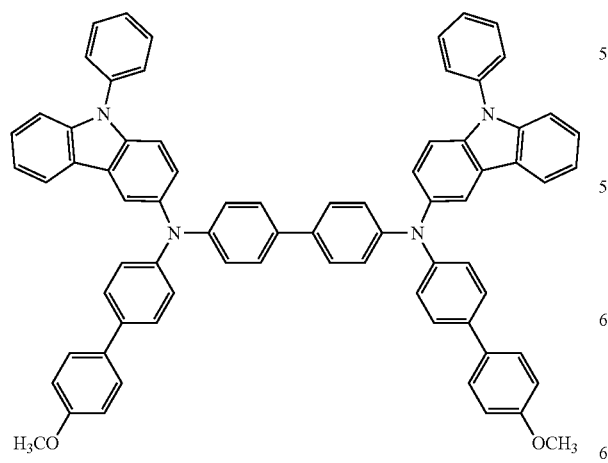
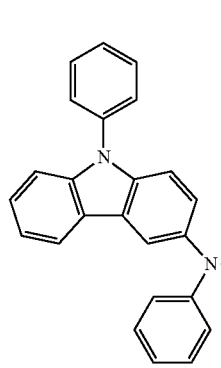

147
-continued
22
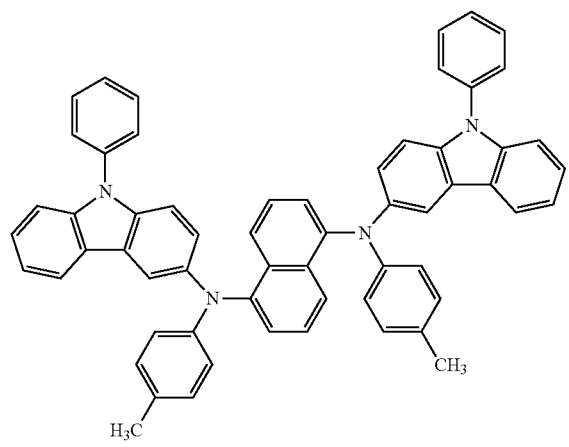
23
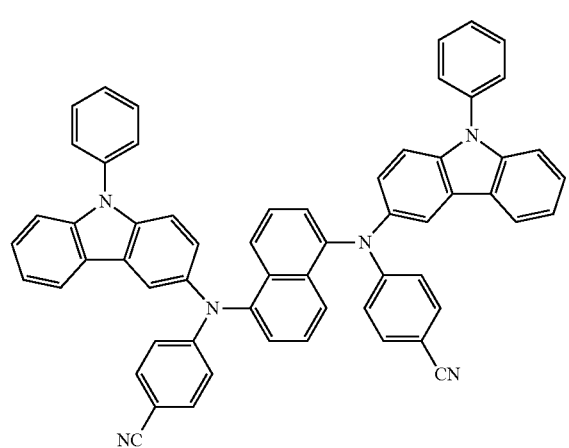
24
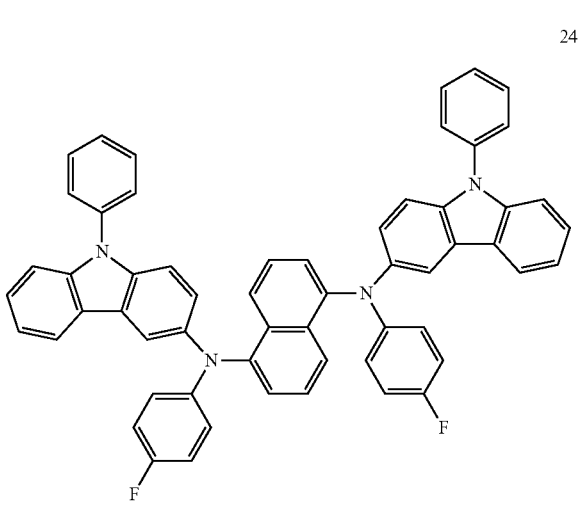
148
-continued
25
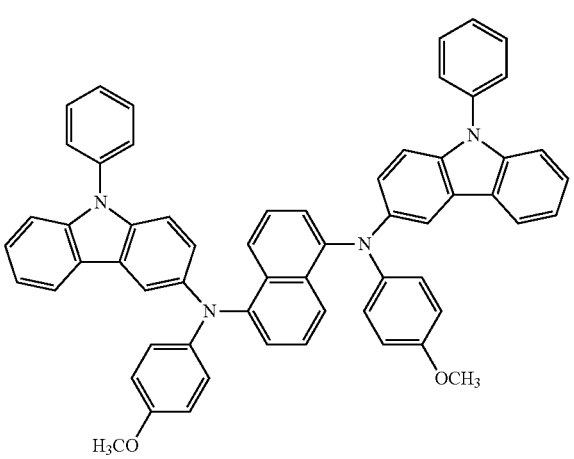
26
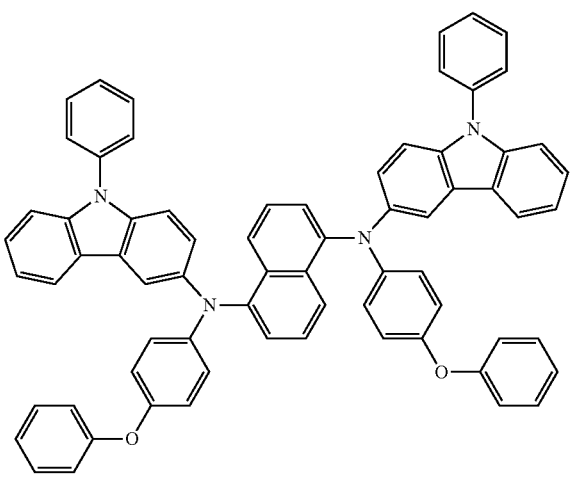
[Formula 63]
27
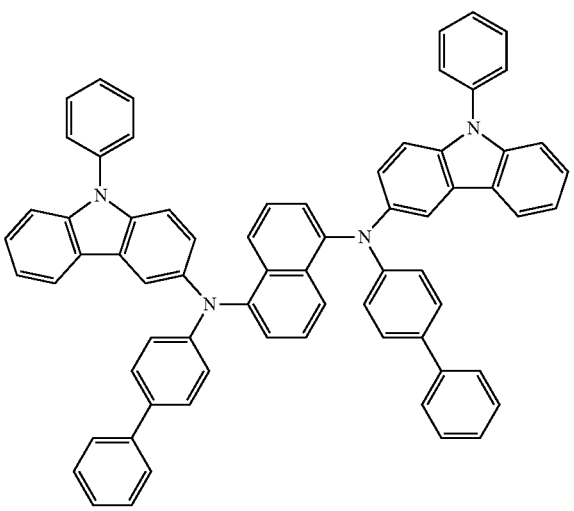

-continued
28
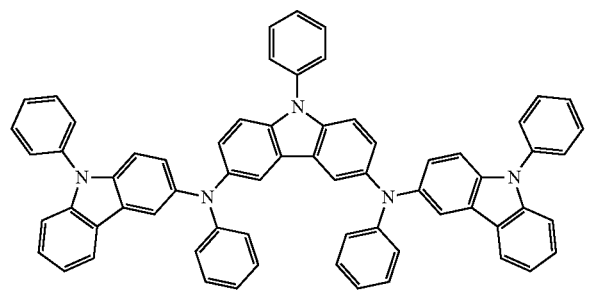
29
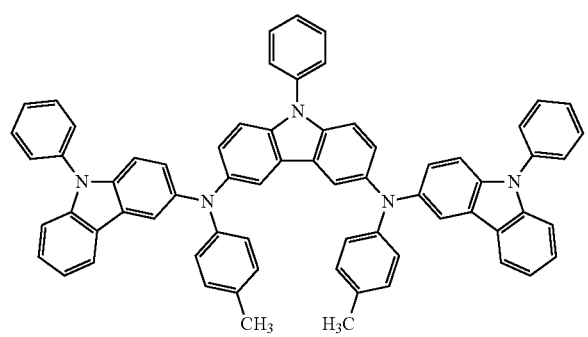
30
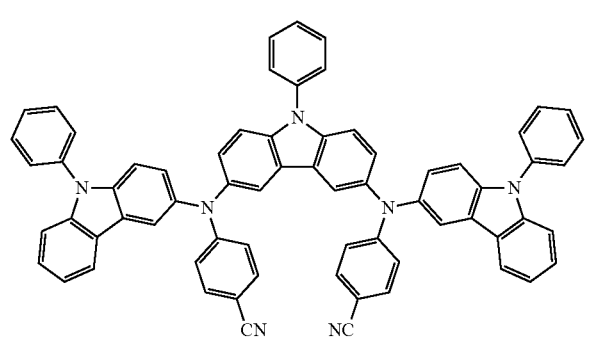
31
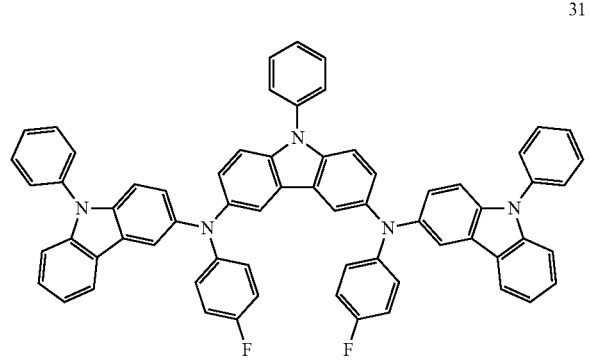
-continued
32
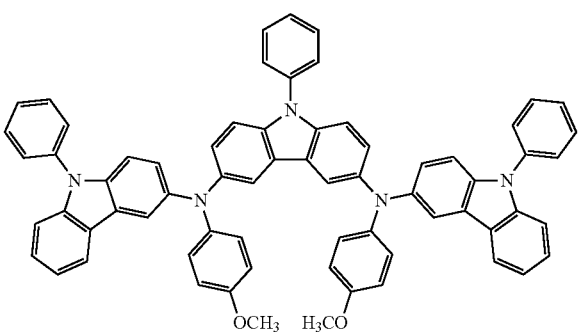
[Formula 64]
33
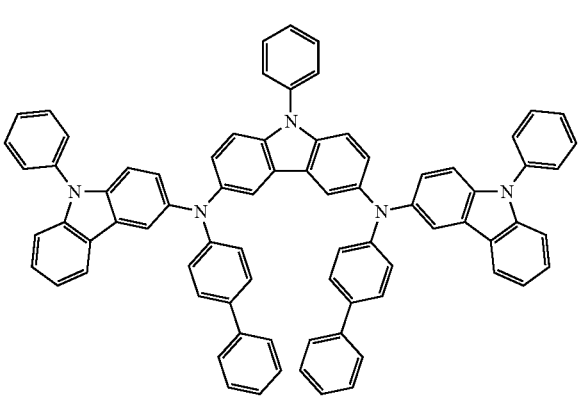
34
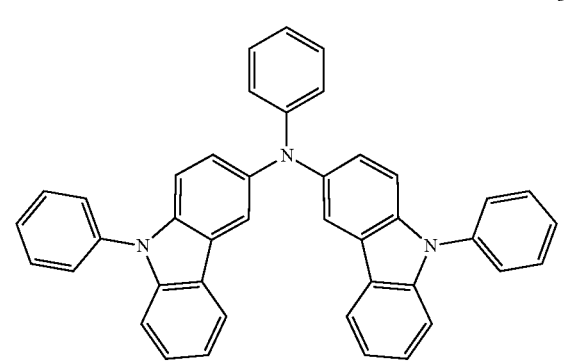
35
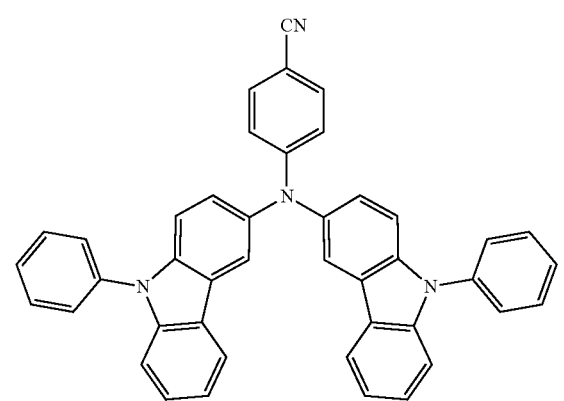

36
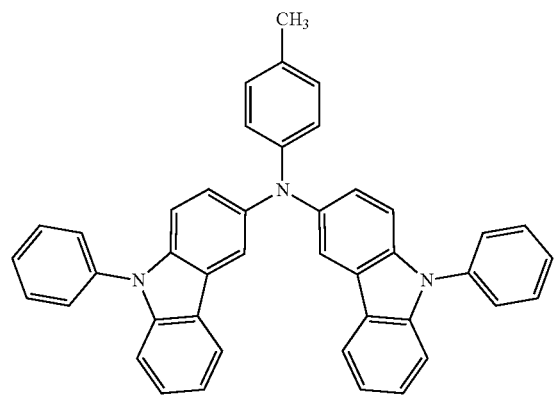
37
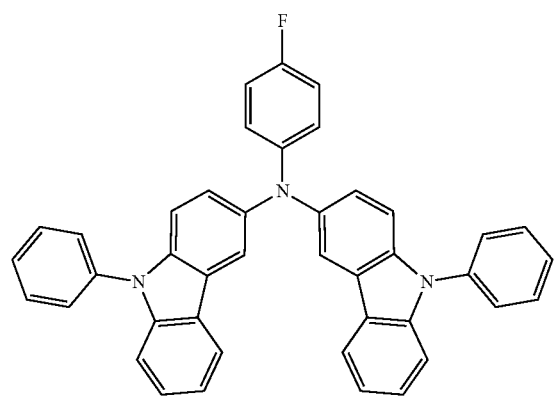
38
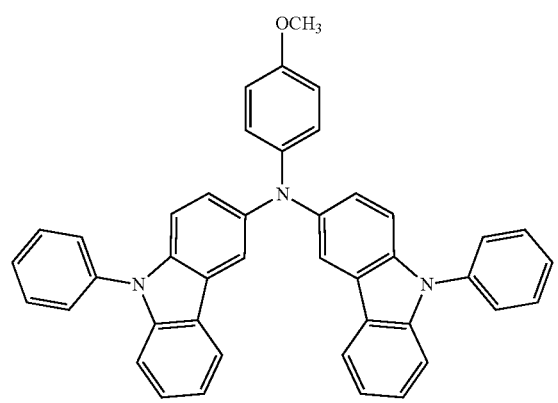
[Formula 65]
39
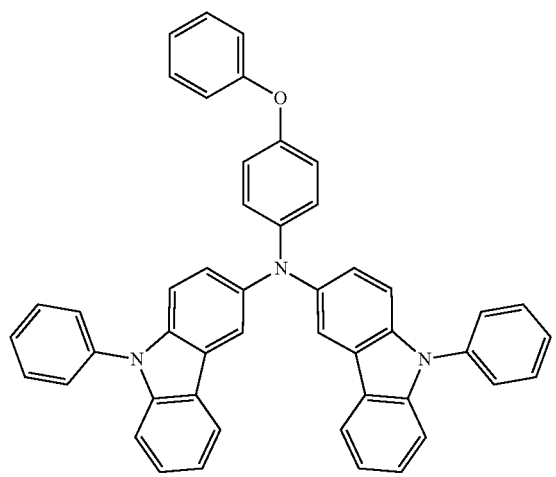
40
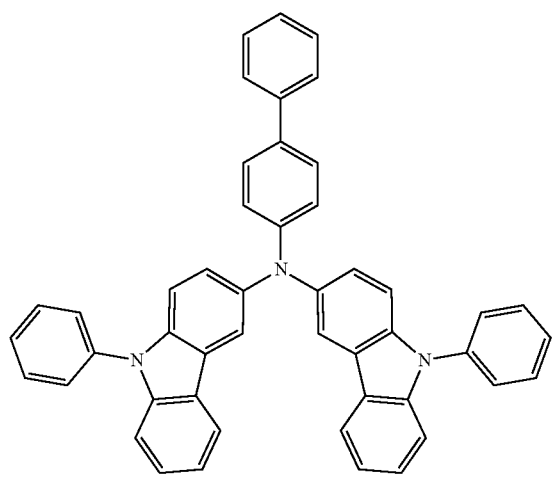
41

[Formula 66]
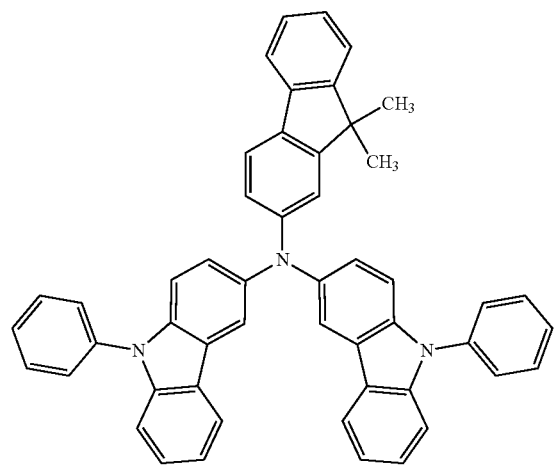
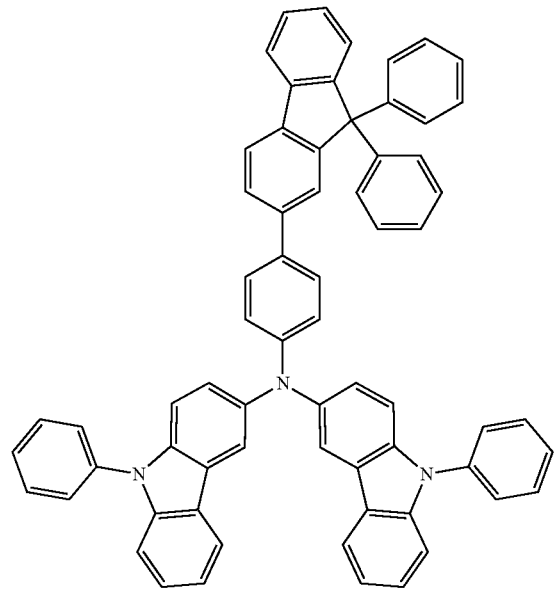
[Formula 67]
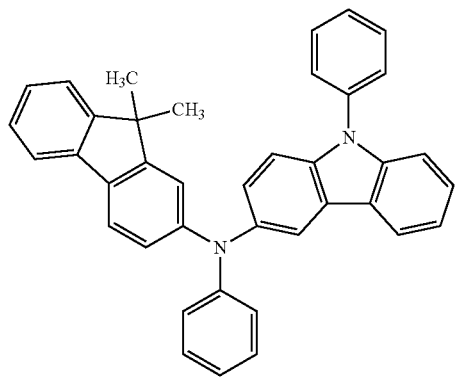
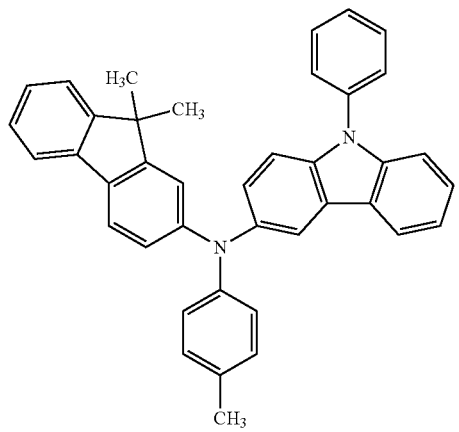

48
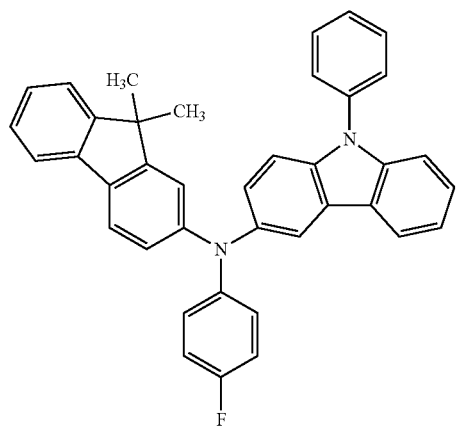
49
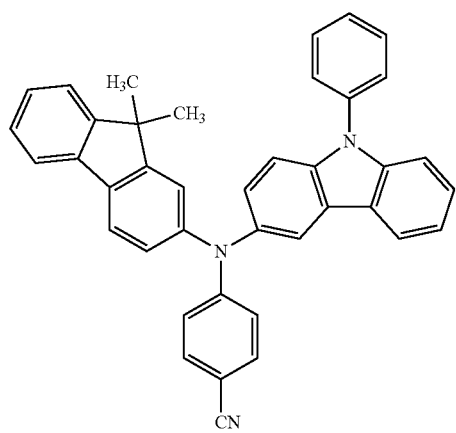
50
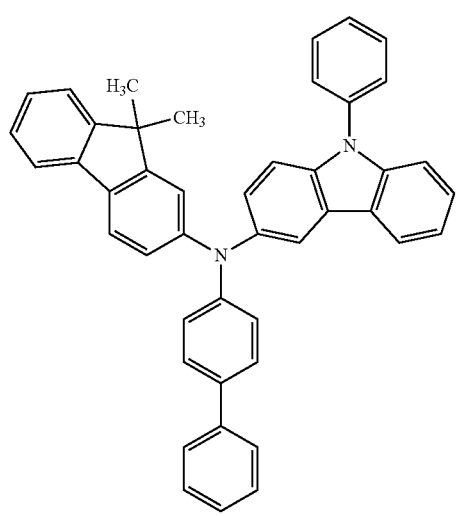
51
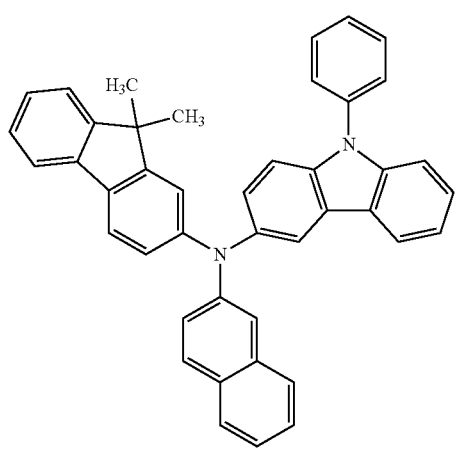
52
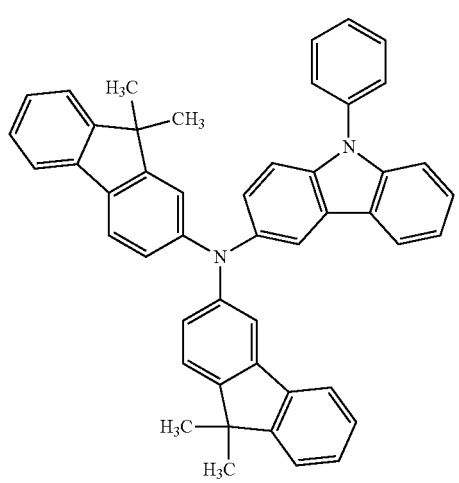
53
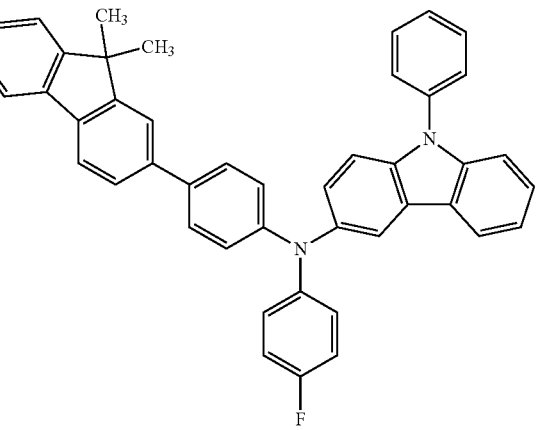

-continued
54
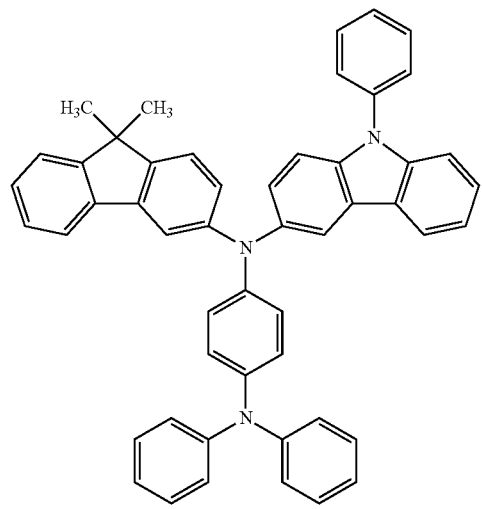
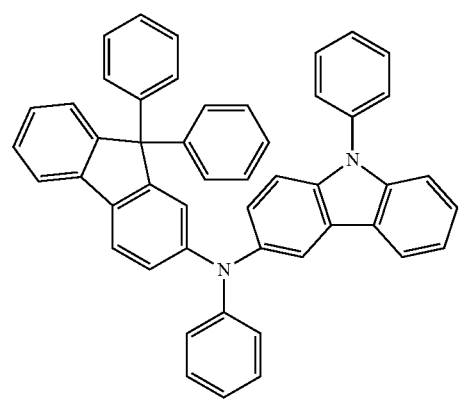
[Formula 68]
56
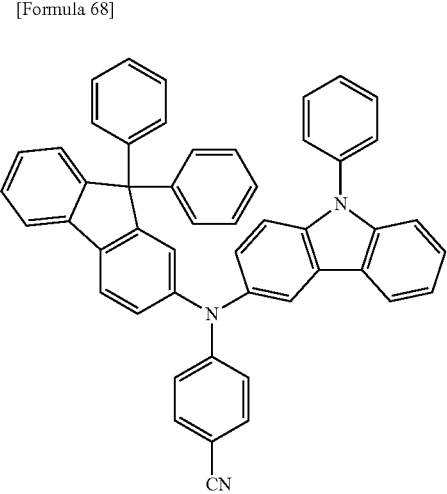
-continued
57
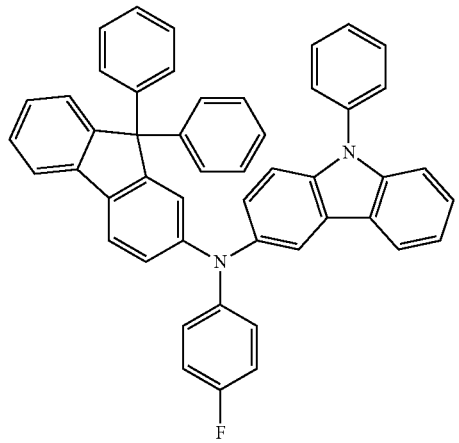
58
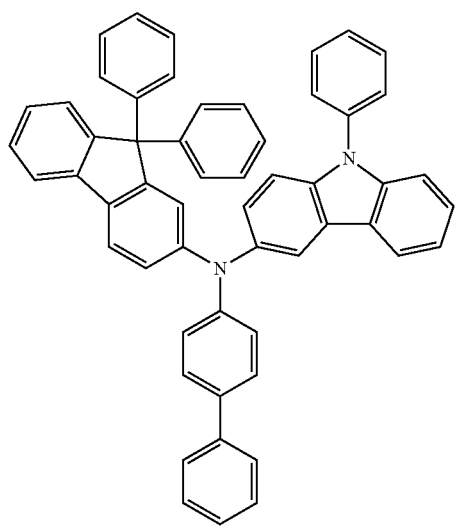
59
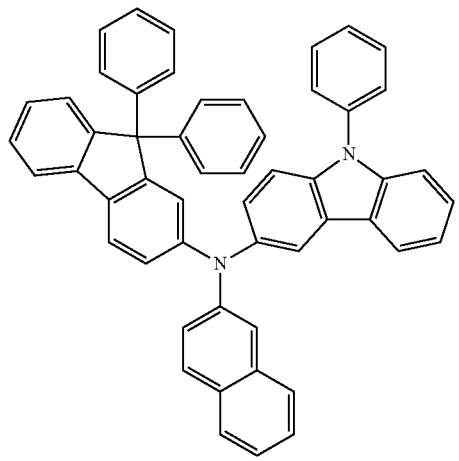

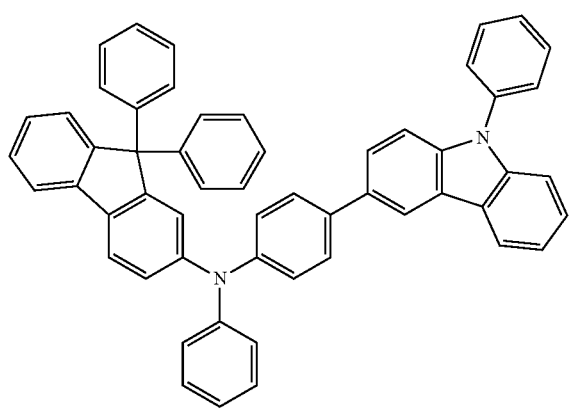

60

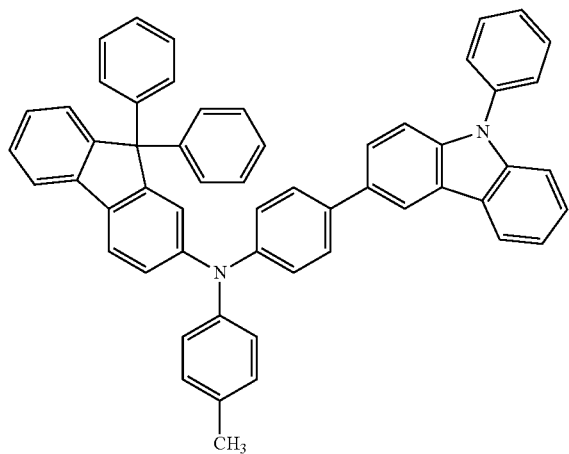

61

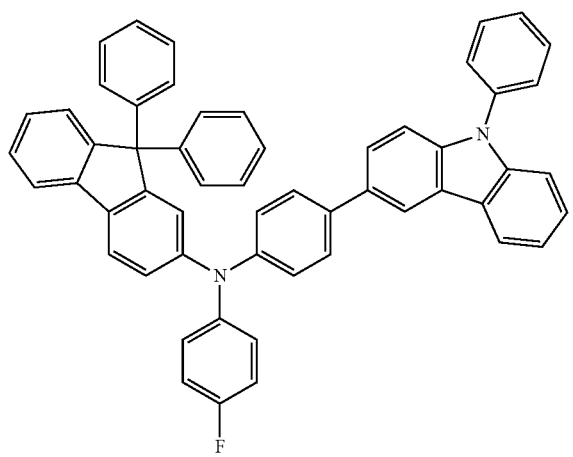

62

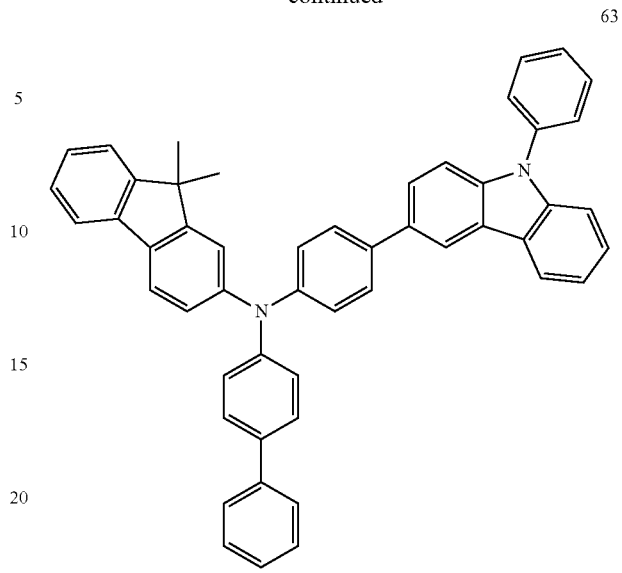

63

The compounds expressed by general formulas (Sa-1), (Sb-1), and (Sc-1) can be synthesized by the methods disclosed in Japanese Unexamined Patent Application 2007-318101. After synthesizing, purification is performed by column chromatography, recrystallization, re-precipitation, or the like, and then purification is preferably performed by sublimation purification. Not only can organic impurities be separated, but inorganic salt, residual solvents, water, and the like can be effectively removed by sublimation purification.

With the light emitting element of the present invention, the compounds expressed by general formulas (Sa-1), (Sb-1), and (Sc-1) are preferably included in an organic layer between the light emitting layer and the anode, but are more preferably included in the layer on the anode side that is adjacent to the light emitting layer, and are particularly preferably electron hole transport materials that are included in the electron hole transport layer.

The compounds expressed by the general formulas (Sa-1), (Sb-1), and (Sc-1) are preferably included at a level of 70 to 100 mass % with regards to the total mass of the added organic layer, and are more preferably included at a level of 85 to 100 mass %.

[Compound Expressed by General Formula (M-3)]

In the organic electroluminescent element of the present invention, an example of (A) the material that is particularly preferably used in the organic layer that is preferably disposed between the cathode and the light emitting layer is at least one type of compound expressed by general formula (M-3).

The compound expressed by general formula (M-3) is more preferably included in the organic layer adjacent to the light emitting layer between the light emitting layer and the anode, but there is no restriction to this use, and this compound can also be included in any layer of the organic layer. The introduction layer for the compound expressed by general formula (M-3) can include any one of the light emitting layer, the electron hole injection layer, the electron hole transport layer, the electron transport layer, the electron injection layer, and the electric charge blocking layer, or a plurality thereof.

The organic layer that is adjacent to the light emitting layer between the light emitting layer and the anode and that includes the compound expressed by general formula (M-3) is more preferably an electron blocking layer or an electron hole transport layer.

[Formula 69]

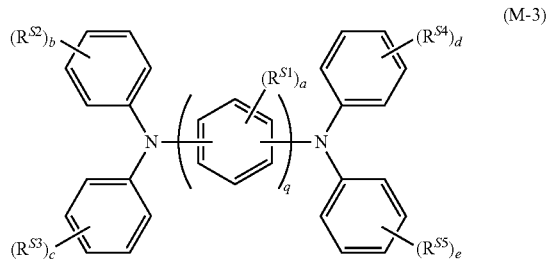

In general formula (M-3), $R^{S1}$ through $R^{S5}$ individually represent an alkyl group, cycloalkyl group, alkenyl group, alkynyl group, —CN, perfluoro alkyl group, trifluoro vinyl group, —CO$_2$R, —C(O)R, —NR$_2$, NO$_2$, —OR, a halogen atom, an aryl group, or a heteroaryl group. R independently represents a hydrogen atom, alkyl group, perhaloalkyl group, alkenyl group, alkynyl group, hetero alkyl group, aryl group, or heteroaryl group. If there are a plurality of $R^{S1}$ through $R^{S5}$, these groups can be bonded together to form a ring, and may also have a substitution group Z.

a represents an integer from 0 to 4, and if there are a plurality of $R^{S1}$, these groups may be the same or different, and may be bonded together to form a ring. b through e represent an integer from 0 to 5, and if there are a plurality of $R^{S1}$ through $R^{S5}$, these groups may be the same or different, and any two may be bonded together to form a ring.

q represents an integer from 1 to 5, and if q is 2 or higher, the plurality of $R^{S1}$ can be the same or different, and can be bonded together to form a ring.

The alkyl group may have a substitution group, and can be saturated or unsaturated, and examples of groups that may be substituted include the aforementioned substitution groups Z. The alkyl groups represented by $R^{S1}$ through $R^{S5}$ are preferably alkyl groups with a total of 1 through 8 carbon atoms, more preferably an alkyl group with a total of 1 to 6 carbon atoms, and examples include a methyl group, ethyl group, i-propyl group, cyclohexyl group, t-butyl group, and the like.

The cycloalkyl group may have a substitution group, and can be saturated or unsaturated, and examples of groups that may be substituted include the aforementioned substitution groups Z. The cycloalkyl groups represented by $R^{S1}$ through $R^{S5}$ are preferably cycloalkyl groups with 4 to 7 member rings, more preferably a cycloalkyl group with a total of 5 to 6 carbon atoms, and examples include a cyclopentyl group, cyclohexyl group, and the like. The alkenyl groups represented by $R^{S1}$ through $R^{S5}$ preferably has 2 to 30 carbon atoms, more preferably 2 to 20 carbon atoms, and particularly preferably 2 to 10 carbon atoms, and examples include vinyl, allyl, 1-propenyl, 1-isopropenyl, t-butenyl, 2-butenyl, 3-pentenyl, and the like.

The alkynyl groups represented by $R^{S1}$ through $R^{S5}$ preferably has 2 to 30 carbon atoms, more preferably 2 to 20 carbon atoms, and particularly preferably 2 to 10 carbon atoms, and examples include ethynyl, propargyl, 1-propynyl, 3-pentynyl, and the like.

An example of the perfluroalkyl group represented by $R^{S1}$ through $R^{S5}$ is an alkyl group where all of the hydrogen atoms have been replaced with a fluorine atoms.

The aryl group represented by $R^{S1}$ through $R^{S5}$ preferably includes substituted or unsubstituted aryl groups with 6 to 30 carbon atoms, and examples include a phenyl group, tolyl group, bephenyl group, ter-phenyl group, and the like.

The heteroaryl group represented by $R^{S1}$ through $R^{S5}$ is preferably a heteroaryl group with 5 to 8 carbon atoms, more preferably a substituted or unsubstituted heteroaryl group with 5 to 6 members, and examples include a pyridyl group, pyrazinyl group, pyridazinyl group, pyrimidinyl group, triazinyl group, quinolinyl group, isoquinolinyl group, quinazolinyl group, cinnolinyl group, phthalazinyl group, quinoxalinyl group, pyrrolyl group, indolyl group, furyl group, benzofuryl group, thienyl group, benzothienyl group, pyrazolyl group, imidazolyl group, benzimidazolyl group, triazolyl group, oxazolyl group, benzoxazolyl group, thiadiazolyl group, benzothiazolyl group, isothiazolyl group, benzisothiazolyl group, thiadiazolyl group, isooxazolyl group, benzisooxazolyl group, pyrrolidinyl group, piperidinyl group, piperazinyl group, imidazolidinyl group, thiazolinyl group, sulforanyl group, carbazolyl group, dibenzofuryl group, dibenzothienyl group, pyridoindolyl group, and the like. Preferable examples include a pyridyl group, pyrimidinyl group, imidazolyl group, or thienyl group, and more preferably a pyridyl group or a pyrimidinyl group.

The $R^{S1}$ through $R^{S5}$ is preferably a hydrogen atom, alkyl group, cyano group, trifluoromethyl group, perfluoroalkyl group, dialkyl amino group, perfluoro group, aryl group, or heteroaryl group, more preferably a hydrogen atom, alkyl group, cyano group, trifluoromethyl group, furyl group, or aryl group, and even more preferably a hydrogen atom, alkyl group, or aryl group. The substitution group Z is preferably an alkyl group, alkoxy group, perfluoro group, cyano group, or dialkylamino group, more preferably a hydrogen atom, or alkyl group.

Any two of $R^{S1}$ through $R^{S5}$ may be bonded together to form a condensed 4 to 7 member ring, and the 4 to 7 member ring may be a cycloalkyl group, aryl group, or heteroaryl group, and the condensed 4 to 7 membered ring may also have a substitution group Z. The definition and the preferable range of the cycloalkyl, aryl, or heteroaryl group that is formed are the same as the cycloalkyl group, aryl group, or heteroaryl group that are defined for $R^{S1}$ through $R^{S5}$.

When the compound expressed by general formula (M-3) is used in the electron hole transport layer, the compound expressed by general formula (M-3) is preferably included at a level of 50 to 100 mass %, more preferably 80 to 100 mass %, and particularly preferably 95 to 100 mass %.

Furthermore, if the compound expressed by general formula (M-3) is used in a plurality of organic layers, the amount is preferably within the aforementioned range in each of the layers.

The thickness of the electron hole transport layer that includes the compound expressed by general formula (M-3), is preferably 1 nm to 500 nm, more preferably 3 nm to 200 nm, and even more preferably 5 nm to 100 nm. Furthermore, the electron hole transport layer is preferably provided so as to contact with the light emitting layer.

Specific examples of the compound expressed by general formula (M-3) are provided below, but the present invention is not restricted to these examples.

[Formula 70]
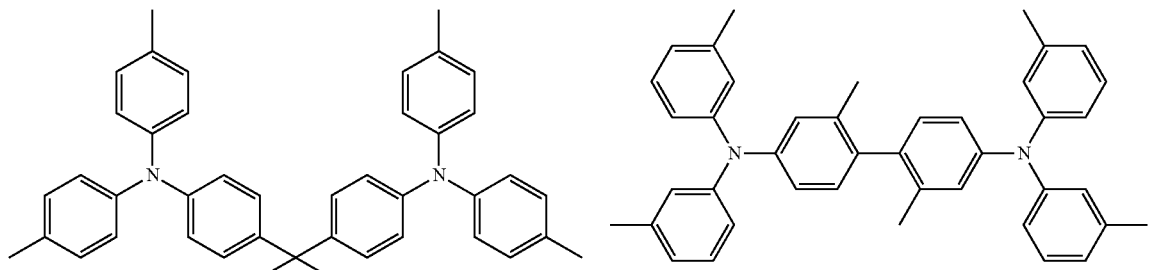
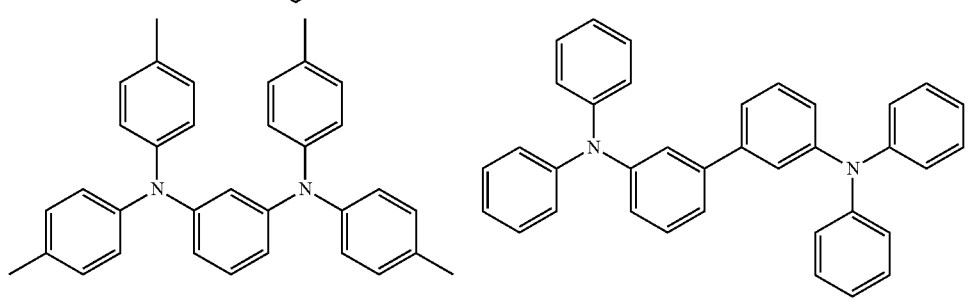
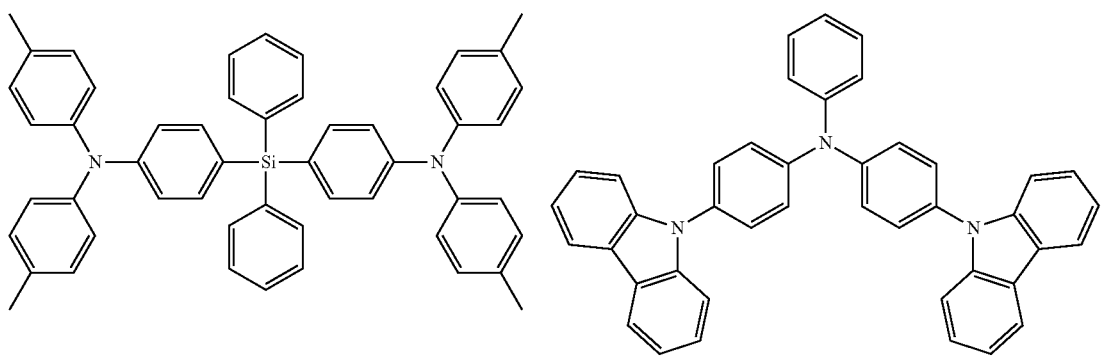
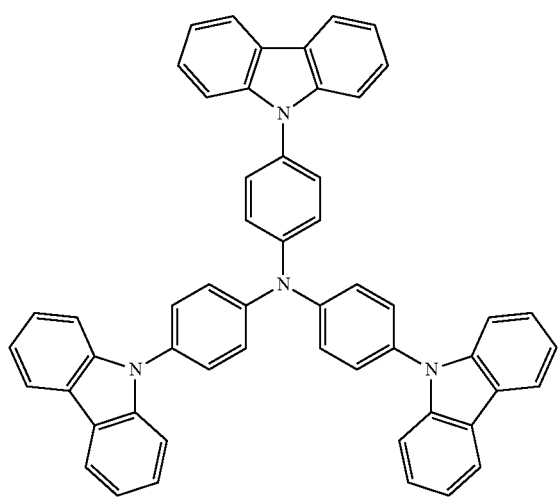

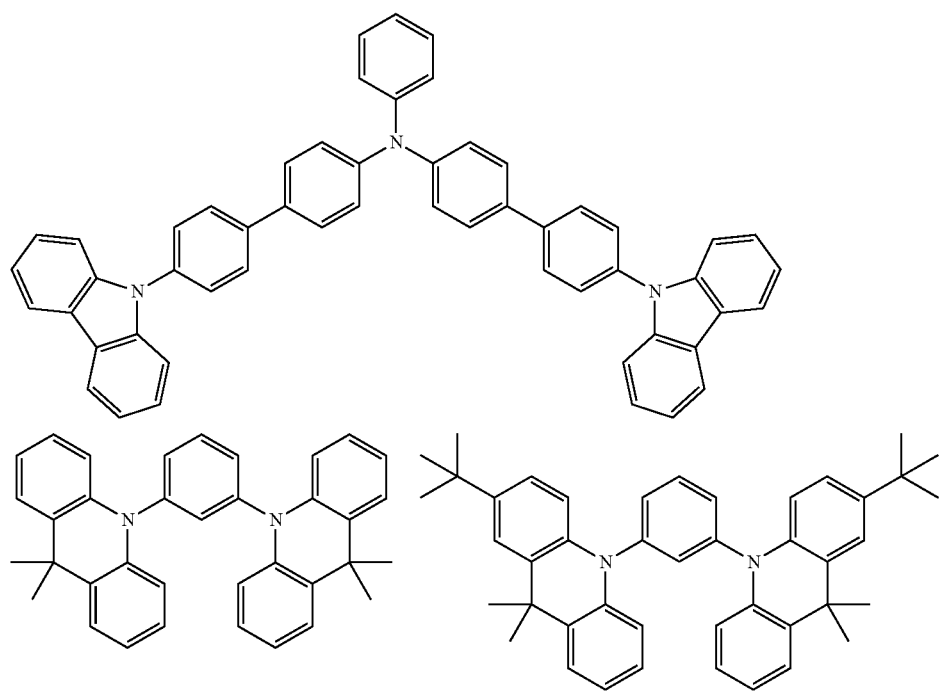
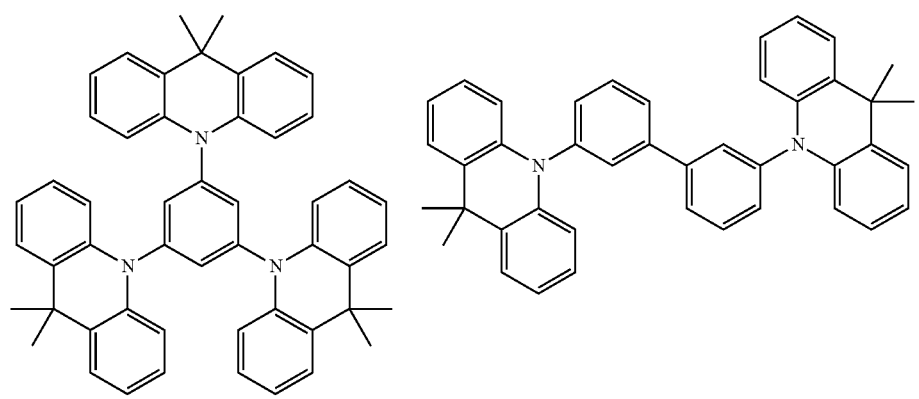
[Formula 71]
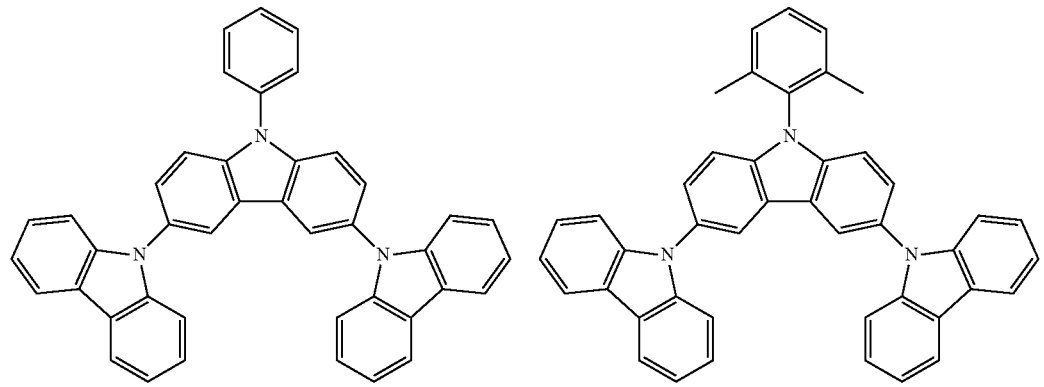

167 168
-continued
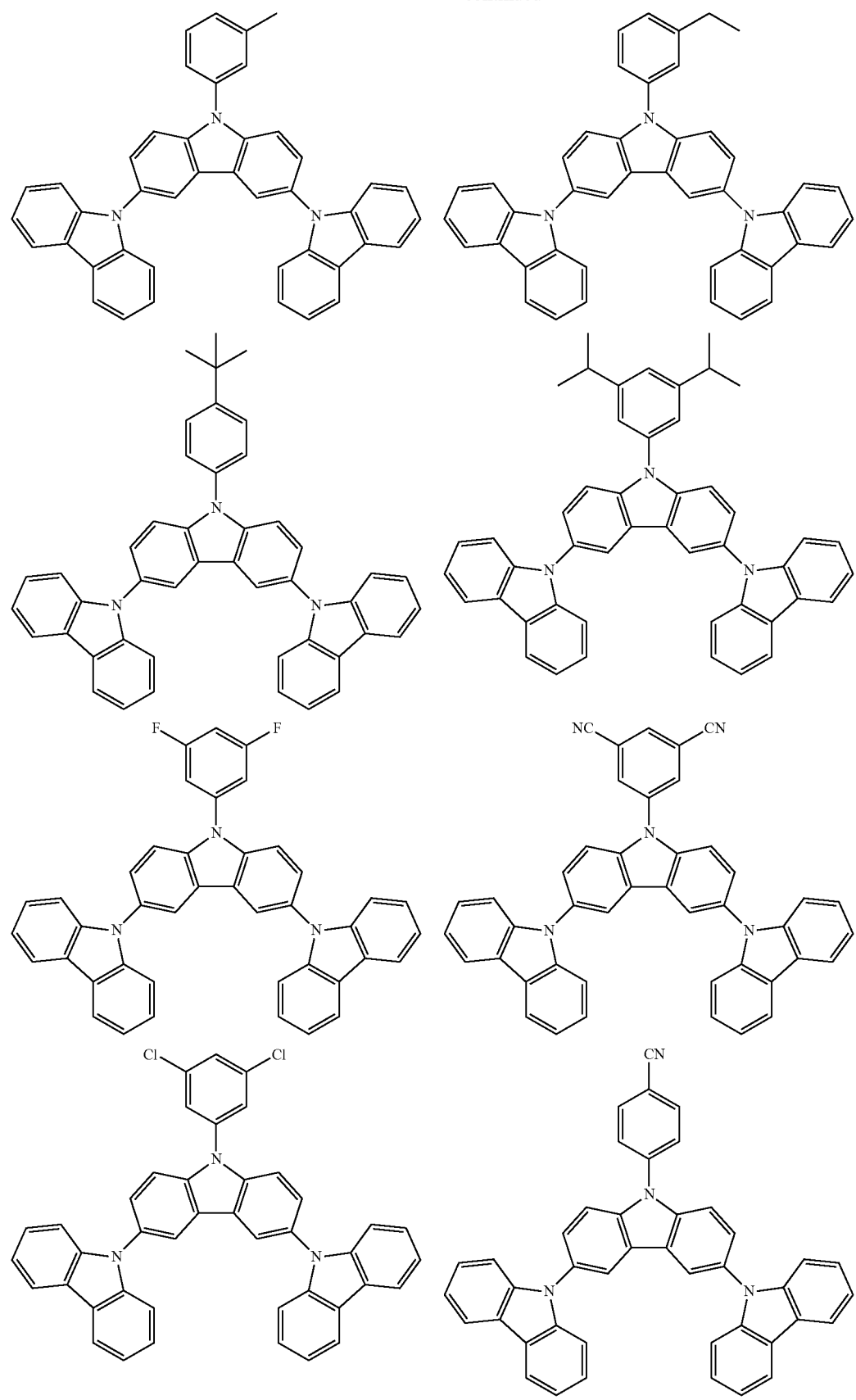

169 170
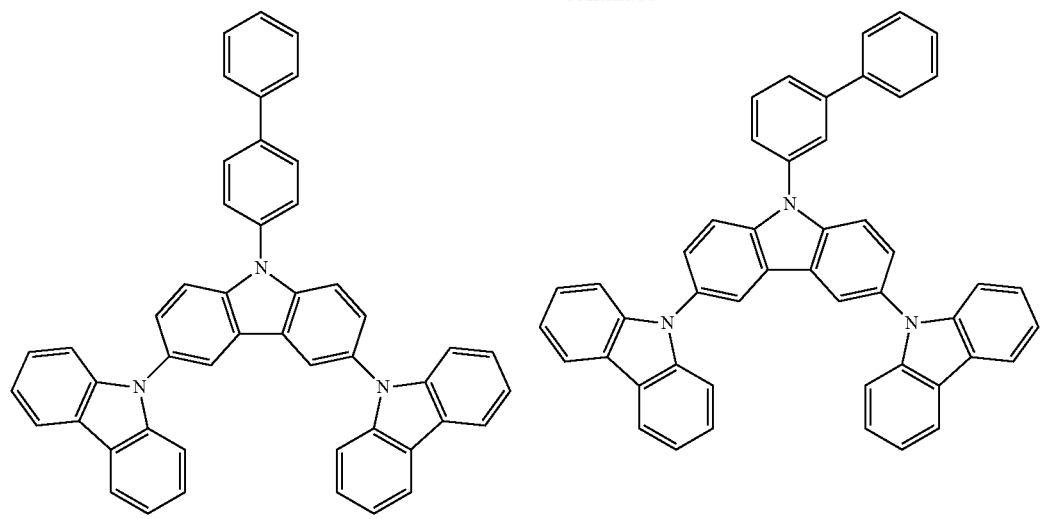
[Formula 72]
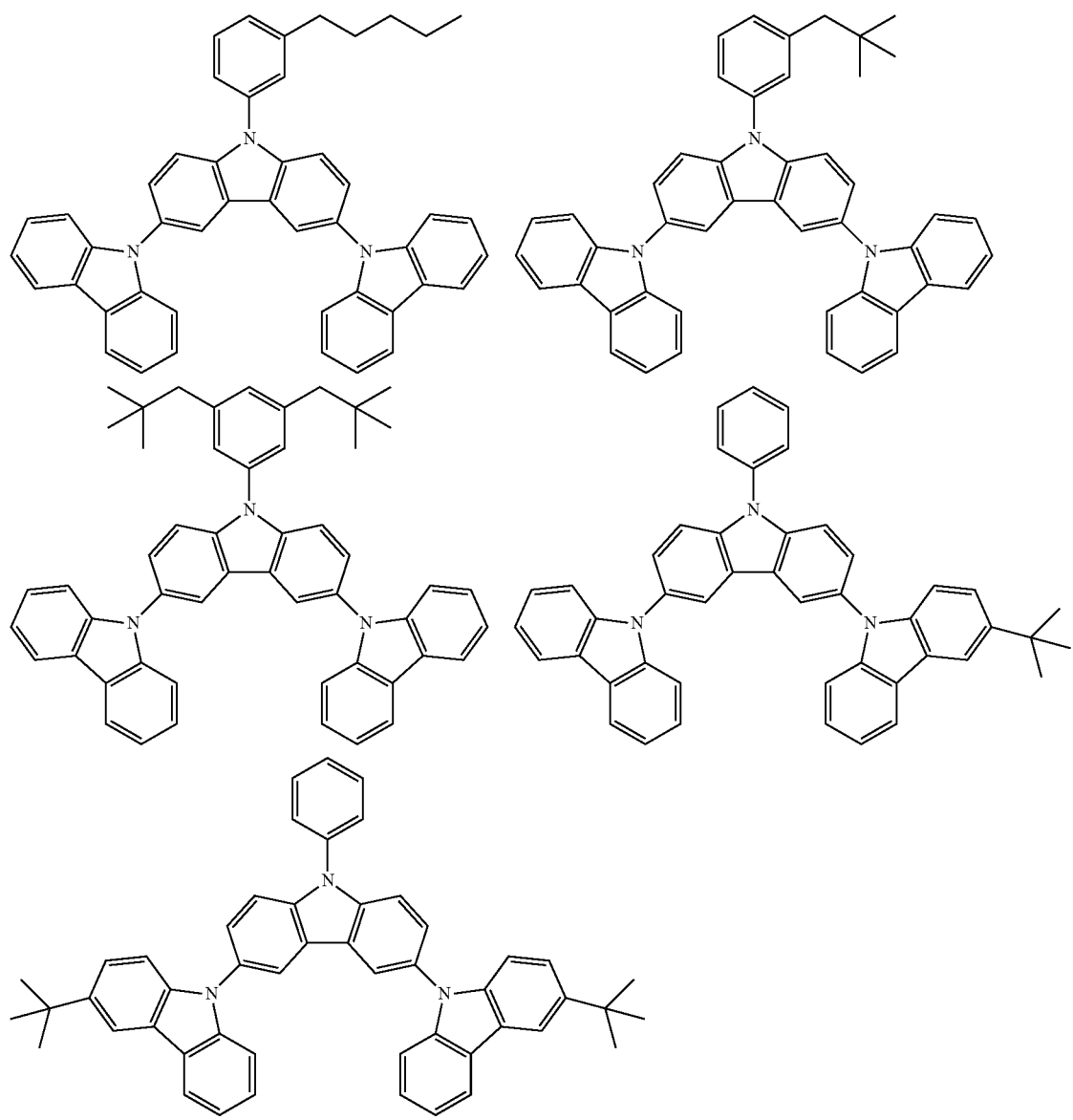

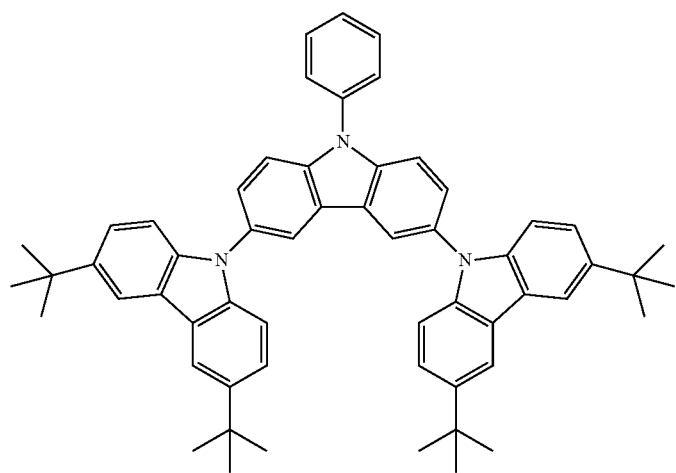 [SMILES: CC(C)(C)c1ccc2c(c1)c1cc(C(C)(C)C)ccc1n2-c1ccc2c(c1)c1cc(-n3c4ccc(C(C)(C)C)cc4c4cc(C(C)(C)C)ccc43)ccc1n2-c1ccccc1]
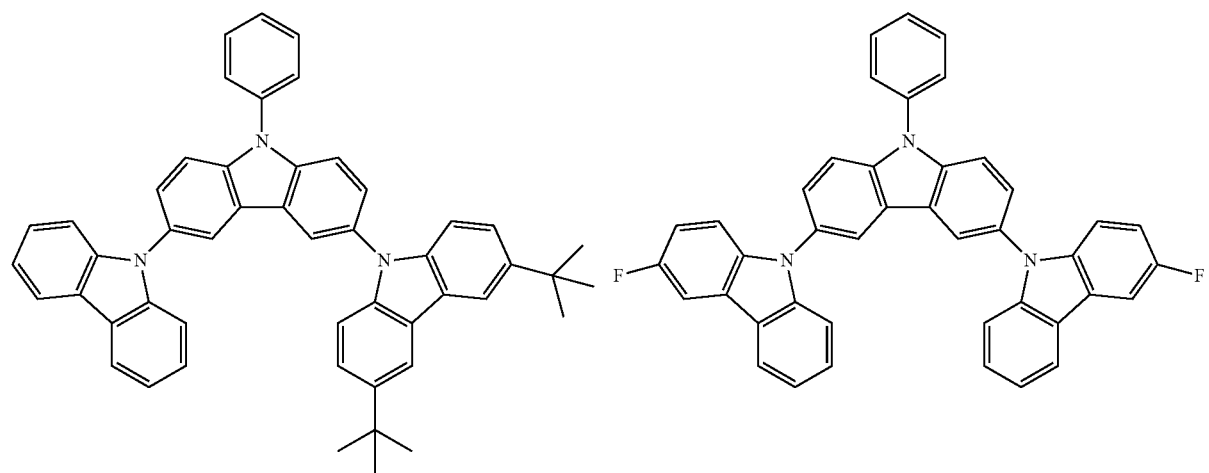
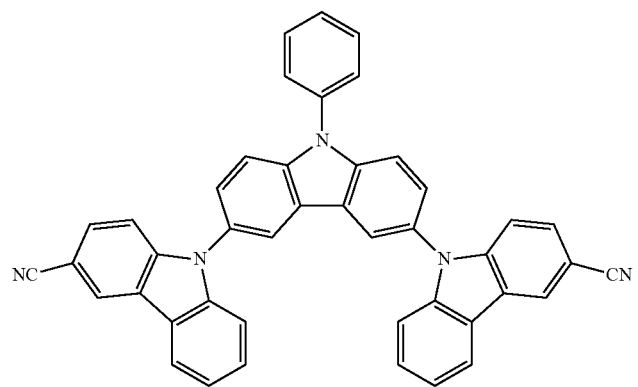

[Formula 73]
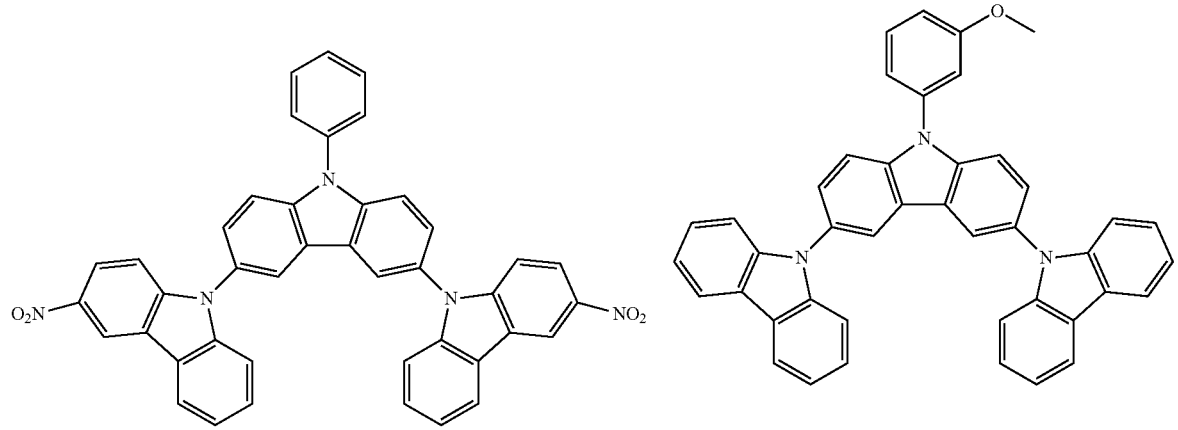
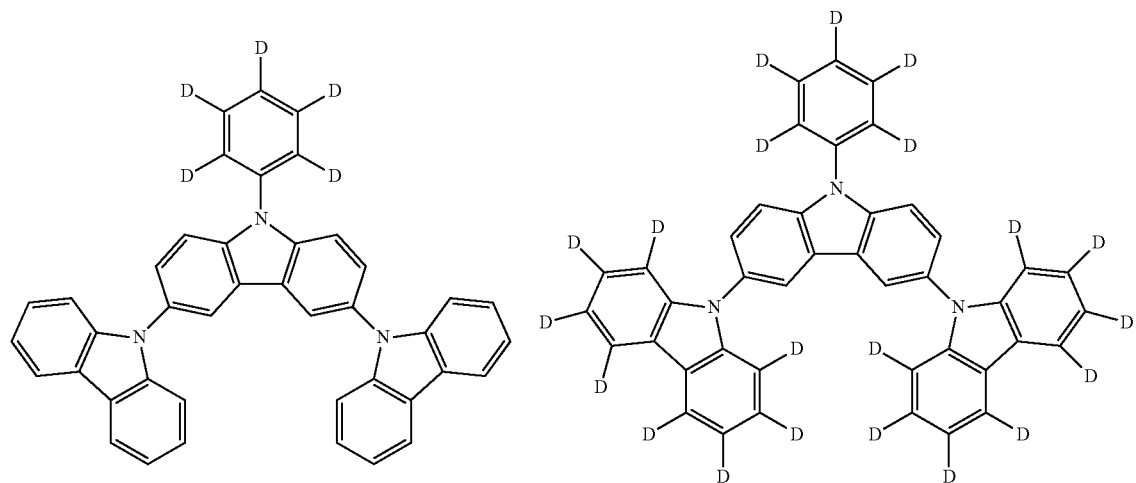
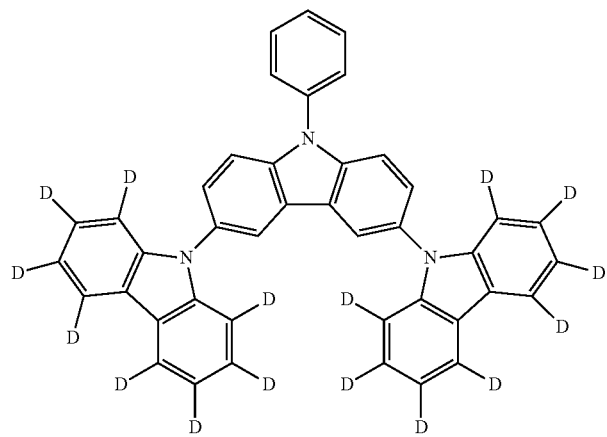

175 176
-continued
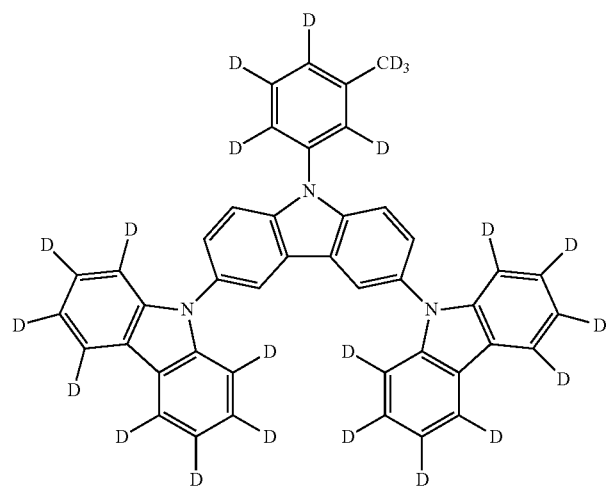
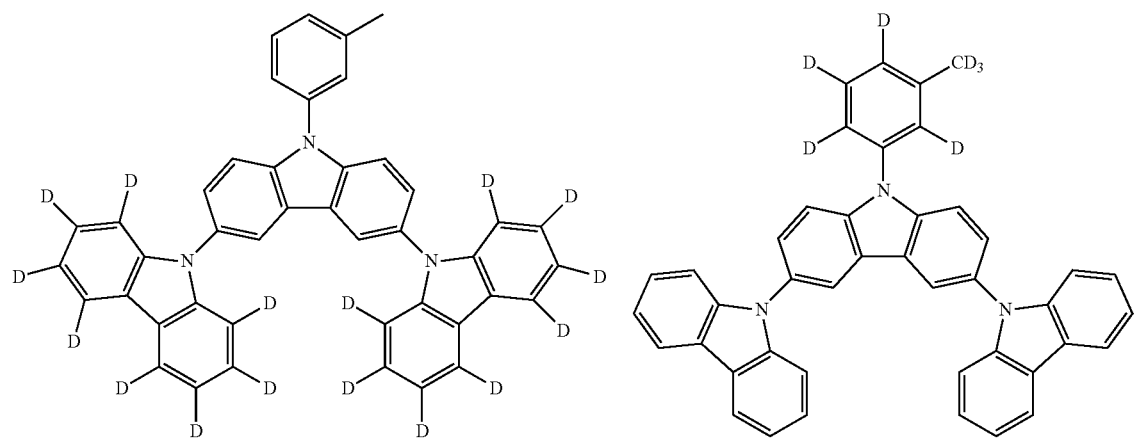
[Formula 74]
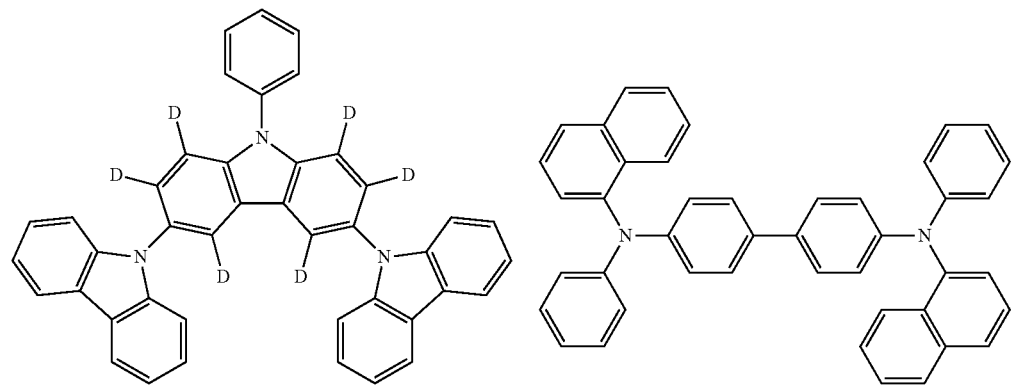

-continued
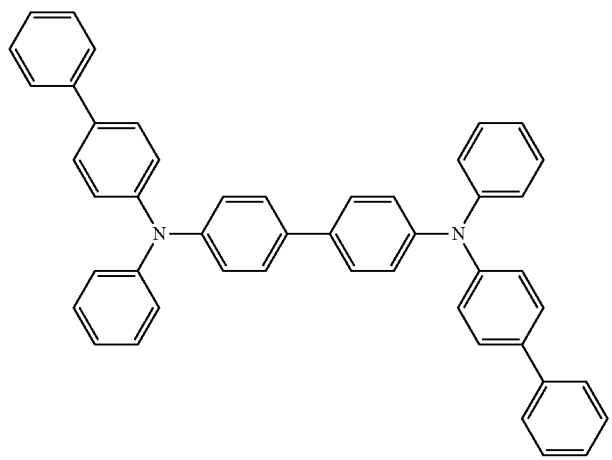
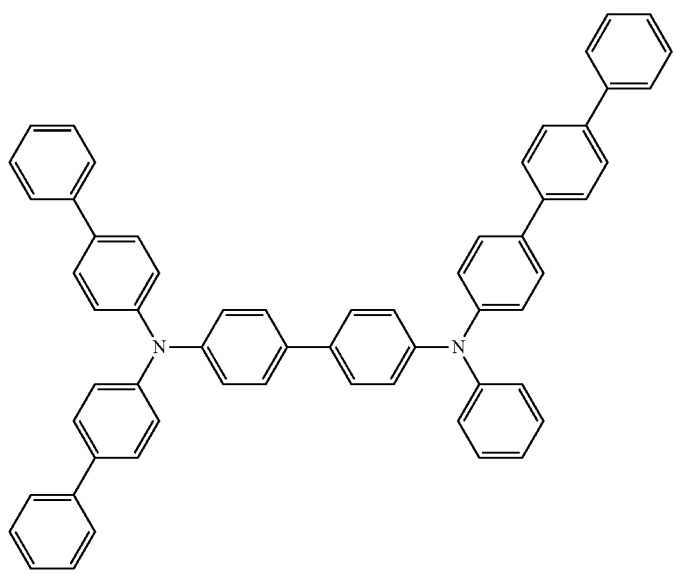
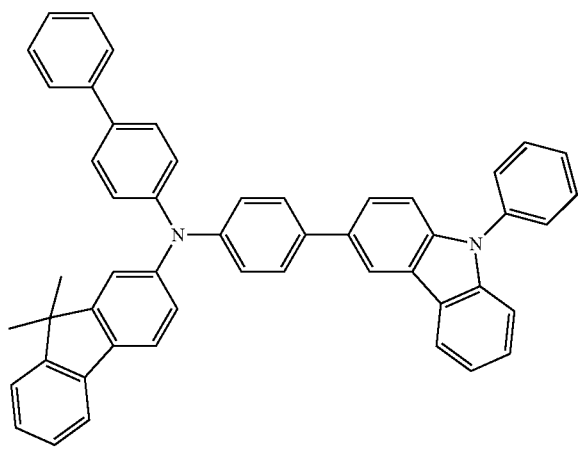

-continued

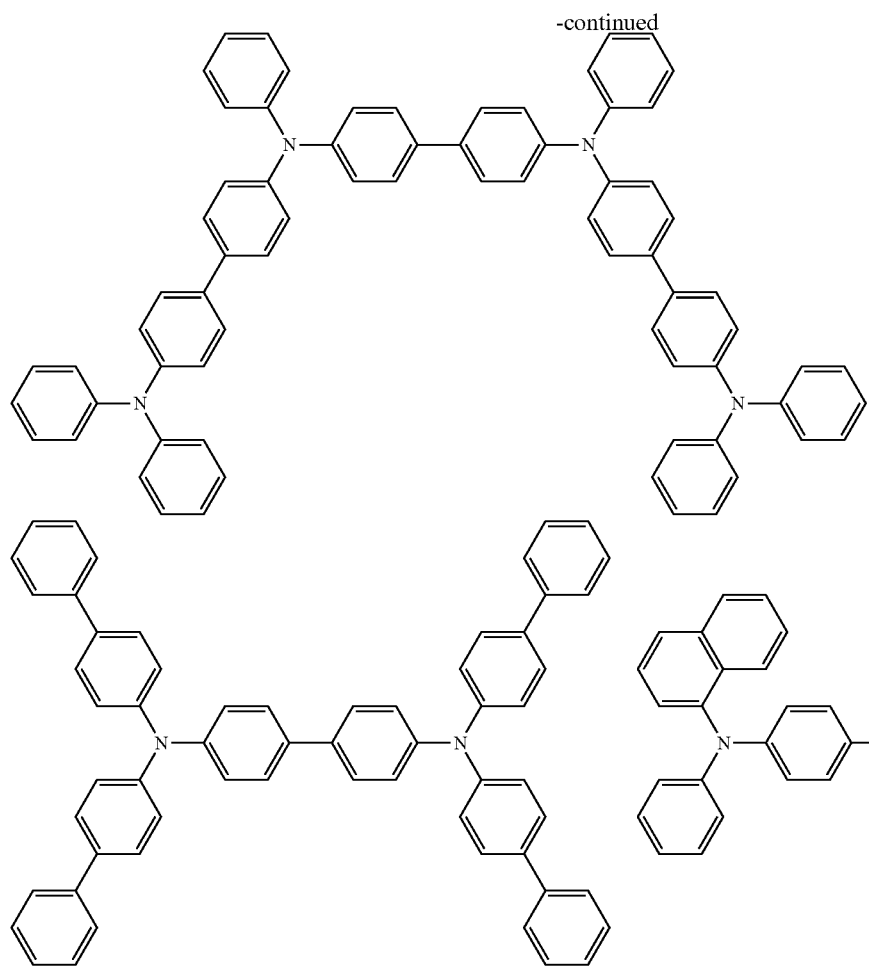
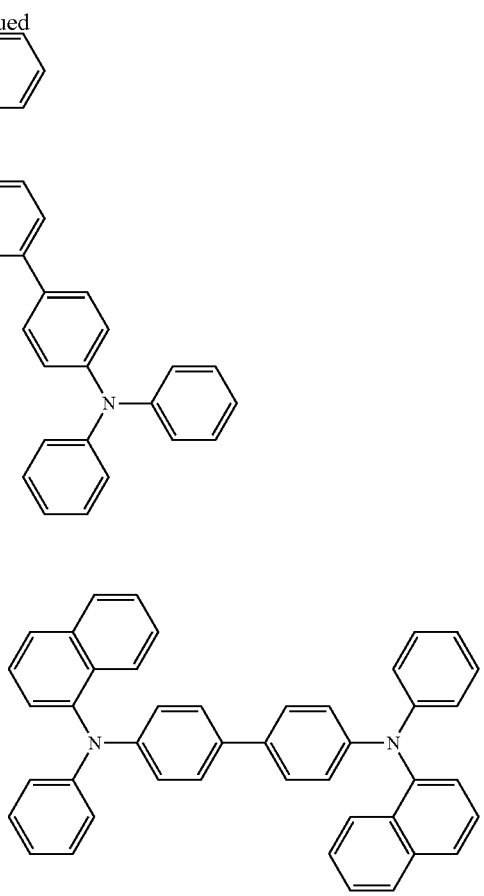

In addition, the elements described in paragraphs [0165] through [0167] of Japanese Unexamined Patent Application 2008-270736 can be applied to the present invention for the electron hole injection layer and the electron hole transport layer. Furthermore, the elements disclosed in [0250] through [0339] of Japanese Unexamined Patent Application 2011-71452 can also be applied to the electron hole injection layer and the electron hole transport layer of the present invention.

The electron hole injection layer may contain an electron receiving dopant. Including the receiving dopant into the electron hole injection layer has effects such as improving electron hole injection, reducing the driving voltage, improving the efficiency, and the like. The electron receiving dopant removes electrons from the doped material, and any organic material or inorganic material that can generate radical cations can be used, and examples include tetracyanoquinodimethane (TCNQ), tetrafluorotetracyanoquinodimethane ($F_4$-TCNQ) and other TCNQ compounds, hexacyanohexaazatriphenylene (HAT-CN) and other hexaazatriphenylene compounds, molybdenum oxide, and the like.

The electron receiving dopant in the electron hole injection layer is preferably included at a level of 0.01 mass % to 50 mass %, more preferably 0.1 mass % to 40 mass %, and even more preferably 0.2 mass % to 30 mass %, based on the total mass of compounds that form the electron hole injection layer.

(A-2) Electron Blocking Layer

The electron blocking layer is a layer that has the functionality of preventing the electrons that have been transported from the cathode side to the light emitting layer from escaping to the anode side. In the present invention, the electron blocking layer can be provided as an organic layer that is adjacent to the light emitting layer on the anode side.

An example of an organic compound that forms the electron blocking layer can be the compounds that were suggested for the aforementioned electron hole transport material.

The thickness of the electron blocking layer is preferably 1 nm to 500 nm, preferably 3 nm to 100 nm, and even more preferably 5 nm to 50 nm.

The electron blocking layer can be a single layer structure formed by one or two types of materials described above, or a multilayer structure formed by a plurality of layers with the same composition or different composition.

The material used in the electron blocking layer is preferably a material with higher $S_1$ energy than the $S_1$ energy of the aforementioned light emitting material, when considering color purity, luminous efficiency, and driving durability. The $S_1$ of the material in the film state used in the electron blocking layer is preferably 0.1 eV or more, more preferably 0.2 eV or more, and most preferably 0.3 eV or more than the $S_1$ of the light emitting material.

(B) Organic layer favorably disposed between the cathode and the light emitting layer Next, (B) the organic layer that is preferably disposed between the cathode and the light emitting layer is described.

(B-1) Electron Injection Layer, Electron Transport Layer

The electron injection layer and the electron transport layer are layers that have the functionality to receive the electron from the cathode or the cathode side and transport the electron to the anode side. The electron injection material and the electron transporting material used in these layers can be a low molecular weight compound or a high molecular weight compound.

For example, the compound represented by the aforementioned general formula (1) can be used as the electron transporting material. Other electron transporting materials are preferably selected from pyridine derivatives, quinoline derivatives, pyrimidine derivatives, pyrazine derivatives, phthalazine derivatives, phenathroline derivatives, triazine derivatives, triazole derivatives, oxazole derivatives, oxadiazole derivatives, imidazole derivatives, benzimidazole derivatives, imidazopyridine derivatives, fluorenone derivatives, anthraquinodimethane derivatives, anthrone derivatives, diphenylquinone derivatives, thiopyrandioxide derivatives, carbodiimide derivatives, fluorenylidenemethane derivatives, distyrylpyrazine derivatives, aromatic tetracarboxylic anhydrides such as naphthalin, perylene, and the like, metallic complexes of phthalocyanine derivatives and 8-quinolinol derivatives, various types of metallic complexes represented by metallic complexes with metal phthalocyanine, benzoxazole, and benzothiazole as ligands, organosilane derivatives represented by silole, and condensed hydrocarbon compounds such as naphthalene, anthracene, phenanthrene, triphenylene, and pyrene, but any of pyridine derivatives, benzimidazole derivatives, imidazopyridine derivatives, metallic complexes, and condensed hydrocarbon compounds are more preferable.

The thickness of the electron injection layer and the electron transport layer is preferably 500 nm or less from the perspective of lowering the driving voltage.

The thickness of the electron transport layer is preferably 1 nm through 500 nm, more preferably 5 nm through 200 nm, and even more preferably 10 nm through 100 nm.

Furthermore, the thickness of the electron injection layer is preferably 0.1 nm to 200 nm, more preferably 0.2 nm to 100 nm, and even more preferably 0.5 nm to 50 nm.

The electron injection layer and the electron transport layer can be a single layer structure formed by one or two types of materials described above, or a multilayer structure formed by a plurality of layers with the same composition or with different compositions.

An electron donating dopant is preferably included in the electron injection layer. Including the electron donating dopant into the electron injection layer has effects such as improved electron injection, lower driving voltage, improved efficiency, and the like. Organic materials or inorganic materials can be used as the electron donating dopant if the material can produce radical anions when electrons are added to the material to be doped, and examples include dihydroimidazole compounds such as tetrathiafulvalene (TTF), tetrathianaphthacene (TTT), and bis-[1,3 diethyl-2-methyl-1,2-dihydro-benzimidazolyl], as well as lithium and cesium.

The electron donating dopant in the electron injection layer is preferably 0.01 mass % through 50 mass %, more preferably 0.1 mass % through 40 mass %, and even more preferably 0.5 mass % through 30 mass %, based on the total mass of all compounds that form the electron injection layer.

(B-2) Electron Hole Blocking Layer

The electron hole blocking layer is the layer that has the functionality to prevent electron holes that are transported from the anode side to the light emitting layer from passing through to the cathode side. In the present invention, the electron hole blocking layer can be provided as the organic layer adjacent to the light emitting layer on the cathode side.

The $S_1$ energy in a film state that configures the electron hole blocking layer is preferably higher than the $S_1$ energy of the light emitting material to prevent the energy transfer of an exciton produced in the light emitting layer and to prevent the luminous efficiency from decreasing.

An example of the organic compound that forms the electron hole blocking layer can be the compound represented by the aforementioned general formula (1).

Examples of other organic compounds that configure the electron hole blocking layer other than the compounds represented by the aforementioned general formula (1) are aluminium (III) bis(2-methyl-8-quinolinato) 4-phenyl phenolate (Aluminum (III) bis(2-methyl-8-quinolinato) 4-phenylphenolate (abbreviated as BAlq)) and other aluminium complexes, and triazole derivatives, 2,9-dimethyl-4,7-diphenyl-1,10-phenanthroline (abbreviated as BCP), and other phenanthroline derivatives.

The thickness of the electron hole blocking layer is preferably 1 nm to 500 nm, preferably 3 nm to 100 nm, and even more preferably 5 nm to 50 nm.

The electron hole blocking layer can be a single layer structure formed by one or two types of materials described above, or a multilayer structure formed by a plurality of layers with the same composition or different composition.

For the material used in the electron hole blocking layer, using a material with higher $S_1$ energy than the $S_1$ energy of the aforementioned light emitting material is preferable considering color purity, luminous efficiency, and driving durability. The $S_1$ of the material in the film state used in the electron hole blocking layer is preferably 0.1 eV or more, more preferably 0.2 eV or more, and even more preferably 0.3 eV or more, than the $S_1$ of the light emitting material.

(B-3) Material Most Favorably Used as the Organic Layer Favorably Placed Between the Cathode and the Light Emitting Layer As the (B) material that is most favorably used as the organic layer that is favorably placed between the cathode and the light emitting layer, the organic electroluminescent element of the present invention can be the compound represented by the aforementioned general formula (1), the compound represented by the following general formula (P-1), or the compound represented by the following general formula (O-1).

The compound represented by the general formula (O-1) and the compound represented by the general formula (P-1) are described below.

In the organic electroluminescent element of the present invention, including at least one layer of the organic layer between the light emitting layer and the cathode is preferable, and including at least one type of compound represented by the general formula (O-1) below into the organic layer is preferable from the perspective of efficiency and driving voltage of the element. The general formula (O-1) is described below.

[Formula 75]

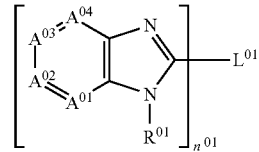

General Formula (O-1)

(In general formula (O-1), $R^{O1}$ represents an alkyl group, aryl group, or heteroaryl group. $A^{O1}$ through $A^{O4}$ independently represent a C—$R^A$ or a nitrogen atom. $R^A$ represents a hydrogen atom, an alkyl group, an aryl group, or a heteroaryl group, and a plurality of $R^A$ can be the same or different. $L^{O1}$ represents a bivalent to hexavalent linking group containing an aryl ring or a heteroaryl ring. $n^{O1}$ represents an integer of 2 to 6.)

$R^{O1}$ represents an alkyl group (preferably 1 to 8 carbon atoms), aryl group (preferably 6 to 30 carbon atoms), or heteroaryl group (preferably 4 to 12 carbon atoms), and these groups can also contain a substitution group selected from the aforementioned group of substitution groups A. An aryl group or the heteroaryl group is preferable and an aryl group is more preferable. When the aryl group of $R^{O1}$ contains a substitution group, an alkyl group, aryl group, and cyano group are preferable, an alkyl group and aryl group are more preferable, and an aryl group is most preferable. When the aryl group of the $R^{O1}$ contains a plurality of substitution groups, the plurality of substitution groups can connect to one another and form a 5 or 6 membered ring. The aryl group of $R^{O1}$ is preferably a phenyl group that can contain a substitution group selected from the group of substitution groups A, more preferably a phenyl group which can be substituted with an alkyl group or aryl group, and even more preferably an unsubstituted phenyl group or a 2-phenyl group.

$A^{O1}$ through $A^{O4}$ independently represent $C-R^A$ or a nitrogen atom. Preferably between 0 and 2 of $A^{O1}$ through $A^{O4}$ are nitrogen atoms, and more preferably between 0 and 1 are nitrogen atoms. Preferably all of $A^{O1}$ through $A^{O4}$ are $C-R^A$, or $A^{O1}$ is a nitrogen atom and $A^{O2}$ through $A^{O4}$ are $C-R^A$, more preferably $A^{O1}$ is a nitrogen atom and $A^{O2}$ through $A^{O4}$ are $C-R^A$, and even more preferably $A^{O1}$ is a nitrogen atom, $A^{O2}$ through $A^{O4}$ are $C-R^A$, and all of $R^A$ are hydrogen atoms.

$R^A$ represents an alkyl group (preferably 1 to 8 carbon atoms), aryl group (preferably 6 to 30 carbon atoms), or heteroaryl group (preferably 4 to 12 carbon atoms), and these groups can also have a substitution group selected from the aforementioned group of substitution groups. Furthermore, a plurality of $R^A$ can be the same or different. For $R^A$, an aryl group or a heteroaryl group is preferable, and an aryl group is more preferable.

$L^{O1}$ represents a bivalent to hexavalent linking group containing an aryl ring (preferably with 6 to 30 carbon atoms) or a heteroaryl ring (preferably with 4 to 12 carbon atoms). $L^{O1}$ is preferably an arylene group, heteroarylene group, or aryltriyl group, more preferably a phenylene group, biphenylene group, or benzenetriyl group, and even more preferably a biphenylene group or benzenetriyl group. $L^{O1}$ can contain a substitution group selected from the aforementioned group of substitution groups A, and if containing a substitution group, the substitution group is preferably an alkyl group, aryl group, or cyano group. Specific examples of $L^{O1}$ can include the following.

[Formula 76]

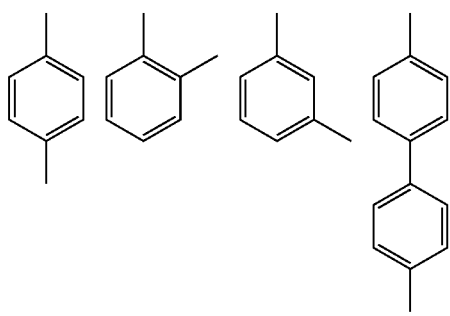

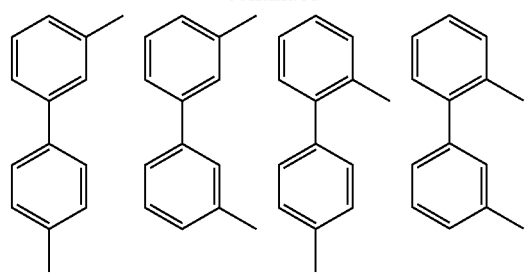

-continued

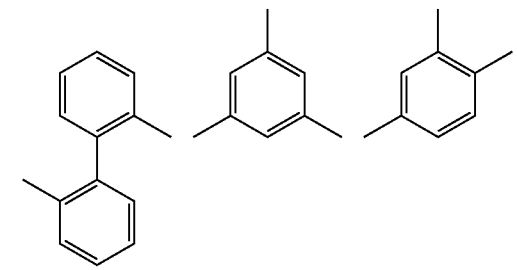

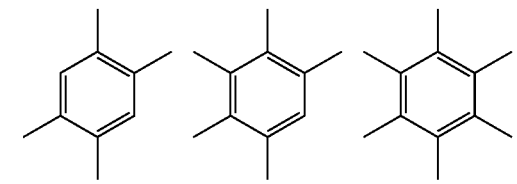

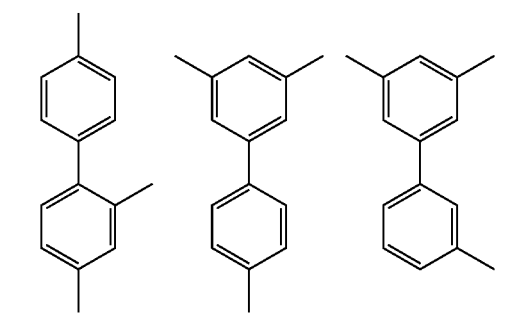

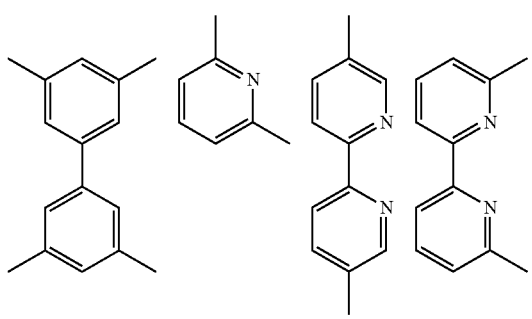

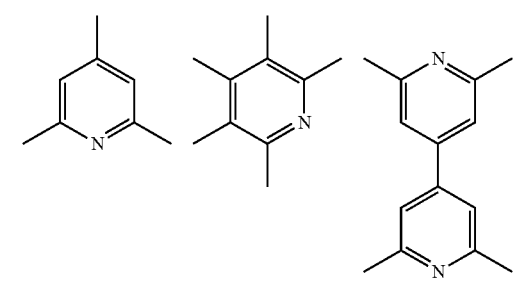

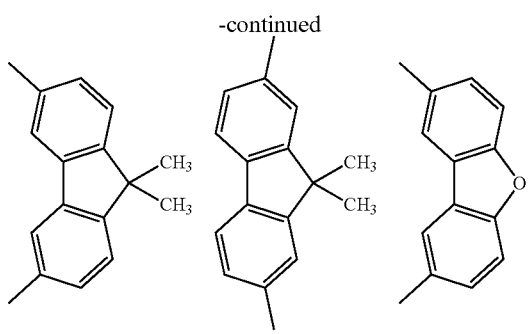

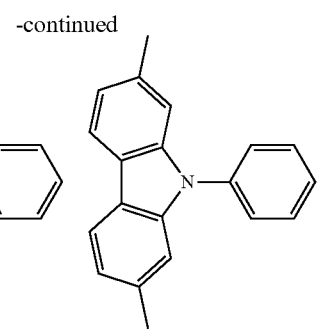

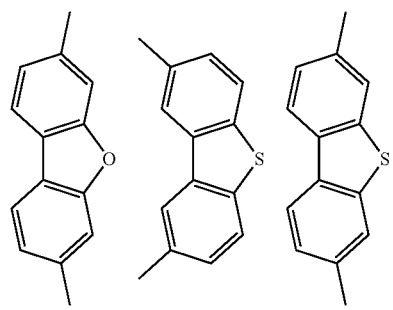

$n^{O1}$ represents an integer of 2 through 6, preferably an integer of 2 through 4, and more preferably 2 or 3. From the perspective of element efficiency, $n^{O1}$ is most preferably 3, and from the perspective of element durability, most preferably 2.

From the perspective of stability during high temperature storage, and stable operation against heating when driving or during high temperature driving, the glass transition temperature (Tg) of the compound represented by the general formula (O-1) is preferably 100° C. through 300° C., more preferably 120° C. through 300° C., even more preferably 120° C. through 300° C., and even more preferably 140° C. through 300° C.

Specific examples of the compound represented by general formula (O-1) are shown below, but the compounds represented by general formula (O-1) that can be used in the present invention should not be interpreted to be limited to these specific examples.

[Formula 77]

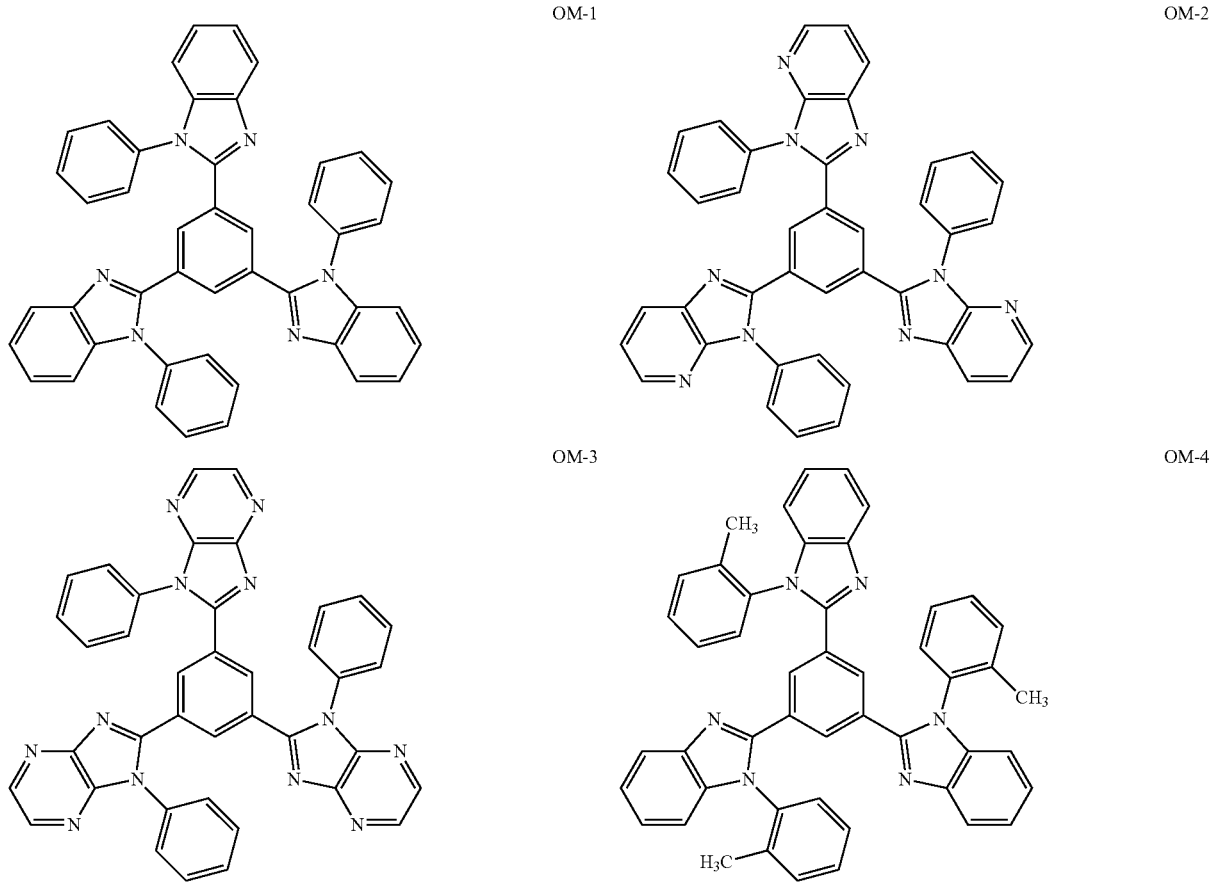

-continued
OM-5
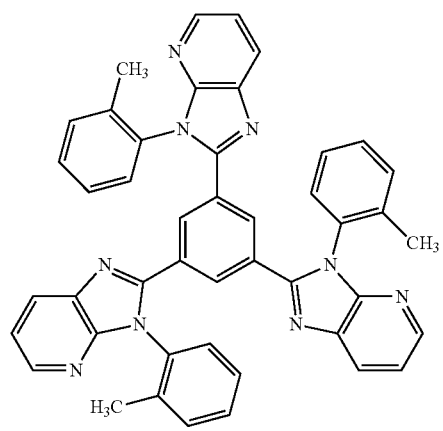
OM-6
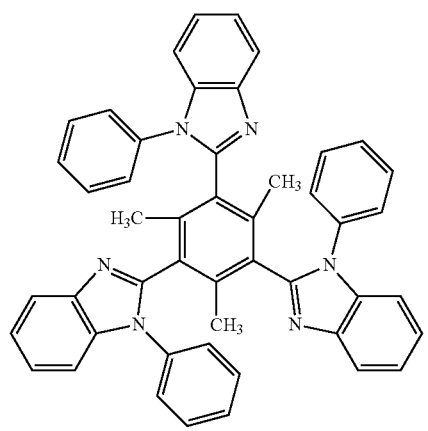
OM-7
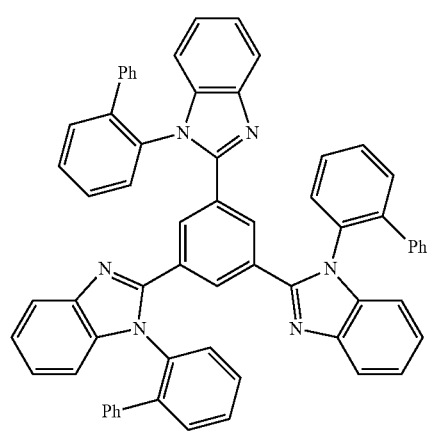
OM-8
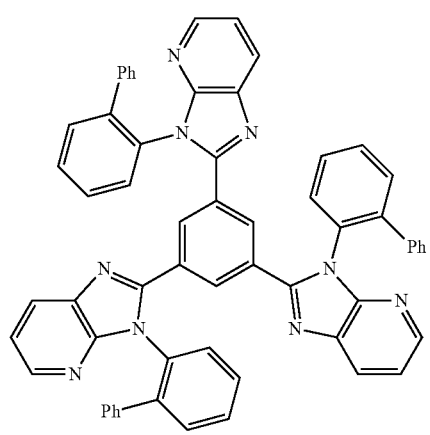
OM-9
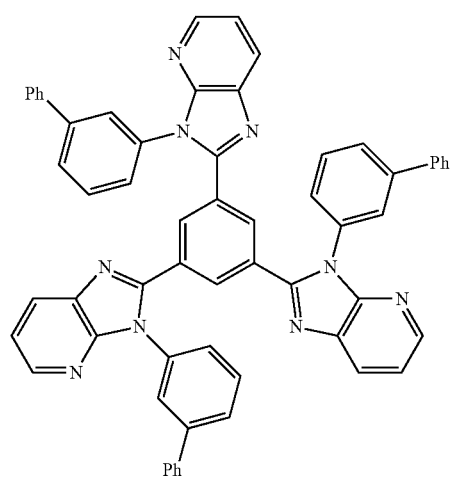

[Formula 78-1]
OM-10
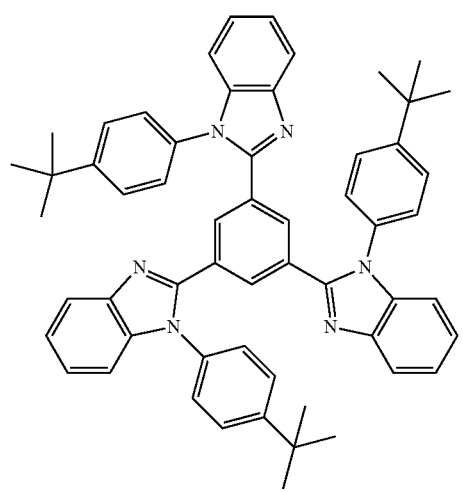
OM-11
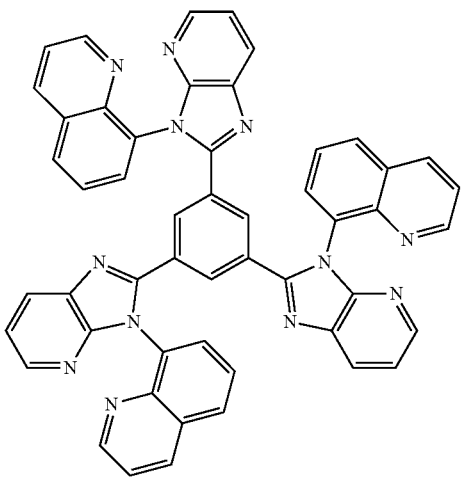
OM-12
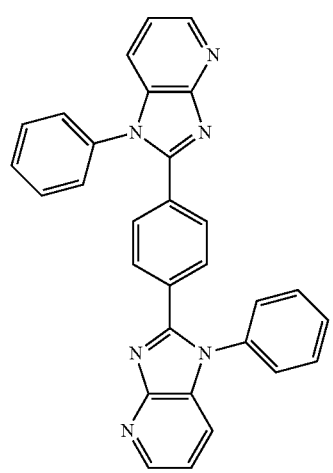
OM-13
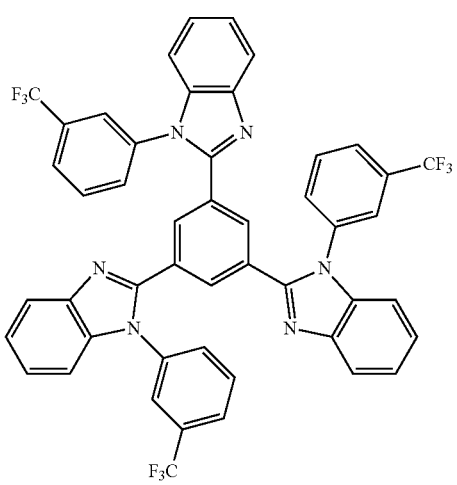
OM-14
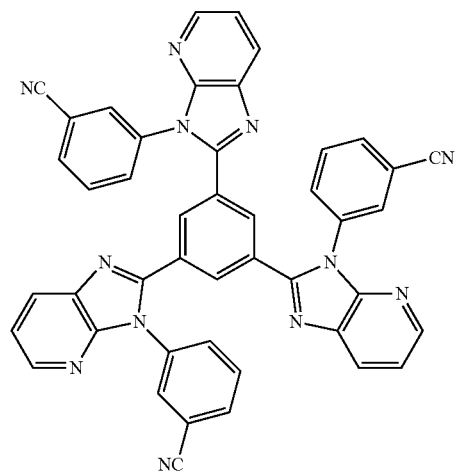
OM-15
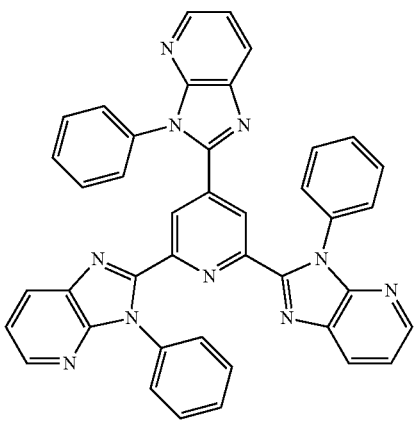

-continued
OM-16
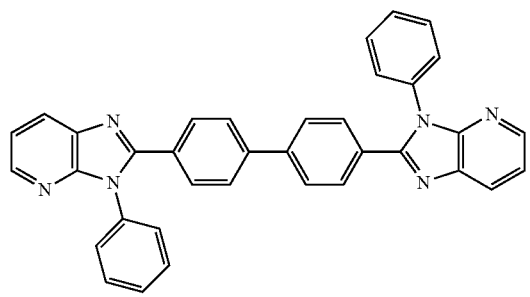
OM-17
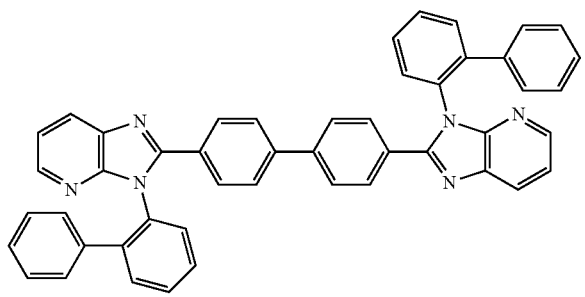
OM-18
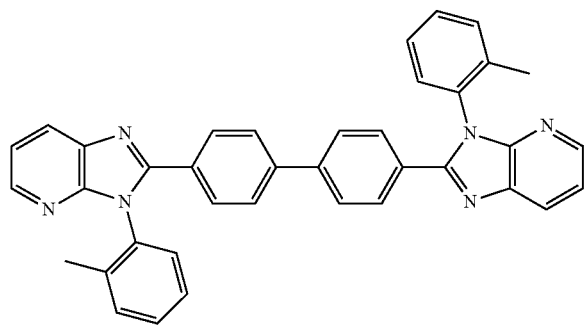
OM-19
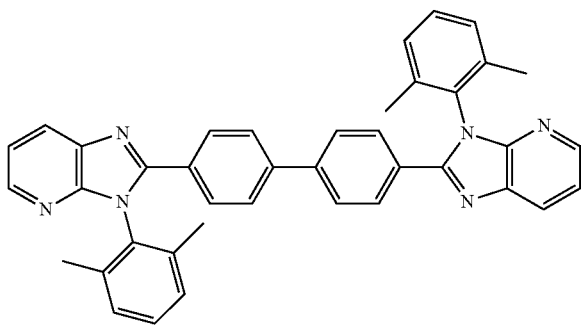
OM-20
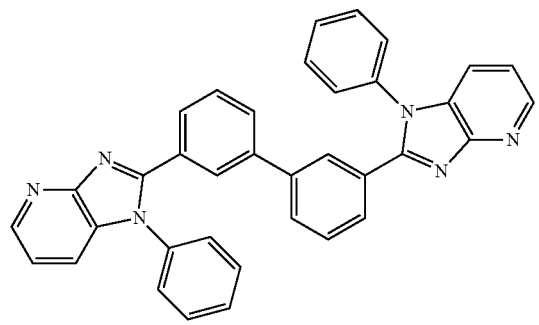
OM-21
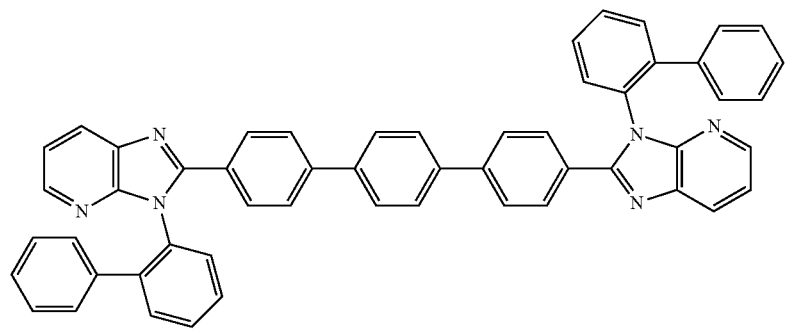
OM-22
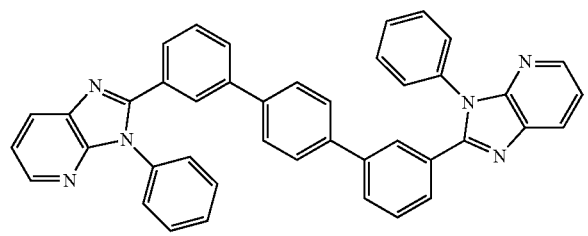

[Formula 78-2]

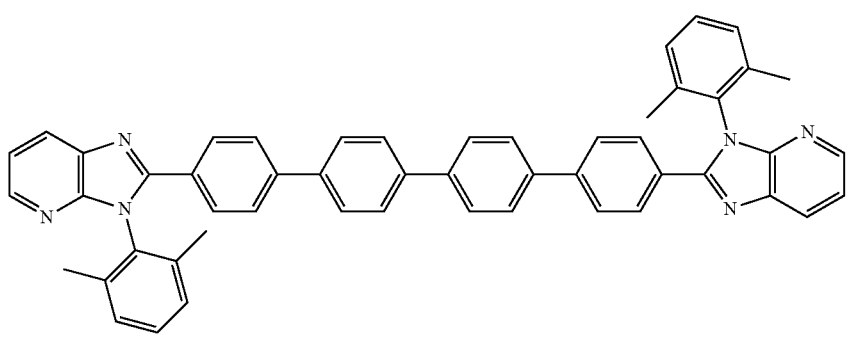

OM-23

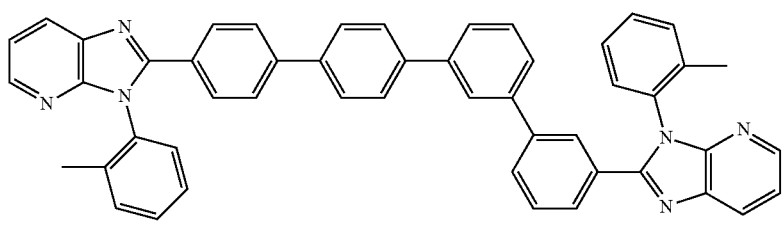

OM-24

The compounds represented by general formula (O-1) can be synthesized using a method described in Japan Unexamined Patent Application 2001-335776. After synthesis, and after purification by column chromatography, recrystallization, and reprecipitation, purification by deposition purification is preferable. Not only can deposition purification separate organic impurities but can also effectively remove inorganic salts, residual solvents, moisture, and the like.

In the organic electroluminescent element of the present invention, the compound represented by general formula (O-1) is preferably included into the organic layer between the light emitting layer and the cathode, but more preferably included into the layer on the cathode side that is adjacent to the light emitting layer.

The amount of the compound represented by general formula (O-1) is preferably 70 to 100 mass %, and more preferably 85 to 100 mass %, based on the total mass of the added organic layer.

In the organic electroluminescent element of the present invention, including at least one layer of the organic layer between the light emitting layer and the cathode is preferable, and including at least one type of compound represented by the following general formula (P) into the organic layer is preferable from the perspective of efficiency and driving voltage of the element. General formula (P) is described below.

[Formula 79]

General Formula (P)

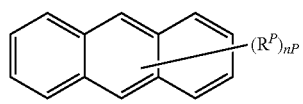

In general formula (P), $R^P$ represents an alkyl group (preferably with 1 to 8 carbon atoms), an aryl group (preferably with 6 to 30 carbon atoms), or a heteroaryl group (preferably with 4 to 1 carbon atoms), and these groups can have a substitution group selected from the aforementioned group of substitution groups.

nP represents an integer of 0 through 4, and if plural, the plurality of $R^P$ may be the same or different. At least one of $R^P$ is a substitution group represented by the general formula (P-1) through (P-5) below.

[Formula 80]

General Formula (P-1)

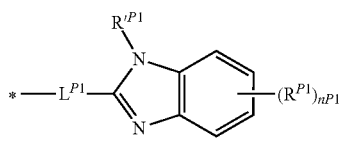

General Formula (P-2)

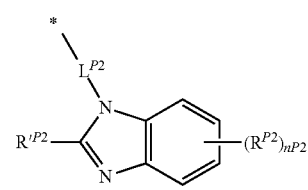

General Formula (P-3)

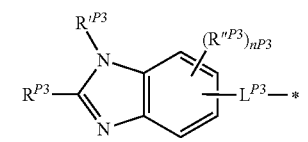

General Formula (P-4)

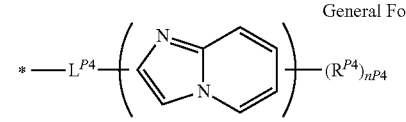

General Formula (P-5)

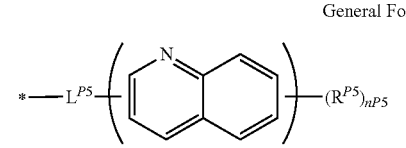

General formula (P-4) is preferably the following general formula (P-4').

[Formula 81]

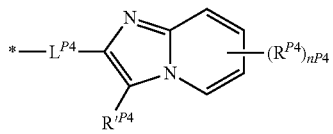

General Formula (P-4')

General formula (P-5) is preferably the following general formula (P-5').

[Formula 82]

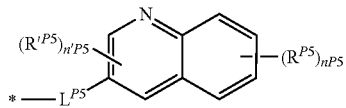

General Formula (P-5')

(In general formula (P-1) through (P-5), $R^{P1}$ through $R^{P5}$, through $R'^{P3}$, $R'^{P5}$, and $R''^{P3}$ each represent an alkyl group (preferably 1 to 8 carbon atoms), aryl group (preferably 6 to 30 carbon atoms), or heteroaryl group (preferably 4 to 12 carbon atoms), and these can contain the substitution group selected from the aforementioned group of substitution groups A. $n^{P1}$ through $n^{P2}$, $n^{P4}$, and $n^{P5}$ represent an integer 0 through 4, $n^{P3}$ and $n^{P5}$ represent an integer 0 through 2, and if $R^{P1}$ through $R^{P5}$, $R'^{P1}$ through $R'^{P3}$, $R'^{P5}$, and $R''^{P3}$ are a plurality, these groups can be the same or different. $L^{P1}$ through $L^{P5}$ represent a single bond or either an aryl ring or heteroaryl ring that form a bivalent linking group.

* represents a site for bonding to the anthracene ring of general formula (P).)

For $R^P$, a substitution group other than the substitution group represented by (P-1) through (P-5) is preferably an aryl group, more preferably any of a phenyl group, biphenyl group, terphenyl group, and naphthyl group, and is even more preferably a naphthyl group. $R^{P1}$ through $R^{P5}$, $R'^{P1}$ through $R'^{P3}$, $R'^{P5}$, and $R''^{P3}$ are preferably either an aryl group or heteroaryl group, more preferably an aryl group, even more preferably any of a phenyl group, biphenyl group, terphenyl group, and naphthyl group, and most preferably a phenyl group. $L^{P1}$ through $L^{P5}$ are preferably either a single bond or aryl ring that forms a bivalent linking group, more preferably any of a single bond, phenylene, biphenylene, terphenylene, or naphthylene, and even more preferably any of a single bond, phenylene, and naphthylene.

Specific examples of the compound expressed by general formula (P) are exemplified below, but the compound expressed by general formula (P) that can be used in the present invention should not be interpreted as to be restricted to these specific examples.

[Formula 83]

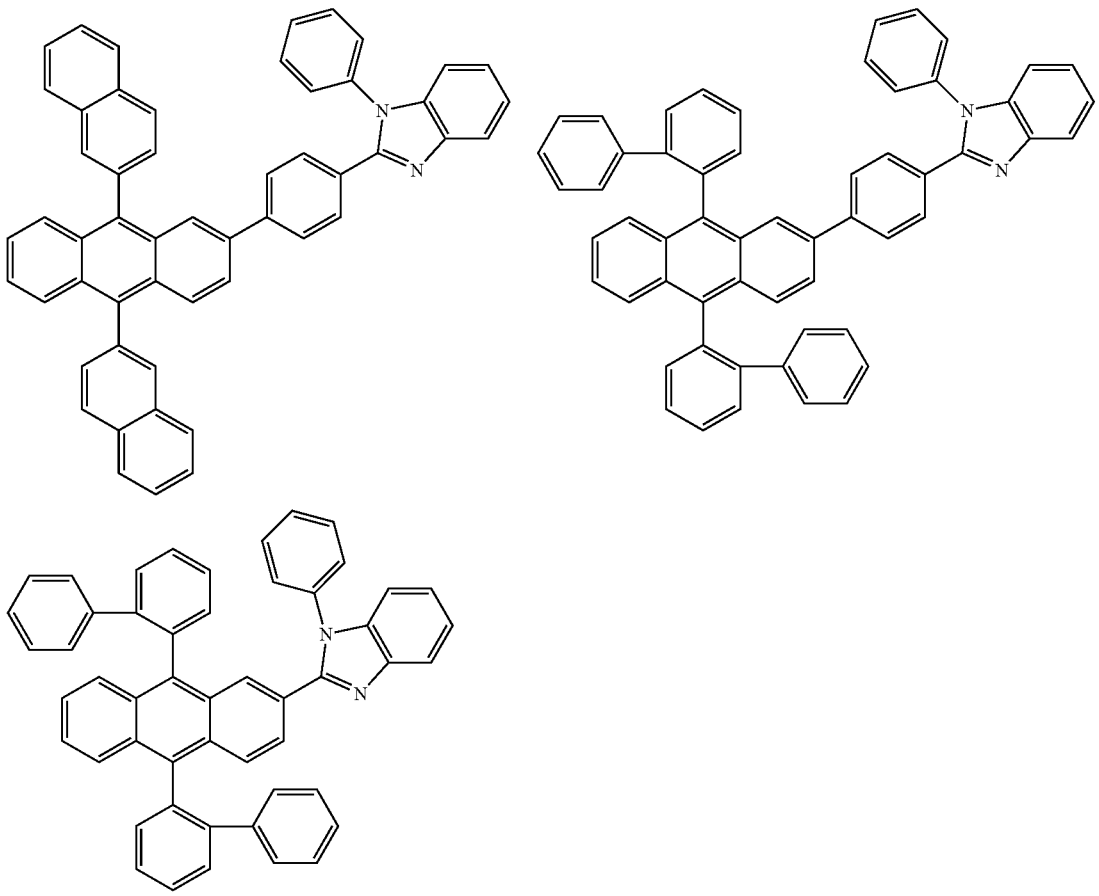

-continued
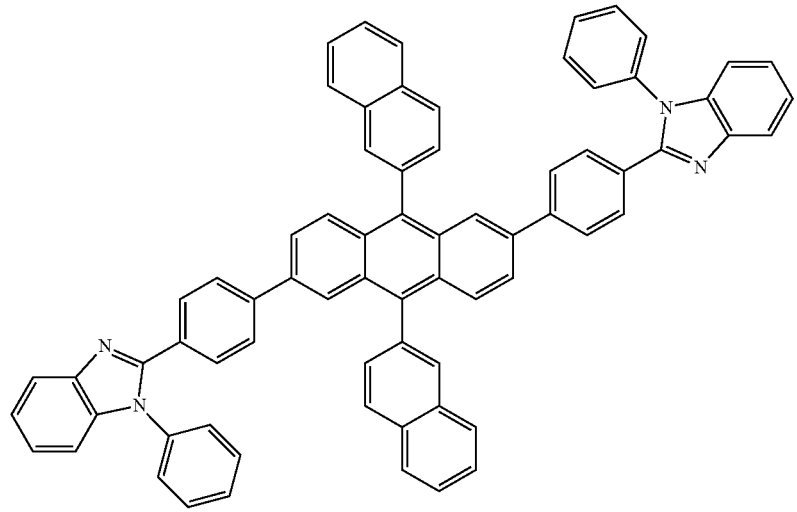
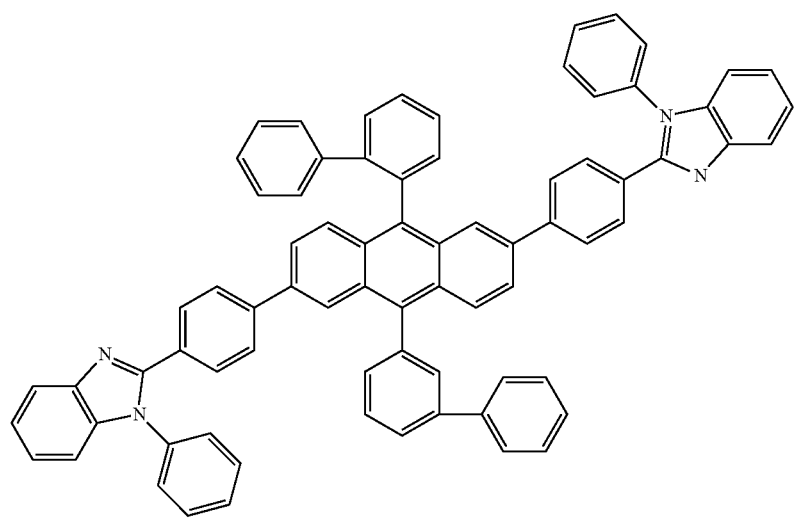
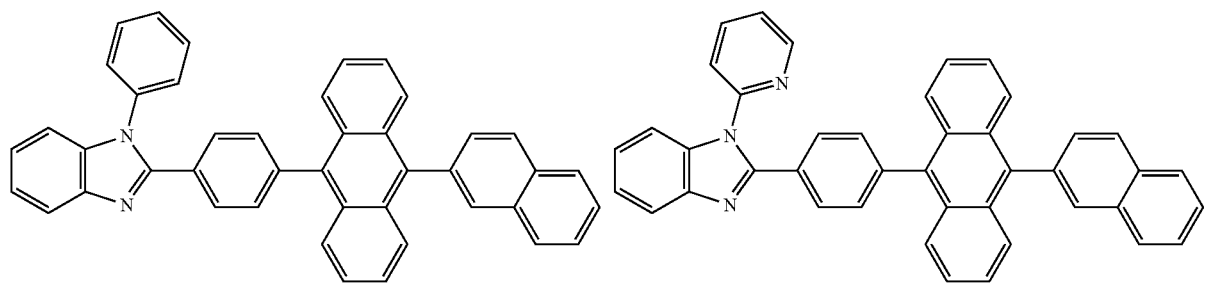
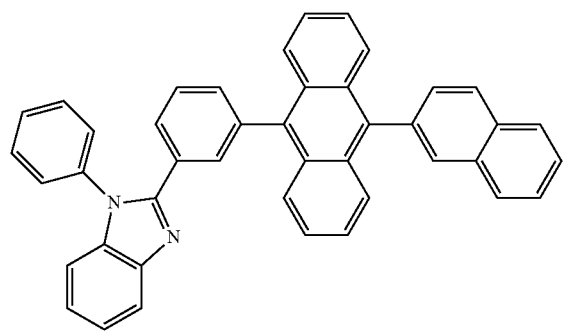

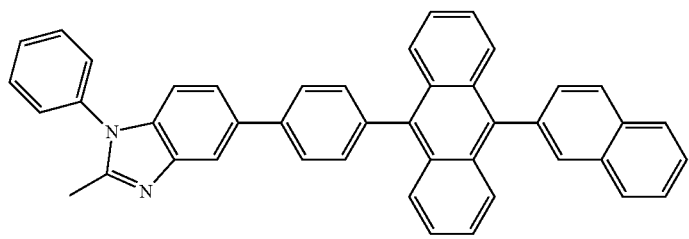
[Formula 84]
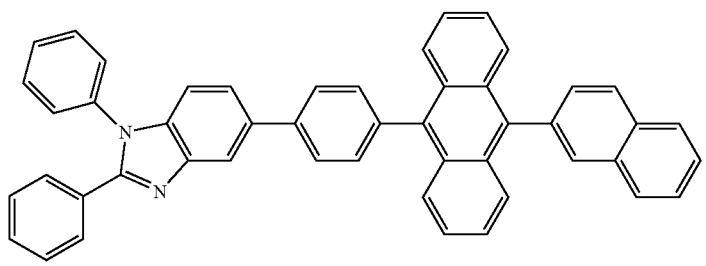
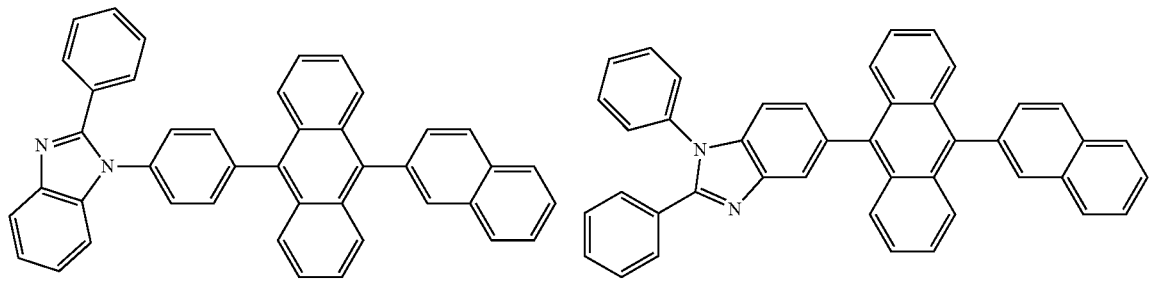
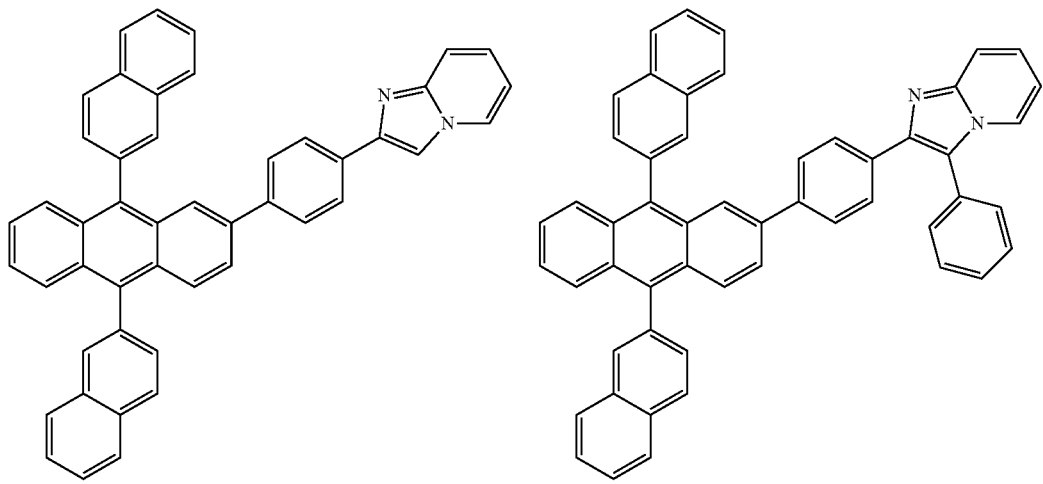

-continued
201
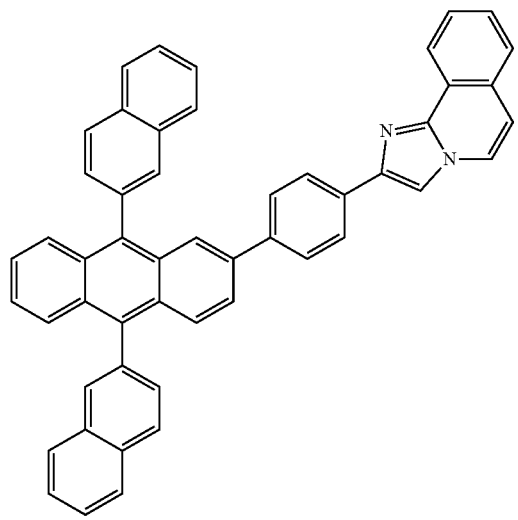
202
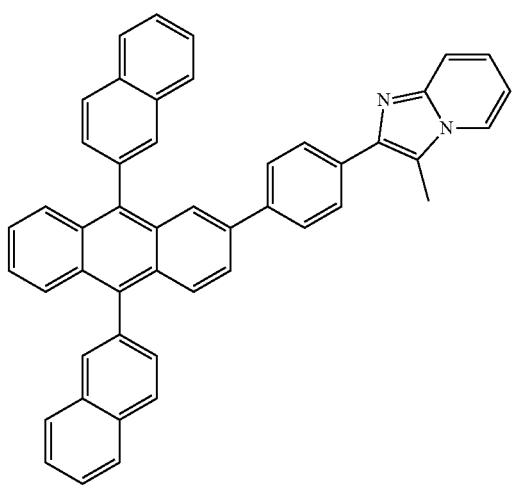
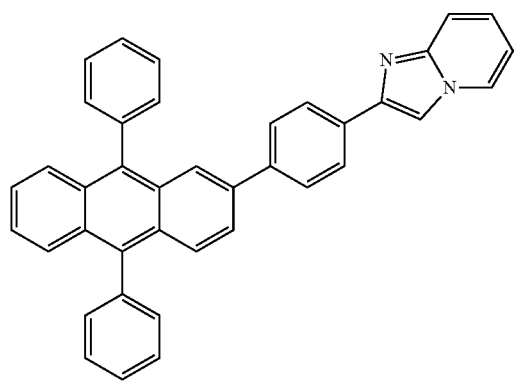
[Formula 85]
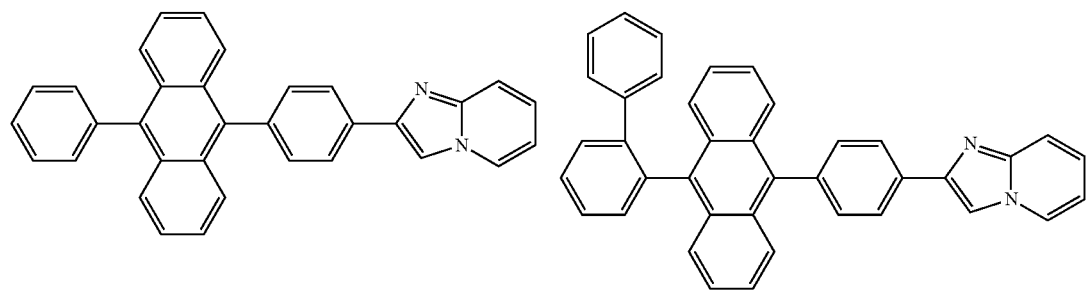
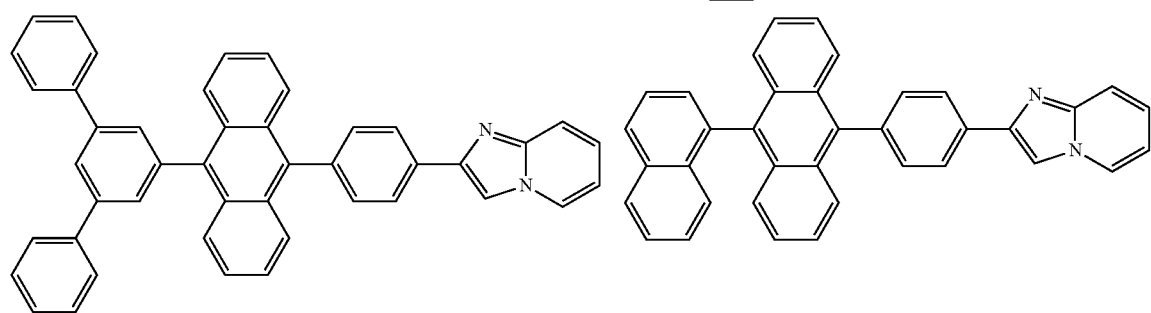

203 204
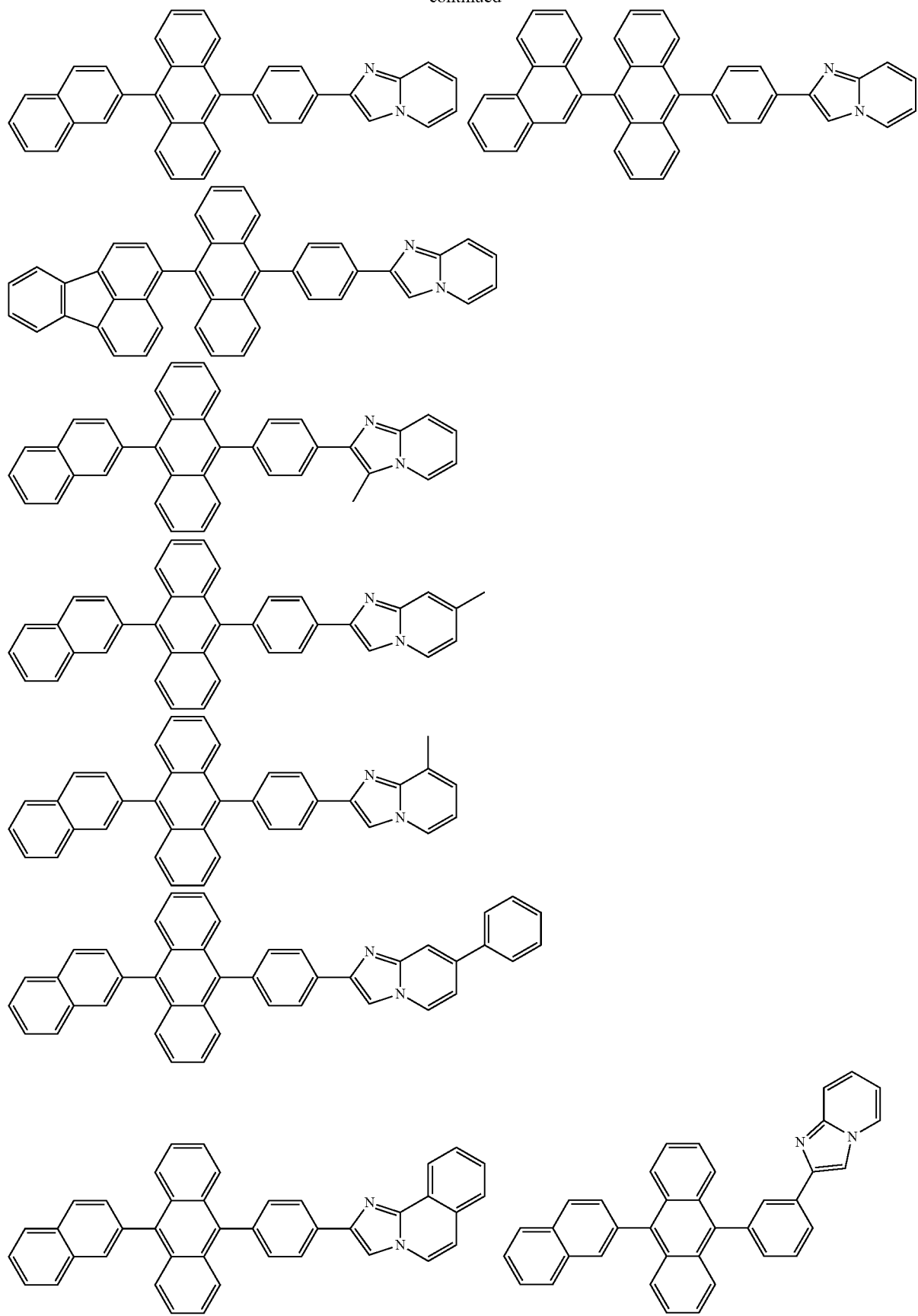
-continued

-continued
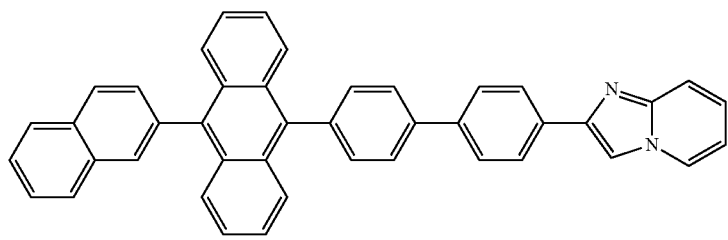
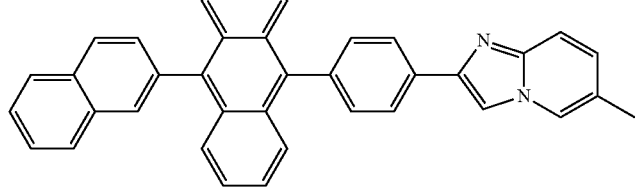
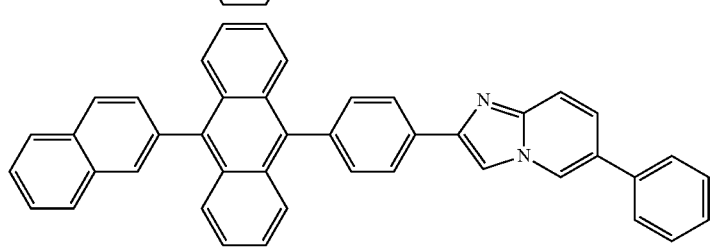
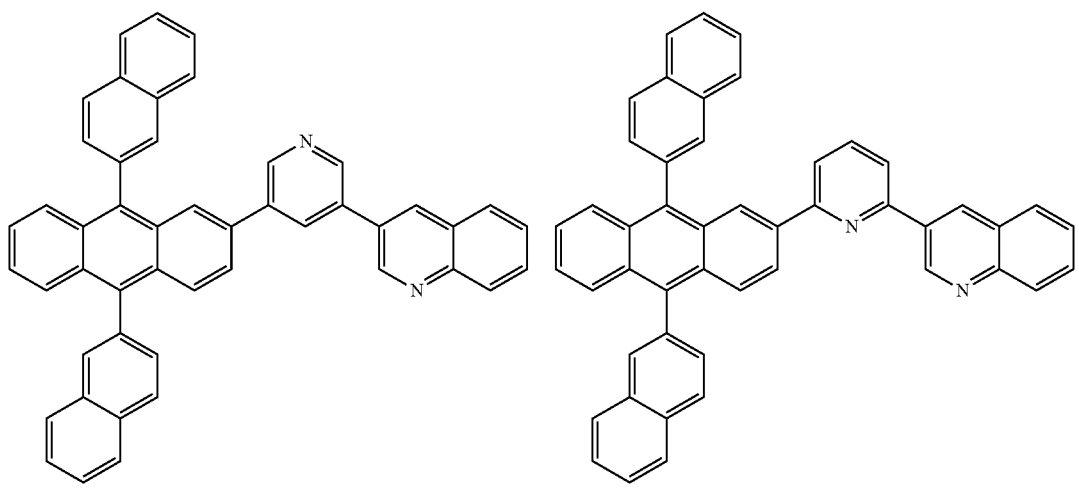
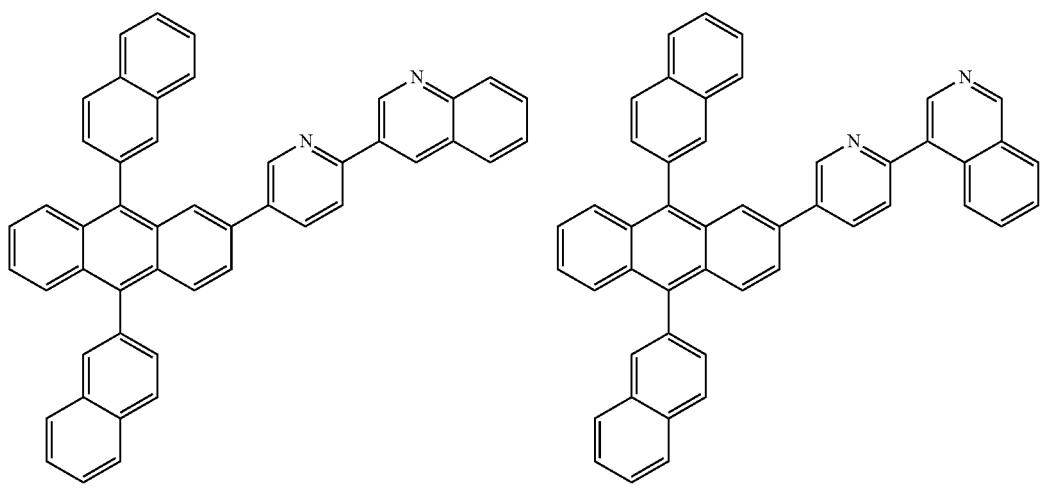

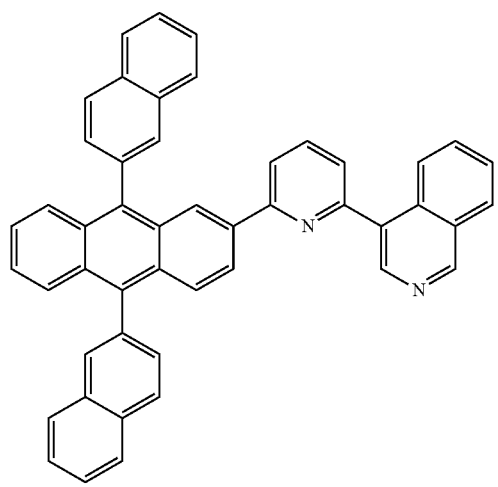
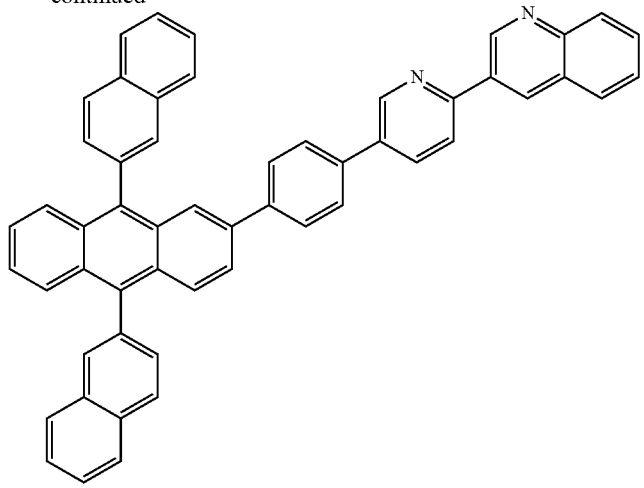

The compound expressed by general formula (P) can be synthesized by the method disclosed in WO 2003/060956 or WO 2004/080975. After synthesizing, purification is performed by column chromatography, recrystallization, reprecipitation, or the like, and then purification is preferably performed by sublimation purification. Not only can organic impurities be separated, but inorganic salt, residual solvents, water, and the like can be effectively removed by sublimation purification.

In the organic electroluminescent element of the present invention, the compound expressed by general formula (P) preferably is included in the organic layer between the light emitting layer and the cathode, but is more preferably included in the layer adjacent to the cathode. The compound expressed by the general formula (P) is preferably included at a level of 70 to 100 mass % with regards to the total mass of the added organic layer, and are more preferably included at a level of 85 to 100 mass %.

Other materials that can be used as an electron injection layer or an electron transport layer in the organic electroluminescent element, can be, for example, a silole compound described in Japanese Unexamined Patent Application H9-194487 or the like, a phosphine oxide compound described in Japanese Unexamined Patent Application 2006-73581 or the like, an aromatic heterocyclic six-membered ring compound containing nitrogen described in Japanese Unexamined Patent Application 2005-276801, Japanese Unexamined Patent Application 2006-225320, WO2005/085387, and the like, an aromatic heterocyclic 6 membered ring structure containing nitrogen and a compound having a carbazol structure described in WO02003/080760, WO2005/085387, and the like, and an aromatic hydrocarbon compound described in US2009/0009065, WO2010/134350, and Japanese PCT patent application 2010-535806, and the like (naphthalene compound, anthracene compound, triphenylene compound, phenanthrene compound, pyrene compound, fluoranthene compound, and the like).

<Protective Layer>

In the present invention, the organic field element as a whole can be protected by a protective layer. Items described in paragraphs [0169] to [0170] in Japanese Unexamined Patent Application 2008-270736 can be applied to the present invention for the protective layer. Furthermore, the material of the protective layer can be inorganic or organic.

<Sealing Container>

The whole element of the organic electroluminescent element of the present invention can be sealed using a sealing container.

An item described in paragraph [0171] of Japanese Unexamined Patent Application 2008-270736 can be applied to the present invention for the sealing container.

<Driving Method>

The organic electroluminescent element of the present invention can achieve light emission by applying a direct current (frequency component can be included if necessary) voltage (normally 2 to 15 volts) or a constant current between the anode and the cathode.

The driving method described in each specification or the like of Japanese Unexamined Patent Applications H2-148687, H6-301355, H5-29080, H7-134558, H7-134558, H8-234685, H8-241047, U.S. Pat. Nos. 2,784, 615, 5,828,459, and 6,023,308 can be applied for the driving method of the organic electroluminescent element of the present invention.

The external quantum efficiency of the organic electroluminescent element of the present invention is preferably 5% or more, more preferably 6% or more, and even more preferably 7% or more. The maximum value of the external quantum efficiency when an element is driven at 20° C. or the external quantum efficiency of approximately 300 through 400 cd/m$^2$ when an element is driven at 20° C. can be used for the numerical value of the external quantum efficiency.

The internal quantum efficiency of the organic electroluminescent element of the present invention is preferably 30% or higher, more preferably 50% or higher, and even more preferably 70% or higher. The internal quantum efficiency of an element is calculated by dividing the light extraction efficiency of the external quantum efficiency. The light extraction efficiency of a normal organic EL element is approximately 20%, but by improvising the form of the substrate, the form of the electrode, the film thickness of the inorganic layer, the refractive index of the organic layer, the refractive index of the inorganic layer, and the like, the light extraction efficiency can be 20% or more.

<Light Emission Wavelength>

There are no restrictions for the light emission wavelength of the organic electroluminescent element of the present invention, but the element is preferably used for blue or white light emission. Of these, using a compound represented by the aforementioned general equation (1) as the light emitting material and emitting light is preferable, and emitting blue light is more preferable for the organic electroluminescent element of the present invention.

<Application of the Organic Electroluminescent Element of the Present Invention>

The organic electroluminescent element of the present invention can favorably be used for a display element, a display, backlight, electrophotography, an illumination light source, a record light source, an exposure light source, a reading light source, an indicator, a signboard, an interior decoration, or for optical communication. The element can be favorably used especially on devices that are driven at a high range of light emitting brightness such as a light emitting device, an illumination device, a display device, and the like.

[Light Emitting Device]

The light emitting device of the present invention has a characteristic of containing the organic electroluminescent element of the present invention.

The light emitting device of the present invention is described next while referring to FIG. 2.

The light emitting device of the present invention is formed by using the organic electroluminescent element.

FIG. 2 is a cross section diagram that schematically illustrates an example of the light emitting device of the present invention. The light emitting device 20 of FIG. 2 is configured from a transparent substrate (support substrate) 2, an organic electroluminescent element 10, a sealing container 16, and the like.

The organic electroluminescent element 10 is configured with an anode (primary electrode) 3, an organic layer 11, and a cathode (secondary electrode) 9 laminated in that order onto a substrate 2. Furthermore, a protective layer 12 is laminated onto the cathode 12, and moreover, the sealing container 16 is provided through an adhesion layer 14 onto the protective layer 12. Note that a part of each electrode 3 and 9, the diaphragm, the insulating layer, and the like are omitted.

Herein, a light curing adhesive or a heat curing adhesive such as an epoxy resin can be used as the adhesion layer 14, and for example, a thermosetting adhesive sheet can also be used.

There are no particular restrictions for the use of the light emitting device of the present invention, and the device can be an illumination device as well as a display device such as a television, a personal computer, a mobile phone, electronic paper, and the like.

[Lighting Device]

The lighting device of the present invention has a characteristic of containing the organic electroluminescent element of the present invention.

The lighting device of the present invention is described next while referring to FIG. 3. FIG. 3 is a cross section diagram that schematically illustrates an example of the lighting device of the present invention. The lighting device 40 of the present invention has the aforementioned organic EL element 10 and an optical scattering member 30 as illustrated in FIG. 3. More specifically, the lighting device 40 is configured such that the substrate 2 of the organic EL element 10 is in contact with the optical scattering member 30.

The optical scattering member 30 is not particularly restricted as long as the member can scatter light, but in FIG. 3, the optical scattering member has particles 32 dispersed by a transparent substrate 31. A glass substrate can be favorably suggested as the transparent substrate 31. The fine particles 32 are preferably transparent resin fine particles. Any known glass substrate or transparent resin particle can be used. In this illumination device 40, the light emitting from the organic electroluminescent element 10 enters the light incident surface 30A of the scattering member 30, the incident light is scattered by the optical scattering member 30, and the scattered light exits the light exit surface 30B as illumination light.

[Display Device]

The display device of the present invention has a characteristic of containing the organic electroluminescent element of the present invention.

The display device of the present invention can be a television, a personal computer, a mobile phone, electronic paper, and the like.

EXAMPLES

Characteristics of the present invention are described in further detail while citing examples and comparative examples below. Material, consumption, ratio, processing content, procedure, and the like indicated in the examples below can be changed as long as the change does not depart from the spirit of the present invention. Therefore, the scope of the present invention should not be interpreted to be limited to the specific examples indicated below.

The structural formula of the compound used in the examples and the comparative examples are all indicated below.

[Formula 86]

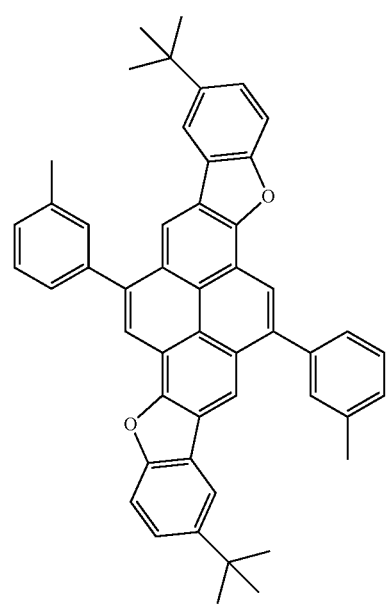

Compound 1

Compound 2
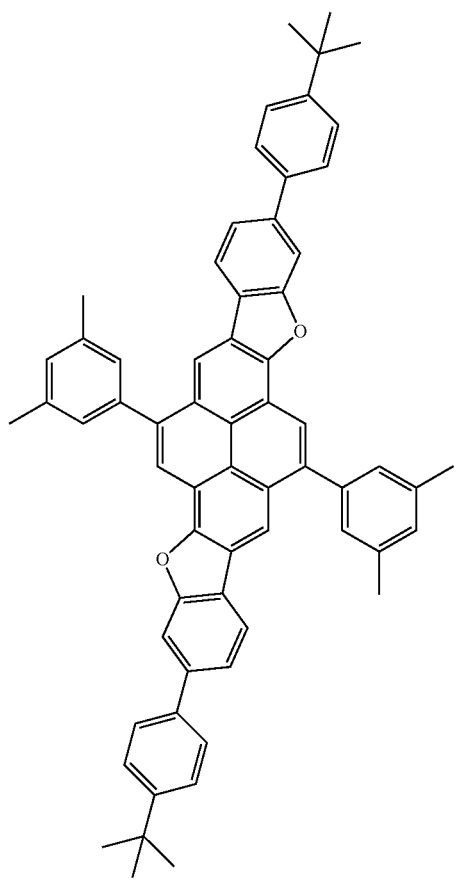
Compound 3
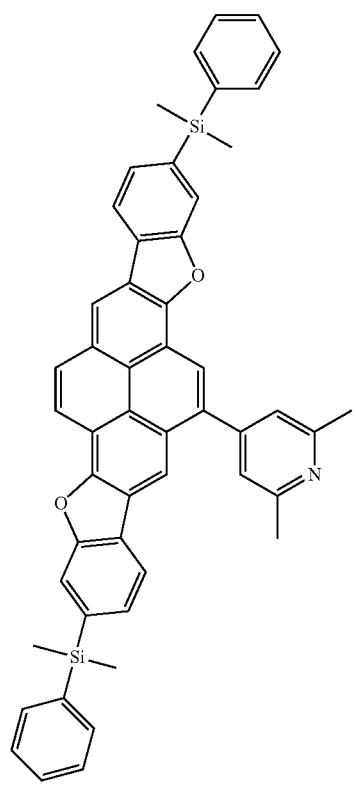
Compound 4
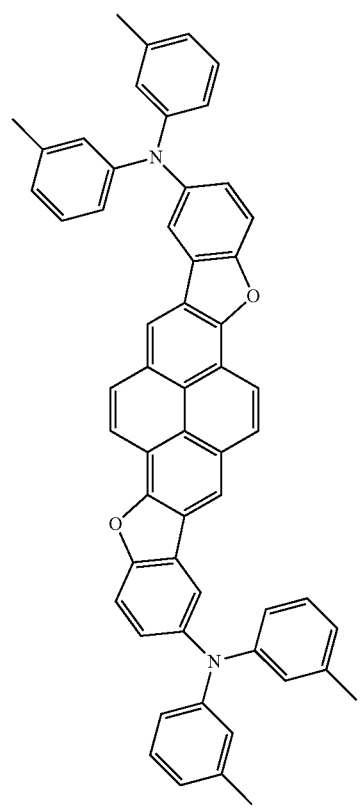
Compound 5
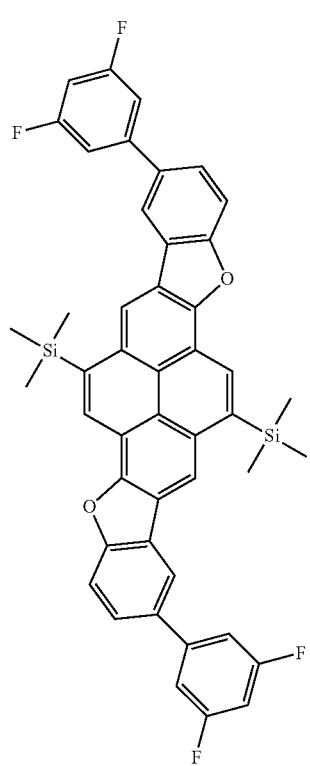

-continued
Compound 6
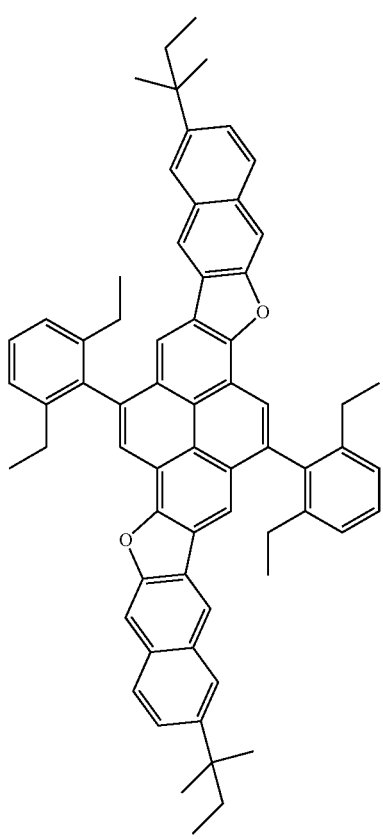
[Formula 87]
Compound 7
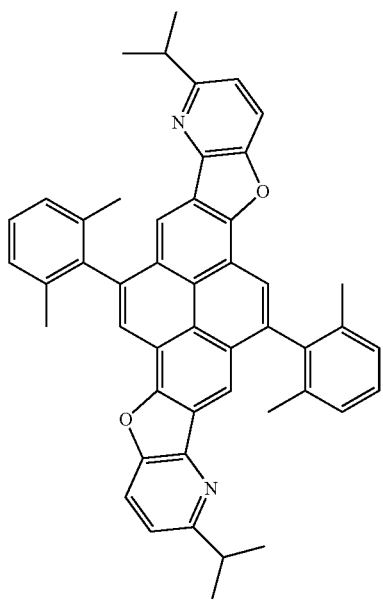
-continued
Compound 8
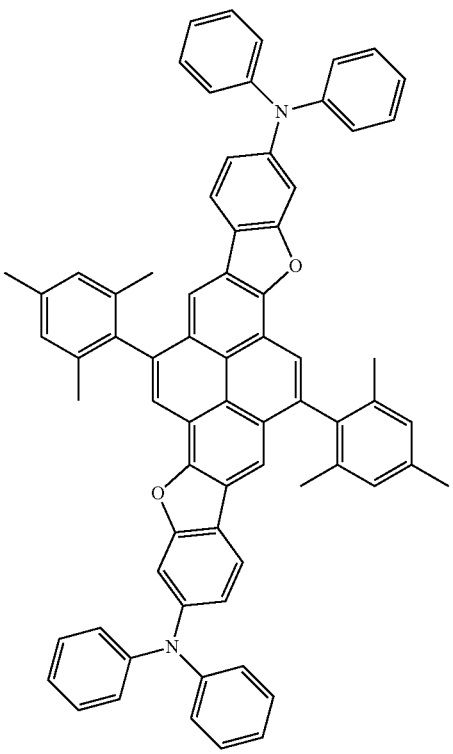
Compound 9
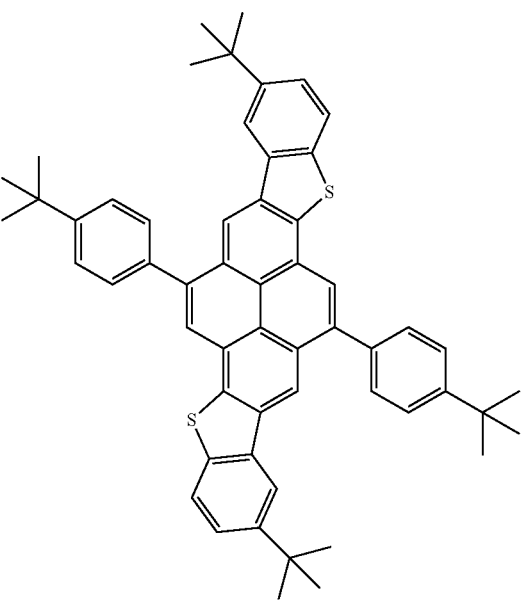

Compound 10
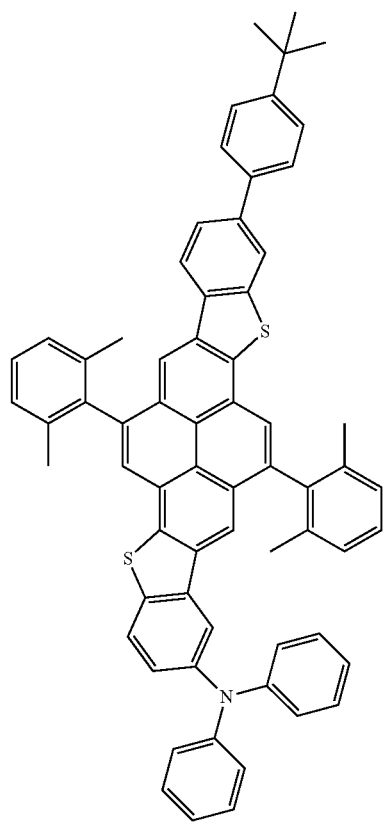
[Formula 88-1]
Compound 12
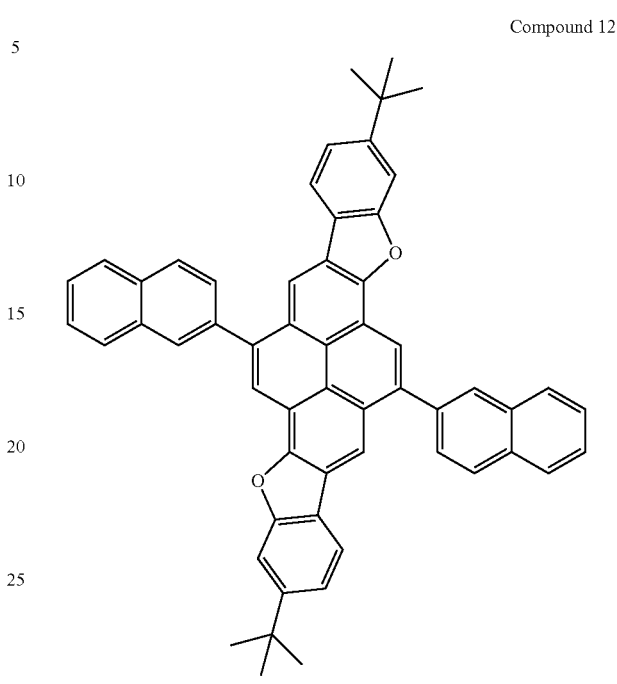
Compound 11
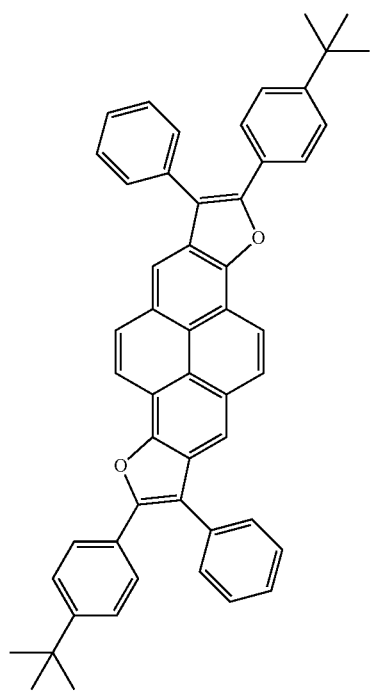
Compound 13
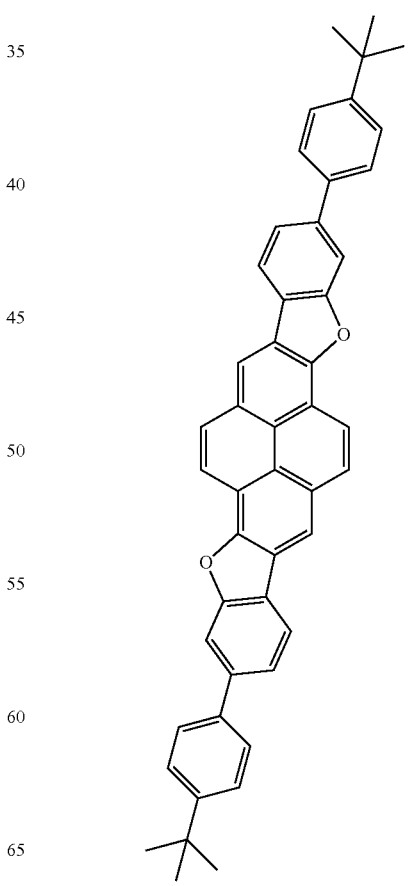

Compound 14
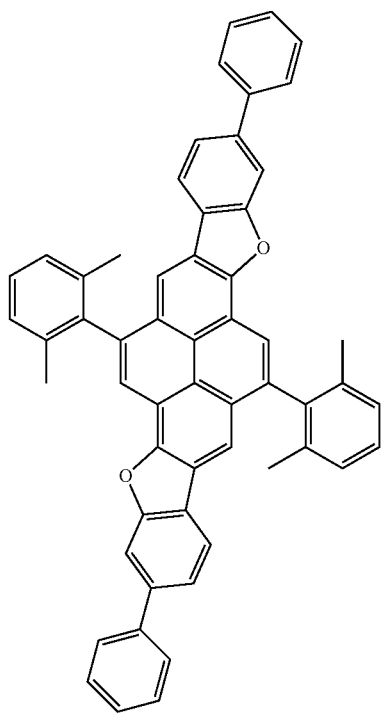
Compound 15
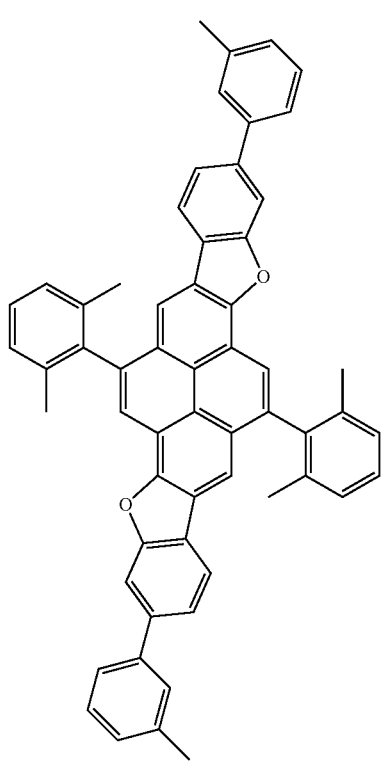
Compound 16
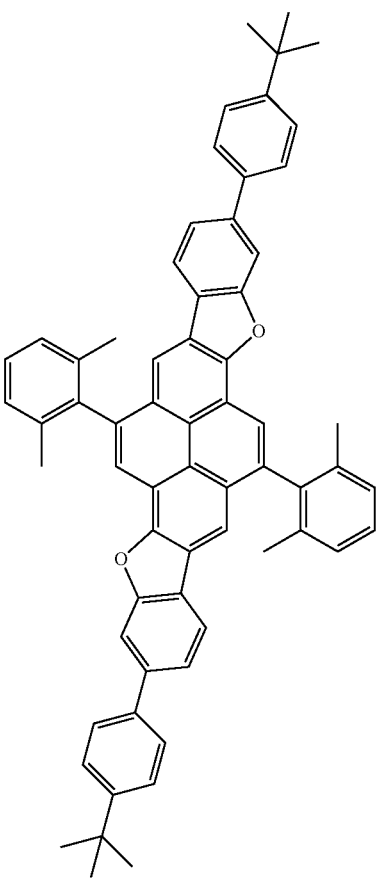
Compoound 17
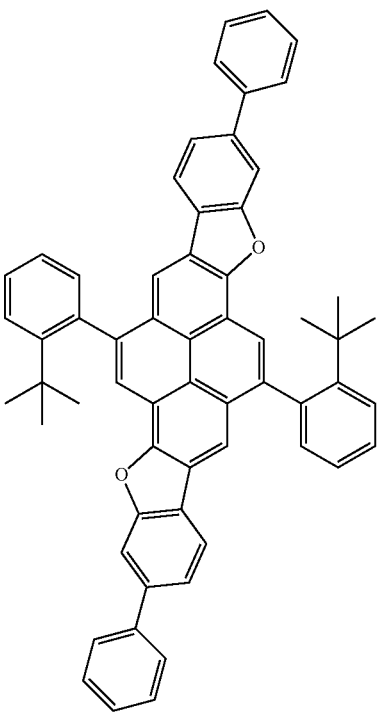

-continued
Compound 18
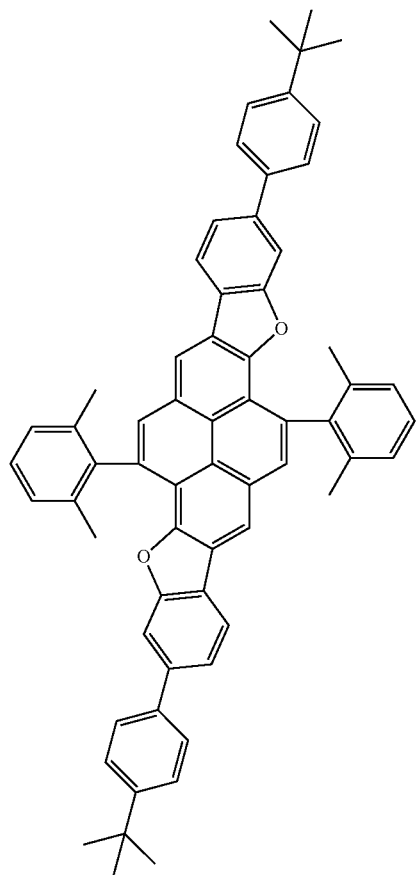
Compound 19
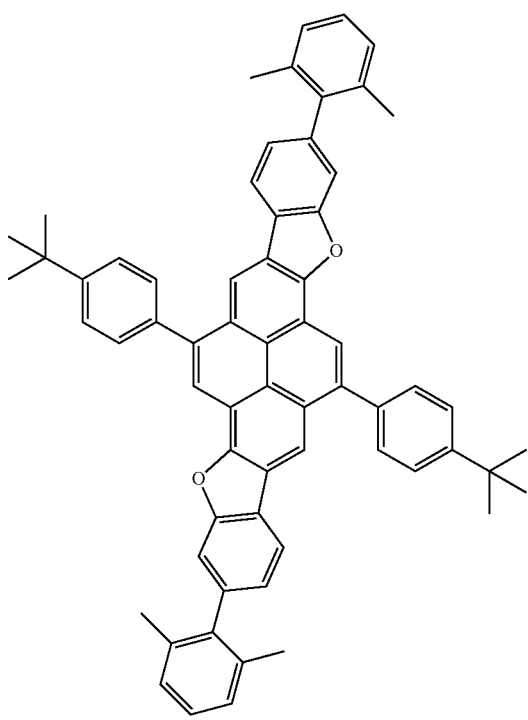
-continued
Compound 20
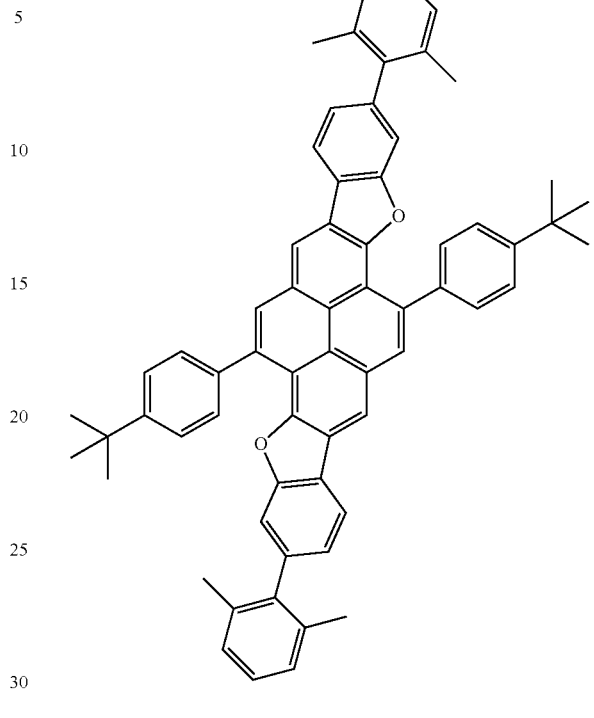
[Formula 88-2]
Compound 21
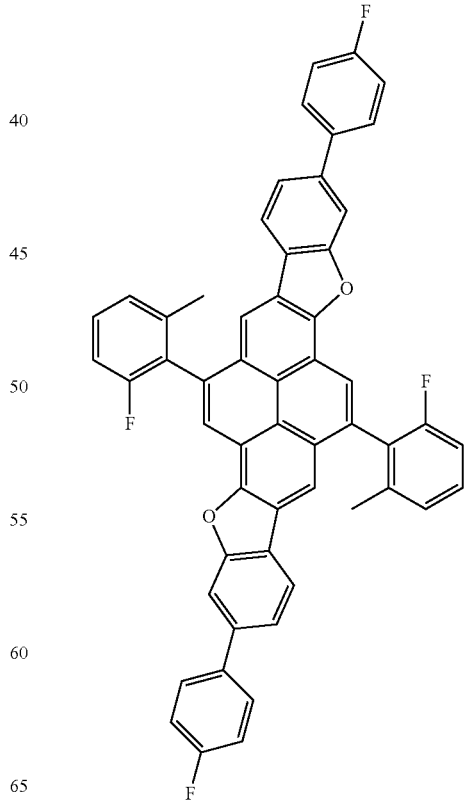

Compound 22
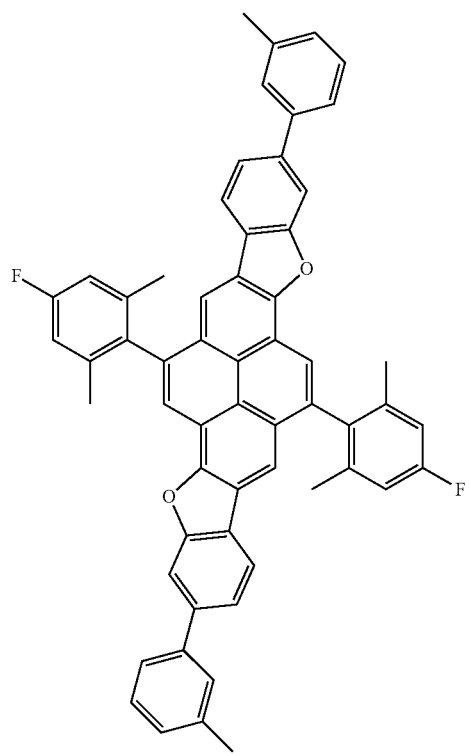
Compound 23
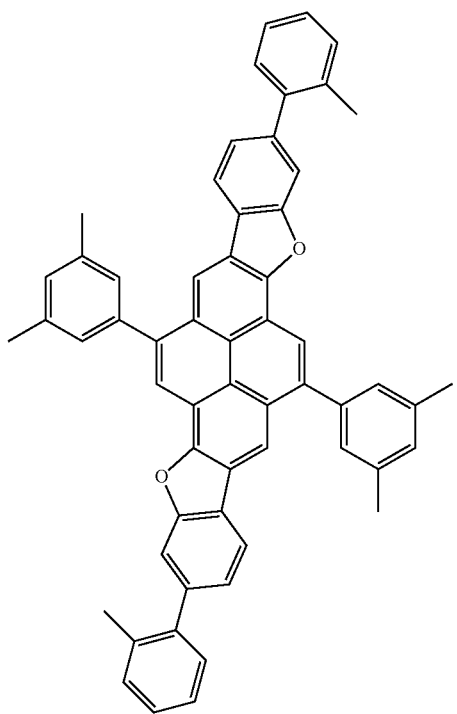
Compound 24
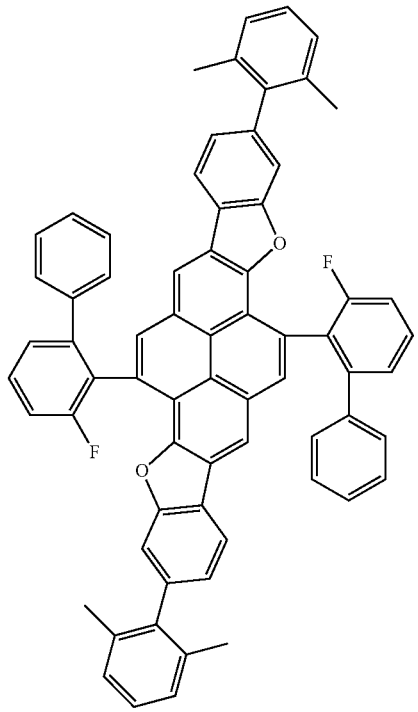
Compound 25
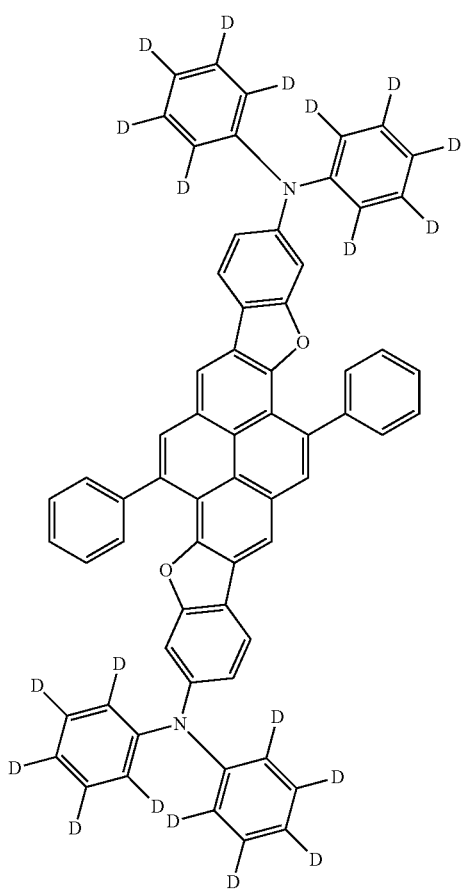

Compound 26
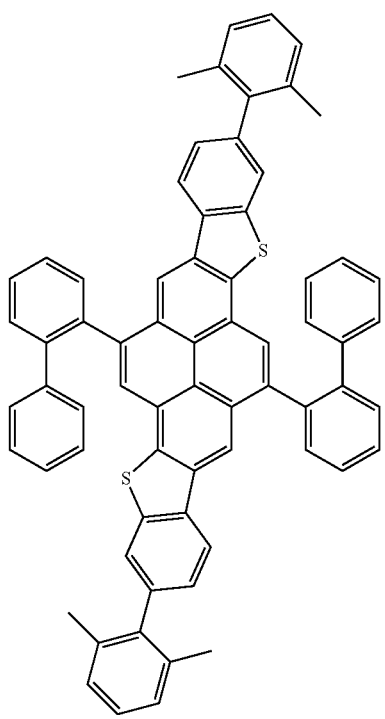
Compound 27
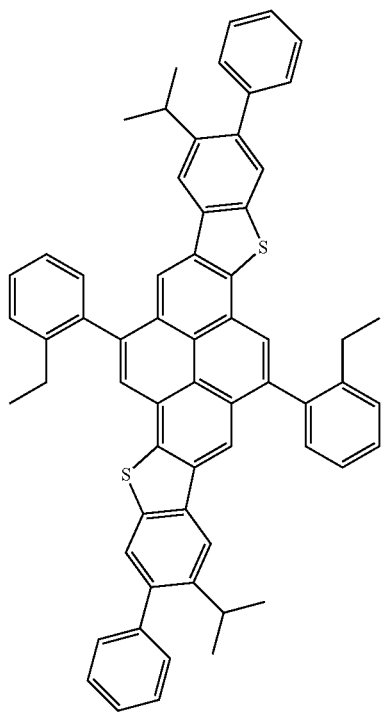
Compound 28
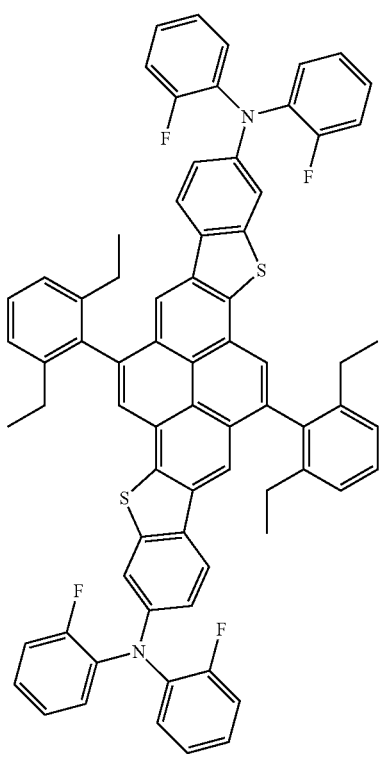
[Formula 89]
Comparative Compound 1
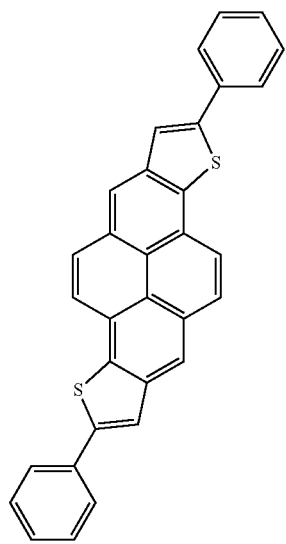

Comparative Compound 2

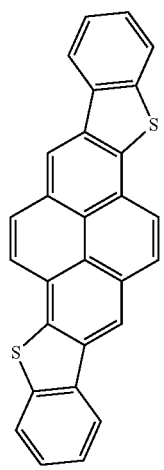

Comparative Compound 3

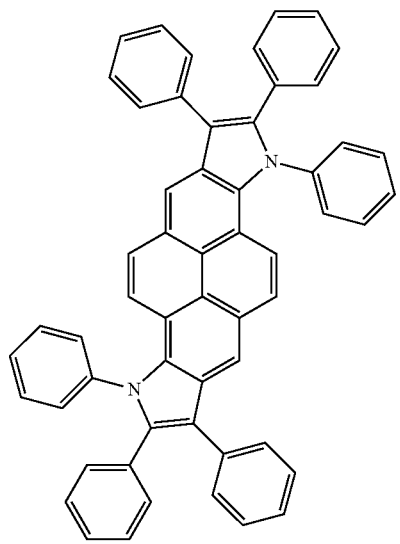

Comparative Compound 4

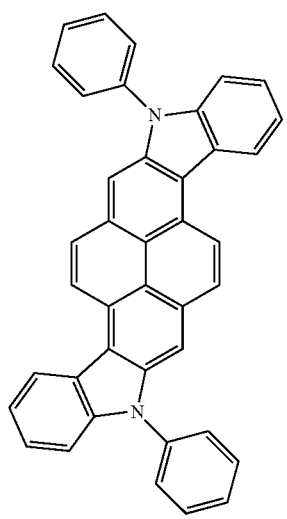

Comparative Compound 5

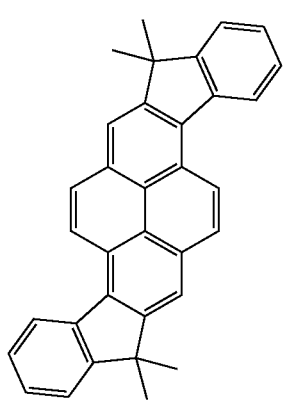

Comparative Compound 6

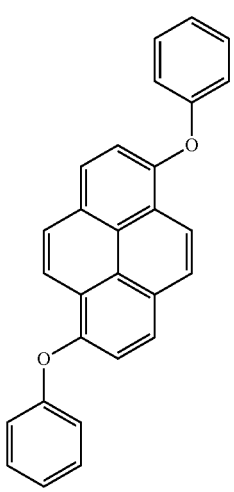

Comparative compound 1 and 2 are compounds described in Japanese Unexamined Patent Application 2010-205986, comparative compound 3 is a compound described in Japanese Unexamined Patent Application 2011-51984, comparative compound 4 is described in Japanese Unexamined Patent Application 2011-205986, KR20110006915, and KR20110041726, comparative compound 5 is a compound described in WO2010012328, and comparative compound 6 is a compound described in Japanese Unexamined Patent Application H2-120747.

[Formula 90]
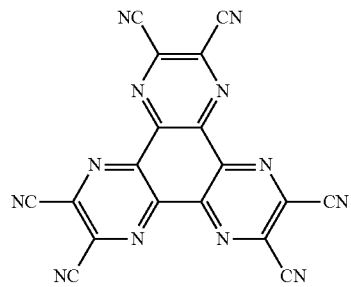
HAT-CN
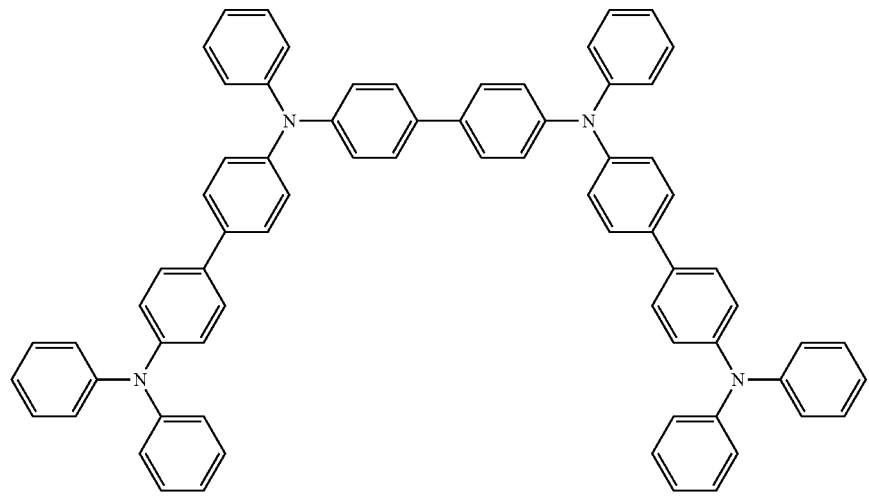
HI-1
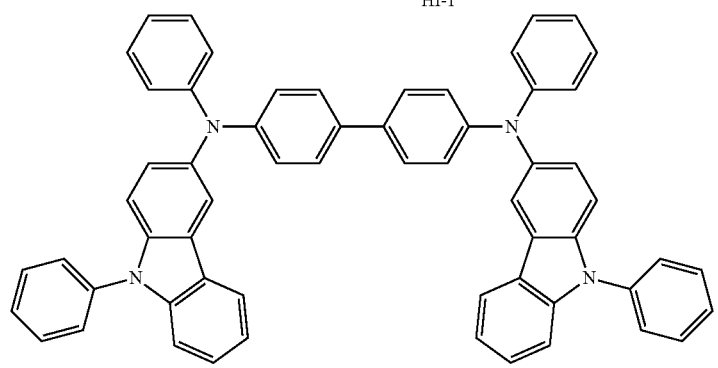
HI-2
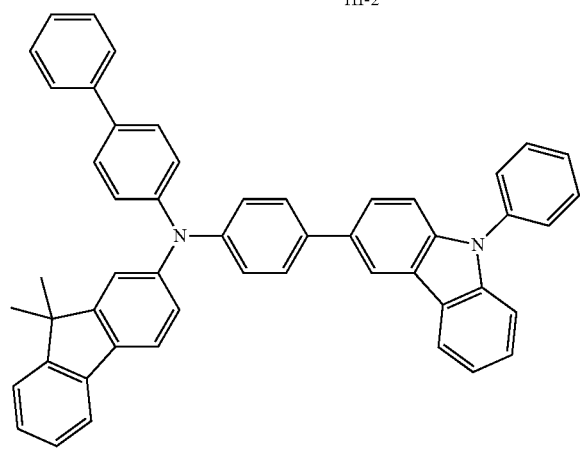
HT-1

-continued
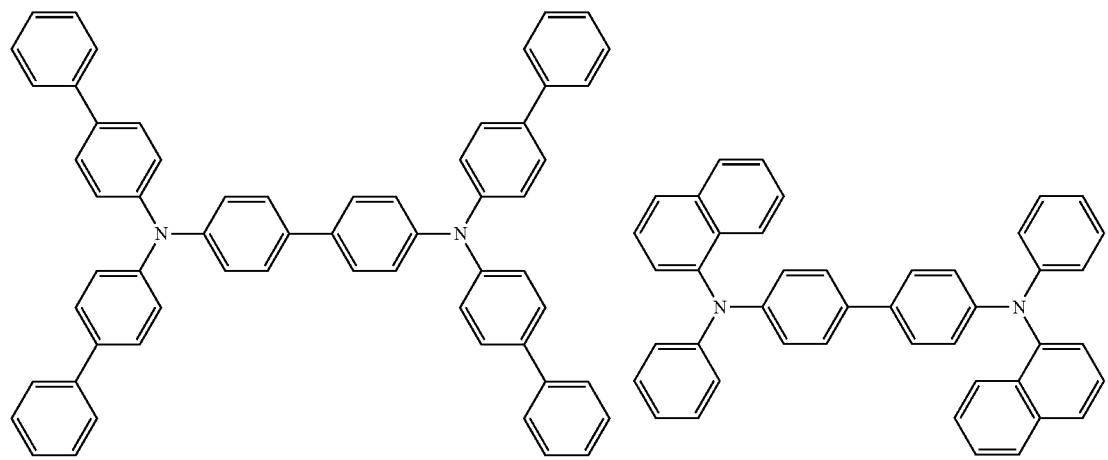
HT-2
NPD
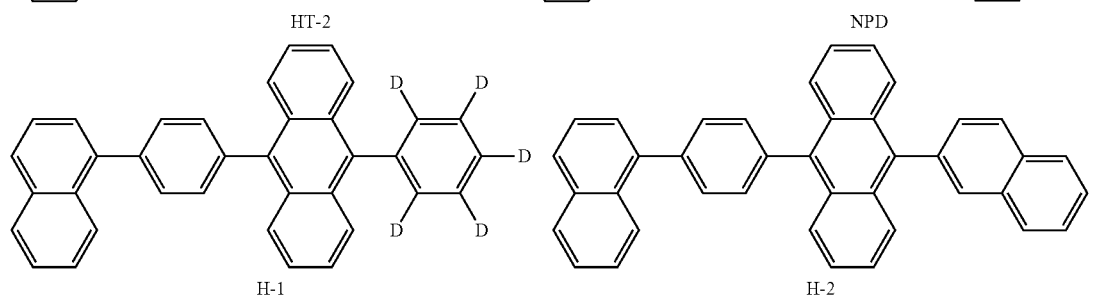
H-1
H-2
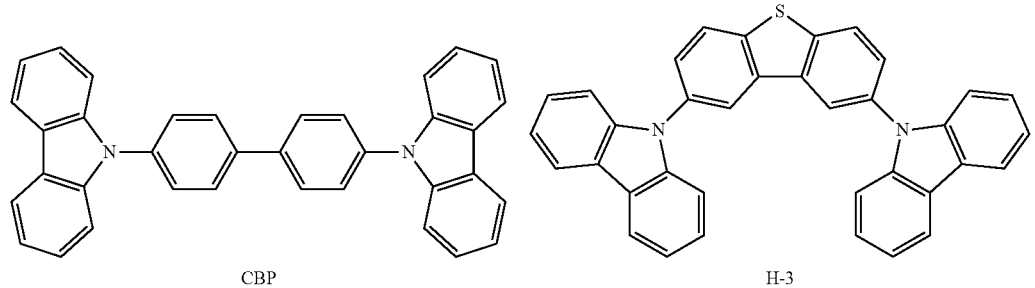
CBP
H-3
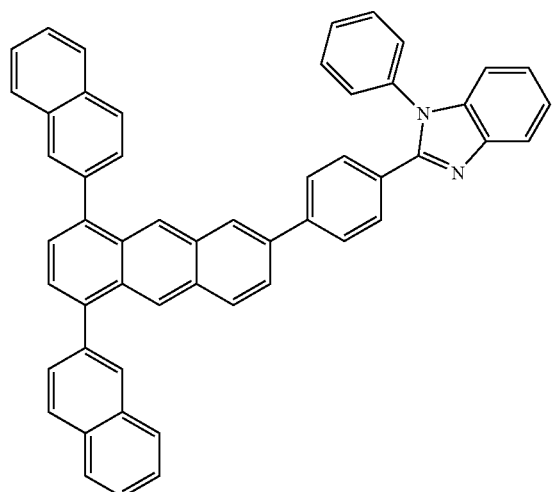
ET-1

-continued
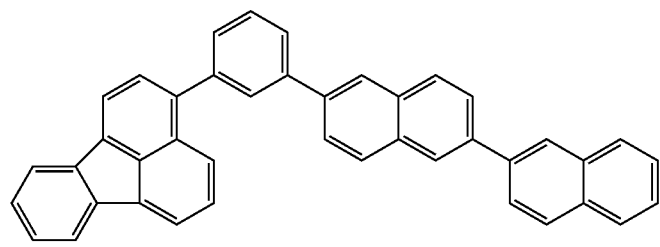
ET-2
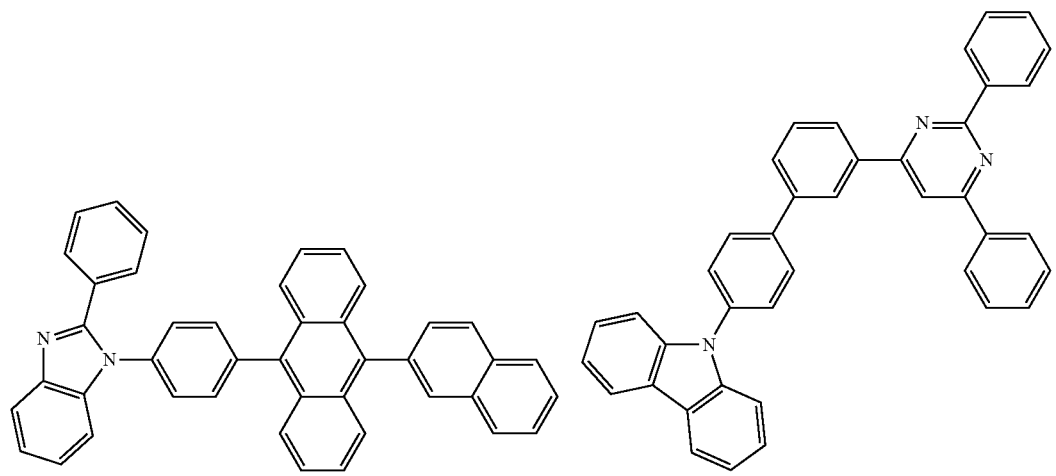
ET-3  ET-4
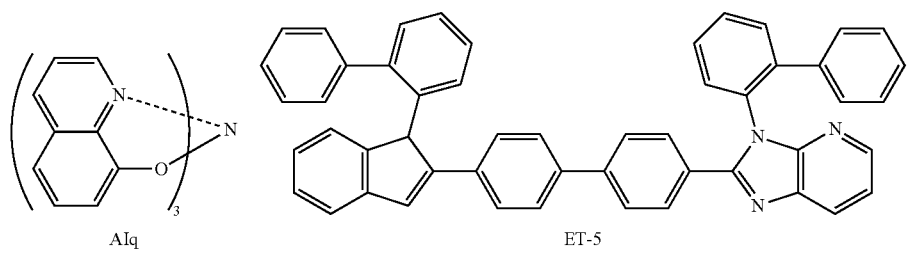
Alq  ET-5
[Formula 91]
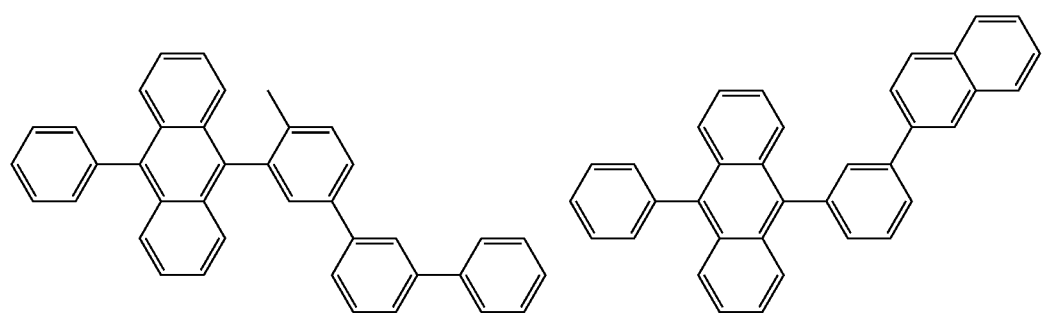
H-4  H-5
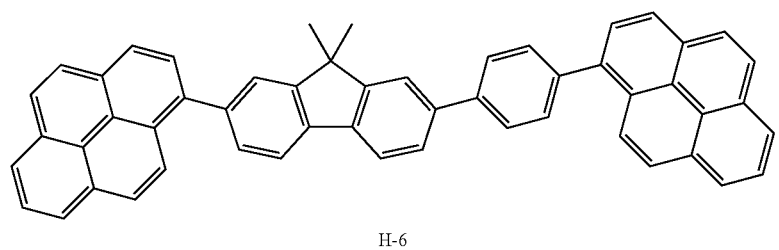
H-6

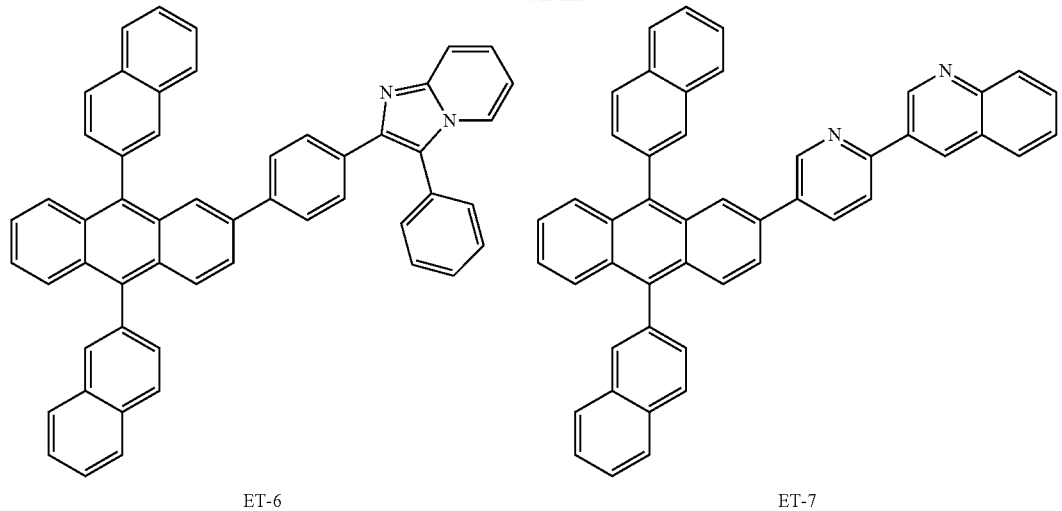

ET-6   ET-7

Example 1

1. Compound Synthesis Represented by General Equation (1)

The compound represented by general equation (1) can be synthesized by the method described in the present specification, in combination with other known reactions. A representative example of a detailed synthesis procedure of the compound represented by general equation (1) is described below.

(Synthesis of Compound 1)

[Formula 92]

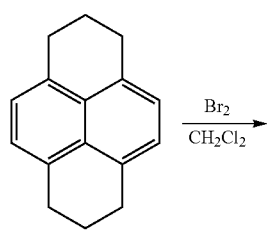

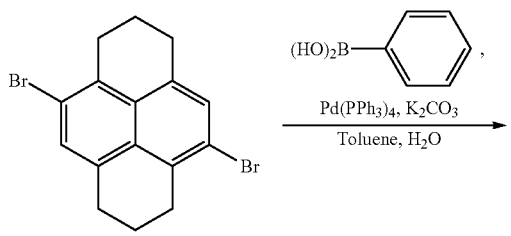

Synthesis Intermediate 1

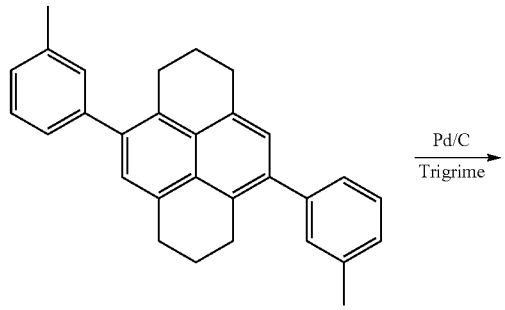

Synthesis Intermediate 2

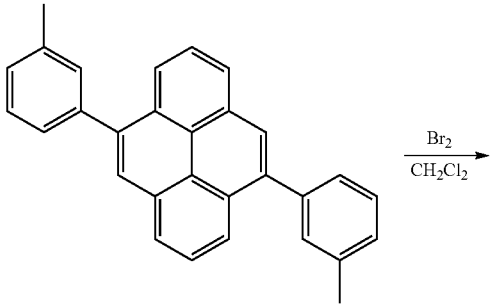

Synthesis Intermediate 3

-continued

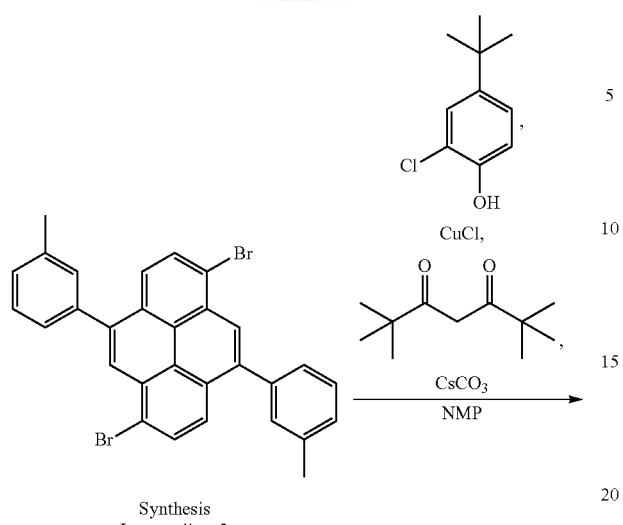

Synthesis
Intermediate 3

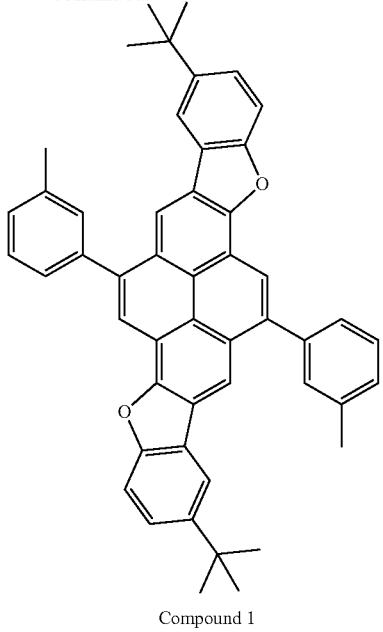

Compound 1

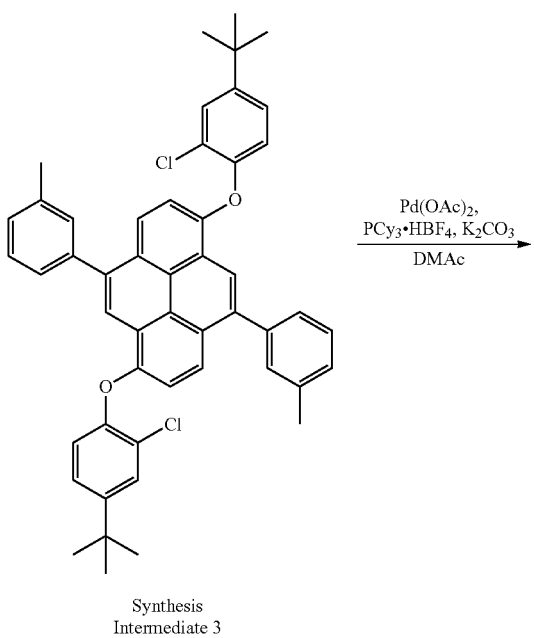

Synthesis
Intermediate 3

A synthesis intermediate 3 was synthesized according to the synthesis scheme, while referring to known documents. Next, the compound 1 was synthesized using the method below. 1.80 g (2.41 mmol) of synthesis intermediate 3, 108 mg (0.482 mmol) of palladium acetate, 355 mg (0.964 mmol) of tricyclohexylphosphonium phosphonium tetrafluoroborate, 1.33 g (9.64 mmol) of potassium carbonate, and 18 mL of dehydrated N,N-dimethylacetamide were mixed and stirred for 3 hours at 130° C. under a nitrogen atmosphere. After the reaction, the reaction liquid was returned to room temperature and then methanol was added, and then the deposition substance was washed successively in pure water and methanol. This solid substance was purified by chromatography (developing solvent: toluene), and then purified by recrystallizing with toluene/isopropanol (1:1) three times, and 1.08 g of compound 1 was achieved.

$^1$H NMR (400 MHz, in CDCl$_3$); δ (ppm)=8.77 (s, 2H), 8.59 (s, 2H), 8.13 (d, 2H), 7.68 (d, 6H), 7.63-7.57 (m, 4H), 7.45 (d, 2H), 2.61 (s, 6H), 1.49 (s, 18H) ppm.

The aforementioned compounds 2 to 28 used in the examples were also synthesized using a similar method as compound 1. Comparative compounds 1 to 6 were synthesized while referring to known documents that describe each compound. Identification data of compound 13 and compound 22 are shown below as a representative example.

(Compound 13)

$^1$H NMR (400 MHz, in THF-d$_8$); δ (ppm)=8.93 (s, 2H), 8.66 (d, 4H), 8.47 (d, 2H), 8.39 (d, 2H), 8.14 (s, 2H), 7.83 (d, 4H), 7.77 (d, 2H), 7.57 (d, 2H), 5.77 (s, 18H) ppm.

(Compound 22)

$^1$H NMR (400 MHz, in CDCl$_3$); δ (ppm)=8.81 (s, 2H), 8.63 (s, 2H), 8.18 (d, 2H), 7.74 (s, 2H), 7.48 (s, 4H), 7.42-7.29 (m, 12H), 2.54 (s, 12H), 2.37 (s, 6H) ppm.

2. Material Property Evaluation

<Material Property Evaluation>

A thin film with a film thickness of 50 nm was formed by vapor deposition on a 0.7 mm thick, 2.5 cm$^2$ quartz glass substrate using a vacuum vapor deposition method, such that the mCBP represented by the structural formula below and each light emitting material would be at a mass ratio of (95:5). UV light at 350 nm was irradiated on the achieved film, the emission spectrum during emission was measured with a fluorescence spectrophotometer (JASCO Corporation FP-6300), the emission wavelength (nm) and the spectrum half-value width (the energy difference (eV) of the short wavelength and the long wavelength that are 0.5 when the light emission maximum value is 1) was calculated, and each was described in three levels of ○, ×, and Δ, shown below.

(Emission Wavelength)
○: 440 nm or more, less than 460 nm
Δ: Less than 440 nm
×: 460 nm or more (Spectrum Half-Value Width)
○: Less than 0.27 eV
Δ: 0.27 eV or more, less than 0.32 eV
×: 0.32 eV or more

[Formula 93]

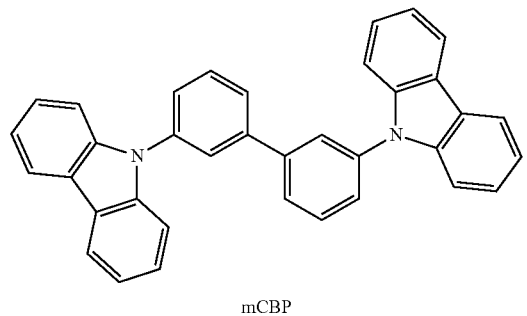

mCBP

TABLE 1

| Light emitting material | Emission wavelength | Spectrum half-value width | Note |
|---|---|---|---|
| Compound 1 | ○ | ○ | Present invention |
| Compound 2 | ○ | ○ | Present invention |
| Compound 3 | ○ | ○ | Present invention |
| Compound 4 | ○ | ○ | Present invention |
| Compound 5 | ○ | ○ | Present invention |
| Compound 6 | ○ | ○ | Present invention |
| Compound 7 | ○ | ○ | Present invention |
| Compound 8 | ○ | ○ | Present invention |
| Compound 9 | ○ | ○ | Present invention |
| Compound 10 | ○ | ○ | Present invention |
| Compound 11 | ○ | Δ | Present invention |
| Compound 12 | ○ | ○ | Present invention |
| Compound 13 | ○ | Δ | Present invention |
| Compound 14 | ○ | ○ | Present invention |
| Compound 15 | ○ | ○ | Present invention |
| Compound 16 | ○ | ○ | Present invention |
| Compound 17 | ○ | ○ | Present invention |
| Compound 18 | ○ | ○ | Present invention |
| Compound 19 | ○ | ○ | Present invention |
| Compound 20 | ○ | ○ | Present invention |
| Compound 21 | ○ | ○ | Present invention |
| Compound 22 | ○ | ○ | Present invention |
| Compound 23 | ○ | ○ | Present invention |
| Compound 24 | ○ | ○ | Present invention |
| Compound 25 | ○ | ○ | Present invention |
| Compound 26 | ○ | ○ | Present invention |
| Compound 27 | ○ | ○ | Present invention |
| Compound 28 | ○ | ○ | Present invention |
| Comparative compound 1 | Δ | × | Comparative example |
| Comparative compound 2 | Δ | × | Comparative example |
| Comparative compound 3 | × | Δ | Comparative example |
| Comparative compound 4 | × | Δ | Comparative example |
| Comparative compound 5 | Δ | × | Comparative example |
| Comparative compound 6 | Δ | × | Comparative example |

Example 2

<Element Preparation and Evaluation>

The materials used in element preparation were all subjected to sublimation purification and were confirmed to have 99.9% purity or higher (absorption intensity surface ratio of 254 nm) by high performance liquid chromatography (Tosoh Corporation TSKgel ODS-100Z).

A glass substrate with a 0.5 mm thick, 2.5 cm² ITO film (Geomatic Corporation, electrical surface resistance 10Ω/□) was placed in a cleaning container and was subjected to ultrasonic cleaning in 2-propanol, and then UV-ozone treated for 30 minutes. The organic compound layers below were successively vapor deposited onto the transparent anode (ITO film) using the vacuum vapor deposition method.

First layer: HAT-CN: Film thickness of 10 nm
Second layer: HT-1: Film thickness of 30 nm
Third layer: H-1 and the light emitting material described in Table 2 (mass ratio 96:4): Film thickness of 30 nm
Fourth layer: ET-1: Film thickness of 30 nm 1 nm of lithium fluoride and 100 nm of metallic aluminum were successively vapor deposited thereon to form the cathode.

The achieved laminated body was placed in a glove box purged with nitrogen gas without contacting air, sealed using a glass sealing can and an ultraviolet hardening type adhesive (XNR5516HV, made by Nagase Chiba Corporation), and the organic electroluminescent elements 1-1 to 1-7 with a light emitting part that was 2 mm×2 mm square, and organic electroluminescent elements 1-1 to 1-4 for comparison were achieved. The tests below were performed on each achieved organic electroluminescent element. The results of evaluating in terms of luminous efficiency, color purity, and driven color change are shown below in Table 2.

(a) Luminous Efficiency

A direct current volt was applied to each element using a Source Measure Unit 2400 made by Toyo Corporation, light was emitted, and the brightness was measured using a brightness photometer (BM-8 TOPCON Corporation). The emission spectrum and the emission wavelength were measured using a spectrum analyzer PMA-11 made by Hamamatsu Photonics. Based on this, the external quantum efficiency (q) with a brightness near 1000 cd/m² was calculated by brightness conversion. In Table 2, relative values are shown, with the value for the external quantum efficiency of comparative element 1-1 being 1.0. A larger number is favorable because a larger number indicates improved efficiency.

(b) Color Purity

Chromaticity (x, y) was calculated from the emission spectrum when each organic electroluminescent element emitted light with a brightness of 1000 cd/m² (CIE 1931 color system). The y value was evaluated into four levels using the criteria below.
⊚: 0.03 or more, 0.08 or less
○: 0.025 or more, less than 0.03, 0.08 or more, less than 0.12
Δ: 0.02 or more, less than 0.025, 0.12 or more, less than 0.18
×: Less than 0.02, 0.18 or more.
(c) Driven Chromaticity Change Direct current voltage was applied to each organic electroluminescent element such that the brightness would be 1000 cd/m² and continuously emit light, and the chromaticity (x', y') of when the brightness decreased to 500 cd/m² was calculated from the emission spectrum. The change Δy (=|y'−Δyl) in the y value before and after a driving deterioration was evaluated into four levels using the criteria below.
⊚: Less than 0.01
○: 0.01 or more, less than 0.02
Δ: 0.02 or more, less than 0.03
×: 0.03 or more

TABLE 2

| Element No. | Light emitting material | Light emission color | Color purity | Luminous efficiency (relative value) | Driven chromaticity change |
|---|---|---|---|---|---|
| Element 1-1 | Compound 1 | Blue | ⊚ | 1.4 | ⊚ |
| Element 1-2 | Compound 3 | Blue | ⊚ | 1.4 | ○ |
| Element 1-3 | Compound 5 | Blue | ⊚ | 1.4 | ○ |
| Element 1-4 | Compound 7 | Blue | ⊚ | 1.4 | ○ |
| Element 1-5 | Compound 8 | Blue | ⊚ | 1.5 | ⊚ |
| Element 1-6 | Compound 9 | Blue | ⊚ | 1.3 | ⊚ |
| Element 1-7 | Compound 11 | Blue | ○ | 1.3 | ○ |
| Element 1-8 | Compound 13 | Blue | ○ | 1.5 | ○ |
| Element 1-9 | Compound 14 | Blue | ⊚ | 1.5 | ⊚ |
| Element 1-10 | Compound 18 | Blue | ⊚ | 1.5 | ⊚ |
| Element 1-11 | Compound 20 | Blue | ⊚ | 1.4 | ⊚ |
| Element 1-12 | Compound 24 | Blue | ⊚ | 1.5 | ⊚ |
| Element 1-13 | Compound 26 | Blue | ⊚ | 1.4 | ⊚ |
| Comparative element 1-1 | Comparative compound 1 | Blue | Δ | 1.0 | X |
| Comparative element 1-2 | Comparative compound 2 | Blue-green | X | 0.9 | X |
| Comparative element 1-3 | Comparative compound 4 | Blue-green | X | 1.2 | Δ |
| Comparative element 1-4 | Comparative compound 6 | Blue | Δ | 0.6 | X |

Example 3

Each organic electroluminescent element of element 2-1 to 2-5 and comparative element 2-1 to 2-3 were prepared and the same evaluation as Example 2 was performed with the layer configurations the same as example 2 except for the changes indicated below. The results are shown below in Table 3. Furthermore, the luminous efficiency in Table 3 is displayed in relative value with the external quantum efficiency value of the comparative element 2-1 being 1.0.
First layer: HI-2: Film thickness of 50 nm
Second layer: HT-2: Film thickness of 45 nm
Third layer: H-2 and the light emitting material described in Table 3 (mass ratio 96:4):
Film thickness of 25 nm
Fourth layer: ET-2: Film thickness of 5 nm
Fifth layer: ET-3: Film thickness of 20 nm

TABLE 3

| Element No. | Light emitting material | Light emission color | Color purity | Luminous efficiency (relative value) | Driven chromaticity change |
|---|---|---|---|---|---|
| Element 2-1 | Compound 1 | Blue | ⊚ | 1.5 | ⊚ |
| Element 2-2 | Compound 2 | Blue | ⊚ | 1.6 | ⊚ |
| Element 2-3 | Compound 4 | Blue | ⊚ | 1.6 | ○ |
| Element 2-4 | Compound 7 | Blue | ⊚ | 1.5 | ○ |
| Element 2-5 | Compound 10 | Blue | ⊚ | 1.4 | ⊚ |
| Element 2-6 | Compound 12 | Blue | ⊚ | 1.5 | ⊚ |
| Element 2-7 | Compound 16 | Blue | ⊚ | 1.6 | ⊚ |
| Element 2-8 | Compound 17 | Blue | ⊚ | 1.6 | ⊚ |
| Element 2-9 | Compound 21 | Blue | ⊚ | 1.6 | ⊚ |
| Element 2-10 | Compound 22 | Blue | ⊚ | 1.6 | ⊚ |
| Element 2-11 | Compound 25 | Blue | ⊚ | 1.7 | ⊚ |

TABLE 3-continued

| Element No. | Light emitting material | Light emission color | Color purity | Luminous efficiency (relative value) | Driven chromaticity change |
|---|---|---|---|---|---|
| Element 2-12 | Compound 28 | Blue | ◉ | 1.5 | ◉ |
| Comparative element 2-1 | Comparative compound 2 | Blue-green | X | 1.0 | X |
| Comparative element 2-2 | Comparative compound 3 | Blue | Δ | 1.3 | X |
| Comparative element 2-3 | Comparative compound 5 | Blue | Δ | 0.8 | X |

Example 4

Each organic electroluminescent element of element 3-1 to 3-5 and comparative element 3-1 to 3-4 were prepared and the same evaluation as Example 1 was performed with the same layer configurations as example 2 except for the changes indicated below. The results are shown below in Table 4. Furthermore, the luminous efficiency in Table 4 is displayed as relative values with the external quantum efficiency value of the organic electroluminescent elements of the comparative element 3-1 being 1.0.

First layer: HI-2: Film thickness of 10 nm
Second layer: NPD: Film thickness of 30 nm
Third layer: Host material and light emitting material described in Table 4 (96:4): Film thickness of 30 nm
Fourth layer: ET-4: Film thickness of 10 nm
Fourth layer: Electron-transport material described in Table 4: Film thickness of 20 nm Example 5

(Organic EL Element Evaluation (Coating))
—Preparation of Coating Solution for Forming Light Emitting Layer—
A coating solution for forming light emitting layer 1 was achieved by mixing a MEK (methyl ethyl ketone) (98.99 mass %) with the compound 1 (0.1 mass %), and a host material H-1 (0.9 mass %).
(Element Preparation Procedure)
—Preparation of Organic Electroluminescent Element 4-1—
ITO was vapor deposited to form a film with a thickness of 150 nm onto a 25 mm×25 mm×0.7 mm glass substrate to form a transparent supporting substrate. The transparent supporting substrate was etched and cleansed.
Two mass parts of PTPDES-2 (made by Chemipro Kasei, Tg=205° C.) represented by the structural formula below were dissolved in 98 mass parts of cyclohexanone (made by

TABLE 4

| Element No. | Host material | Light emitting material | Electron-transport material | Light emission color | Color purity | Luminous efficiency (relative value) | Driven chromaticity change |
|---|---|---|---|---|---|---|---|
| Element 3-1 | CBP | Compound 4 | Alq | Blue | ◉ | 1.6 | ○ |
| Element 3-2 | H-3 | Compound 5 | ET-5 | Blue | ◉ | 1.5 | ○ |
| Element 3-3 | CBP | Compound 6 | Alq | Blue | ◉ | 1.5 | ◉ |
| Element 3-4 | CBP | Compound 9 | ET-5 | Blue | ◉ | 1.4 | ◉ |
| Element 3-5 | H-3 | Compound 10 | ET-5 | Blue | ◉ | 1.4 | ◉ |
| Element 3-6 | H-4 | Compound 1 | ET-6 | Blue | ◉ | 1.4 | ◉ |
| Element 3-7 | H-5 | Compound 2 | ET-6 | Blue | ◉ | 1.6 | ◉ |
| Element 3-8 | H-5 | Compound 5 | ET-7 | Blue | ◉ | 1.4 | ○ |
| Element 3-9 | H-6 | Compound 8 | ET-7 | Blue | ◉ | 1.7 | ◉ |
| Element 3-10 | H-6 | Compound 14 | ET-5 | Blue | ◉ | 1.6 | ◉ |
| Element 3-11 | CBP | Compound 15 | Er-5 | Blue | ◉ | 1.6 | ◉ |
| Element 3-12 | H-3 | Compound 19 | ET-6 | Blue | ◉ | 1.6 | ◉ |
| Element 3-13 | H-5 | Compound 23 | ET-6 | Blue | ◉ | 1.6 | ◉ |
| Element 3-14 | H-5 | Compound 24 | ET-7 | Blue | ◉ | 1.6 | ◉ |
| Element 3-15 | H-6 | Compound 27 | ET-7 | Blue | ◉ | 1.3 | ○ |
| Element 3-16 | H-6 | Compound 28 | ET-5 | Blue | ◉ | 1.4 | ○ |
| Comparative element 3-1 | CBP | Comparative compound 1 | Alq | Blue | Δ | 1.0 | X |
| Comparative element 3-2 | H-3 | Comparative compound 4 | Alq | Blue-green | X | 1.3 | X |
| Comparative element 3-3 | CBP | Comparative compound 5 | ET-5 | Blue | Δ | 0.9 | X |
| Comparative element 3-4 | H-3 | Comparative compound 6 | ET-5 | Blue | Δ | 0.8 | X |

Kanto Kagaku) for electronic industries and spin coated (2,000 rpm for 20 seconds) so that the thickness would be approximately 40 nm onto the ITO glass substrate, and dried for 30 minutes in 120° C. and annealing processed for 10 minutes in 160° C. to form a film of an electron hole injection layer.

[Formula 94]

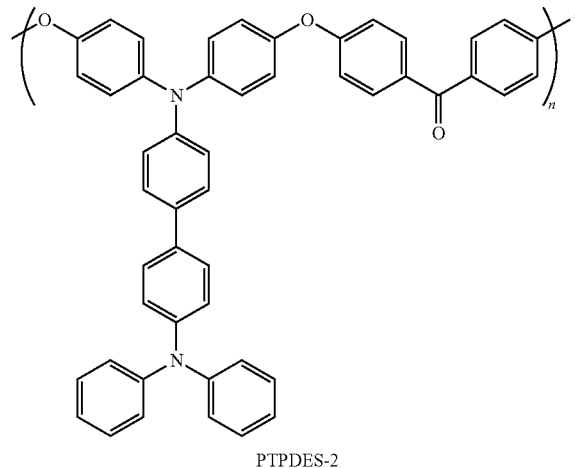

PTPDES-2

The aforementioned coating solution for forming light emitting layer 1 was spin coated so that the thickness would be approximately 40 nm (1,300 rpm for 30 seconds) onto the electron hole injection layer to form the light emitting layer.

Next, a BAlq (bis-(2-methyl-8-quinolinolato)-4-(phenyl-phenolate)-aluminium (III)) represented by the structural formula below was formed as the electron transport layer onto the light emitting layer using the vacuum vapor deposition method so that the thickness was 40 nm.

[Formula 95]

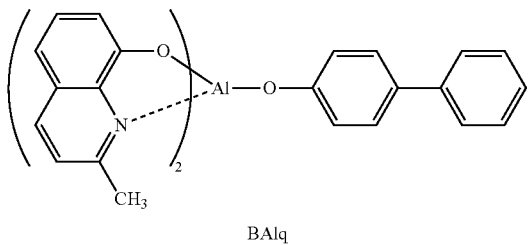

BAlq

Lithium fluoride (LiF) was formed as the electron injection layer onto the electron transporting using the vacuum vapor deposition method so that the thickness was 1 nm. Furthermore, 70 nm of metallic aluminum was vapor deposited to form the cathode. The laminated body prepared as described above was placed in a glove box substituted with argon gas and sealed using a stainless sealing can and an ultraviolet hardening type adhesive (XNR5516HV, made by Nagase Chiba Corporation) to prepare the organic electroluminescent element 4-1.

In the coating solution for forming light emitting layer 1, the coating solution prepared in the same way except for the compound 1 changed to the compound described in table 5 was used to achieve the organic electroluminescent element 4-2 and 4-3, and comparative element 4-1 and 4-2.

The same evaluation as Example 1 was performed on the organic electroluminescent element 4-1 to 4-3, and comparative element 4-1 and 4-2. The results are shown below in Table 5. Note that the luminous efficiency of Table 5 is displayed as a relative value with the external quantum efficiency value of the organic electro fluorescent element for comparison 4-1 being 1.0.

TABLE 5

| Element No. | Light emitting material | Light emission color | Color purity | Luminous efficiency (relative value) | Driven chromaticity change |
|---|---|---|---|---|---|
| Element 4-1 | Compound 1 | Blue | ○ | 1.5 | ○ |
| Element 4-2 | Compound 5 | Blue | ○ | 1.2 | Δ |
| Element 4-3 | Compound 7 | Blue | ○ | 1.4 | Δ |
| Comparative element 4-1 | Comparative compound 1 | Blue | Δ | 1.0 | X |
| Comparative element 4-2 | Comparative compound 5 | Blue | Δ | 0.8 | X |

From the results of each table above, the compound of the present invention was found to have high luminous efficiency, excellent blue color purity, and small chromaticity change involving drive deterioration.

On the other hand, each comparative element using the comparative compound 1 described in Japanese Unexamined Patent Application 2010-205986 was found to have less chromaticity change involving drive deterioration.

Similarly, each comparative element using the comparative compound 2 described in Japanese Unexamined Patent Application 2010-205986 was found to have inferior color purity and color change related to drive deterioration.

Comparative elements using the comparative compound 3 described in Japanese Unexamined Patent Application 2011-51984 was found to have inferior color change related to drive deterioration.

The comparative element using the comparative compound 4 described in Japanese Unexamined Patent Application 2011-205986, KR 20110006915 and KR 20110041726 was found to have inferior color purity and inferior color change related to drive deterioration. The comparative element using the comparative compound 5 described in WO 2010012328 was found to have inferior color purity and inferior color change related to drive deterioration. The comparative element using the comparative compound 5 described in Japanese Unexamined Patent Application H2-120747 was found to have inferior color purity and inferior color change related to drive deterioration.

DESCRIPTION OF SYMBOLS

2 . . . Substrate
3 . . . Anode
4 . . . Electron hole injection layer
5 . . . Electron hole transport layer
6 . . . Light emitting layer
7 . . . Electron hole blocking layer
8 . . . Electron transport layer
9 . . . Cathode
10 . . . Organic electroluminescent element
11 . . . Organic layer
12 . . . Protective layer
14 . . . Adhesion layer
16 . . . Sealing layer
20 . . . Light emitting device
30 . . . Optical scattering member
31 . . . Transparent substrate
30 A . . . Light entrance surface
30 B . . . Light exit surface
32 . . . Particle
40 . . . Illumination device

The invention claimed is:

1. An organic electroluminescent element, comprising:
a substrate;
a pair of electrodes including an anode and a cathode, disposed on the substrate; and
at least one organic layer which is arranged between the electrodes and which includes a light emitting layer;
wherein the organic layer contains a compound expressed by general formula (1) in at least one layer:

[Formula 1]

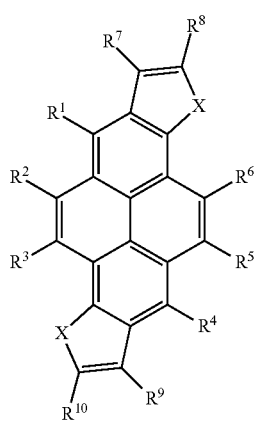

General Formula (1)

wherein in general formula (1), the two X's represent the same linking group, and either both represent oxygen atoms or both represent sulfur atoms, $R^1$ through $R^{10}$ independently represent a hydrogen atom or a substitution group, and $R^1$ through $R^{10}$ may jointly form a ring; however, if the two X's represent sulfur atoms, at least one of $R^2$, $R^3$, $R^5$, and $R^6$ represents a substitution group.

2. The organic electroluminescent element according to claim 1, wherein the compound expressed by general formula (1) is expressed by general formula (2):

[Formula 2]

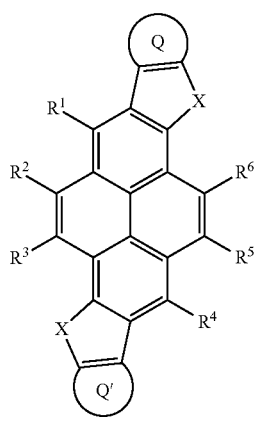

General Formula (2)

wherein in general formula (2), the two X's represent the same linking group, and either both represent oxygen atoms or both represent sulfur atoms, $R^1$ through $R^6$ independently represent a hydrogen atom or a substitution group, and $R^1$ through $R^6$ may jointly form a ring; Q and Q' independently represent an aromatic five membered ring or an aromatic six-membered ring; however, if the two X's represent sulfur atoms, at least one of $R^2$, $R^3$, $R^5$, and $R^6$ represents a substitution group.

3. The organic electroluminescent element according to claim 2, wherein the compound expressed by general formula (2) is expressed by general formula (3):

[Formula 3]

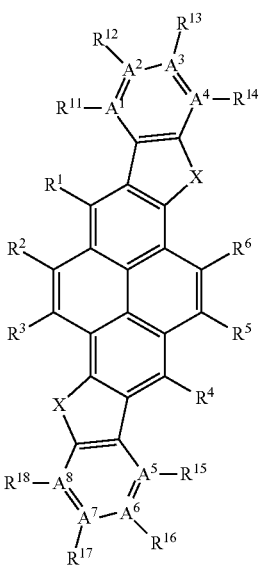

General Formula (3)

wherein in general formula (3), the two X's represent the same linking group, and either both represent oxygen atoms or both represent sulfur atoms, $R^1$ through $R^6$ independently represent a hydrogen atom or a substitution group, and $R^1$ through $R^6$ may jointly form a ring $R^{11}$ through $R^{18}$ independently represent a hydrogen atom or a substitution group; $A^1$ through $A^8$ independently represent a carbon atom or a nitrogen atom, and if $A^1$ through $A^8$ represent a nitrogen atom, $R^{11}$ through $R^{18}$ that bonds thereto does not exist; however, if the two X's represent sulfur atoms, at least one of $R^2$, $R^3$, $R^5$, and $R^6$ represents a substitution group.

4. The organic electroluminescent element according to claim 3, wherein the compound expressed by general formula (3) is expressed by general formula (4):

[Formula 4]

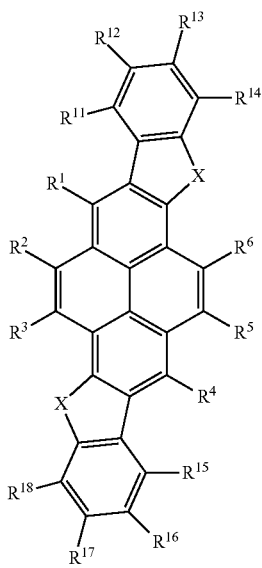

General Formula (4)

wherein in general formula (4), the two X's represent the same linking group, and either both represent oxygen atoms or both represent sulfur atoms, $R^1$ through $R^6$ independently represent a hydrogen atom or a substitution group, and $R^1$ through $R^6$ may jointly form a ring; $R^{11}$ through $R^{18}$ independently represent a hydrogen atom or a substitution group; however, if the two X's represent sulfur atoms, at least one of $R^2$, $R^3$, $R^5$, and $R^6$ represents a substitution group.

5. The organic electroluminescent element according to claim 4, wherein in general formula (4), at least one of $R^1$ through $R^6$ and $R^{11}$ through $R^{18}$ is a substitution group containing one of a fluorine atom, alkyl group, silyl group, or amino group.

6. The organic electroluminescent element according to claim 4, wherein the compound expressed by general formula (4) is expressed by general formula (5):

[Formula 5]

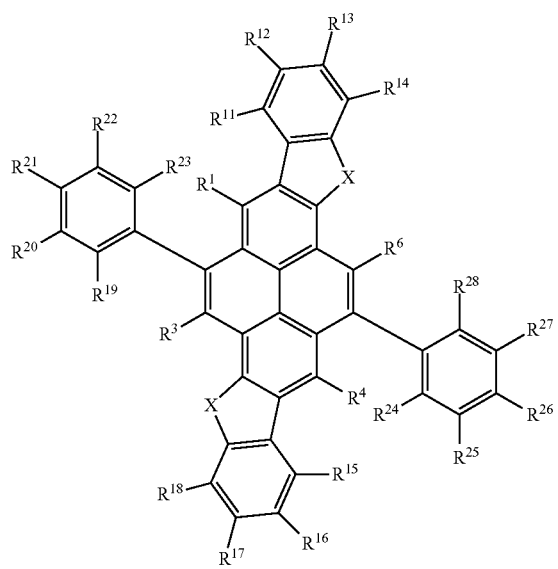

General Formula (5)

wherein in general formula (5), the two X's represent the same linking group, and either both represent oxygen atoms or both represent sulfur atoms, and $R^1$, $R^3$, $R^4$, and $R^6$ independently represent a hydrogen atom or a substitution group; $R^{11}$ through $R^{28}$ independently represent a hydrogen atom or a substitution group; however, at least one of $R^3$ through $R^6$ and $R^{11}$ through $R^{18}$ is a substitution group containing one of a fluorine atom, alkyl group, silyl group, or amino group, or at least one of $R^{19}$ through $R^{28}$ is a fluorine atom, alkyl group, silyl group, or amino group.

7. The organic electroluminescent element according to claim 6, wherein in general formula (5), $R^{13}$ is a substitution group.

8. The organic electroluminescent element according to claim 6, wherein the compound expressed by general formula (5) is expressed by general formula (6):

[Formula 6]

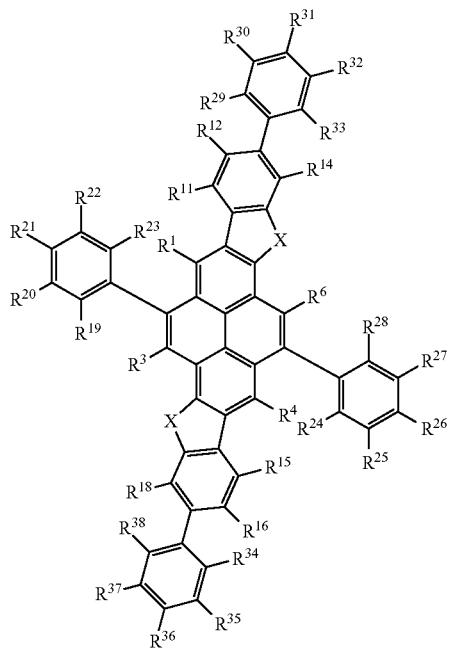

General Formula (6)

wherein in general formula (6), the two X's represent the same linking group, and either both represent oxygen atoms or both represent sulfur atoms, and $R^1$, $R^3$, $R^4$, and $R^6$ independently represent a hydrogen atom or a substitution group; $R^{11}$ through $R^{38}$ independently represent a hydrogen atom or a substitution group.

9. The organic electroluminescent element according to claim 4, wherein the compound expressed by general formula (4) is expressed by general formula (7):

[Formula 7]

General Formula (7)

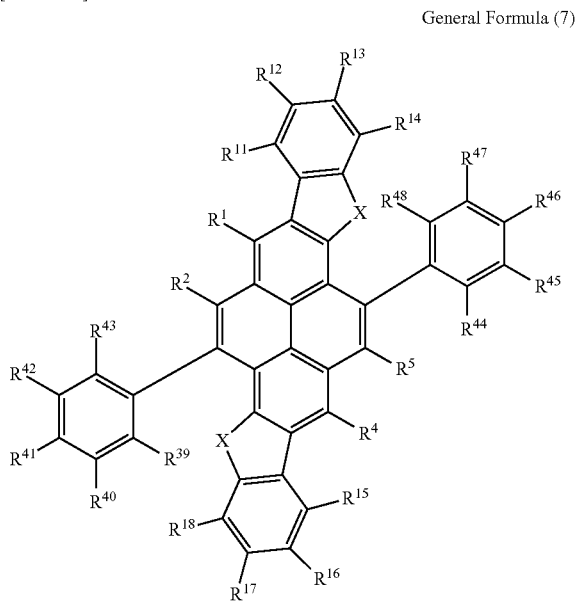

wherein in general formula (7), the two X's represent the same linking group, and either both represent oxygen atoms or both represent sulfur atoms, and $R^1$, $R^2$, $R^4$, and $R^5$ independently represent a hydrogen atom or a substitution group; a ring may be jointly formed by a plurality of $R^1$, $R^2$, $R^4$, and $R^5$; $R^{11}$ through $R^{48}$ independently represent a hydrogen atom or a substitution group.

10. The organic electroluminescent element according to claim 9, wherein in general formula (7), $R^{13}$ is a substitution group.

11. The organic electroluminescent element according to claim 9, wherein the compound expressed by general formula (7) is expressed by general formula (8):

[Formula 8]

General Formula (8)

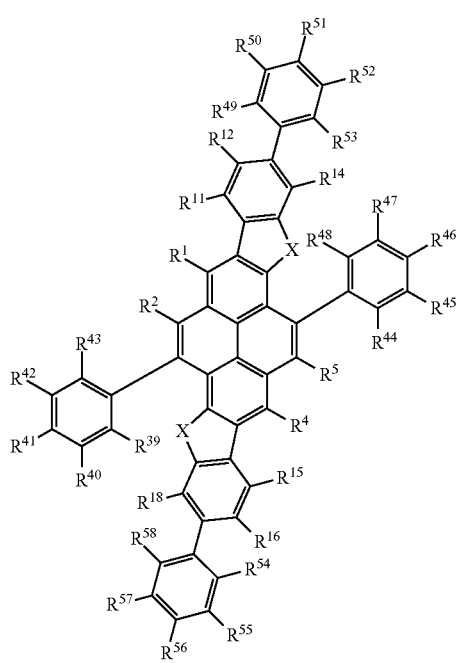

wherein in general formula (8), the two X's represent the same linking group, and either both represent oxygen atoms or both represent sulfur atoms, and $R^1$, $R^2$, $R^4$, and $R^5$ independently represent a hydrogen atom or a substitution group; a ring may be jointly formed by a plurality of $R^1$, $R^2$, $R^4$, and $R^5$; $R^{11}$ through $R^{58}$ independently represent a hydrogen atom or a substitution group.

12. The organic electroluminescent element according to claim 4, wherein the compound expressed by general formula (4) is expressed by general formula (9):

[Formula 9]

General Formula (9)

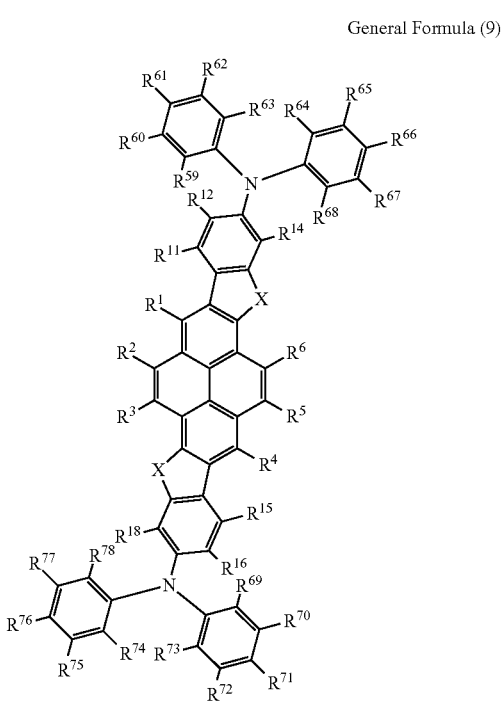

wherein in general formula (9), the two X's represent the same linking group, and either both represent oxygen atoms or both represent sulfur atoms, and $R^1$ through $R^6$ independently represent a hydrogen atom or a substitution group; a ring may be jointly formed by a plurality of $R^1$ through $R^6$; $R^{11}$ through $R_{78}$ independently represent a hydrogen atom or a substitution group.

13. The organic electroluminescent element according to claim 12, wherein in general formula (9), at least one of $R^2$, $R^3$, $R^5$, and $R^6$ is a substitution group.

14. The organic electroluminescent element according to claim 1, where in general formula (1), both X's represent oxygen atoms.

15. The organic electroluminescent element according to claim 1, wherein at least one layer of the organic layer containing the compound expressed by general formula (1) is a light emitting layer.

16. The organic electroluminescent element according to claim 1, wherein the light emitting layer is formed using a vacuum vapor deposition process.

17. The organic electroluminescent element according to claim 1, wherein the light emitting layer is formed using a wet process.

18. A light emitting device comprising the organic electroluminescent element according to claim 1.

19. A display device comprising the organic electroluminescent element according to claim 1.

20. A lighting device comprising the organic electroluminescent element according to claim 1.

* * * * *